US009643971B2

(12) United States Patent
Dax et al.

(10) Patent No.: US 9,643,971 B2
(45) Date of Patent: May 9, 2017

(54) BREATHING CONTROL MODULATING COMPOUNDS, AND METHODS OF USING SAME

(71) Applicant: GALLEON PHARMACEUTICALS, INC., Horsham, PA (US)

(72) Inventors: Scott Dax, Landenberg, PA (US); James Joseph Mencel, North Wales, PA (US); Vita Ozola, Adazu Nov. (LV); Kirill Shubin, Riga (LV); Marina Martjuga, Riga (LV); Edgars Suna, Riga (LV)

(73) Assignee: Galleon Pharmaceuticals, Inc., Doylestown, PA (US)

( * ) Notice: Subject to any disclaimer, the term of this patent is extended or adjusted under 35 U.S.C. 154(b) by 0 days.

(21) Appl. No.: 14/776,391

(22) PCT Filed: Mar. 13, 2014

(86) PCT No.: PCT/US2014/025792
§ 371 (c)(1),
(2) Date: Sep. 14, 2015

(87) PCT Pub. No.: WO2014/151462
PCT Pub. Date: Sep. 25, 2014

(65) Prior Publication Data
US 2016/0046635 A1 Feb. 18, 2016

Related U.S. Application Data

(60) Provisional application No. 61/792,185, filed on Mar. 15, 2013.

(51) Int. Cl.
*A61K 31/519* (2006.01)
*C07D 487/04* (2006.01)
*A61K 45/06* (2006.01)
*C07D 519/00* (2006.01)
*A61K 9/48* (2006.01)
*A61K 9/50* (2006.01)
*A61K 31/5377* (2006.01)
*A61K 31/541* (2006.01)

(52) U.S. Cl.
CPC .............. *C07D 487/04* (2013.01); *A61K 9/48* (2013.01); *A61K 9/4891* (2013.01); *A61K 9/5084* (2013.01); *A61K 31/519* (2013.01); *A61K 31/5377* (2013.01); *A61K 31/541* (2013.01); *A61K 45/06* (2013.01); *C07D 519/00* (2013.01)

(58) Field of Classification Search
CPC .... A61K 9/4891; A61K 45/06; A61K 31/519; C07D 487/04
USPC ................... 424/452, 490; 514/228.1, 234.2; 544/118, 58.2
See application file for complete search history.

(56) References Cited

U.S. PATENT DOCUMENTS

| 3,031,450 A * | 4/1962 | Fischer ................ C07D 487/04 540/600 |
| 5,075,290 A | 12/1991 | Findley et al. |
| 6,232,312 B1 | 5/2001 | Pamukcu et al. |
| 2005/0159414 A1* | 7/2005 | Nickolaus ............ A61K 31/519 514/227.8 |
| 2010/0255087 A1* | 10/2010 | Coulter ................ A61K 9/5015 424/457 |

FOREIGN PATENT DOCUMENTS

| JP | 49011897 A | 2/1974 |
| WO | 9009996 A1 | 9/1990 |
| WO | 9514478 A1 | 6/1995 |
| WO | 2012074999 A1 | 6/2012 |

OTHER PUBLICATIONS

Johnson, title: Molecular mechanisms of β-adrenergic receptor function, response, and regulation; Journal of Allergy and Clinical Immunology; vol. 117, Issue 1, Jan. 2006, pp. 18-24.*
International Search Report issued for PCT International Application No. PCT/US2014/025792 dated Jul. 30, 2014.
Pubchem SureCN7939019, CID 350861, pp. 1-3, create date: Mar. 26, 2005. Retrieved from internet: <URL: http://pubchem.ncbi.nlm.nih.gov/summary/summary.cgi?cid=350861&loc=ec_rcs>.
Pubchem SureCN7930960, CID 350874, pp. 1-3, create date: Mar. 26, 2005. Retrieved from the internet: <URL: http://pubchem.ncbi.nlm.nih.gov/summary/summary.cgi?cid=350874&loc=ec_rcs>.
Barlow, et al., "Resistance-Modifying Agents. Part 7: 2,6-disubstituted-4,8-dibenzylaminopyrimido[5,4-d]pyrimidines that Inhibit Nucleoside Transport in the Presence of Alpha1-acid Glycoprotein (AGP)", Bioorganic & Medicinal Chemistry Letters, vol. 10, No. 6, 2000, pp. 585-589.
Curtin, et al., "Resistance-Modifying Agents. 11. Pyrimido[5,4-d]pyrimidine Modulators of Antitumor Drug Activity. Synthesis and Structure-Activity Relatinoships for Nucleoside Transport Inhibtion and Binding to alpha1-Acid Glycoprotein", Journal of Medicinal Chemistry, vol. 47, No. 20, 2004, pp. 4905-4922.

(Continued)

*Primary Examiner* — Yanzhi Zhang
(74) *Attorney, Agent, or Firm* — Saul Ewing LLP; Kathryn Doyle; Domingos J. Silva

(57) ABSTRACT

The present invention includes pyrimido[5,4-d]pyrimidines that are useful in the prevention and/or treatment of breathing control diseases or disorders in a subject in need thereof. The present invention also includes a method of preventing and/or treating a respiratory disease or disorder in a subject in need thereof, comprising administering to the subject a therapeutically effective amount of at least one compound of the invention. The present invention further includes a method of preventing destabilization or stabilizing breathing rhythm in a subject in need thereof, comprising administering to the subject a therapeutically effective amount of at least one compound of the invention.

70 Claims, 17 Drawing Sheets

(56) References Cited

OTHER PUBLICATIONS

Lin, et al., "Synthesis, Flow Cytometric Evaluation, and Identification of Highly Potent Dipyridamole Analogues as Equilibrative Nucleoside Transporter 1 Inhibitors", Journal of Medicinal Chemistry, vol. 50, No. 16, 2007, pp. 3906-3920.

Nepomuceno, et al., "Antioxidant Effect of Dipyridamole and its Derivative RA-25 in Mitochondria: Correlation of Activity and Location in the Membrane", Biochimica et Biophysica Acta, vol. 1418, No. 2, 1999, pp. 285-294.

\* cited by examiner

Apneas/hr

Apneas/hr

* p<0.05 different to vehicle

Apneas/hr

Apneas/hr

* p<0.05 different to vehicle

BREATHING CONTROL MODULATING COMPOUNDS, AND METHODS OF USING SAME

CROSS-REFERENCE TO RELATED APPLICATIONS

The present application is a 35 U.S.C. §371 national phase application of International Application No. PCT/US2014/025792, filed Mar. 13, 2014, and published under PCT Article 21(2) in English, which claims priority under 35 U.S.C. §119(e) to U.S. Provisional Application No. 61/792,185, filed Mar. 15, 2013, all of which applications are incorporated herein by reference in their entireties.

BACKGROUND OF THE INVENTION

Normal control of breathing is a complex process that involves, in part, the body's interpretation and response to chemical stimuli such as carbon dioxide, pH and oxygen levels in blood, tissues and the brain. Normal breathing control is also affected by other factors such as wakefulness (i.e., whether the patient is awake or sleeping), emotion, posture and vocalization. Within the brain medulla, there are respiratory control centers that interpret various feed-forward and feed-back signals that affect respiration by issuing commands to the muscles that perform the work of breathing. Key muscle groups are located in the abdomen, diaphragm, pharynx and thorax. Sensors located centrally and peripherally then provide input to the brain's central respiration control areas that enables response to changing metabolic requirements.

For example, ventilation sufficient to meet the body's metabolic needs is maintained primarily by the body's rapid response to changes in carbon dioxide ($CO_2$) levels. Increased $CO_2$ levels (hypercapnia) signal the body to increase breathing rate and depth, resulting in higher blood oxygen levels and subsequent lower blood $CO_2$ levels. Conversely, low $CO_2$ levels (hypocapnia) can result in periods of hypopnea (decreased breathing) or, in the extreme case, apnea (no breathing) since the stimulation to breathe is diminished.

There are many diseases in which loss of normal breathing control is a primary or secondary feature of the disease. Examples of diseases with a primary loss of breathing control are sleep apneas (central, mixed or obstructive; where the breathing repeatedly stops for 10 to 60 seconds) and congenital central hypoventilation syndrome. Secondary loss of breathing control may be due to chronic cardiopulmonary diseases (e.g., heart failure, chronic bronchitis, emphysema, and impending respiratory failure), excessive weight (e.g., obesity-hypoventilation syndrome), certain drugs (e.g., anesthetics, sedatives, sleeping aids, anxiolytics, hypnotics, alcohol, and narcotic analgesics and/or factors that affect the neurological system (e.g., stroke, tumor, trauma, radiation damage, and ALS). In chronic obstructive pulmonary diseases where the body is exposed to chronically high levels of carbon dioxide, the body adapts to the respiratory acidosis (lower pH) by a kidney mediated retention of bicarbonate, which has the effect of partially neutralizing the $CO_2$/pH respiratory stimulation. Thus, the patient is unable to mount a normal ventilatory response to changes in metabolic demand.

Sleep disordered breathing is an example of where abnormalities in the control of breathing lead to a serious and prevalent disease in humans. Sleep apnea is characterized by frequent periods of no or partial breathing. Key factors that contribute to these apneas include anatomical factors (e.g., obesity), decreased hypercapnic and hypoxic ventilatory responses (e.g., decreased response to high carbon dioxide and low oxygen levels, respectively) and loss of "wakefulness" (i.e., respiratory drive to both lungs and/or to pharyngeal dilator muscles during sleep). Apneic events result in hypoxia (and the associated oxidative stress) and eventually severe cardiovascular consequences (high blood pressure, stroke, heart attack).

Estimates for U.S. individuals afflicted with conditions wherein there is compromised respiratory control include sleep apneas (15-20 millions); obesity-hypoventilation syndrome (3-5 millions); chronic heart disease (5 millions); chronic obstructive pulmonary disease (COPD)/chronic bronchitis (10 millions); drug-induced hypoventilation (2-10 millions); and mechanical ventilation weaning (0.5 million).

Drugs are most often eliminated by biotransformation and/or excretion into urine, feces or bile. The liver is the major organ for xenobiotic biotransformation, and is thereby important in characterizing the metabolic stability, toxicology, and drug-drug interaction properties of drugs. Drug metabolism is achieved via two major liver-located enzyme reactions: Phase I and Phase II reactions. Phase I enzymes include the cytochrome $P^{450}$ (CYP450) family of enzymes, which are located in the smooth endoplasmic reticulum. The basic processes in Phase I reactions are oxidation, reduction and/or hydrolysis, many of which are catalyzed by the CYP450 system and require NADPH as a cofactor. Phase II enzymes are located in the cytoplasm and endoplasmic reticulum, and perform conjugation reactions including glucuronic acid, glutathione, sulfate, and glutamine conjugations. Phase II reactions generally inactivate the drug if it is not already therapeutically inactive following Phase I metabolism, and also make the drug more water soluble to facilitate its elimination. Some drugs are metabolized by Phase I or Phase II enzymes alone, whereas others are metabolized by both Phase I and Phase II enzymes (Baranczewski et al., 2006, Pharmacol. Rep. 58:453-472). Microsomes are subcellular liver tissue fractions (membrane vesicles of the smooth endoplasmic reticulum) and contain the Phase I CYP450 family of enzymes. Compounds undergo only Phase I metabolism in liver microsomes in the presence of NADPH cofactors. Significant parent-drug disappearance in the presence of liver microsomes thus indicates that the drug will be significantly modified by the CYP450 enzymes in the body (Rodrigues, 1994, Biochem, Pharm. 48(12):2147).

The purpose of a pharmacokinetic (PK) study is to use drug concentration-time profiles and associated pharmacokinetic parameters to understand how the drug is processed, modified, distributed and/or eliminated upon administration to an animal. In drug discovery, a pharmacokinetic study is performed to (1) guide dosage regimen design for animal efficacy and toxicity studies, (2) understand and interpret pharmacology and toxicology study results, and (3) select the drug candidates with desired pharmacokinetic properties for the disease indication intended. The PK data from the animal studies can be extrapolated to predict PK profiles in humans so as to select and optimize dosage regimens for a drug candidate in human clinical trials.

There is a need in the art for novel compounds useful for restoring all or part of the body's normal breathing control system in response to changes in $CO_2$ and/or oxygen levels, with minimal side effects. Further, there is a need in the art for novel compounds useful for restoring all or part of the body's normal breathing control system, that possess suitable metabolic stability and suitable pharmacokinetic properties, such as oral bioavailability. Further, there is a need in the art for novel compounds useful for restoring all or part of the body's normal breathing control system, that can be administered orally and used in a chronic manner, as well as acutely, via methods including intravenous administration. The present invention addresses and meets these needs.

BRIEF SUMMARY OF THE INVENTION

The invention provides a compound or salt thereof. The invention further provides a pharmaceutical composition comprising the compound of the invention and at least one pharmaceutically acceptable carrier. The invention further provides a method of preventing or treating a breathing control disorder or disease in a subject in need thereof, the method comprising administering to the subject an effective amount of a pharmaceutical composition comprising at least one pharmaceutically acceptable carrier and at least one compound of the invention or salt thereof. The invention further provides a method of preventing destabilization or stabilizing breathing rhythm in a subject in need thereof, the method comprising administering to the subject an effective amount of a pharmaceutical composition comprising at least one pharmaceutically acceptable carrier and at least one compound of the invention or salt thereof. The invention further provides a method of preparing $N^2$-$N^6$-bis-cyclopropylmethyl $N^4$,$N^8$-dimethyl-pyrimido[5,4-d]pyrimidine-2,4,6,8-tetraamine (84).

In certain embodiments, the compound is selected from the group consisting of:
a compound of formula (I):

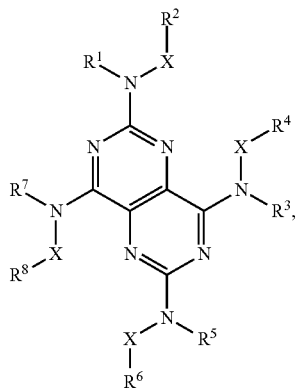

wherein in formula (I):
$R^1$, $R^2$, $R^3$, $R^4$, $R^5$, $R^6$, $R^7$ and $R^8$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$, $R^3$ and $R^4$, $R^5$ and $R^6$, or $R^7$ and $R^8$ independently combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl; each occurrence of X is independently selected from the group consisting of bond, NH, NR$^9$ and O; and, each occurrence of X is independently alkyl or substituted alkyl;

a compound of formula (II):

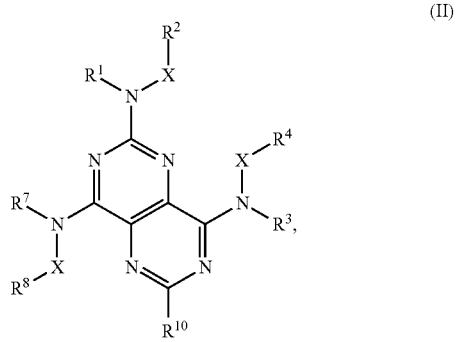

wherein in formula (II):
$R^1$, $R^2$, $R^3$, $R^4$, $R^7$ and $R^8$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$, $R^3$ and $R^4$, $R^5$ and $R^6$, or $R^7$ and $R^8$ independently combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl; each occurrence of X is independently selected from the group consisting of bond, NH, NR$^9$ and O; each occurrence of R$^9$ is independently alkyl, or substituted alkyl; $R^{10}$ is H, halogen, CN, amidino, amido, carboxy, carboxamido, hydrazino, OH, alkyl or substituted alkyl, alkoxy or substituted alkoxy, or thioalkoxy or substituted thioalkoxy; and, a compound of formula (III):

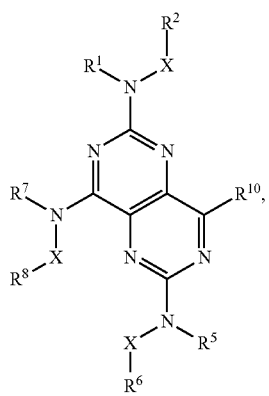

wherein in formula (III):
$R^1$, $R^2$, $R^3$, $R^4$, $R^7$ and $R^8$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$, $R^3$ and $R^4$, $R^5$ and $R^6$, or $R^7$ and $R^8$ independently combine as to form a biradical selected from the group consisting of 3-hydroxy-pentane-1,5-diyl, 6-hydroxy-cycloheptane-1,4- diyl, propane-1,3-diyl, butane-1,4-diyl and pentane-1,5-diyl; each occurrence of X is independently selected from the group consisting of: bond, NH, $NR^9$ and O; each occurrence of $R^9$ is independently alkyl or substituted alkyl; and $R^{10}$ is H, halogen, CN, amidino, amido, carboxy, carboxamido, hydrazino, OH, alkyl or substituted alkyl, alkoxy or substituted alkoxy, or thioalkoxy or substituted thioalkoxy; and any combinations thereof.

In certain embodiments, the compound is selected from the group consisting of: $N^2,N^6$-Dimethyl-$N^4,N^8$-di-n-propyl-pyrimido[5,4-d]pyrimidine-2,4,6,8-tetraamine; $N^2,N^4,N^6,N^8$-Tetra-n-propyl-pyrimido[5,4-d]pyrimidine-2,4,6,8-tetraamine; $N^2,N^6$-Di-n-butyl-$N^4$, $N^8$-di-n-propyl-pyrimido[5,4-d]pyrimidine-2,4,6,8-tetraamine; $N^2,N^6$-Di-i-propyl-$N^4$, $N^8$-di-n-propyl-pyrimido[5,4-d]pyrimidine-2,4,6,8-tetraamine; $N^2,N^6$-Dimethyl-$N^4$-n-propyl-$N^8$-prop-2-ynyl-pyrimido[5,4-d]pyrimidine-2,4,6,8-tetraamine; $N^2,N^6$-Bis-(N-methoxy(N-methyl)amino)-$N^4$, $N^8$-bis-n-propylamino-pyrimido[5,4-d]pyrimidine; N-(6-Chloro-4,8-bis-propylamino-pyrimido[5,4-d]pyrimidin-2-yl)-O,N-dimethyl-hydroxylamine; $N^2,N^6$-Bis-(N-Methoxy(N-methyl)amino)-$N^4,N^8$-bis-n-propylamino-pyrimido[5,4-d]pyrimidine; $N^2$-Methyl-$N^4,N^8$-di-n-propyl-pyrimido[5,4-d]pyrimidine-2,4,8-triamine; O,N-Dimethyl-N-(6-methylamino-4,8-bis-n-propylamino-pyrimido[5,4-d]pyrimidin-2-yl)-hydroxylamine; $N^4,N^8$-Dimethyl-$N^2,N^6$-di-n-propyl-pyrimido[5,4-d]pyrimidine-2,4,6,8-tetraamine; $N^2,N^2,N^6$-Trimethyl-$N^4,N^8$-di-n-propyl-pyrimido[5,4-d]pyrimidine-2,4,6,8-tetraamine; 6-Chloro-$N^2$-methyl-$N^4,N^8$-di-n-propylpyrimido[5,4-d]pyrimidine-2,4,8-triamine; $N^2,N^2$-Diethyl-$N^6$-methyl-$N^4,N^8$-di-n-propyl-pyrimido[5,4-d]pyrimidine-2,4,6,8-tetraamine; 2-(4,8-Bis-n-propylamino-6-methylamino-pyrimido[5,4-d]pyrimidin-2-yl-amino)-ethanol; $N^2$-(2-Methoxy-ethyl)-$N^6$-methyl-$N^4,N^8$-di-n-propyl-pyrimido[5,4-d]pyrimidine-2,4,6,8-tetraamine; $N^2$-(2-Isopropoxy-ethyl)-$N^6$-methyl-$N^4,N^8$-di-n-propyl-pyrimido[5,4-d]pyrimidine-2,4,6,8-tetraamine; $N^8$-Methyl-$N^4,N^6$-di-n-propyl-$N^2$-(3,3,3-trifluoropropyl)-pyrimido[5,4-d]pyrimidine-2,4,6,8-tetraamine; $N^2$-Methyl-$N^4,N^8$-di-n-propyl-6-(morpholin-4-yl)-pyrimido[5,4-d]pyrimidine-2,4,8-triamine; $N^2$-Methyl-$N^4,N^8$-di-n-propyl-6-(piperidin-1-yl)-pyrimido[5,4-d]pyrimidine-2,4,8-triamine; $N^2$-Methyl-$N^4,N^8$-di-n-propyl-6-pyrrolidin-1-yl-pyrimido[5,4-d]pyrimidine-2,4,8-triamine; $N^2$-Methyl-$N^4,N^8$-di-n-propyl-6-(4-methoxy-piperidin-1-yl)-pyrimido[5,4-d]pyrimidine-2,4,8-triamine; $N^2$-(3-Chloro-2-methyl-benzyl)-$N^6$-methyl-$N^4,N^8$-di-n-propyl-pyrimido[5,4-d]pyrimidine-2,4,6,8-tetraamine; $N^2$-(3,4-Dichlorobenzyl)-$N^6$-methyl-$N^4,N^8$-di-n-propyl-pyrimido[5,4-d]pyrimidine-2,4,6,8-tetraamine; $N^2$-(4-Fluorobenzyl)-$N^6$-methyl-$N^4,N^8$-di-n-propyl-pyrimido[5,4-d]pyrimidine-2,4,6,8-tetraamine; 6-Chloro-$N^4$, $N^8$-dimethyl-$N^2$-n-propyl-pyrimido[5,4-d]pyrimidine-2,4,8-triamine; $N^2,N^2,N^4,N^8$-Tetramethyl-$N^6$-n-propyl-pyrimido[5,4-d]pyrimidine-2,4,6,8-tetraamine; $N^2,N^2$-Diallyl-$N^4,N^8$-dimethyl-$N^6$-n-propyl-pyrimido[5,4-d]pyrimidine-2,4,6,8-tetraamine; 2-[(4,8-Bis-methylamino-6-n-propylamino-pyrimido[5,4-d]pyrimidin-2-yl)-methyl-amino]-ethanol; $N^2$-(2-Isopropoxy-ethyl)-$N^4,N^8$-dimethyl-$N^6$-n-propyl-pyrimido[5,4-d]pyrimidine-2,4,6,8-tetraamine; 2-[N-(2-Dimethylamino-ethyl)-N-methyl]amino-$N^4,N^8$-dimethyl-$N^6$-n-propyl-pyrimido[5,4-d]pyrimidine-4,6,8-triamine; 2-[(4,8-Bis-methylamino-6-n-propylamino-pyrimido[5,4-d]pyrimidin-2-yl)-(2-hydroxy-ethyl)-amino]-ethanol; $N^2,N^2$-Bis-(2-methoxyethyl)-$N^4,N^8$-dimethyl-$N^6$-n-propyl-pyrimido[5,4-d]pyrimidine-2,4,6,8-tetraamine; 6-(4-Oxo-piperidin-1-yl)-$N^4,N^8$-dimethyl-$N^2$-n-propylamino-pyrimido-[5,4-d]pyrimidine-2,4,8-triamine; $N^2$-(3-Trifluoromethyl-piperidin-1-yl)-$N^4,N^8$-dimethyl-6-n-propylamino-pyrimido-[5,4-d]pyrimidine-2,4,8-triamine; $N^2$-6-n-Propylamino-$N^4,N^8$-dimethyl-2-(1,1-dioxo-thiomorpholin-4-yl)-pyrimido-[5,4-d]pyrimidine-2,4,8-triamine; $N^2$-n-Propyl-$N^4$, $N^8$-dimethyl-6-(4,4-difluoro-piperidin-1-yl)-pyrimido[5,4-d]pyrimidine-2,4,8-triamine; $N^2,N^4,N^6,N^8$-Tetramethyl-pyrimido[5,4-d]pyrimidine-2,4,6,8-tetraamine; $N^2,N^6$-Diethyl-$N^4,N^8$-dimethyl-pyrimido[5,4-d]pyrimidine-2,4,6,8-tetraamine; $N^2,N^6$-Di-n-butyl-$N^4$, $N^8$-dimethyl-pyrimido[5,4-d]pyrimidine-2,4,6,8-tetraamine; $N^2,N^6$-Bis-cyclopropylmethyl-$N^4$, $N^8$-dimethyl-pyrimido[5,4-d]pyrimidine-2,4,6,8-tetraamine; $N^2,N^6$-Diisobutyl-$N^4$, $N^8$-dimethyl-pyrimido[5,4-d]pyrimidine-2,4,6,8-tetraamine; $N^2,N^6$-Diallyl-$N^4$, $N^8$-dimethyl-pyrimido[5,4-d]pyrimidine-2,4,6,8-tetraamine; 2-Chloro-6-(N,N'-dimethyl-hydrazino)-$N^4$, $N^8$-dimethyl-pyrimido[5,4-d]pyrimidine-4,8-diamine; 6-(N,N'-Dimethyl-hydrazino)-$N^2$, $N^2,N^4,N^8$-tetramethyl-pyrimido[5,4-d]pyrimidine-2,4,8-triamine; $N^4,N^8$-Dimethyl-6-propoxy-$N^2$-n-propyl-pyrimido[5,4-d]pyrimidine-2,4,8-triamine; $N^4,N^8$-Dimethyl-$N^2$-n-propyl-6-propylsulfanyl-pyrimido[5,4-d]pyrimidine-2,4,8-triamine; 6-Benzyloxy-$N^4,N^8$-dimethyl-$N^2$-n-propyl-pyrimido[5,4-d]pyrimidine-2,4,8-triamine; 4,8-Bis-methylamino-6-n-propylamino-pyrimido[5,4-d]pyrimidin-2-ol; 4,8-Bis-methylamino-6-n-propylamino-pyrimido[5,4-d]pyrimidine-2-carbonitrile; $N^4,N^8$-Dimethyl-$N^2$-n-propyl-6-(aminomethyl)-pyrimido[5,4-d]pyrimidine-2,4,8-triamine; 6-Carbamoyl-$N^4,N^8$-dimethyl-$N^2$-n-propyl-pyrimido[5,4-d]pyrimidine-2,4,8-triamine; 4,8-Bis-methylamino-6-n-propylamino-pyrimido[5,4-d]pyrimidine-2-carboxylic acid; N-(n-Propyl)-[4,8-bis-methylamino-6-n-propylamino-pyrimido[5,4-d]pyrimidin-2-yl]-amidine; $N^4,N^8$-Dimethyl-$N^2$-n-propyl-6-(4-fluorophenyl)-pyrimido[5,4-d]pyrimidine-2,4,8-triamine; $N^2$-Methyl-$N^4,N^8$-di-n-propyl-6-(4-fluorophenyl)-pyrimido[5,4-d]pyrimidine-2,4,8-triamine; $N^4,N^8$-Dimethyl-$N^2$-n-propyl-pyrimido[5,4-d]pyrimidine-2,4,8-triamine; 6-n-Butyl-$N^2$-methyl-$N^4,N^8$-di-n-propyl-pyrimido[5,4-d]pyrimidine-2,4,8-triamine; 6-Methoxy-$N^2$-Methyl-$N^4,N^8$-di-n-propyl-pyrimido[5,4-d]pyrimidine-2,4,8-triamine; 6-Methylamino-4,8-bis-n-propylamino-pyrimido[5,4-d]pyrimidine-2-carbonitrile; $N^2,N^4,N^6,N^8$-Tetraethyl-pyrimido[5,4-d]pyrimidine-2,4,6,8-tetraamine 2,6-Dichloro-$N^4,N^8$-diethyl-pyrimido[5,4-d]pyrimidine-4,8-diamine; $N^4,N^8$-Diethyl-$N^2,N^6$-Di-n-propyl-pyrimido[5,4-d]pyrimidine-2,4,6,8-tetraamine; $N^2,N^6$-Bis-cyclopropylmethyl-$N^4,N^8$-diethyl-pyrimido[5,4-d]pyrimidine-2,4,6,8-tetraamine; $N^2,N^6$-Diethyl-$N^4,N^8$-bis-cyclopropylmethyl-pyrimido[5,4-d]pyrimidine-2,4,6,8-tetraamine; $N^2,N^2,N^6$-Triethyl-$N^4,N^8$-bis-cyclopropylmethyl-pyrimido[5,4-d]pyrimidine-2,4,6,8-tetraamine; 6-Chloro-$N^2$-ethyl-$N^4,N^8$-bis-cyclopropylmethyl-pyrimido[5,4-d]pyrimidine-2,4,8-triamine; $N^2,N^6$-Diethyl-$N^4,N^8$-di-n-propyl-pyrimido[5,4-d]pyrimidine-2,4,6,8-tetraamine; $N^2,N^6$-Dicyclopropyl-$N^4$, $N^8$-di-n-propyl-pyrimido[5,4-d]pyrimidine-2,4,6,8-tetraamine; $N^2,N^6$-Bis-cyclopropylmethyl-$N^4,N^8$-di-n-propyl-pyrimido[5,4-d]pyrimidine-2,4,6,8-tetraamine; $N^2,N^2,N^6,N^6$-Tetramethyl-$N^4,N^8$-di-n-propyl-pyrimido[5,4-d]pyrimidine-2,4,6,8-tetraamine; $N^4,N^8$-Diallyl-$N^2,N^6$-dimethyl-pyrimido[5,4-d]pyrimidine-2,4,6,8-tetraamine; $N^2,N^4$, $N^8$-Triallyl-6-[4-(4-fluorobenzyl)-piperazin-1-yl]-pyrimido[5,4-d]pyrimidine-2,4,8-triamine; 6-Chloro-$N^2,N^4,N^8$-triallyl-pyrimido[5,4-d]pyrimidine-2,4,8-triamine; $N^2,N^4$, $N^8$-Triallyl-6-{4-[bis-(4-fluorophenyl)-methyl]-piperazin-1-yl}-pyrimido[5,4-d]pyrimidine-2,4,8-triamine; $N^2,N^2,N^6$-Triethyl-$N^4,N^8$-di-n-propyl-pyrimido[5,4-d]pyrimidine-2,4,6,8-tetraamine; (4,8-Bis-methylamino-6-n-propylamino-pyrimido[5,4-d]pyrimidin-2-ylamino)-acetic acid tert-butyl ester; (4,8-Bis-methylamino-6-n-propylamino-pyrimido[5,4-d]pyrimidin-2-ylamino)-acetic acid; N-n-Propyl-[2-(4,8-bis-methylamino-6-propylamino-pyrimido[5,4-d]pyrimidin-2-ylamino)]-acetamide; (6-Chloro-4,8-bis-methylamino-pyrimido[5,4-d]pyrimidin-2-ylamino)-acetic acid ethyl ester; a salt or solvate thereof, and any combinations thereof.

In certain embodiments, the salt is selected from the group consisting of sulfate, hydrogen sulfate, hemisulfate, chloride, bromide, iodide, nitrate, carbonate, phosphate, hydrogen phosphate, dihydrogen phosphate, formate, acetate, propionate, succinate, glycolate, gluconate, lactate, malate, tartrate, citrate, ascorbate, glucuronate, maleate, fumarate, pyruvate, aspartate, glutamate, benzoate, anthranilate, 4-hydroxybenzoate, phenylacetate, mandelate, pamoate, methanesulfonate, ethanesulfonate, benzenesulfonate, pantothenate, trifluoromethanesulfonate, 2-hydroxyethanesulfonate, p-toluenesulfonate, sulfanilate, cyclohexylaminosulfonate, stearate, alginate, β-hydroxybutyrate, salicylate, galactarate, galacturonate, saccharin, saccharate, glycerophosphonate, and any combinations thereof.

In certain embodiments, the composition of the invention further comprises at least one agent selected from the group consisting of doxapram and enantiomers thereof, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, armodafinil, and inhaled therapeutics. In other embodiments, the compound and the agent are physically mixed in the composition. In yet other embodiments, the compound and the agent are physically separated in the composition.

In certain embodiments, the composition of the invention further comprises at least one agent known to cause changes in breathing control. In other embodiments, the at least one agent is selected from the group consisting of opioid narcotics, benzodiazepines, sedatives, sleeping aids, hypnotics, propofol, and any combinations thereof. In yet other embodiments, the compound and the agent are physically mixed in the composition. In yet other embodiments, the compound and the agent are physically separated in the composition.

In certain embodiments, the composition allows for modified delivery of the compound following oral administration to a subject. In other embodiments, the composition minimizes delivery of the compound to the stomach of the subject and maximizes delivery of the compound to the intestine of the subject. In yet other embodiments, the composition includes an enteric coating. In yet other embodiments, the compound is contained in a pharmaceutically suitable capsule. In yet other embodiments, the capsule contains granules or powder of the compound, or an admixture of the compound with an excipient. In yet other embodiments, the excipient comprises a binder, disintegrant, diluent, buffer, lubricant, glidant, antioxidant, antimicrobial preservative, colorant, or flavorant. In yet other embodiments, the capsule is enterically coated but the granules or powders of the compound are not enterically coated. In yet other embodiments, the granules or powders of the compound are coated with an enteric coating before being placed into the capsule. In yet other embodiments, the granules or powders of the compound are coated with a multiplicity of enteric coatings, as to provide delivery of drug to different regions of the intestine of the subject. In yet other embodiments, at least a portion of the granules or powders of the compound are enterically coated. In yet other embodiments, the capsule is coated with an enteric coating that is different from the enteric coating that coats the granules or powders of the compound. In yet other embodiments, the compound is coated onto a base particle, whereby a core comprising the drug as a coating over the base particle is formed. In yet other embodiments, the base particle is not enterically coated and the composition is contained in a pharmaceutically acceptable capsule that is enterically coated. In yet other embodiments, the core is coated with an enteric coating, thereby forming an enterically coated bead. In yet other embodiments, the enterically coated bead is contained in a pharmaceutically acceptable capsule. In yet other embodiments, the capsule contains beads coated with a multiplicity of enteric coatings, so that the capsule provides delivery of the compound to different regions of the intestine of the subject. In yet other embodiments, the contents of the capsule are dissolved or suspended in a pharmaceutically acceptable liquid as to provide a liquid-filled capsule. In yet other embodiments, the capsule is enterically coated but the liquid formulation contained within does not comprise an enteric coating. In yet other embodiments, the granules or powders of the compound are enterically coated. In yet other embodiments, the granules or powders of the compound are coated with a multiplicity of enteric coatings, as to provide delivery of drug to different regions of the intestine of the subject. In yet other embodiments, the enteric coating applied to the capsule differs from the enteric coating applied to any of the granules or powders of the compound. In yet other embodiments, the compound is coated onto a base particle to form a core comprising the compound as a coating over the base particle, wherein the core is suspended in a pharmaceutically acceptable liquid, and wherein the suspended core is placed in a capsule. In yet other embodiments, the capsule is enterically coated but the core is not enterically coated. In yet other embodiments, the capsule and the core are enterically coated.

In certain embodiments, the destabilization is associated with a breathing control disorder or disease.

In certain embodiments, the breathing control disorder or disease is selected from the group consisting of respiratory depression, sleep apnea, apnea of prematurity, obesity-hypoventilation syndrome, primary alveolar hypoventilation syndrome, dyspnea, altitude sickness, hypoxia, hypercapnia, chronic obstructive pulmonary disease (COPD), sudden infant death syndrome (SIDS), congenital central hypoventilation syndrome, Alzheimer's disease, Parkinson's disease, stroke, Duchenne muscular dystrophy, and brain and spinal cord traumatic injury. In other embodiments, the respiratory depression is caused by an anesthetic, a sedative, a sleeping aid, an anxiolytic agent, a hypnotic agent, alcohol or a narcotic.

In certain embodiments, the subject is further administered at least one additional agent useful for treating the breathing disorder or disease. In other embodiments, the at least one additional agent is selected from the group consisting of doxapram and enantiomers thereof, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, armodafinil, and inhaled therapeutics. In yet other embodiments, the compound and the agent are separately administered to the subject. In yet other embodiments, the compound and the agent are co-administered to the subject, further wherein the compound and the agent are physically mixed or physically separated when administered to the subject.

In certain embodiments, the subject is further administered at least one additional therapeutic agent known to change normal breathing control in the subject. In other embodiments, the at least one additional agent is selected from the group consisting of opioid narcotics, benzodiazepines, sedatives, sleeping aids, hypnotics, propofol, and any combinations thereof. In yet other embodiments, the composition is administered in conjunction with the use of a mechanical ventilation device or positive airway pressure device on the subject.

In certain embodiments, the subject is a mammal or bird. In other embodiments, the mammal is a human. In yet other embodiments, the composition is administered to the subject by a nasal, inhalational, topical, oral, buccal, rectal, pleural, peritoneal, vaginal, intramuscular, subcutaneous, transdermal, epidural, intrathecal, intratracheal, otic, intraocular or intravenous route. In yet other embodiments, the composition is orally administered to the subject.

In certain embodiment, the compound is $N^2$—$N^6$-bis-cyclopropylmethyl-$N^4$,$N^8$-dimethyl-pyrimido[5,4-d]pyrimidine-2,4,6,8-tetraamine and wherein the X-ray powder diffraction spectrum of the compound comprises 2Θ values (in degrees) of about 8.12, 9.59, 12.60, 15.02, 16.33, 17.40, 18.98, 20.68, 21.72, 22.28, 23.98, 25.24, and 26.70.

In certain embodiments, the method of preparing (84) comprises reacting 2,6-dichloro-$N^4$,$N^8$-dimethyl-pyrimido[5,4-d]pyrimidine-4,8-diamine and cyclopropylmethylamine in a solvent. In other embodiments, the reaction is run under heating and (84) precipitates from the solvent once the reaction system is cooled to room temperature. In yet other embodiments, the solvent comprises n-butanol. In yet other embodiments, the precipitated (84) is recrystallized from n-butanol. In yet other embodiments, the recrystallized (84) has a X-ray powder diffraction spectrum comprising 2θ values (in degrees) of about 8.12, 9.59, 12.60, 15.02, 16.33, 17.40, 18.98, 20.68, 21.72, 22.28, 23.98, 25.24, and 26.70. In yet other embodiments, the 2,6-dichloro-$N^4$,$N^8$-dimethyl-pyrimido[5,4-d]pyrimidine-4,8-diamine is prepared by reacting 2,4,6,8-tetrachloro-pyrimido[5,4-d]pyrimidine and methylamine in a solvent. In yet other embodiments, the ratio of equivalents of 2,4,6,8-tetrachloro-pyrimido[5,4-d]pyrimidine to methylamine is about 1:4.5.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
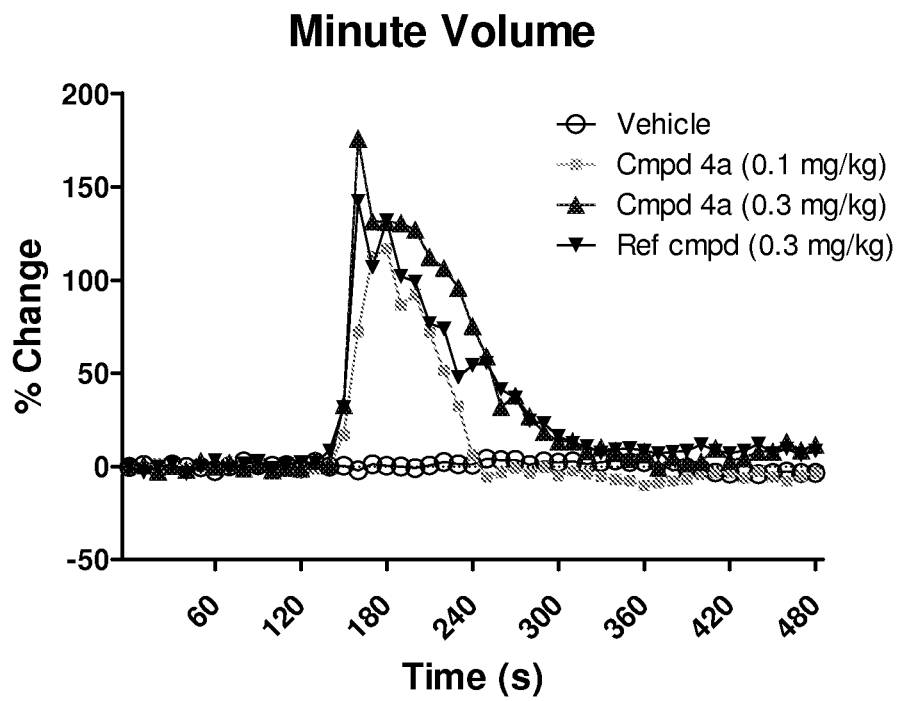
FIG. 1 is a graph illustrating the effect of compound (4a) on minute volume in an anesthetized rat spirometry screening assay.

The present invention relates to the discovery that the compounds of the invention are orally bioavailable breathing control modulators and useful in the prevention or treatment of breathing control disorders or diseases. Further, the compounds of the invention are orally bioavailable breathing control modulators suitable for chronic use in the prevention or treatment of breathing control disorders or diseases. Further, the compounds of the invention are breathing control modulators and useful in the prevention or treatment of breathing control disorders or diseases upon oral administration.

In one aspect, the compounds of the invention prevent changes to the body's normal breathing control system, as a result of disorders and diseases and in response to changes in $CO_2$ and/or oxygen levels, with minimal side effects. In another aspect, the compounds of the invention decrease the incidence and severity of breathing control disturbances, such as sleep apneas. In yet another aspect, the compounds of the invention decrease the incidence of apneic events and/or decrease the duration of apneic events. In yet another aspect, the compounds of the invention have good metabolic stability and oral bioavailability. In yet another aspect, the compounds of the invention do not interfere with the effectiveness of therapies that may cause changes to breathing control, such as opioid analgesia. Such breathing control-altering therapies benefit from administration of agents that support or restore normal breathing function.

In one aspect, the compounds of the invention represent an improvement over previously reported breathing control modulating compounds, such as the compounds disclosed in U.S. application Ser. No. 13/306,349. In one aspect, the compounds of the invention have improved microsomal stability and metabolic stability over the compounds taught in the prior art. In another aspect, the compounds of the invention have improved oral bioavailability over the compounds taught in the prior art. In another aspect, the compounds of the invention have improved pharmacological activities over the compounds taught in the prior art. In yet another aspect, the compounds of the invention display a developable cytochrome P450 profile (metabolism) and low activity at cardiac channels such as, but not limited to, hERG.

In one embodiment, the breathing control disorder or disease is selected from the group consisting of respiratory depression, sleep apnea, apnea of prematurity, obesity-hypoventilation syndrome, primary alveolar hypoventilation syndrome, dyspnea, altitude sickness, hypoxia, hypercapnia, chronic obstructive pulmonary disease (COPD) and sudden infant death syndrome (SIDS). In another embodiment, the respiratory depression is caused by an anesthetic, sedative, sleeping aid, anxiolytic agent, hypnotic agent, alcohol or narcotic. In yet another embodiment, the respiratory depression is caused by genetic factors as manifested in congenital central hypoventilation syndrome. In yet another embodiment, the respiratory depression is caused by neurological conditions such as Alzheimer's disease, Parkinson's disease, stroke, Duchenne muscular dystrophy, and brain or spinal cord traumatic injury.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, a "subject" may be a human or non-human mammal or a bird. Non-human mammals include, for example, livestock and pets, such as ovine, bovine, porcine, canine, feline and murine mammals. Preferably, the subject is human.

In a non-limiting embodiment, the following terminology used to report blood gas measurements is well known to those skilled in the art and may be defined as such: minute ventilation (MV) is a measure of breathing volume per unit time and is given herein as mL/min; $pCO_2$ is partial pressure of carbon dioxide (gas) in (arterial) blood measured in mm Hg (millimeters of Hg); $pO_2$ is partial pressure of oxygen (gas) in (arterial) blood measured in mmHg (millimeters of Hg); $SaO_2$ is the percentage of oxyhemoglobin saturation (oxygen gas bound to hemoglobin) that correlates to the percentage of hemoglobin binding sites in the bloodstream occupied by oxygen; end-tidal $CO_2$ is the measurement of exhaled carbon dioxide gas as detected using calorimetry, capnometry, or capnography techniques.

As used herein, the term $ED_{50}$ refers to the effective dose of a formulation that produces 50% of the maximal effect in subjects that are administered that formulation.

As used herein, the term "CYP450" or "P450" as applied to enzymes refers to cytochrome P450 (or P450) family of enzymes.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, an "effective amount," "therapeutically effective amount" or "pharmaceutically effective amount" of a compound is that amount of compound that is sufficient to provide a beneficial effect to the subject to which the compound is administered.

The terms "treat," "treating" and "treatment," as used herein, means reducing the frequency or severity with which symptoms of a disease or condition are experienced by a subject by virtue of administering an agent or compound to the subject.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein, the term "composition" or "pharmaceutical composition" refers to a mixture of at least one compound useful within the invention with a pharmaceutically acceptable carrier. The pharmaceutical composition facilitates administration of the compound to a subject.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

In one aspect, the terms "co-administered" and "co-administration" as relating to a subject refer to administering to the subject a compound of the invention or salt thereof along with a compound that may also treat breathing control disorders and/or with a compound that is useful in treating other medical conditions but which in themselves may alter breathing control. In one embodiment, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

By the term "specifically bind" or "specifically binds," as used herein, is meant that a first molecule preferentially binds to a second molecule (e.g., a particular receptor or enzyme), but does not necessarily bind only to that second molecule.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "cycloalkyl" by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl" employed alone or in combination with other terms means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" employed alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—$N(CH_3)$—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Preferred is aryl-$CH_2$— and aryl-$CH(CH_3)$—.

The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

The following abbreviations are used herein:
δ (delta): delta (ppm); μL (μl): microliter;
ABG: arterial blood gas; AcOH: acetic acid;
ASV: adaptive servo ventilation; AUC: area under (the) curve;
BiPAP: bi-level positive airway pressure; nBuOH: n-butanol;
2-BuOH: 2-butanol; $CHCl_3$: chloroform;
$CDCl_3$: chloroform-d; $CH_2Cl_2$: dichloromethane or methylene chloride;
CPAP: continous positive airway pressure; DIPEA: N,N-diisopropylethylamine;
DMAc: N,N-dimethylacetamide; DMSO: dimethylsulfoxide;
EPAP: expiratory positive airway pressure; EtOAc: ethyl acetate;
EtOH: ethanol; $Et_2O$: (di)ethyl ether;
f: frequency (of respiration); F (%): bioavailability (percent)
HCl: hydrochloric acid or a hydrochloride salt;
hERG: human Ether-a-go-go Related Gene (Kv11.1 ion channel)
$H_2SO_4$: sulfuric acid; HLM: human liver microsomes;
HPLC: high pressure liquid chromatography;
ICU: intensive care unit; IPA: isopropanol (or 2-propanol);
IPAP: inspiratory positive airway pressure;
LCMS: liquid chromatography-mass spectrometry;
MBP: mean blood pressure; MeCN or $CH_3CN$: acetonitrile;
MEK: methyl ethyl ketone; MeOH or $CH_3OH$: methanol;
MIBK: methyl iso-butyl ketone; min: minute
mL (or mL): milliliter; mpk: mg/kg;
MTBE: methyl-tert-butyl ether; MV: minute volume;
MS: mass spectrometry; NaCl: sodium chloride;
NaHMDS: sodium hexamethyldisilazide; $NaHCO_3$: sodium bicarbonate;
NaOH: sodium hydroxide; $Na_2SO_4$: sodium sulfate;
NAVA: neurally adjusted ventilatory assist;
NIPPV: non-invasive positive pressure ventilation;
NMR: nuclear magnetic resonance; PAV: proportional assist ventilation;
PE or pet ether: petroleum ether; ppm: part per million;
iPrOAc: isopropyl acetate; nPrOH: n-propanol;
RLM: rat liver microsomes; RR: respiratory rate;
THF: tetrahydrofuran; TV: tidal volume;
$V_E$: minute (expired) volume; XRPD: x-ray powder diffraction (spectrum);
% y: percent yield.

"Instructional material" as that term is used herein includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Compounds and Compositions of the Invention

The invention includes a compound of formula (I) or a salt thereof:

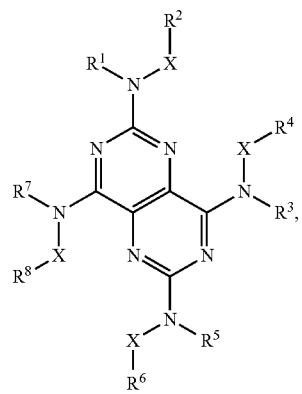

(I)

wherein:

$R^1$, $R^2$, $R^3$, $R^4$, $R^5$, $R^6$, $R^7$ and $R^8$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl;

or $R^1$ and $R^2$, $R^3$ and $R^4$, $R^5$ and $R^6$, or $R^7$ and $R^8$ independently combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

each occurrence of X is independently selected from the group consisting of bond, NH, $NR^9$ and O; and, each occurrence of X is independently alkyl or substituted alkyl.

In one embodiment, $R^1$, $R^3$, $R^5$ and $R^7$ are H.

In one embodiment, $R^1$, $R^3$, $R^5$ and $R^7$ are H; X is O; and $R^2$, $R^4$, $R^6$ and $R^8$ are alkyl or substituted alkyl. In another embodiment, $R^1$, $R^3$, $R^5$ and $R^7$ are H; X is O; and $R^2$, $R^4$, $R^6$ and $R^8$ are H. In yet another embodiment, $R^1$, $R^3$, $R^5$ and $R^7$ are alkyl or substituted alkyl; X is O; and $R^2$, $R^4$, $R^6$ and $R^8$ are H.

In one embodiment, $R^1$, $R^3$, $R^5$ and $R^7$ are H; X is NH; and $R^2$, $R^4$, $R^6$ and $R^8$ are alkyl or substituted alkyl. In another embodiment, $R^1$, $R^3$, $R^5$ and $R^7$ are H; X is NH; and $R^2$, $R^4$, $R^6$ and $R^8$ are H.

In one embodiment, $R^1$, $R^3$, $R^5$ and $R^7$ are H; X is $NR^9$; and $R^2$, $R^4$, $R^6$ and $R^8$ are alkyl or substituted alkyl. In another embodiment, $R^1$, $R^3$, $R^5$ and $R^7$ are H; X is $NR^9$; and $R^2$, $R^4$, $R^6$ and $R^8$ are H. In yet another embodiment, $R^1$, $R^3$, $R^5$ and $R^7$ are alkyl or substituted alkyl; X is $NR^9$; and $R^2$, $R^4$, $R^6$ and $R^8$ are alkyl or substituted alkyl.

In one embodiment, $R^1$, $R^3$, $R^5$ and $R^7$ are H; X is bond; and $R^2$, $R^4$, $R^6$ and $R^8$ are alkyl or substituted alkyl.

The invention also includes a compound of formula (II) or a salt thereof:

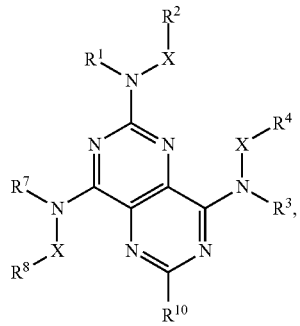

(II)

wherein:

$R^1$, $R^2$, $R^3$, $R^4$, $R^7$ and $R^8$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl;

or $R^1$ and $R^2$, $R^3$ and $R^4$, $R^5$ and $R^6$, or $R^7$ and $R^8$ independently combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

each occurrence of X is independently selected from the group consisting of bond, NH, $NR^9$ and O;

each occurrence of $R^9$ is independently alkyl or substituted alkyl;

$R^{10}$ is H, halogen, CN, amidino, amido, carboxy, carboxamido, hydrazino, OH, alkyl or substituted alkyl, alkoxy or substituted alkoxy, or thioalkoxy or substituted thioalkoxy.

The invention also includes a compound of formula (III) or a salt thereof:

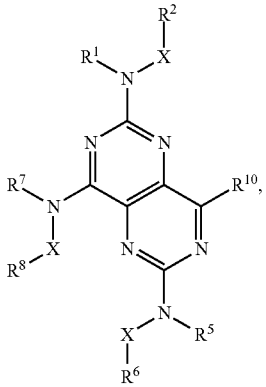

(III)

wherein:

R$^1$, R$^2$, R$^3$, R$^4$, R$^7$ and R$^8$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl;

or R$^1$ and R$^2$, R$^3$ and R$^4$, R$^5$ and R$^6$, or R$^7$ and R$^8$ independently combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

each occurrence of X is independently selected from the group consisting of bond, NH, NR$^9$ and O;

each occurrence of R$^9$ is independently alkyl or substituted alkyl;

R$^{10}$ is H, halogen, CN, amidino, amido, carboxy, carboxamido, hydrazino, OH, alkyl or substituted alkyl, alkoxy or substituted alkoxy, or thioalkoxy or substituted thioalkoxy.

In one embodiment, the compound of the invention is selected from the group consisting of:

N$^2$,N$^6$-Dimethyl-N$^4$,N$^8$-di-n-propyl-pyrimido[5,4-d]pyrimidine-2,4,6,8-tetraamine;
N$^2$,N$^4$,N$^6$,N$^8$-Tetra-n-propyl-pyrimido[5,4-d]pyrimidine-2,4,6,8-tetraamine;
N$^2$,N$^6$-Di-n-butyl-N$^4$,N$^8$-di-n-propyl-pyrimido[5,4-d]pyrimidine-2,4,6,8-tetraamine;
N$^2$,N$^6$-Di-i-propyl-N$^4$,N$^8$-di-n-propyl-pyrimido[5,4-d]pyrimidine-2,4,6,8-tetraamine;
N$^2$,N$^6$-Dimethyl-N$^4$-n-propyl-N$^8$-prop-2-ynyl-pyrimido[5,4-d]pyrimidine-2,4,6,8-tetraamine;
N$^2$,N$^6$-Bis-(N-methoxy(N-methyl)amino)-N$^4$,N$^8$-bis-n-propylamino-pyrimido[5,4-d]pyrimidine;
N-(6-Chloro-4,8-bis-propylamino-pyrimido[5,4-d]pyrimidin-2-yl)-O,N-dimethyl-hydroxylamine;
N$^2$,N$^6$-Bis-(N-Methoxy(N-methyl)amino)-N$^4$,N$^8$-bis-n-propylamino-pyrimido[5,4-d]pyrimidine;
N$^2$-Methyl-N$^4$,N$^8$-di-n-propyl-pyrimido[5,4-d]pyrimidine-2,4,8-triamine;
O,N-Dimethyl-N-(6-methylamino-4,8-bis-n-propylamino-pyrimido[5,4-d]pyrimidin-2-yl)-hydroxylamine;
N$^4$,N$^8$-Dimethyl-N$^2$,N$^6$-di-n-propyl-pyrimido[5,4-d]pyrimidine-2,4,6,8-tetraamine;
N$^2$,N$^2$,N$^6$-Trimethyl-N$^4$,N$^8$-di-n-propyl-pyrimido[5,4-d]pyrimidine-2,4,6,8-tetraamine;
6-Chloro-N$^2$-methyl-N$^4$,N$^8$-di-n-propylpyrimido[5,4-d]pyrimidine-2,4,8-triamine;
N$^2$,N$^2$-Diethyl-N$^6$-methyl-N$^4$,N$^8$-di-n-propyl-pyrimido[5,4-d]pyrimidine-2,4,6,8-tetraamine;
2-(4,8-Bis-n-propylamino-6-methylamino-pyrimido[5,4-d]pyrimidin-2-yl-amino)-ethanol;
N$^2$-(2-Methoxy-ethyl)-N$^6$-methyl-N$^4$,N$^8$-di-n-propyl-pyrimido[5,4-d]pyrimidine-2,4,6,8-tetraamine;
N$^2$-(2-Isopropoxy-ethyl)-N$^6$-methyl-N$^4$N$^8$-di-n-propyl-pyrimido[5,4-d]pyrimidine-2,4,6,8-tetraamine;
N$^8$-Methyl-N$^4$,N$^6$-di-n-propyl-N$^2$-(3,3,3-trifluoropropyl)-pyrimido[5,4-d]pyrimidine-2,4,6,8-tetraamine
N$^2$-Methyl-N$^4$,N$^8$-di-n-propyl-6-(morpholin-4-yl)-pyrimido[5,4-d]pyrimidine-2,4,8-triamine;
N$^2$-Methyl-N$^4$,N$^8$-di-n-propyl-6-(piperidin-1-yl)-pyrimido[5,4-d]pyrimidine-2,4,8-triamine;
N$^2$-Methyl-N$^4$,N$^8$-di-n-propyl-6-pyrrolidin-1-yl-pyrimido[5,4-d]pyrimidine-2,4,8-triamine;
N$^2$-Methyl-N$^4$,N$^8$-di-n-propyl-6-(4-methoxy-piperidin-1-yl)-pyrimido[5,4,-d]pyrimidine-2,4,8-triamine;
N$^2$-(3-Chloro-2-methyl-benzyl)-N$^6$-methyl-N$^4$,N$^8$-di-n-propyl-pyrimido[5,4-d]pyrimidine-2,4,6,8-tetraamine;
N$^2$-(3,4-Dichlorobenzyl)-N$^6$-methyl-N$^4$,N$^8$-di-n-propyl-pyrimido[5,4-d]pyrimidine-2,4,6,8-tetraamine;
N$^2$-(4-Fluorobenzyl)-N$^6$-methyl-N$^4$,N$^8$-di-n-propyl-pyrimido[5,4-d]pyrimidine-2,4,6,8-tetraamine;
6-Chloro-N$^4$,N$^8$-dimethyl-N$^2$-n-propyl-pyrimido[5,4-d]pyrimidine-2,4,8-triamine;
N$^2$,N$^2$,N$^4$,N$^8$-Tetramethyl-N$^6$-n-propyl-pyrimido[5,4-d]pyrimidine-2,4,6,8-tetraamine;
N$^2$,N$^2$-Diallyl-N$^4$,N$^8$-dimethyl-N$^6$-n-propyl-pyrimido[5,4-d]pyrimidine-2,4,6,8-tetraamine;
2-[(4,8-Bis-methylamino-6-n-propylamino-pyrimido[5,4-d]pyrimidin-2-yl)-methyl-amino]-ethanol;
N$^2$-(2-Isopropoxy-ethyl)-N$^4$,N$^8$-dimethyl-N$^6$-n-propyl-pyrimido[5,4-d]pyrimidine-2,4,6,8-tetraamine;
2-[N-(2-Dimethylamino-ethyl)-N-methyl]amino-N$^4$,N$^8$-dimethyl-N$^6$-n-propyl-pyrimido[5,4-d]pyrimidine-4,6,8-triamine;
2-[(4,8-Bis-methylamino-6-n-propylamino-pyrimido[5,4-d]pyrimidin-2-yl)-(2-hydroxy-ethyl)-amino]-ethanol;
N$^2$,N$^2$-Bis-(2-methoxyethyl)-N$^4$,N$^8$-dimethyl-N$^6$-n-propyl-pyrimido[5,4-d]pyrimidine-2,4,6,8-tetraamine;
6-(4-Oxo-piperidin-1-yl)-N$^4$,N$^8$-dimethyl-N$^2$-n-propylamino-pyrimido-[5,4-d]pyrimidine-2,4,8-triamine;
N$^2$-(3-Trifluoromethyl-piperidin-1-yl)-N$^4$,N$^8$-dimethyl-6-n-propylamino-pyrimido-[5,4-d]pyrimidine-2,4,8-triamine;
N$^2$-6-n-Propylamino-N$^4$,N$^8$-dimethyl-2-(1,1-dioxo-thiomorpholin-4-yl)-pyrimido-[5,4-d]pyrimidine-2,4,8-triamine;
N$^2$-n-Propyl-N$^4$,N$^8$-dimethyl-6-(4,4-difluoro-piperidin-1-yl)-pyrimido[5,4-d]pyrimidine-2,4,8-triamine;
N$^2$,N$^4$,N$^6$,N$^8$-Tetramethyl-pyrimido[5,4-d]pyrimidine-2,4,6,8-tetraamine;
N$^2$,N$^6$-Diethyl-N$^4$,N$^8$-dimethyl-pyrimido[5,4-d]pyrimidine-2,4,6,8-tetraamine;
N$^2$,N$^6$-Di-n-butyl-N$^4$,N$^8$-dimethyl-pyrimido[5,4-d]pyrimidine-2,4,6,8-tetraamine;
N$^2$,N$^6$-Bis-cyclopropymethyl-N$^4$,N$^8$-dimethyl-pyrimido[5,4-d]pyrimidine-2,4,6,8-tetraamine;
N$^2$,N$^6$-Diisobutyl-N$^4$,N$^8$-dimethyl-pyrimido[5,4-d]pyrimidine-2,4,6,8-tetraamine;
N$^2$,N$^6$-Diallyl-N$^4$,N$^8$-dimethyl-pyrimido[5,4-d]pyrimidine-2,4,6,8-tetraamine;
2-Chloro-6-(N,N'-dimethyl-hydrazin)-N$^4$,N$^8$-dimethy-pyrimido[5,4-d]pyrimidine-4,8-diamine;
6-(N,N'-Dimethyl-hydrazino)-N$^2$,N$^2$,N$^4$,N$^8$-tetramethyl-pyrimido[5,4-d]pyrimidine-2,4,8-triamine;
N$^4$,N$^8$-Dimethyl-6-propoxy-N$^2$-n-propyl-pyrimido[5,4-d]pyrimidine-2,4,8-triamine;
N$^4$,N$^8$-Dimethyl-N$^2$-n-propyl-6-propylsulfanyl-pyrimido[5,4-d]pyrimidine-2,4,8-triamine;
6-Benzyloxy-N$^4$,N$^8$-dimethyl-N$^2$-n-propyl-pyrimido[5,4-d]pyrimidine-2,4,8-triamine;
4,8-Bis-methylamino-6-n-propylamino-pyrimido[5,4-d]pyrimidin-2-ol;
4,8-Bis-methylamino-6-n-propylamino-pyrimido[5,4-d]pyrimidine-2-carbonitrile;
N$^4$,N$^8$-Dimethyl-N$^2$-n-propyl-6-(aminomethyl)-pyrimido[5,4-d]pyrimidine-2,4,8-triamine;
6-Carbamoyl-N$^4$,N$^8$-dimethyl-N$^2$-n-propyl-pyrimido[5,4-d]pyrimidine-2,4,8-triamine;
4,8-Bis-methylamino-6-n-propylamino-pyrimido[5,4-d]pyrimidine-2-carboxylicacid;
N-(n-Propyl)-[4,8-bis-methylamino-6-n-propylamino-pyrimido[5,4-d]pyrimidin-2-yl]-amidine;

$N^4,N^8$-Dimethyl-$N^2$-n-propyl-6-(4-fluorophenyl)-pyrimido[5,4-d]pyrimidine-2,4,8-triamine;
$N^2$-Methyl-$N^4,N^8$-di-n-propyl-6-(4-fluorophenyl)-pyrimido[5,4-d]pyrimidine-2,4,8-triamine;
$N^4,N^8$-Dimethyl-$N^2$-n-propyl-pyrimido[5,4-d]pyrimidine-2,4,8-triamine;
6-n-Butyl-$N^2$-methyl-$N^4,N^8$-di-n-propyl-pyrimido[5,4-d]pyrimidine-2,4,8-triamine;
6-Methoxy-$N^2$-Methyl-$N^4,N^8$-di-n-propyl-pyrimido[5,4-d]pyrimidine-2,4,8-triamine;
6-Methylamino-4,8-bis-n-propylamino-pyrimido[5,4-d]pyrimidine-2-carbonitrile;
$N^2,N^4,N^6,N^8$-Tetraethyl-pyrimido[5,4-d]pyrimidine-2,4,6,8-tetraamine
2,6-Dichloro-$N^4,N^8$-diethyl-pyrimido[5,4-d]pyrimidine-4,8-diamine;
$N^4,N^8$-Diethyl-$N^2,N^6$-Di-n-propyl-pyrimido[5,4-d]pyrimidine-2,4,6,8-tetraamine;
$N^2,N^6$-Bis-cyclopropylmethyl-$N^4,N^8$-diethyl-pyrimido[5,4-d]pyrimidine-2,4,6,8-tetraamine;
$N^2,N^6$-Diethyl-$N^4,N^8$-bis-cyclopropylmethyl-pyrimido[5,4-d]pyrimidine-2,4,6,8-tetraamine;
$N^2,N^2,N^6$-Triethyl-$N^4,N^8$-bis-cyclopropylmethyl-pyrimido[5,4-d]pyrimidine-2,4,6,8-tetraamine;
6-Chloro-$N^2$-ethyl-$N^4,N^8$-bis-cyclopropylmethyl-pyrimido[5,4-d]pyrimidine-2,4,8-triamine;
$N^2,N^6$-Diethyl-$N^4,N^8$-di-n-propyl-pyrimido[5,4-d]pyrimidine-2,4,6,8-tetraamine;
$N^2,N^6$-Dicyclopropyl-$N^4,N^8$-di-n-propyl-pyrimido[5,4-d]pyrimidine-2,4,6,8-tetraamine;
$N^2,N^6$-Bis-cyclopropylmethyl-$N^4N^8$-di-n-propyl-pyrimido[5,4-d]pyrimidine-2,4,6,8-tetraamine;
$N^2,N^2,N^6,N^6$-Tetramethyl-$N^4,N^8$-di-n-propyl-pyrimido[5,4-d]pyrimidine-2,4,6,8-tetraamine;
$N^4,N^8$-Diallyl-$N^2,N^6$-dimethyl-pyrimido[5,4-d]pyrimidine-2,4,6,8-tetraamine;
$N^2,N^4,N^8$-Triallyl-6-{4-(4-fluorobenzyl)-piperazin-1-yl}-pyrimido[5,4-d]pyrimidine-2,4,8-triamine;
6-Chloro-$N^2,N^4,N^8$-triallyl-pyrimido[5,4-d]pyrimidine-2,4,8-triamine;
$N^2,N^4,N^8$-Triallyl-6-{4-[bis-(4-fluorophenyl)-methyl]-piperazin-1-yl}-pyrimido[5,4-d]pyrimidine-2,4,8-triamine;
$N^2,N^2,N^6$-Triethyl-$N^4,N^8$-di-n-propyl-pyrimido[5,4-d]pyrimidine-2,4,6,8-tetraamine;
(4,8-Bis-methylamino-6-n-propylamino-pyrimido[5,4-d]pyrimidin-2-ylamino)-acetic acid tert-butyl ester;
(4,8-Bis-methylamino-6-n-propylamino-pyrimido[5,4-d]pyrimidin-2-ylamino)-acetic acid;
N-n-Propyl-[2-(4,8-bis-methylamino-6-propylamino-pyrimido[5,4-d]pyrimidin-2-ylamino)]-acetamide;
(6-Chloro-4,8-bis-methylamino-pyrimido[5,4-d]pyrimidin-2-ylamino)-acetic acid ethyl ester;
any salt or solvate thereof, and any combinations thereof.

In one embodiment, the salt is selected from the group consisting of sulfate, hydrogen sulfate, chloride, bromide, iodide, nitrate, carbonate, phosphate, hydrogen phosphate, dihydrogen phosphate, formate, acetate, propionate, succinate, glycolate, gluconate, lactate, malate, tartrate, citrate, ascorbate, glucuronate, maleate, fumarate, pyruvate, aspartate, glutamate, benzoate, anthranilate, 4-hydroxybenzoate, phenylacetate, mandelate, pamoate, methanesulfonate, ethanesulfonate, benzenesulfonate, pantothenate, trifluoromethanesulfonate, 2-hydroxyethanesulfonate, p-toluenesulfonate, sulfanilate, cyclohexylaminosulfonate, stearate, alginate, β-hydroxybutyrate, salicylate, galactarate, galacturonate, saccharin, saccharate, and glycerophosphonate. In certain embodiments, salts may be comprised of one or more molar equivalent of salt former with respect to any molecule of the invention.

In one embodiment, the at least one compound of the invention is a component of a pharmaceutical composition further including at least one pharmaceutically acceptable carrier.

The compounds of the invention may possess one or more stereocenters, and each stereocenter may exist independently in either the (R) or (S) configuration. In one embodiment, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form. In one embodiment, the compounds of the invention exist as tautomers. All tautomers are included within the scope of the compounds recited herein.

In one embodiment, compounds described herein are prepared as prodrugs. A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, the isotope comprises deuterium. In certain embodiments, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed. Isotopical labeling should not eb construed to be limited to the compounds of the invention, but rather applies to the compounds that may be used in combination with the compounds of the invention, such as but not limited to acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, armodafinil, and inhaled therapeutics. In certain embodiments, the oxybate salt is isotopically labeled with one or more deuteriums at the C-α position.

In one embodiment, the compounds described herein are labeled by other means, including, but not limited to, the use of chromophores or fluorescent moieties, bioluminescent labels, or chemiluminescent labels.

Preparation of the Compounds of the Invention

The compounds of the invention may be prepared according to the general methodology illustrated in the synthetic schemes described below. The reagents and conditions described herein may be modified to allow the preparation of the compounds of the invention, and such modifications are known to those skilled in the art. The scheme included herein are intended to illustrate but not limit the chemistry and methodologies that one skilled in the art may use to make compounds of the invention.

In a non-limiting example, compounds of formula (I) may be prepared by the additions of: (i) a primary alkylamine or a secondary alkylamine or an allylic amine or a propargylic amine, or (ii) a N-alkoxy-N-alkylamine, or (iii) an appropriately substituted hydrazine to suitably chlorinated intermediate (A) (Scheme 1).

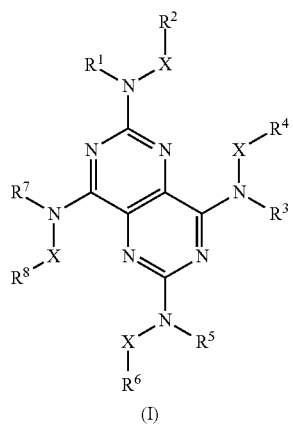

(n = 1, 3, 5 and 7)

In a non-limiting example, compounds of formulae (I)-(III) may be prepared by the successive additions of: (i) a primary alkylamine or a secondary alkylamine or an allylic amine or a propargylic amine, and (ii) a N-alkoxy-N-alkylamine or (iii) an appropriately substituted hydrazine to suitably chlorinated intermediate (A) (Scheme 2). Reaction temperature can be used to direct the order of installation of substituents onto the pyrimido[5,4-d]pyrimidine core. For example, low temperatures, such as 0° C. to ambient temperature (approximately 20° C.) selectively installs substituents at centers adjacent to the ring junction (alpha positions), yielding compound (B), whereas higher temperatures (approximately 80-100° C.) add substituents to positions farther removed (beta positions) from the ring junction and less activated towards nucleophilic displacement. Thus, tetra-substituted pyrimido[5,4-d]pyrimidine compounds (C) may be obtained with dissimilar substituents (Scheme 2). Quenching the reaction appropriately may afford tri-substituted pyrimido[5,4-d]pyrimidine compounds.

Scheme 1.

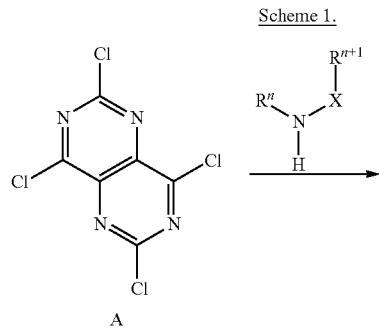

A

Scheme 2.

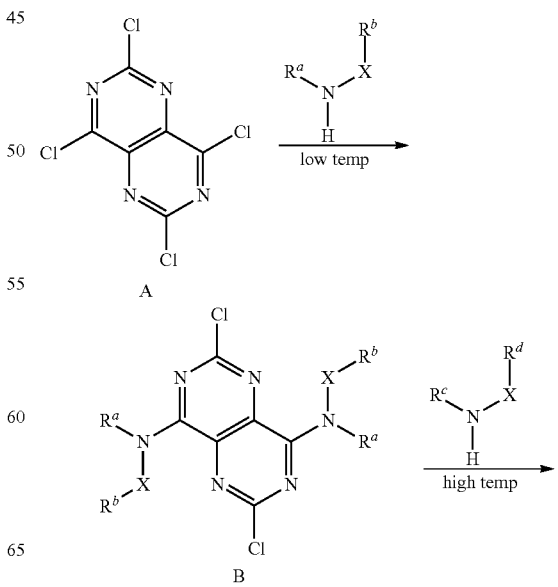

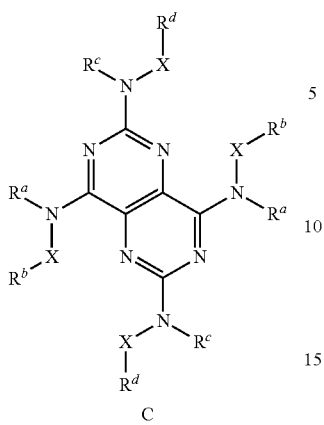

C

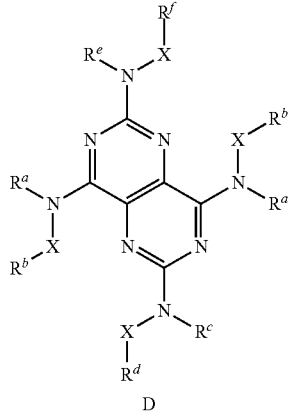

D

In a non-limiting example, compounds of formula (I) may be obtained with dissimilar substituents (D, Scheme 3) by attaching two identical alkylamino substituents in the first step and then attaching a third alkylamino substituent, dissimilar to the previous groups, in the second step and lastly, attaching a fourth alkylamino substituent that is dissimilar from the previous groups.

In a non-limiting example, compounds of formula (II)-(III) may be prepared by the successive additions of: (i) a primary alkylamine or a secondary alkylamine or an allylic amine or a propargylic amine, and (ii) a N-alkoxy-N-alkylamine or (iii) an appropriately substituted hydrazine to suitably chlorinated intermediate (A), to provide monochloro pyrimido[5,4-d]pyrimidine compounds (E), which may be further dehalogenated/reduced to produce tri-substituted pyrimido[5,4-d]pyrimidine compounds (F) of formula (II) (Scheme 4).

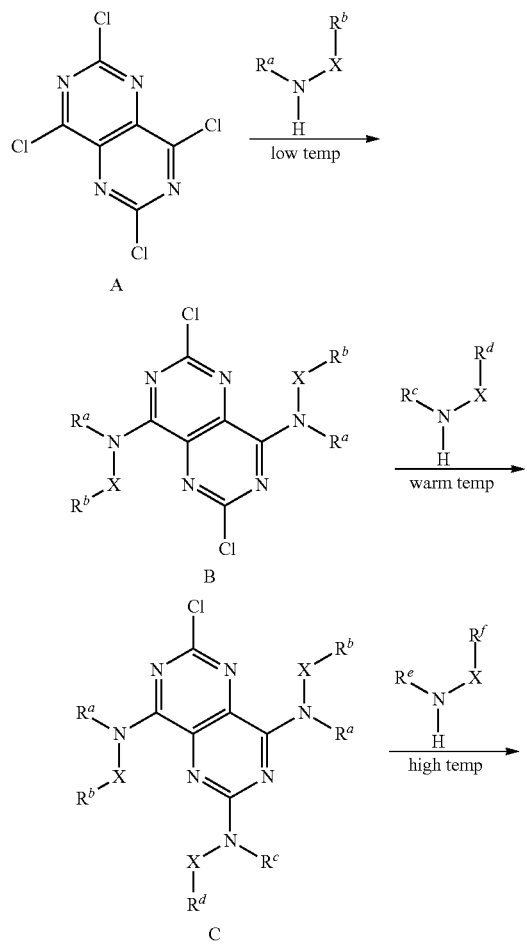

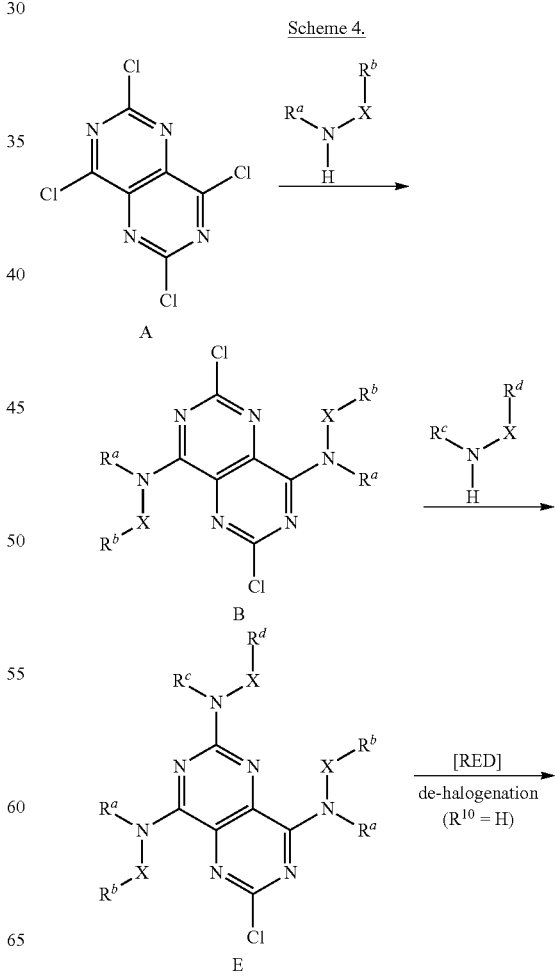

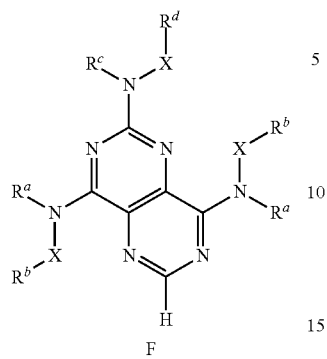

F

In a non-limiting example, compounds of formulae (I)-(III) may be obtained via halide displacement with nucleophiles to produce pyrimido[5,4-d]pyrimidine compounds which contain halogen, cyano, amidino, amido, hydrazino, hydroxyl, alkyl, substituted alkyl, alkoxy or substituted alkoxy, carboxylic acid, carboxamido, ether or thioether substituents.

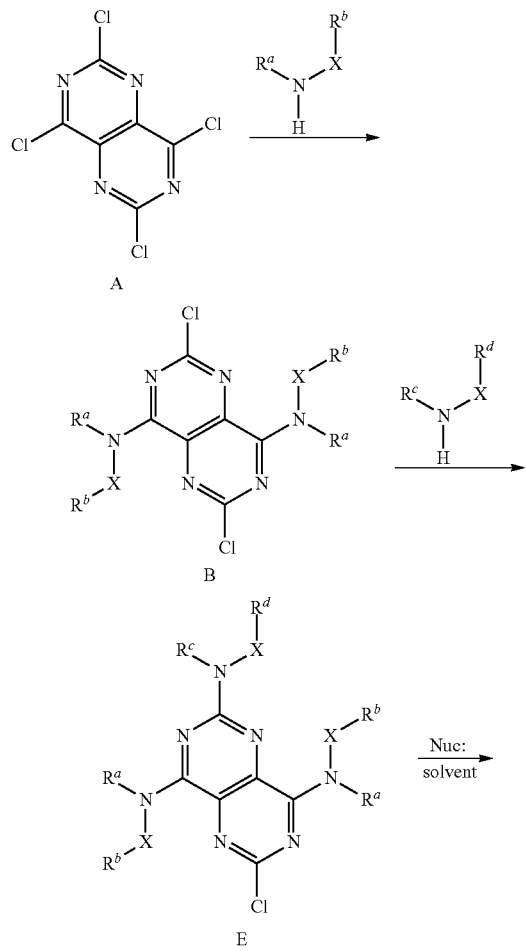

In a non-limiting example, compounds of formulae (I)-(III) may be obtained via reductive amination of amino-substituted pyrimido[5,4-d]pyrimidine compounds.

Scheme 6.

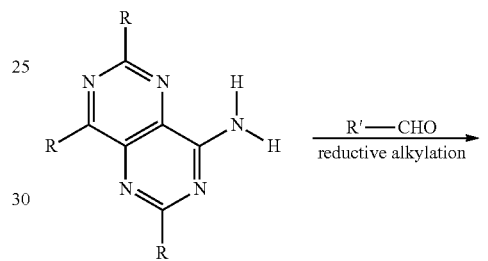

Salts

The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Molecules of the invention may be isolated as crystalline or amorphous free bases. Such crystalline or amorphous free bases may be obtained directly during the processing step wherein the final amine is attached during the synthetic process, and may also or alternatively be obtained by separately dissolving and crystallizing, and/or precipating, the free base from a suitable solvent or mixture of solvents. Suitable solvents may include, but are not limited to, MeCN, MEK, MIBK, EtOAc, iPrOAc, water, heptane, MTBE, cyclohexane, toluene, MeOH, EtOH, n-PrOH, IPA, nBuOH, 2-BuOH, isoamyl alcohol, and THF.

Combination and Concurrent Therapies

In one embodiment, the compounds of the invention are useful in the methods of present invention when used concurrently with at least one additional compound useful for preventing and/or treating breathing control disorders.

In one embodiment, the compounds of the invention are useful in the methods of present invention in combination with at least one additional compound useful for preventing and/or treating breathing control disorders.

These additional compounds may comprise compounds of the present invention or other compounds, such as commercially available compounds, known to treat, prevent, or reduce the symptoms of breathing disorders. In one embodiment, the combination of at least one compound of the invention or a salt thereof and at least one additional compound useful for preventing and/or treating breathing disorders has additive, complementary or synergistic effects in the prevention and/or treatment of disordered breathing, and in the prevention and/or treatment of sleep-related breathing disorders.

In a non-limiting example, the compounds of the invention or a salt thereof may be used concurrently or in combination with one or more of the following drugs: doxapram, enantiomers of doxapram, acetazolamide, almitrine, theophylline, caffeine, methylprogesterone and related compounds, sedatives that increase arousal threshold in sleep disordered breathing patients (such as eszopiclone and zolpidem), benzodiazepine receptor agonists (e.g., zolpidem, zaleplon, estazolam, flurazepam, quazepam, temazepam, triazolam) orexin antagonists (e.g., suvorexant), tricyclic antidepressants (e.g., doxepin), serotonergic modulators, adenosine and adenosine receptor and nucleoside transporter modulators, cannabinoids (such as, but not limited to, dronabinol), orexins, melatonin agonists (such as ramelteon), compounds known as ampakines, sodium oxybate, modafinil, and armodafinil.

In a non-limiting example, the compounds of the invention or a salt thereof may be used concurrently or in combination with inhaled therapeutics such as oxygen and carbon dioxide as for the treatment of sleep disordered breathing.

Non-limiting examples of ampakines are the pyrrolidine derivative racetam drugs such as piracetam and aniracetam; the "CX-" series of drugs which encompass a range of benzoylpiperidine and benzoylpyrrolidine structures, such as CX-516 (6-(piperidin-1-yl-carbonyl)quinoxaline), CX-546 (2,3-dihydro-1,4-benzodioxin-7-yl-(1-piperidyl)-methanone), CX-614 (2H,3H,6aH-pyrrolidino(2,1-3',2')-1,3-oxazino-(6',5'-5,4)benzo(e)1,4-dioxan-10-one), CX-691 (2,1,3-benzoxadiazol-6-yl-piperidin-1-yl-methanone), CX-717, CX-701, CX-1739, CX-1763, and CX-1837; benzothiazide derivatives such as cyclothiazide and IDRA-21 (7-chloro-3-methyl-3,4-dihydro-2H-1,2,4-benzothiadiazine 1,1-dioxide); biarylpropylsulfonamides such as LY-392,098, LY-404,187 (N-[2-(4'-cyanobiphenyl-4-yl)propyl]propane-2-sulfonamide), LY-451,646 and LY-503,430 (4'-{(1S)-1-fluoro-2-[(isopropylsulfonyl)amino]-1-methylethyl}-N-methylbiphenyl-4-carboxamide).

In one embodiment, the invention includes a composition comprising a compound of the invention and at least one agent selected from the group consisting of doxapram, enantiomers of doxapram, enantiomers of doxapram, acetazolamide, almitrine, theophylline, caffeine, methylprogesterone and related compounds, sedatives that increase arousal threshold in sleep disordered breathing patients (such as eszopiclone or zolpidem), benzodiazepine receptor agonists (such as zolpidem, zaleplon, estazolam, flurazepam, quazepam, temazepam, or triazolam), orexin antagonists (e.g. suvorexant), tricyclic antidepressants (such as doxepin), serotonergic modulators, adenosine and adenosine receptor and nucleoside transporter modulators, cannabinoids (such as but not limited to dronabinol), orexins, melatonin agonists (such as ramelteon), compounds known as ampakines, sodium oxybate, modafinil, armodafinil, and inhaled therapeutics such as oxygen and carbon dioxide gases.

In another non-limiting example, the compounds of the invention or a salt thereof may be used concurrently or in combination with one or more of the following drugs and drug classes known to cause changes in breathing control: opioid narcotics (such as morphine, fentanyl, codeine, hydromorphone, hydrocodone, oxymorphone, oxycodone, meperidine, butorphanol, carfentanil, buprenorphine, methadone, nalbuphine, propoxyphene, pentazocine, remifentanil, alfentanil, sufentanil and tapentadol); benzodiazepines (such as midazolam); and sedatives (such as zolipidem and eszopiclone); propofol; sodium oxybate, modafinil, and armodafinil. In one embodiment, the invention includes a composition comprising a compound of the invention and at least one agent known to cause changes in breathing control. In one embodiment, the at least one agent is selected from the group consisting of opioid narcotics, benzodiazepines, sedatives, sleeping aids and propofol.

In another non-limiting example, the compounds of the invention or a salt thereof may be used concurrently or in combination with one or more of the following drugs and drug classes known to either aid the onset of sleep, maintain sleep and/or alter arousal threshold: zolipidem, zaleplon, eszopiclone, ramelteon, estazolam, temazepam doxepin, phenobarbital and other barbiturates, diphenhydramine, doxylamine and related compounds, sodium oxybate, modafinil and armodafinil, for example. The combination of a sleep promoting/stabilizing drug and the compounds of the invention may act additively or synergistically to improve indices of sleep disordered breathing. In one embodiment, the compounds of the invention stabilize respiratory pattern (i.e., decrease variation in respiratory rate and tidal volume on a breath by breath basis) and respiratory drive (i.e., decrease fluctuations in the neural control of the respiratory muscles), thereby decreasing the incidence of central and obstructive apneas whilst the sleep promoting/stabilizing drug prevents patient arousal from sleep if residual apneas persist. Blood gas derangements associated with a residual apnea may elicit chemoreceptor stimulation, which in turn elicits generalized central nervous system arousal. Patients with a low arousal threshold from sleep wake early and often (i.e., experience sleep fragmentation), and these patients experience a ventilatory overshoot due to the sudden awakening in excess of the level of chemoreceptor stimulation. Sleep promoting/stabilizing drugs delay cortical arousal and permit a more appropriate ventilatory response to apnea-induced chemoreceptor stimulation. The patient benefits from delayed arousal from sleep because sleep fragmentation decreases and hyperventilation-driven central apneas decrease.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

In one embodiment, the compound and the agent are physically mixed in the composition. In another embodiment, the compound and the agent are physically separated in the composition.

In one embodiment, the compound of the invention is co-administered with a compound that is used to treat another disorders but causes loss of breathing control. In this aspect, the compound of the invention blocks or otherwise reduces depressive effects on normal breathing control caused by the compound with which they are co-administered. Such compound that treats another disorder but depresses breathing control includes but is not limited to anesthetics, sedatives, sleeping aids, anxiolytics, hypnotics, alcohol, and narcotic analgesics. The co-administered compound may be administered individually, or a combined composition as a mixture of solids and/or liquids in a solid, gel or liquid formulation or as a solution, according to methods known to those familiar with the art.

In one embodiment, a compound of the present invention may be co-administered with at least one additional compound useful for treating breathing control disorders and with at least one compound that is used to treat other disorder but causes a loss of breathing control. In this aspect, the compound of the invention works in an additive, complementary or synergistic manner with the co-administered breathing control agent to block or otherwise reduce depressive effects on normal breathing control caused by other compounds with which they are combined.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In one embodiment, a compound of the present invention may be packaged with at least one additional compound useful for treating breathing control disorders. In another embodiment, a compound of the present invention may be packaged with a therapeutic agent known to cause changes in breathing control, such as, but not limited to, anesthetics, sedatives, anxiolytics, hypnotics, alcohol, and narcotic analgesics. A co-package may be based upon, but not limited to, dosage units.

Methods of the Invention

In one aspect, the present invention includes a method of preventing or treating a breathing control disorder or disease in a subject in need thereof. The method includes administering to the subject an effective amount of a pharmaceutical formulation comprising at least a pharmaceutically acceptable carrier and at least one compound or salt thereof selected from the group consisting of:

a compound of formula (I):

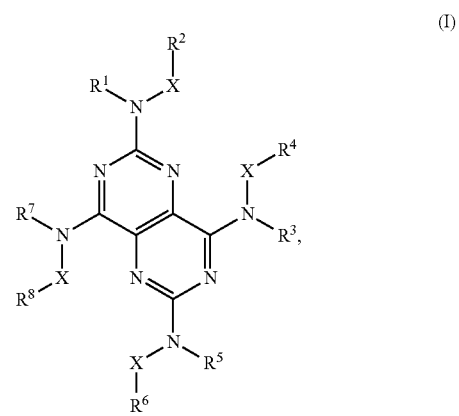

wherein in formula (I)

$R^1$, $R^2$, $R^3$, $R^4$, $R^5$, $R^6$, $R^7$ and $R^8$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl;

or $R^1$ and $R^2$, $R^3$ and $R^4$, $R^5$ and $R^6$, or $R^7$ and $R^8$ independently combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl; each occurrence of X is independently selected from the group consisting of bond, NH, $NR^9$ and O; and, each occurrence of $R^9$ is independently alkyl or substituted alkyl;

a compound of formula (II):

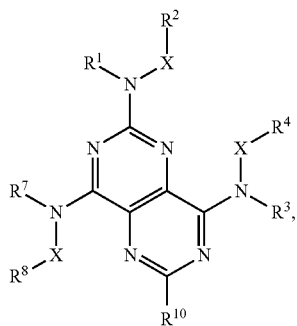

wherein in formula (II):

R$^1$, R$^2$, R$^3$, R$^4$, R$^7$ and R$^8$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl;

or R$^1$ and R$^2$, R$^3$ and R$^4$, R$^5$ and R$^6$, or R$^7$ and R$^8$ independently combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

each occurrence of X is independently selected from the group consisting of bond, NH, NR$^9$ and O;

each occurrence of R$^9$ is independently alkyl or substituted alkyl;

R$^{10}$ is H, halogen, CN, amidino, amido, carboxy, carboxamido, hydrazino, OH, alkyl or substituted alkyl, alkoxy or substituted alkoxy, or thioalkoxy or substituted thioalkoxy; and, a compound of formula (III):

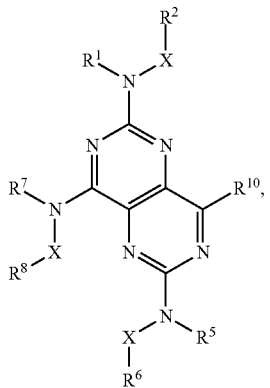

wherein in formula (III):

R$^1$, R$^2$, R$^3$, R$^4$, R$^7$ and R$^8$ are independently H, alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl;

or R$^1$ and R$^2$, R$^3$ and R$^4$, R$^5$ and R$^6$, or R$^7$ and R$^8$ independently combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

each occurrence of X is independently selected from the group consisting of bond, NH, NR$^9$ and O;

each occurrence of R$^9$ is independently alkyl or substituted alkyl;

R$^{10}$ is H, halogen, CN, amidino, amido, carboxy, carboxamido, hydrazino, OH, alkyl or substituted alkyl, alkoxy or substituted alkoxy, or thioalkoxy or substituted thioalkoxy.

In another aspect, the present invention includes a method of preventing destabilization of or stabilizing breathing rhythm in a subject in need thereof. The method includes administering to the subject an effective amount of a pharmaceutical formulation comprising at least a pharmaceutically acceptable carrier and at least one compound of the invention or a salt thereof.

In one embodiment, administering the formulation of the invention stabilizes the breathing rhythm of the subject. In another embodiment, administering the formulation of the invention increases minute ventilation in the subject.

In one embodiment, the destabilization is associated with a breathing control disorder or disease.

In one embodiment, the breathing disorder or disease is selected from the group consisting of narcotic-induced respiratory depression, anesthetic-induced respiratory depression, sedative-induced respiratory depression, sleeping aid-induced respiratory depression, anxiolytic-induced respiratory depression, hypnotic-induced respiratory depression, alcohol-induced respiratory depression, analgesic-induced respiratory depression, sleep apnea (includes but not limited to mixed central, obstructive, anatomical), apnea of prematurity, obesity-hypoventilation syndrome, primary alveolar hypoventilation syndrome, dyspnea, altitude sickness, hypoxia, hypercapnia, chronic obstructive pulmonary disease (COPD), sudden infant death syndrome (SIDS), Alzheimer's disease, Parkinson's disease, stroke, Duchenne muscular dystrophy, and brain and spinal cord traumatic injury. In another embodiment, the respiratory depression is caused by an anesthetic, a sedative, an anxiolytic agent, a hypnotic agent, alcohol or a narcotic. In yet another embodiment, the compounds of the invention or a salt thereof may be used concurrently or in combination with one or more of the following drugs and drug classes known to either aid the onset of sleep, maintain sleep and/or alter arousal threshold: zolipidem, zaleplon, eszopiclone, ramelteon, estazolam, temazepam doxepin, phenobarbital and other barbiturates, diphenhydramine, doxylamine and related compounds for example.

In one embodiment, the subject is further administered at least one additional compound useful for preventing or treating the breathing disorder or disease. In another embodiment, the at least one additional compound is selected from the group consisting of doxapram, enantiomers of doxapram, acetazolamide, almitrine, theophylline, caffeine, methylprogesterone and related compounds, sedatives such as eszopiclone and zolpidem, benzodiazepine receptor agonists (e.g., zolpidem, zaleplon, estazolam, flurazepam, quazepam, temazepam, triazolam), orexin antagonists (e.g., suvorexant), tricyclic antidepressants (e.g., doxepin), serotonergic modulators, adenosine and adenosine receptor and nucleoside transporter modulators, cannabinoids (such as but not limited to dronabinol), orexins, melatonin agonists (such as ramelteon), compounds known as ampakines, sodium oxybate, modafinil, armodafinil, and inhaled therapeutics.

In yet another embodiment, the formulation is administered to the subject in conjunction with the use of a mechanical ventilation device or positive airway pressure device. In one embodiment, the formulation is administered to the subject by an inhalational, topical, oral, nasal, buccal, rectal, pleural, peritoneal, vaginal, intramuscular, subcutaneous, transdermal, epidural, intrathecal, intratracheal, otic, intraocular or intravenous route. In another embodiment, the subject is a bird or a mammal including but not limited to mouse, rat, ferret, guinea pig, non-human primate (such as monkey), dog, cat, horse, cow, pig and other farm animals. In one embodiment, the subject is a human.

In one embodiment, the compound of the invention is selected from the group consisting of:

$N^2,N^6$-Dimethyl-$N^4,N^8$-di-n-propyl-pyrimido[5,4-d]pyrimidine-2,4,6,8-tetraamine;

$N^2,N^4,N^6,N^8$-Tetra-n-propyl-pyrimido[5,4-d]pyrimidine-2,4,6,8-tetraamine;

$N^2,N^6$-Di-n-butyl-$N^4,N^8$-di-n-propyl-pyrimido[5,4-d]pyrimidine-2,4,6,8-tetraamine;

$N^2,N^6$-Di-i-propyl-$N^4,N^8$-di-n-propyl-pyrimido[5,4-d]pyrimidine-2,4,6,8-tetraamine;

$N^2,N^6$-Dimethyl-$N^4$-n-propyl-$N^8$-prop-2-ynyl-pyrimido[5,4-d]pyrimidine-2,4,6,8-tetraamine;

$N^2,N^6$-Bis-(N-methoxy(N-methyl)amino)-$N^4,N^8$-bis-n-propylamino-pyrimido[5,4-d]pyrimidine;

N-(6-Chloro-4,8-bis-propylamino-pyrimido[5,4-d]pyrimidin-2-yl)-O,N-dimethyl-hydroxylamine;

$N^2,N^6$-Bis-(N-Methoxy(N-methyl)amino)-$N^4,N^8$-bis-n-propylamino-pyrimido[5,4-d]pyrimidine;

$N^2$-Methyl-$N^4,N^8$-di-n-propyl-pyrimido[5,4-d]pyrimidine-2,4,8-triamine;

O,N-Dimethyl-N-(6-methylamino-4,8-bis-n-propylamino-pyrimido[5,4-d]pyrimidin-2-yl)-hydroxylamine;

$N^4,N^8$-Dimethyl-$N^2,N^6$-di-n-propyl-pyrimido[5,4-d]pyrimidine-2,4,6,8-tetraamine;

$N^2,N^2,N^6$-Trimethyl-$N^4,N^8$-di-n-propyl-pyrimido[5,4-d]pyrimidine-2,4,6,8-tetraamine;

6-Chloro-$N^2$-methyl-$N^4,N^8$-di-n-propylpyrimido[5,4-d]pyrimidine-2,4,8-triamine;

$N^2,N^2$-Diethyl-$N^6$-methyl-$N^4,N^8$-di-n-propyl-pyrimido[5,4-d]pyrimidine-2,4,6,8-tetraamine;

2-(4,8-Bis-n-propylamino-6-methylamino-pyrimido[5,4-d]pyrimidin-2-yl-amino)-ethanol;

$N^2$-(2-Methoxy-ethyl)-$N^6$-methyl-$N^4,N^8$-di-n-propyl-pyrimido[5,4-d]pyrimidine-2,4,6,8-tetraamine;

$N^2$-(2-Isopropoxy-ethyl)-$N^6$-methyl-$N^4,N^8$-di-n-propyl-pyrimido[5,4-d]pyrimidine-2,4,6,8-tetraamine;

$N^8$-Methyl-$N^4,N^6$-di-n-propyl-$N^2$-(3,3,3-trifluoropropyl)-pyrimido[5,4-d]pyrimidine-2,4,6,8-tetraamine $N^2$-Methyl-$N^4,N^8$-di-n-propyl-6-(morpholin-4-yl)-pyrimido[5,4-d]pyrimidine-2,4,8-triamine;

$N^2$-Methyl-$N^4,N^8$-di-n-propyl-6-(piperidin-1-yl)-pyrimido[5,4-d]pyrimidine-2,4,8-triamine;

$N^2$-Methyl-$N^4,N^8$-di-n-propyl-6-pyrrolidin-1-yl-pyrimido[5,4-d]pyrimidine-2,4,8-triamine;

$N^2$-Methyl-$N^4,N^8$-di-n-propyl-6-(4-methoxy-piperidin-1-yl)-pyrimido[5,4-d]pyrimidine-2,4,8-triamine;

$N^2$-(3-Chloro-2-methyl-benzyl)-$N^6$-methyl-$N^4,N^8$-di-n-propyl-pyrimido[5,4-d]pyrimidine-2,4,6,8-tetraamine;

$N^2$-(3,4-Dichlorobenzyl)-$N^6$-methyl-$N^4,N^8$-di-n-propyl-pyrimido[5,4-d]pyrimidine-2,4,6,8-tetraamine;

$N^2$-(4-Fluorobenzyl)-$N^6$-methyl-$N^4,N^8$-di-n-propyl-pyrimido[5,4-d]pyrimidine-2,4,6,8-tetraamine;

6-Chloro-$N^4,N^8$-dimethyl-$N^2$-n-propyl-pyrimido[5,4-d]pyrimidine-2,4,8-triamine;

$N^2,N^2N^4,N^8$-Tetramethyl-$N^6$-n-propyl-pyrimido[5,4-d]pyrimidine-2,4,6,8-tetraamine;

$N^2,N^2$-Diallyl-$N^4,N^8$-dimethyl-$N^6$-n-propyl-n-propyl-pyrimido[5,4-d]pyrimidine-2,4,6,8-tetraamine;

2-[(4,8-Bis-methylamino-6-n-propylamino-pyrimido[5,4-d]pyrimidin-2-yl)-methyl-amino]-ethanol;

$N^2$-(2-Isopropoxy-ethyl)-$N^4,N^8$-dimethyl-$N^6$-n-propyl-pyrimido[5,4-d]pyrimidine-2,4,6,8-tetraamine;

2-[N-(2-Dimethylamino-ethyl)-N-methyl]amino-$N^4,N^8$-dimethyl-$N^6$-n-propyl-pyrimido[5,4-d]pyrimidine-4,6,8-triamine;

2-[(4,8-Bis-methylamino-6-n-propylamino-pyrimido[5,4-d]pyrimidin-2-yl)-(2-hydroxy-ethyl)-amino]-ethanol;

$N^2,N^2$-Bis-(2-methoxyethyl)-$N^4,N^8$-dimethyl-$N^6$-n-propyl-pyrimido[5,4-d]pyrimidine-2,4,6,8-tetraamine;

6-(4-Oxo-piperidin-1-yl)-$N^4,N^8$-dimethyl-$N^2$-n-propylamino-pyrimido-[5,4-d]pyrimidine-2,4,8-triamine;

$N^2$-(3-Trifluoromethyl-piperidin-1-yl)-$N^4,N^8$-dimethyl-6-n-propylamino-pyrimido-[5,4-d]pyrimidine-2,4,8-triamine;

$N^2$-6-n-Propylamino-$N^4,N^8$-dimethyl-2-(1,1-dioxo-thiomorpholin-4-yl)-pyrimido-[5,4-d]pyrimidine-2,4,8-triamine;

$N^2$-n-Propyl-$N^4,N^8$-dimethyl-6-(4,4-difluoro-piperidin-1-yl)-pyrimido[5,4-d]pyrimidine-2,4,8-triamine;

$N^2,N^4,N^6,N^8$-Tetramethyl-pyrimido[5,4-d]pyrimidine-2,4,6,8-tetraamine;

$N^2,N^6$-Diethyl-$N^4,N^8$-dimethyl-pyrimido[5,4-d]pyrimidine-2,4,6,8-tetraamine;

$N^2,N^6$-Di-n-butyl-$N^4,N^8$-dimethyl-pyrimido[$_{5,4}$-d]pyrimidine-2,4,6,8-tetraamine;

$N^2,N^6$-Bis-cyclopropylmethyl-$N^4,N^8$-dimethyl-pyrimido[5,4-d]pyrimidine-2,4,6,8-tetraamine;

$N^2,N^6$-Diisobutyl-$N^4,N^8$-dimethyl-pyrimido[5,4-d]pyrimidine-2,4,6,8-tetraamine;

$N^2,N^6$-Diallyl-$N^4,N^8$-dimethyl-pyrimido[5,4-d]pyrimidine-2,4,6,8-tetraamine;

2-Chloro-6-(N,N'-dimethyl-hydrazino)-$N^4,N^8$-dimethyl-pyrimido[5,4-d]pyrimidine-4,8-diamine;

6-(N,N'-Dimethyl-hydrazino)-$N^2,N^2,N^4,N^8$-tetramethyl-pyrimido[5,4-d]pyrimidine-2,4,8-triamine;

$N^4,N^8$-Dimethyl-6-propoxy-$N^2$-n-propyl-pyrimido[5,4-d]pyrimidine-2,4,8-triamine;

$N^4,N^8$-Dimethyl-$N^2$-n-propyl-6-propylsulfanyl-pyrimido[5,4-d]pyrimidine-2,4,8-triamine;

6-Benzyloxy-$N^4,N^8$-dimethyl-$N^2$-n-propyl-pyrimido[5,4-d]pyrimidine-2,4,8-triamine;

4,8-Bis-methylamino-6-n-propylamino-pyrimido[5,4-d]pyrimidin-2-ol;

4,8-Bis-methylamino-6-n-propylamino-pyrimido[5,4-d]pyrimidine-2-carbonitrile;

$N^4,N^8$-Dimethyl-$N^2$-n-propyl-6-(aminomethyl)-pyrimido[5,4-d]pyrimidine-2,4,8-triamine;

6-Carbamoyl-$N^4,N^8$-dimethyl-$N^2$-n-propyl-pyrimido[5,4-d]pyrimidine-2,4,8-triamine;

4,8-Bis-methylamino-6-n-propylamino-pyrimido[5,4-d]pyrimidine-2-carboxylic acid;

N-(n-Propyl)-[4,8-bis-methylamino-6-n-propylamino-pyrimido[5,4-d]pyrimidin-2-yl]-amidine;

$N^4,N^8$-Dimethyl-$N^2$-n-propyl-6-(4-fluorophenyl)-pyrimido[5,4-d]pyrimidine-2,4,8-triamine;

$N^2$-Methyl-$N^4,N^8$-di-n-propyl-6-(4-fluorophenyl)-pyrimido[5,4-d]pyrimidine-2,4,8-triamine;

$N^4,N^8$-Dimethyl-$N^2$-n-propyl-pyrimido[5,4-d]pyrimidine-2,4,8-triamine;

6-n-Butyl-N$^2$-methyl-N$^4$,N$^8$-di-n-propyl-pyrimido[5,4-d]pyrimidine-2,4,8-triamine;
6-Methoxy-N$^2$-Methyl-N$^4$,N$^8$-di-n-propyl-pyrimido[5,4-d]pyrimidine-2,4,8-triamine;
6-Methylamino-4,8-bis-n-propylamino-pyrimido[5,4-d]pyrimidine-2-carbonitrile;
N$^2$,N$^4$,N$^6$,N$^8$-Tetraethyl-pyrimido[5,4-d]pyrimidine-2,4,6,8-tetraamine
2,6-Dichloro-N$^4$,N$^8$-diethyl-pyrimido[5,4-d]pyrimidine-4,8-diamine;
N$^4$,N$^8$-Diethyl-N$^2$,N$^6$-Di-n-propyl-pyrimido[5,4-d]pyrimidine-2,4,6,8-tetraamine;
N$^2$,N$^6$-Bis-cyclopropylmethyl-N$^4$,N$^8$-diethyl-pyrimido[5,4-d]pyrimidine-2,4,6,8-tetraamine;
N$^2$,N$^6$-Diethyl-N$^4$,N$^8$-bis-cyclopropylmethyl-pyrimido[5,4-d]pyrimidine-2,4,6,8-tetraamine;
N$^2$,N$^2$,N$^6$-Triethyl-N$^4$,N$^8$-bis-cyclopropylmethyl-pyrimido[5,4-d]pyrimidine-2,4,6,8-tetraamine;
6-Chloro-N$^2$-ethyl-N$^4$,N$^8$-bis-cyclopropylmethyl-pyrimido[5,4-d]pyrimidine-2,4,8-triamine;
N$^2$,N$^6$-Diethyl-N$^4$,N$^8$-di-n-propyl-pyrimido[5,4-d]pyrimidine-2,4,6,8-tetraamine;
N$^2$,N$^6$-Dicyclopropyl-N$^4$,N$^8$-di-n-propyl-pyrimido[5,4-d]pyrimidine-2,4,6,8-tetraamine;
N$^2$,N$^6$-Bis-cyclopropylmethyl-N$^4$,N$^8$-di-n-propyl-pyrimido[5,4-d]pyrimidine-2,4,6,8-tetraamine;
N$^2$,N$^2$,N$^6$,N$^6$-Tetramethyl-N$^4$,N$^8$-di-n-propyl-pyrimido[5,4-d]pyrimidine-2,4,6,8-tetraamine;
N$^4$,N$^8$-Diallyl-N$^2$,N$^6$-dimethyl-pyrimido[5,4-d]pyrimidine-2,4,6,8-tetraamine;
N$^2$,N$^4$,N$^8$-Triallyl-6-[4-(4-fluorobenzyl)-piperazin-1-yl]-pyrimido[5,4-d]pyrimidine-2,4,8-triamine;
6-Chloro-N$^2$,N$^4$,N$^8$-triallyl-pyrimido[5,4-d]pyrimidine-2,4,8-triamine;
N$^2$,N$^4$,N$^8$-Triallyl-6-{4-[bis-(4-fluorophenyl)-methyl]-piperazin-1-yl}-pyrimido[5,4-d]pyrimidine-2,4,8-triamine;
N$^2$,N$^2$,N$^6$-Triethyl-N$^4$,N$^8$-di-n-propyl-pyrimido[5,4-d]pyrimidine-2,4,6,8-tetraamine;
(4,8-Bis-methylamino-6-n-propylamino-pyrimido[5,4-d]pyrimidin-2-ylamino)-acetic acid tert-butyl ester;
(4,8-Bis-methylamino-6-n-propylamino-pyrimido[5,4-d]pyrimidin-2-ylamino)-acetic acid;
N-n-Propyl-[2-(4,8-bis-methylamino-6-propylamino-pyrimido[5,4-d]pyrimidin-2-ylamino)]-acetamide;
(6-Chloro-4,8-bis-methylamino-pyrimido[5,4-d]pyrimidin-2-ylamino)-acetic acid ethyl ester; any salt thereof, and any combinations thereof.

Pharmaceutical Compositions and Formulations

The invention also encompasses the use of pharmaceutical compositions of at least one compound of the invention or a salt thereof to practice the methods of the invention.

Such a pharmaceutical composition may consist of at least one compound of the invention or a salt thereof, in a form suitable for administration to a subject, or the pharmaceutical composition may comprise at least one compound of the invention or a salt thereof, and one or more pharmaceutically acceptable carriers, one or more additional ingredients, or some combination of these. The at least one compound of the invention may be present in the pharmaceutical composition in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intratracheal, otic, intraocular, intravenous or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations. Additionally, constituents and or processes useful within the methods of the invention enables the pharmaceutical compositions of at least one compound of the invention or a salt thereof to be combined or processed with other substances into a pharmaceutical matrix to easily process insoluble materials, to improve the bioavailability of compounds of the inventions or salts, the ability to create controlled and or sustained release product, and the ability to create compounds that are extremely homogeneous. By way of example, implementing hot melt extrusion, solid solutions, solid dispersions, size reduction technologies, molecular complexes (e.g. cyclodextrins, and others), microparticulate, particle and formulation coating processes. It is understood that in all the constituents and or process a skill artisan can utilize amorphous or crystalline phases. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g. Recombumin®), solubilized gelatins (e.g. Gelofusine®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia and other ionic or non ionic surfactants. Known preservatives include, but are not limited to, methyl, ethyl, or n-propyl para-hydroxybenzoates, ascorbic acid, and sorbic acid.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a breathing disorder event. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a breathing control disorder in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of breathing disorders in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 μg to about 7,500 mg, about 20 μg to about 7,000 mg, about 40 μg to about 6,500 mg, about 80 μg to about 6,000 mg, about 100 μg to about 5,500 mg, about 200 μg to about 5,000 mg, about 400 μg to about 4,000 mg, about 800 μg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 μg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of breathing disorder in a patient.

The term "container" includes any receptacle for holding the pharmaceutical composition or to add protection to manage stability and or water-uptake. For example, in one embodiment, the container is the packaging that contains the pharmaceutical composition such as liquid (solution and suspension), semisolid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a breathing disorder in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, intratracheal, otic, intraocular, subcutaneous, intramuscular, intradermal, intraarterial, intravenous, intrabronchial, inhalation, and topical administration.

Suitable compositions and dosage forms include, for example, tablets, capsules, caplets, pills, gel caps, troches, emulsions, dispersions, suspensions, solutions, sterile solutions for injection, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

In one embodiment, compounds of the invention may be formulated to prepare a pharmaceutical composition for oral administration. In further embodiments, the composition for oral administration may be designed to promote a modified release of the drug, such that the location, extent and rate of exposure of the compound when ingested are modulated. Factors that affect the target zone for exposure of a drug may be the drug's pH or enzymatic stability, reactivity with other drugs (e.g., certain antibiotics), solubility as a salt or free base, ionization behavior, and pharmacodynamic and pharmacokinetic behaviors in specific environments. Some drugs are better absorbed in the duodenum or other intestinal locations.

Delayed release is a particularly useful mode of modified release that delivers drug in its most concentrated form to the duodenum or other intestinal location. In a preferred embodiment, compounds of the present invention are formulated to promote delivery to the duodenum and, optionally, other intestinal locations. Delayed release may be achieved using compositions that include a enteric coatings. Enteric coatings are insoluble in highly acidic environments, with the polyacidic coating remaining non-ionized and intact at gastric pH. However, under mildly acidic (>pH 5.5), neutral or mildly alkaline conditions (pH 6.5-7.6) of the duodenum or other intestinal regions, the coating ionizes, swells and breaks down, exposing the coated entity to the environment. Coating options exist to allow ionization at or near a specific pH (e.g. Eudragit L-110, ionization threshold pH 6.0; Eudragit S-100, ioization threshold pH 7.0).

In a further embodiment, compounds of the present invention may be formulated with an enteric coating which has been modified by adding plasticizers to the polymer before coating. The plasticizers may be added to adjust resistance to chipping or cracking of the coating, while also lowering the glass transition temperature of the coating to enable smooth and even spreadability of the coating during its application. Suitable plasticizers include polyethylene glycol 8000 (PEG 8000), triethyl citrate (TEC), and triacetin, which may be incorporated into the polymeric enteric coating agent.

Compounds of the present invention may be enterically formulated under a variety of dosage forms, including (but not limited to) capsules, granules of the active drug itself, beads, and tablets. In one embodiment, the composition may comprise a drug encapsulated in a capsule that is enterically coated to release the drug in the duodenum or other intestinal environment. In one aspect of the invention, pharmaceutically acceptable capsules include hard capsules, which may be composed of plant derived polysaccharides, starches, and cellulose, or gelatin. In another embodiment, pharmaceutically acceptable capsules include soft gelatin capsules. The gelatin capsule may be composed of animal-derived collagen or from a hypromellose, a modified form of cellulose, and manufactured using optional mixtures of gelatin, water and plasticizers such as sorbitol or glycerol In one embodiment, molecules of the invention may be encapsulated in pure granular or powdered form, with no carriers, excipients or other pharmaceutically acceptable additives. In other embodiments, molecules of the invention may be encapsulated together with one or more pharmaceutically acceptable carriers, excipients, antioxidants (e.g., sodium metabisulfite, butylated hydroxy toluene [BHT]), antifungals, (e.g., benzoic and ascorbic acids and their salts, and phenolic compounds such as methyl, ethyl, propyl and butyl p-hydroxybenzoate (parabens)), antimicrobial preservatives (e.g., sodium benzoate, sorbic acid), colorants, and flavorants. The excipients may aid in capsule-filling behavior, stability, and in the distribution of the drug when the capsule disintegrates in the body. In another embodiment, granules and/or powders of compounds of the present invention may be enterically coated before being placed in a capsule. The enterically coated granules and/or powders placed in the capsule may feature one or several types of enteric coating to enable delivery of the drug to different regions of the intestine. The capsule may lack enteric coating or may be coated with an enteric coating matching or differing entirely from the coating applied to any of the enterically coated material inside the capsule.

In a further embodiment, molecules of the invention may be encapsulated in a liquid in the form of a solution or suspension in water or various pharmaceutically acceptable oils or other dispersion medium (e.g., mineral oil, sesame oil, safflower oil, coconut oils), optionally with such excipients as cosolvents (e.g., propylene glycol, glycerol), solubility enhancers (e.g., sorbitol, dextrose), wetting agents (e.g.; polysorbates [Tweens], sorbitan esters [Span], hydrophobic colloids [cellulose derivatives], thickening agents (e.g., methylcellulose, microcrystalline cellulose), buffers (e.g., disodium hydrogen phosphate), antioxidants (e.g., butylated hydroxy toluene [BHT], citric acid, potassium sorbate), antifungals (e.g., benzoic and ascorbic acids and their salts, and phenolic compounds such as methyl, ethyl, propyl and butyl p-hydroxybenzoate (parabens)) antimicrobial preservatives (e.g., sodium benzoate, sorbic acid), colorants and flavorants. In some embodiments, compounds of the present invention may be formulated for liquid filled capsules in the form of the pure drug as granules and/or powders in the liquid. In a related embodiment, the capsule contained the drug in liquid may be enterically coated. In another embodiment, granules and/or powders of compounds of the invention may be enterically coated before being placed in a liquid and the combination placed in a capsule. The enterically coated granules and/or powder may feature one or several types of enteric coating to enable deliver of the drug to different regions of the intestine. The capsule may lack enteric coating or may be coated with an enteric coating matching or differing entirely from the coating applied to any of the enterically coated material inside the capsule.

In another embodiment, molecules of the present invention may be encapsulated in a capsule comprised of material which affords post-gastric drug delivery without the need for the separate application of an enteric coating (e.g., Entericare enteric softgels). The molecules may be encapsulated in such capsules as granules or powders with or without excipients, and as solutions or suspensions as described above.

In some embodiments, the solid particles of the compounds of the present invention, as a variety of particle sizes and particle size distributions, may be admixed with excipients such as microcrystalline cellulose or lactose and formed as a bead which comprise the drug-containing core onto which the enteric coating is applied. In some embodiments, molecules of the current invention may be formed as a suspension or solution including, optionally, buffers (e.g., aq. 1 N HCl with tris hydroxymethyl aminomethane [TRIS]), and binders (e.g., Opadry Clear Coat Powder) and coated onto a base particle, for example sugar beads (e.g., Sugar Spheres, NF particles) to form a bead. In another embodiment, the beads may be enterically coated. In yet another embodiment, molecules of the invention may be formulated as enterically coated beads, as described above, and the beads further formulated by encapsulation. In a further embodiment, a combination of beads with different types of enteric coating may be encapsulated, such that once released from the capsule, compounds of the invention are made available in a controlled manner at different regions ranging from the duodenum to other parts of the intestine. The capsule may lack enteric coating or may be coated with an enteric coating matching or differing entirely from the coating applied to any of the enterically coated material inside the capsule.

In a further embodiment, compounds of the present invention may be formulated as tablets or caplets which alone or in combination with other formulation components deliver drug to the duodenum or other intestinal region. In one embodiment, compounds of the invention are formulated as tablets or caplets which are enterically coated and which constitute the dosage form administered. In another embodiment, tablets or caplets of suitable size and shape may be placed inside a capsule. In one such embodiment, the capsule may be enterically coated and contain non-enterically coated tablets or caplets which are released from the capsule in the duodenum or other intestinal region. In yet another such embodiment, the capsule may be designed to disintegrate in the stomach and release entericallly coated tablets or caplets for subsequent delivery to duodenum or other intestinal regions. In yet another such embodiment, the capsule and tablets or caplets contained within may both be enterically coated to provide further control over the release of the tablets or caplets from the capsule, and the subsequent release of the drug from the tablet or caplet. In a further related embodiment, tablets or caplets featuring a variety of enteric coating may combined and place in a capsule which itself may optionally be enterically coated as well. Materials which are useful for enteric coatings for tablets and caplets include but are not limited to those described above for application to capsules.

Enteric coatings may permit premature drug release in acidic media. In a still further embodiment, compounds of the present invention may be formulated such that a sub-coating is applied before the enteric coating is applied. The subcoating may comprise application to the enteric substrate of a soluble subcoating agent, examples of which are hydroxypropylmethylcellulose, povidone, hydroxypropyl cellulose, polyethylene glycol 3350, 4500, 8000, methyl cellulose, pseudo ethylcellulose and amylopectin. A thin subcoating layer on the enteric substrate impedes water penetration through the enteric coating on the capsule shell or into the core where the active ingredient is located, preventing premature drug release. The subcoating may also promote the release of the drug in a basic environment by moderating the acidic microenvironment at the interface between the core and the enteric coating. In some embodiments, compounds of the present invention are formulated with a subcoating containing organic acids intended to promote more rapid polymer dissolution of a capsule as the coating degrades in environments with pH 5-6, promoting a rapid release of the drug in basic media.

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS), pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY—P Type, Aqueous Enteric OY-A Type, OY-PM Type and OPADRY™ White, 32K18400). It is understood that similar type of film coating or polymeric products from other companies can be used.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in a recombinant human albumin, a fluidized gelatin, or in a microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In further embodiments, the composition may be designed to promote controlled release of the drug, such that the location, extent and rate of exposure of the compound when administered are modulated. Factors that affect the target zone for exposure of an orally administered drug may be the drug's pH, enzymatic stability, reactivity with other drugs (e.g., certain antibiotics), solubility as a salt or free base, ionization behavior, and pharmacodynamic and pharmacokinetic behaviors in specific environments.

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, that are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include targeted delivery within the gastrointestinal tract upon oral administration, extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example water, pH, temperature, enzymes, bacteria, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations. The active drug substance can also be coated on an implantable medical device to be eluted or be released using a remotely activated system.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation (drug embedded in polymeric matrices).

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 24 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 24 hours, about 12 hours, about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 24 hours, about 12 hours, about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Some drugs are better absorbed in the duodenum or other intestinal locations. A particularly useful mode of controlled release is one that minimizes release of drug in the stomach while delivering drug in its most concentrated form to the duodenum or other intestinal locations. In a preferred embodiment, compounds of the present invention are formulated to promote delivery to the duodenum and, optionally, other intestinal locations. Controlled release that delivers drug to the duodenum or other intestinal regions may be achieved using compositions that include enteric coatings. Enteric coatings are insoluble in highly acidic environments, often comprising a polyacidic coating which remains non-ionized and intact at gastric pH. However, under mildly acidic (>pH 5.5), neutral or mildly alkaline conditions (pH 6.5-7.6) of the duodenum or other intestinal regions, the coating ionizes, swells and breaks down, exposing the coated entity to the environment. Coating options exist to allow ionization at or near a specific pH (e.g., Eudragit L-110, ionization threshold pH 6.0; Eudragit S-100, ioization threshold pH 7.0). It is understood that similar type or grade of film coating or polymeric products from other companies can be used.

In a further embodiment, compounds of the present invention may be formulated with an enteric coating, which has been modified by adding plasticizers to the polymer before coating. The plasticizers may be added to adjust resistance to chipping or cracking of the coating, while also lowering the glass transition temperature of the coating to enable smooth and even spreadability of the coating during its application. Suitable plasticizers include polyethylene glycol 8000 (PEG 8000), triethyl citrate (TEC), and triacetin, which may be incorporated into the polymeric enteric coating agent.

Compounds of the present invention may be enterically formulated under a variety of dosage forms, including (but not limited to) capsules, granules of the active drug itself, beads, micro spheres, and tablets. In one embodiment, the composition may comprise a drug encapsulated in a capsule that is enterically coated to release the drug in the duodenum or other intestinal environment. In one aspect of the invention, pharmaceutically acceptable capsules include hard capsules. In another embodiment, pharmaceutically acceptable capsules include soft gelatin capsules.

In one embodiment, molecules of the invention may be encapsulated in pure granular or powdered form, with no carriers, excipients or other pharmaceutically acceptable additives. In other embodiments, molecules of the invention may be encapsulated together with one or more pharmaceutically acceptable carriers, excipients, antioxidants, antifungals, (e.g., benzoic and ascorbic acids and their salts, and phenolic compounds such as methyl, ethyl, propyl and butyl p-hydroxybenzoate (parabens)), antimicrobial preservatives, colorants, and flavorants. The excipients may aid in capsule-filling behavior, stability, and in the distribution of the drug when the capsule disintegrates in the body. In another embodiment, granules and/or powders of compounds of the present invention may be enterically coated before being placed in a capsule. The enterically coated granules and/or powders placed in the capsule may feature one or several types of enteric coating to enable delivery of the drug to different regions of the intestine. The capsule may lack enteric coating or may be coated with an enteric coating matching or differing entirely from the coating applied to any of the enterically coated materials inside the capsule.

In a further embodiment, molecules of the invention may be encapsulated in a liquid in the form of a solution or suspension in water or various pharmaceutically acceptable oils or other dispersion medium, optionally with such excipients as cosolvents (e.g., PEG 300, PEG 400, propylene glycol, glycerol, tween 80, ethanol), solubility enhancers (e.g., sorbitol, dextrose), wetting agents (thickening agent, buffers (e.g., disodium hydrogen phosphate), antioxidants, antifungals, preservatives, colorants and flavorants. In some embodiments, compounds of the present invention may be formulated for liquid filled capsules in the form of the pure drug as granules and/or powders in the liquid. In a related embodiment, the capsule containing the drug in liquid may be enterically coated. In another embodiment, granules and/or powders of compounds of the invention may be enterically coated before being placed in a liquid and the combination placed in a capsule. The enterically coated granules and/or powder may feature one or several types of enteric coating to enable delivery of the drug to different regions of the intestine. The capsule may lack enteric coating or may be coated with an enteric coating matching or differing entirely from the coating applied to any of the enterically coated materials inside the capsule.

In another embodiment, molecules of the present invention may be encapsulated in a capsule comprised of material that affords post-gastric drug delivery without the need for the separate application of an enteric coating (e.g., Entericare enteric softgels). The molecules may be encapsulated in such capsules as granules or powders with or without excipients, and as solutions or suspensions as described above.

In some embodiments, the solid particles of the compounds of the present invention, as a variety of particle sizes and particle size distributions, may be admixed with excipients such as microcrystalline cellulose or lactose and formed as a bead which comprises the drug-containing core onto which the enteric coating is applied. In some embodiments, molecules of the current invention may be formed as a suspension or solution including, optionally, buffers (e.g., aq. 1N HCl with trishydroxymethylaminomethane [TRIS]), and binders (e.g., Opadry Clear Coat Powder) and coated onto a base particle, for example sugar beads (e.g., Sugar Spheres, NF particles) to form a bead. In another embodiment, the beads may be enterically coated. In yet another embodiment, molecules of the invention may be formulated as enterically coated beads, as described above, and the beads further formulated by encapsulation. In a further embodiment, a combination of beads with different types of enteric coating may be encapsulated, such that once released from the capsule compounds of the invention are made available in a controlled manner at different regions ranging from the duodenum to other parts of the intestine. The capsule may lack enteric coating or may be coated with an enteric coating matching or differing entirely from the coating applied to any of the enterically coated materials inside the capsule.

In a further embodiment, compounds of the present invention may be formulated as tablets or caplets which alone or in combination with other formulation components deliver drug to the duodenum or other intestinal region. In one embodiment, compounds of the invention are formulated as tablets or caplets which are enterically coated and which constitute the dosage form administered. In another embodiment, tablets or caplets of suitable size and shape may be placed inside a capsule. In one such embodiment, the capsule may be enterically coated and contain non-enterically coated tablets or caplets which are released from the capsule in the duodenum or other intestinal region. In yet another such embodiment, the capsule may be designed to disintegrate in the stomach and release entericallly coated tablets or caplets for subsequent delivery to duodenum or other intestinal regions. In yet another such embodiment, the capsule and tablets or caplets contained within may both be enterically coated to provide further control over the release of the tablets or caplets from the capsule, and the subsequent release of the drug from the tablet or caplet. In a further related embodiment, tablets or caplets featuring a variety of enteric coating may combined and place in a capsule which itself may optionally be enterically coated as well. Materials which are useful for enteric coatings for tablets and caplets include but are not limited to those described above for application to capsules.

Enteric coatings may permit premature drug release in acidic media. In a still further embodiment, compounds of the present invention may be formulated such that a subcoating is applied before the enteric coating is applied. The subcoating may comprise application to the enteric substrate of a soluble subcoating agent, examples of which are hydroxypropylmethylcellulose, povidone, hydroxypropyl cellulose, polyethylene glycol 3350, 4500, 8000, methyl cellulose, pseudo ethylcellulose and amylopectin. It is understood that similar type of synthetic and semisynthetic polymeric products from other companies can be used. A thin subcoating layer on the enteric substrate impedes water penetration through the enteric coating on the capsule shell or into the core where the active ingredient is located, preventing premature drug release. The subcoating may also promote the release of the drug in a basic environment by moderating the acidic microenvironment at the interface between the core and the enteric coating. In some embodiments, compounds of the present invention are formulated with a subcoating containing organic acids intended to promote more rapid polymer dissolution of a capsule as the coating degrades in environments with pH 5-6, promoting a rapid release of the drug in basic media.

Mechanical Devices

In one aspect of the invention, a method of treating a patient without normal ventilation and normal breathing control comprises administering the composition useful within the invention as described herein, and additionally treating the patient using a device to support breathing. Such devices include, but are not limited to, ventilation devices, CPAP and BiPAP devices.

Mechanical ventilation is a method to mechanically assist or replace spontaneous breathing. Mechanical ventilation is typically used after an invasive intubation, a procedure wherein an endotracheal or tracheostomy tube is inserted into the airway. It is normally used in acute settings, such as in the ICU, for a short period of time during a serious illness. It may also be used at home or in a nursing or rehabilitation institution, if patients have chronic illnesses that require long-term ventilation assistance. The main form of mechanical ventilation is positive pressure ventilation, which works by increasing the pressure in the patient's airway and thus forcing air into the lungs. Less common today are negative pressure ventilators (for example, the "iron lung") that create a negative pressure environment around the patient's chest, thus sucking air into the lungs. Mechanical ventilation is often a life-saving intervention, but carries many potential complications including pneumothorax, airway injury, alveolar damage, and ventilator-associated pneumonia. For this reason the pressure and volume of gas used is strictly controlled, and discontinued as soon as possible. Types of mechanical ventilation are: conventional positiove pressure ventilation, high frequency ventilation, non-invasive ventilation (non-invasive positive pressure ventilation or NIPPV), proportional assist ventilation (PAV), adaptive servo ventilation (ASV) and neurally adjusted ventilatory assist (NAVA).

Non-invasive ventilation refers to all modalities that assist ventilation without the use of an endotracheal tube. Non-invasive ventilation is primarily aimed at minimizing patient discomfort and the complications associated with invasive ventilation, and is often used in cardiac disease, exacerbations of chronic pulmonary disease, sleep apnea, and neuromuscular diseases. Non-invasive ventilation refers only to the patient interface and not the mode of ventilation used; modes may include spontaneous or control modes and may be either pressure or volume cycled modes. Some commonly used modes of NIPPV include:

(a) Continuous positive airway pressure (CPAP): This kind of machine has been used mainly by patients for the treatment of sleep apnea at home, but now is in widespread use across intensive care units as a form of ventilation support. The CPAP machine stops upper airway obstruction by delivering a stream of compressed air via a hose to a nasal pillow, nose mask or full-face mask, splinting the airway open (keeping it open under air pressure) so that unobstructed breathing becomes possible, reducing and/or preventing apneas and hypopneas. When the machine is turned on, but prior to the mask being placed on the head, a flow of air comes through the mask. After the mask is placed on the head, it is sealed to the face and the air stops flowing. At this point, it is only the air pressure that accomplishes the desired result. This has the additional benefit of reducing or eliminating the extremely loud snoring that sometimes accompanies sleep apnea.

(b) Bi-level positive airway pressure (BIPAP): Pressures alternate between inspiratory positive airway pressure (IPAP) and a lower expiratory positive airway pressure (EPAP), triggered by patient effort. On many such devices, backup rates may be set, which deliver IPAP pressures even if patients fail to initiate a breath.

(c) Intermittent positive pressure ventilation (IPPV), via mouthpiece or mask.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all remaining starting materials were obtained from commercial suppliers and used without purification. Final products are typically isolated as acid addition salts unless noted otherwise.

Example 1

$N^2,N^6$-Dimethyl-$N^4,N^8$-di-n-propyl-pyrimido[5,4-d] pyrimidine-2,4,6,8-tetraamine (3) and corresponding hydrochloride salt (4a) (Scheme 7)

2,6-Dichloro-$N^4,N^8$-di-n-propyl-pyrimido[5,4-d] pyrimidine-4,8-diamine (2)

To a solution of 2,4,6,8-tetrachloro-pyrimido[5,4-d]pyrimidine (1) (2.20 g, 8.15 mmol) in THF (55 mL), n-propylamine (2.68 mL, 32.60 mmol) in THF (15 mL) was added dropwise at 0° C. The reaction mixture was stirred at room temperature for 1 h. After this time, water (50 mL) was added and the resultant precipitate was filtered, washed with water (30 mL) and dried over $P_2O_5$ to yield 2,6-dichloro-$N^4,N^8$-di-n-propyl-pyrimido[5,4-d]pyrimidine-4,8-diamine (2) (2.49 g, 97% y). 400 MHz $^1$H NMR (CDCl$_3$, ppm) δ 6.92-6.85 (2H, m), 3.56 (4H, td, J=7.3, 6.2 Hz), 1.73 (4H, sextet, J=7.3 Hz), 1.02 (6H, t, J=7.3 Hz). ESI-MS (m/z): 315, 317, 319 [M+H]$^+$.

$N^2,N^6$-Dimethyl-$N^4,N^8$-di-n-propyl-pyrimido[5,4-d] pyrimidine-2,4,6,8-tetraamine (3)

The mixture of 2,6-dichloro-$N^4,N^8$-di-n-propyl-pyrimido [5,4-d]pyrimidine-4,8-diamine (2) (316 mg, 1.00 mmol) and methylamine (40% water solution) (2.00 mL, 718 mg, 23.15 mmole) in 1,4-dioxane (3 mL) was heated at 100° C. for 65 h. After this time, the volatiles were removed by evaporation, and the residue was partitioned between $CH_2Cl_2$ (40 mL) and water (20 mL). The water phase was extracted with $CH_2Cl_2$ (2×30 mL). The combined organic extracts were washed with water (50 mL) and dried over solid anhydrous $Na_2SO_4$. After filtration, the solvent was removed and the residue was purified by flash column chromatography using gradient elution from $CH_2Cl_2$ to $CH_2Cl_2$/EtOH (98:2) to yield $N^2,N^6$-dimethyl-$N^4,N^8$-di-n-propyl-pyrimido[5,4-d] pyrimidine-2,4,6,8-tetraamine (3) (220 mg, 72% y). 400 MHz $^1$H NMR (CDCl$_3$, ppm) δ 6.53 (2H, br s), 4.60 (2H, br s), 3.46 (4H, q, J=6.7 Hz), 2.97 (6H, d, J=4.5 Hz), 1.69 (4H, sextet, J=7.5 Hz), 1.00 (6H, t, J=7.5 Hz). ESI-MS (m/z): 305 [M+H]$^+$.

$N^2,N^6$-Dimethyl-$N^4,N^8$-di-n-propyl-pyrimido[5,4-d] pyrimidine-2,4,6,8-tetraamine hydrochloride (4a)

A 2M HCl/diethyl ether solution (0.35 mL, 0.70 mmol) was added to a suspension of $N^2,N^6$-dimethyl-$N^4,N^8$-di-n-propyl-pyrimido[5,4-d]pyrimidine-2,4,6,8-tetraamine (3) (212 mg, 0.70 mmol) in methanol (15 mL). The mixture was stirred for 0.5 h at 0° C. and the resultant precipitate were filtered, washed with methanol (3 mL) to yield $N^2,N^6$-dimethyl-$N^4,N^8$-di-n-propyl-pyrimido[5,4-d]pyrimidine-2, 4,6,8-tetraamine hydrochloride (4a) (230 mg, 96% y). 400 MHz $^1$H NMR (CDCl$_3$, ppm) δ 9.70-9.41 (1H, m), 7.86-7.37 (1H, m), 6.63 (1.3H, br s), 4.97-4.68 (0.7H, m), 3.77-3.38 (4H, m), 3.15-2.86 (6H, m), 1.93-1.68 (4H, m), 1.04 (6H, t, J=7.3 Hz). ESI-MS (m/z): 305 [M+H]$^+$; melting point: 229-232° C.

Scheme 7.

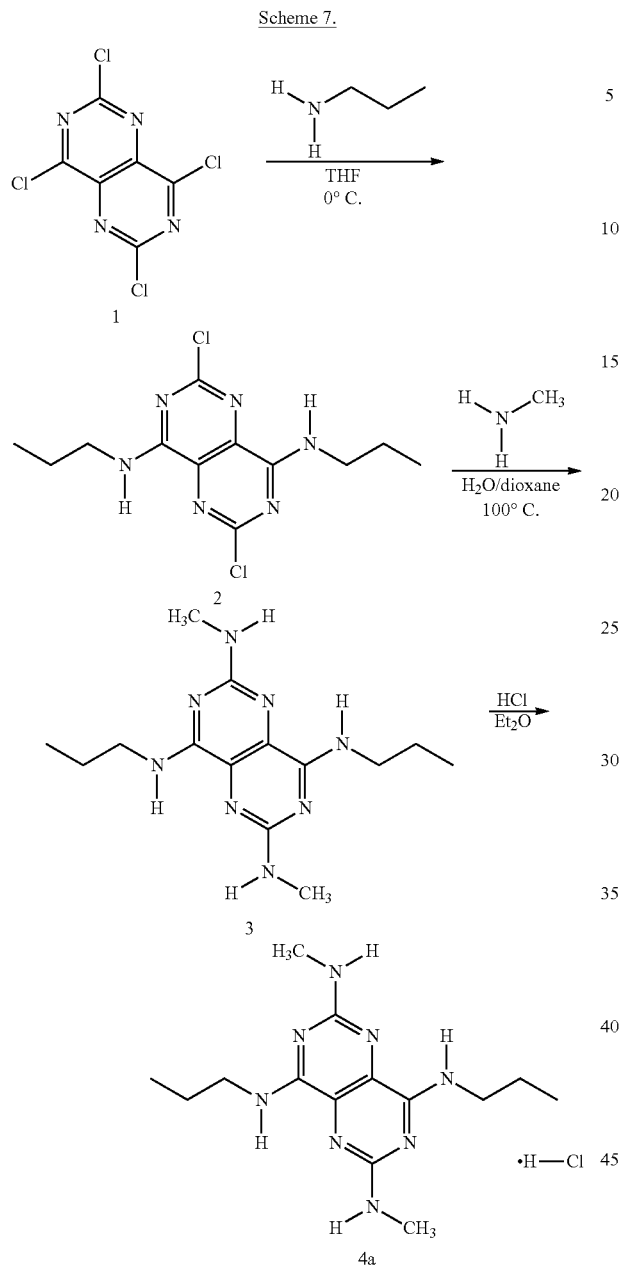

saturated NaHCO₃ solution (30 mL). The water phase was extracted with EtOAc (2×40 mL). The combined organic extracts were washed with water (50 mL), and then with a brine solution (50 mL), and lastly dried over solid anhydrous Na₂SO₄. After filtration, the solvent was removed and the residue was purified by flash column chromatography using gradient elution from CH₂Cl₂ to CH₂Cl₂/EtOH (98:2) to yield $N^2,N^4,N^6,N^8$-tetra-n-propyl-pyrimido[5,4-d]pyrimidine-2,4,6,8-tetraamine (5) (235 mg, 61% y). 400 MHz ¹H NMR (CDCl₃, ppm) δ 6.47 (2H, br s), 4.61 (2H, br s), 3.53-3.40, (4H, m), 3.40-3.26 (4H, m), 1.76-1.54 (8H, m), 1.00 (6H, t, J=7.4 Hz), 0.99 (6H, t, J=7.4 Hz). ESI-MS (m/z): 361 [M+H]⁺.

$N^2,N^4,N^6,N^8$-Tetra-n-propyl-pyrimido[5,4-d]pyrimidine-2,4,6,8-tetraamine hydrochloride (6a)

$N^2,N^4,N^6,N^8$-Tetra-n-propyl-pyrimido[5,4-d]pyrimidine-2,4,6,8-tetraamine (5) and 2M HCl/diethyl ether in CH₂Cl₂/MeOH (15/1) were reacted using the procedure described for compound (4a) to yield $N^2,N^4,N^6,N^8$-tetra-n-propyl-pyrimido[5,4-d]pyrimidine-2,4,6,8-tetraamine hydrochloride (6a) in quantitative yield. 400 MHz ¹H NMR (CDCl₃, ppm): δ 9.55 (0.7H, br s), 7.75-7.36 (1.3H, m), 6.71 (1.3H, s), 4.85 (0.7H, br s), 3.72-3.21 (8H, m), 1.90-1.52 (8H, m), 1.03 (6H, t, J=7.3 Hz), 0.98 (6H, t, J=7.3 Hz). ESI-MS (m/z): 361 [M+H]⁺; melting point: 208-211° C.

Scheme 8.

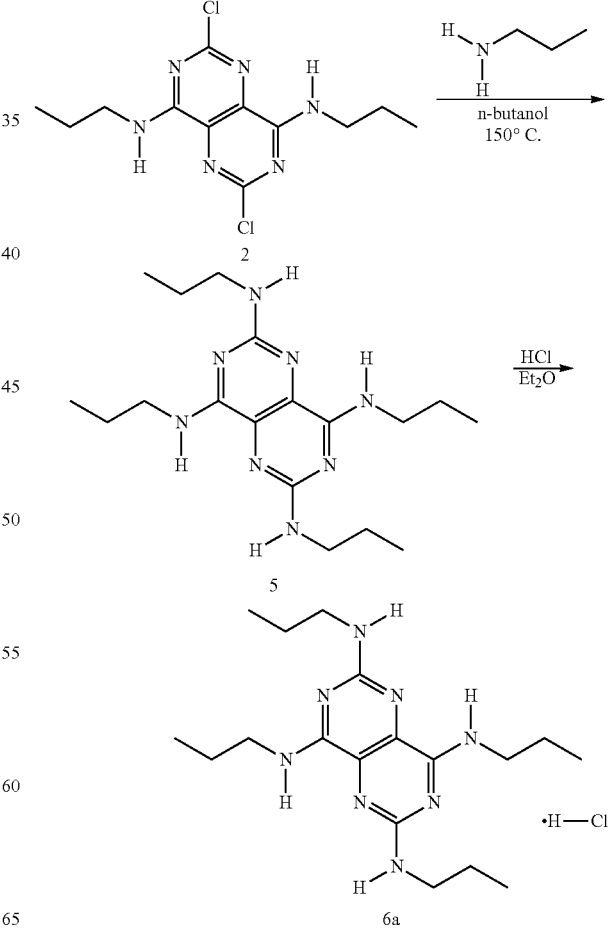

Example 2

$N^2,N^4,N^6,N^8$-Tetra-n-propyl-pyrimido[5,4-d]pyrimidine-2,4,6,8-tetraamine (5) and corresponding hydrochloride salt (6a) (Scheme 8)

$N^2,N^4,N^6,N^8$-Tetra-n-propyl-pyrimido[5,4-d]pyrimidine-2,4,6,8-tetraamine (5)

A mixture of 2,6-dichloro-$N^4,N^8$-di-n-propyl-pyrimido[5,4-d]pyrimidine-4,8-diamine (2) (338 mg, 1.07 mmol), K₂CO₃ (296 mg, 2.14 mmol) and n-propylamine (2.20 mL) in n-butanol (4 mL) was heated at 150° C. for 45 h. After this time, the volatiles were removed by evaporation and the residue was partitioned between EtOAc (50 mL) and a

Example 3

$N^2,N^6$-Di-n-butyl-$N^4,N^8$-di-n-propyl-pyrimido[5,4-d]pyrimidine-2,4,6,8-tetraamine (7) and corresponding hydrochloride salt (8a)

$N^2,N^6$-Di-n-butyl-$N^4,N^8$-di-n-propyl-pyrimido[5,4-d]pyrimidine-2,4,6,8-tetraamine (7)

2,6-Dichloro-$N^4,N^8$-di-n-propyl-pyrimido[5,4-d]pyrimidine-4,8-diamine (2) and n-butylamine were reacted using the procedure described for compound (3) to yield $N^2,N^6$-di-n-butyl-$N^4,N^8$-di-n-propyl-pyrimido[5,4-d]pyrimidine-2,4,6,8-tetraamine (7) in 85% yield. 400 MHz $^1$H NMR (CDCl$_3$, ppm): δ 6.46 (2H, br s), 4.57 (2H, br s), 3.51-3.42 (4H, m), 3.42-3.32 (4H, m), 1.69 (4H, sextet, J=7.4 Hz), 1.63-1.54 (4H, m), 1.48-1.37 (4H, m), 1.00 (6H, t, J=7.4 Hz), 0.96 (6H, t, J=7.4 Hz). ESI-MS (m/z): 389 [M+H]$^+$.

$N^2,N^6$-Di-n-butyl-$N^4,N^8$-di-n-propyl-pyrimido[5,4-d]pyrimidine-2,4,6,8-tetraamine hydrochloride (8a)

$N^2,N^6$-Di-n-butyl-$N^4,N^8$-di-n-propyl-pyrimido[5,4-d]pyrimidine-2,4,6,8-tetraamine hydrochloride (7) and 2M HCl/diethyl ether in CH$_2$Cl$_2$/MeOH (15/1) were reacted using the procedure described for compound (4a) to yield $N^2,N^6$-di-n-butyl-$N^4,N^8$-di-n-propyl-pyrimido[5,4-d]pyrimidine-2,4,6,8-tetraamine hydrochloride (8a) in quantitative yield. 400 MHz $^1$H NMR (CDCl$_3$, ppm): δ 13.95 (0.5H, s), 9.54 (0.5H, br s), 7.67 (1H, br s), 7.45 (1H, br s), 6.69 (1.2H, s), 4.82 (0.8H, br s), 3.69-3.29 (8H, m), 1.85-1.67 (4H, m), 1.65-1.52 (4H, m), 1.41 (4H, sextet, J=7.3 Hz), 1.02 (6H, t, J=7.3 Hz), 0.95 (6H, t, J=7.4 Hz). ESI-MS (m/z): 389 [M+H]$^+$; melting point: 205-208° C.

Example 4

$N^2,N^6$-Di-i-propyl-$N^4,N^8$-di-n-propyl-pyrimido[5,4-d]pyrimidine-2,4,6,8-tetraamine (9) and corresponding hydrochloride salt (10a)

$N^2,N^6$-Di-i-propyl-$N^4,N^8$-di-n-propyl-pyrimido[5,4-d]pyrimidine-2,4,6,8-tetraamine (9)

2,6-Dichloro-$N^4,N^8$-di-n-propyl-pyrimido[5,4-d]pyrimidine-4,8-diamine (2) and i-propylamine were reacted using the procedure described for compound (3) to yield $N^2,N^6$-di-i-propyl-$N^4,N^8$-di-n-propyl-pyrimido[5,4-d]pyrimidine-2,4,6,8-tetraamine (9) in 85% yield. 400 MHz $^1$H NMR (CDCl$_3$, ppm) δ 6.45 (2H, br s), 4.44 (2H, br s), 4.20-4.05 (2H, m), 3.50-3.37 (4H, m), 1.68 (4H, sextet, J=7.4 Hz), 1.23 (12H, d, J=6.5 Hz), 1.00 (6H, t, J=7.4 Hz). ESI-MS (m/z): 361 [M+H]$^+$.

$N^2,N^6$-Di-i-propyl-$N^4,N^8$-di-n-propyl-pyrimido[5,4-d]pyrimidine-2,4,6,8-tetraamine hydrochloride (10a)

$N^2,N^6$-Di-n-propyl-$N^4,N^8$-di-n-propyl-pyrimido[5,4-d]pyrimidine-2,4,6,8-tetraamine hydrochloride (9) and 2M HCl/diethyl ether in CH$_2$Cl$_2$/MeOH (15/1) were reacted using the procedure described for compound (4a) to yield $N^2,N^6$-di-i-propyl-$N^4,N^8$-di-n-propyl-pyrimido[5,4-d]pyrimidine-2,4,6,8-tetraamine hydrochloride (10a) in 81% yield. 400 MHz $^1$H NMR (CDCl$_3$, ppm): δ 13.90 (0.6H, s), 9.58 (0.4H, s), 7.71 (1H, s), 7.48-7.40 (1H, m), 6.50 (1H, d, J=7.4 Hz), 4.68 (1H, d, J=7.4 Hz), 4.29-4.02 (2H, m), 3.64-3.42 (4H, m), 1.80-1.68 (4H, m), 1.28 (7.2H, d, J=6.6 Hz), 1.23 (4.8H, d, J=6.6 Hz), 1.04-0.97 (6H, m). ESI-MS (m/z): 361 [M+H]$^+$; melting point: 158-161° C.

Example 5

$N^2,N^6$-Dimethyl-$N^4$-n-propyl-$N^8$-prop-2-ynyl-pyrimido[5,4-d]pyrimidine-2,4,6,8-tetraamine (12) and corresponding hydrochloride salt (13a) (Scheme 9)

2,6-Dichloro-$N^4$-n-propyl-$N^8$-prop-2-ynyl-pyrimido[5,4-d]pyrimidine-4,8-diamine (11)

n-Propylamine (283 μL, 3.45 mmol) in THF (15 mL) was added dropwise to a mixture of 2,4,6,8-tetrachloro-pyrimido[5,4-d]pyrimidine (1) (930 mg, 3.45 mmol) and K$_2$CO$_3$ (477 mg, 3.45 mmol) in THF (20 mL) at −78° C. during 30 min. The reaction mixture was allowed to reach ambient temperature, and then propargylamine (442 μL, 6.90 mmol) was added. The mixture was stirred for 1 h. After this time, water (50 mL) was added and the resulting suspension was extracted with EtOAc (3×30 mL). The combined organic extracts were washed with water (50 mL), and then with a brine solution (50 mL) and lastly dried over solid anhydrous Na$_2$SO$_4$. After filtration, the solvent was removed and the residue was purified by flash column chromatography using gradient elution from PE/EtOAc (99:1) to PE/EtOAc (9:1) to yield 2,6-dichloro-$N^4$-n-propyl-$N^8$-prop-2-ynyl-pyrimido[5,4-d]pyrimidine-4,8-diamine (11) (740 mg, 70% y). 400 MHz $^1$H NMR (CDCl$_3$, ppm): δ 7.01-6.95 (1H, m), 6.95-6.87 (1H, m), 4.39 (2H, dd, J=5.5, 2.6 Hz), 3.56 (2H, td, J=7.3, 6.1 Hz), 2.33 (1H, t, J=2.6 Hz), 1.73 (2H, sextet, J=7.3 Hz), 1.04 (3H, t, J=7.3 Hz). ESI-MS (m/z): 311, 313, 315 [M+H]+.

$N^2,N^6$-Dimethyl-$N^4$-n-propyl-$N^8$-prop-2-ynyl-pyrimido[5,4-d]pyrimidine-2,4,6,8-tetraamine (12)

A mixture of 2,6-dichloro-$N^4$-n-propyl-$N^8$-prop-2-ynyl-pyrimido[5,4-d]pyrimidine-4,8-diamine (11) (312 mg, 1.00 mmol) and methylamine (40% water solution) (2.00 mL) in 1,4-dioxane (3 mL) was heated at 100° C. for 30 h. The volatiles were removed by evaporation, and the residue was partitioned between CH$_2$Cl$_2$ (40 mL) and water (20 mL). The water phase was then extracted with CH$_2$Cl$_2$ (2×30 mL). The combined organic extracts were washed with water (50 mL) and dried over solid anhydrous Na$_2$SO$_4$. The solvent was removed under vacuum and the residue was purified by flash column chromatography using gradient elution from CH$_2$Cl$_2$ to CH$_2$Cl$_2$/EtOH (98:2) to yield $N^2,N^6$-dimethyl-$N^4$-n-propyl-$N^8$-prop-2-ynyl-pyrimido[5,4-d]pyrimidine-2,4,6,8-tetraamine (12) (150 mg, 50% y). 400 MHz $^1$H NMR (CDCl$_3$, ppm): δ 6.68-6.44 (2H, m), 4.65 (2H, br s), 4.32 (2H, dd, J=5.7, 2.6 Hz), 3.50-3.42 (2H, m), 2.98 (3H, s), 2.97 (3H, s), 2.24 (1H, t, J=2.6 Hz), 1.69 (2H, sextet, J=7.4 Hz), 1.00 (3H, t, J=7.4 Hz). ESI-MS (m/z): 301 [M+H]$^+$.

$N^2,N^6$-Dimethyl-$N^4$-n-propyl-$N^8$-prop-2-ynyl-pyrimido[5,4-d]pyrimidine-2,4,6,8-tetraamine hydrochloride (13a)

$N^2,N^6$-dimethyl-$N^4$-n-propyl-$N^8$-prop-2-ynyl-pyrimido[5,4-d]pyrimidine-2,4,6,8-tetraamine (12) and 2M HCl/diethyl ether in CH$_2$Cl$_2$/MeOH (15/1) were reacted using the procedure described for compound (4a) to yield $N^2,N^6$-dimethyl-$N^4$-n-propyl-$N^8$-prop-2-ynyl-pyrimido[5,4-d]pyrimidine-2,4,6,8-tetraamine hydrochloride (13a) quantitative yield. 400 MHz $^1$H NMR (CDCl$_3$, ppm): δ 10.2-9.4

(1H, m), 8.3-7.4 (1H, m), 6.92-6.45 (1.6H, m), 5.18-74.73 (0.4H, m), 4.48-4.25 (2H, m), 3.70-3.50 (2H, m), 3.19-2.92 (6H, m), 2.36-2.20 (1H, m), 1.90-1.72 (2H, m), 1.04 (3H, t, J=7.4 Hz). ESI-MS (m/z): 301 [M+H]$^+$; melting point: 210-212° C.

Scheme 9.

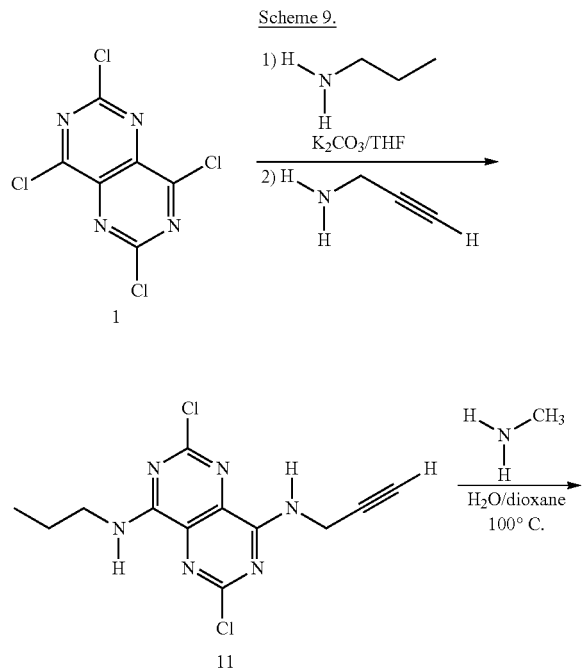

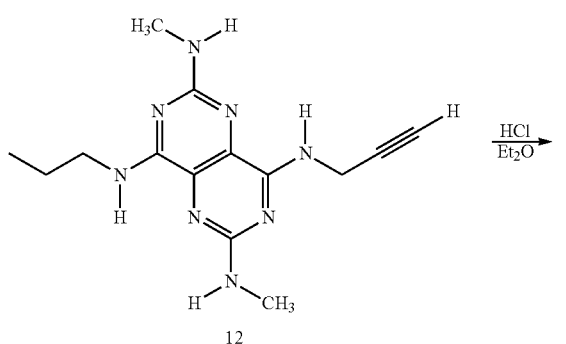

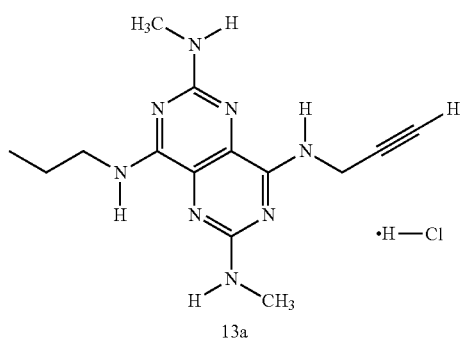

Example 6

N$^2$,N$^6$-Bis(N-methoxy(N-methyl)amino)-N$^4$-n-propylamino-N$^8$-prop-2-ynyl-amino-pyrimido[5,4-d]pyrimidine (14) and corresponding hydrochloride salt (15a)

N$^2$,N$^6$-Bis(methoxy(methyl)amino)-N$^4$-n-propylamino-N$^8$-prop-2-ynylamino-pyrimido[5,4-d]pyrimidine (14)

A mixture of 2,6-dichloro-N$^4$-n-propyl-N$^8$-prop-2-ynyl-pyrimido[5,4-d]pyrimidine-4,8-diamine (11) (350 mg, 1.12 mmol), N,O-dimethylhydroxylamine hydrochloride (3.28 g, 33.60 mmol) and N,N-diisopropylethylamine (5.85 mL, 33.60 mmol) in 1,4-dioxane (15 mL) was heated at 90° C. for 60 h. The reaction mixture was then cooled, and a saturated NaHCO$_3$ solution (30 mL) was added. The resultant precipitate was filtered and dissolved in CH$_2$Cl$_2$. This solution was washed with water (2×20 mL) and dried over solid anhydrous Na$_2$SO$_4$. After filtration, the solvent was removed in vacuo and the residue was purified by flash column chromatography using gradient elution from CH$_2$Cl$_2$ to CH$_2$Cl$_2$/EtOH (95:5) to yield N$^2$,N$^6$-bis(N-methoxy(N-methyl)amino)-N$^4$-n-propylamino-N$^8$-prop-2-ynylamino-pyrimido[5,4-d]pyrimidine (14) (156 mg, 39% y). 400 MHz $^1$H NMR (CDCl$_3$, ppm): δ 6.84 (1H, t, J=5.6 Hz), 6.80 (1H, t, J=6.0 Hz), 4.52 (2H, dd, J=5.6, 2.5 Hz), 4.04 (3H, s), 4.04 (3H, s), 3.71-3.64 (2H, m), 3.49 (3H, s), 3.48 (3H, s), 2.40 (1H, t, J=2.5 Hz), 1.87 (2H, sextet, J=7.4 Hz), 1.16 (3H, t, J=7.4 Hz). ESI-MS (m/z): 361 [M+H]$^+$.

N$^2$,N$^6$-Bis(N-methoxy(N-methyl)amino)-N$^4$-n-propylamino-N$^8$-prop-2-ynylamino-pyrimido[5,4-d] pyrimidine hydrochloride (15a)

N$^2$,N$^6$-Bis(N-methoxy(N-methyl)amino)-N$^4$-n-propylamino-N$^8$-prop-2-ynylamino-pyrimido[5,4-d]pyrimidine (14) and 2M HCl/diethyl ether in MeOH were reacted using the procedure described for compound (4a) to yield N$^2$,N$^6$-bis(N-methoxy (N-methyl)amino)-N$^4$-n-propylamino-N$^8$-prop-2-ynylamino-pyrimido[5,4-d]pyrimidine hydrochloride (15a) in 90% yield. 400 MHz $^1$H NMR (DMSO-d$_6$, ppm): δ 9.63 (1H, br s), 9.29 (1H, br s), 4.31 (2H, dd, J=5.2, 2.3 Hz), 3.82 (3H, s), 3.81 (3H, s), 3.53-3.47 (2H, m), 3.41 (3H, s), 3.38 (3H, s), 3.23 (1H, t, J=2.3 Hz), 1.66 (2H, sextet, J=7.4 Hz), 0.92 (3H, t, J=7.4 Hz). ESI-MS (m/z): 361 [M+H]$^+$; melting point: 176-177° C.

Example 7

N-(6-Chloro-4,8-bis-n-propylamino-pyrimido[5,4-d]pyrimidin-2-yl)-O,N-dimethyl-hydroxylamine (16) and corresponding hydrochloride salt (17a) (Scheme 10)

N-(6-Chloro-4,8-bis-n-propylamino-pyrimido[5,4-d]pyrimidin-2-yl)-O,N-dimethyl-hydroxylamine (16)

A mixture of 2,6-dichloro-N$^4$,N$^8$-di-n-propyl-pyrimido[5,4-d]pyrimidine-4,8-diamine (2) (316 mg, 1.00 mmol), N,O-dimethylhydroxylamine hydrochloride (975 mg, 10.00 mmol) and N,N-diisopropylethylamine (1.74 mL, 10.00 mmol) in 1,4-dioxane (10 mL) was heated at 90° C. for 5 h. The reaction mixture was cooled and a saturated NaHCO$_3$ solution (30 mL) was added. The resulting suspension was extracted with CH$_2$Cl$_2$ (3×20 mL). The combined organic extracts were washed with water (50 mL) and dried over solid anhydrous $Na_2SO_4$. After filtration, the solvent was removed and the residue was purified by flash column chromatography using gradient elution from $CH_2Cl_2$ to $CH_2Cl_2$/EtOH (98:2) to yield N-(6-chloro-4,8-bis-n-propylamino-pyrimido[5,4-d]pyrimidin-2-yl)-O,N-dimethyl-hydroxylamine (16) (237 mg, 70% y). 400 MHz $^1$H NMR ($CDCl_3$, ppm): δ 6.87-6.77 (1H, m), 6.68-6.64 (1H, t, J=5.6 Hz), 3.86 (3H, s), 3.58-3.47 (4H, m), 3.36 (3H, s), 1.77-1.65 (4H, m), 1.02 (3H, t, J=7.4 Hz), 1.00 (3H, t, J=7.4 Hz). ESI-MS (m/z): 340, 342 [M+H]$^+$.

N-(6-Chloro-4,8-bis-n-propylamino-pyrimido[5,4-d]pyrimidin-2-yl)-O,N-dimethyl-hydroxylamine hydrochloride (17a)

N-(6-Chloro-4,8-bis-n-propylamino-pyrimido[5,4-d]pyrimidin-2-yl)-O,N-dimethyl-hydroxylamine (16) and 2M HCl/diethyl ether in diethyl ether were reacted using procedure described for compound (4a) to yield N-(6-chloro-4,8-bis-propylamino-pyrimido[5,4-d]pyrimidin-2-yl)-O,N-dimethyl-hydroxylamine hydrochloride (17a) in 90% yield. 400 MHz $^1$H NMR (DMSO-d6, ppm): δ 9.27-8.15 (2H, m), 3.81 (3H, s), 3.49-3.32 (7H, m), 1.70-1.54 (4H, m), 0.95-0.84 (6H, m). ESI-MS (m/z): 340, 342 [M+H]$^+$; melting point: 142-145° C.

Example 8

$N^2,N^6$-Bis-(N-methoxy(N-methyl)amino)-$N^4,N^8$-bis-n-propylamino-pyrimido[5,4-d]pyrimidine (18) and corresponding hydrochloride salt (19a) (Scheme 11)

$N^2,N^6$-Bis-(N-methoxy(N-methyl)amino)-$N^4,N^8$-bis-n-propylamino-pyrimido[5,4-d]pyrimidine (18)

2,6-Dichloro-$N^4,N^8$-di-n-propyl-pyrimido[5,4-d]pyrimidine-4,8-diamine (2) and N,O-dimethylhydroxylamine hydrochloride were reacted using the procedure described for compound (14) to yield $N^2,N^6$-bis-(N-methoxy(N-methyl)amino)-$N^4,N^8$-bis-n-propylamino-pyrimido[5,4-d]pyrimidine (18) in 94% yield. 400 MHz $^1$H NMR ($CDCl_3$, ppm): d 6.62 (2H, t, J=5.9 Hz), 3.88 (6H, s), 3.55-3.48 (4H, m), 3.32 (6H, s), 1.71 (4H, sextet, J=7.4 Hz), 1.00 (6H, t, J=7.4 Hz). ESI-MS (m/z): 365 [M+H]$^+$.

$N^2,N^6$-Bis-(N-Methoxy(N-methyl)amino)-$N^4,N^8$-bis-n-propylamino-pyrimido[5,4-d]pyrimidine hydrochloride (19a)

$N^2,N^6$-Bis-(N-methoxy(N-methyl)amino)-$N^4,N^8$-bis-n-propylamino-pyrimido[5,4-d]pyrimidine (18) and 2M HCl/diethyl ether in MeOH were reacted using the procedure described for compound (4a) to yield $N^2,N^6$-bis-(N-methoxy(N-methyl)amino)-$N^4$, $N^8$-bis-n-propylamino-pyrimido[5,4-d]pyrimidine (hydrochloride (19a) in 94% yield. 400 MHz $^1$H NMR ($CDCl_3$, ppm): δ 12.79 (1H, br s), 11.7-8.3 (2H, m), 3.94 (6H, s), 3.61-3.50 (4H, m), 3.42 (6H, s), 1.84-1.71 (4H, m), 1.04-0.94 (6H, m). ESI-MS (m/z): 365 [M+H]$^+$.

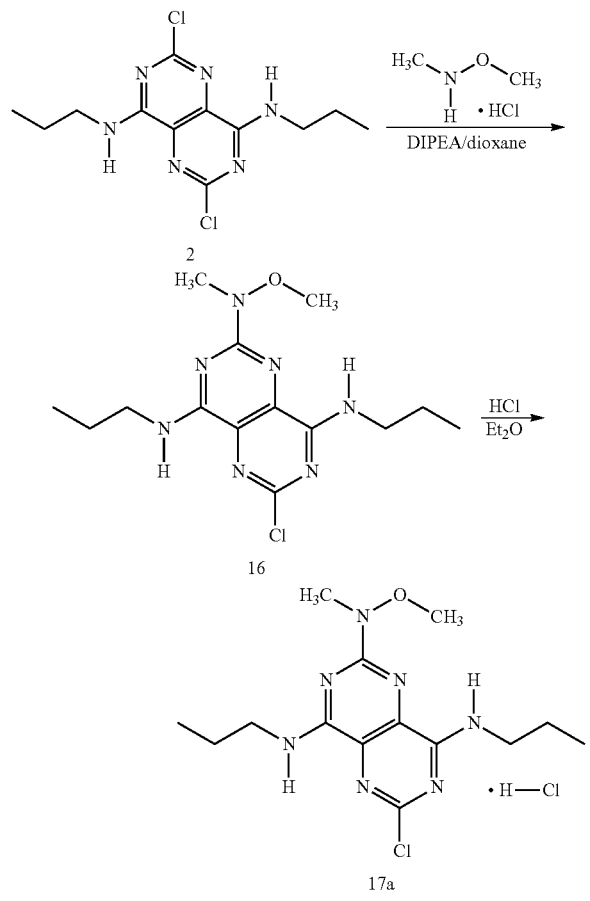

Scheme 10.

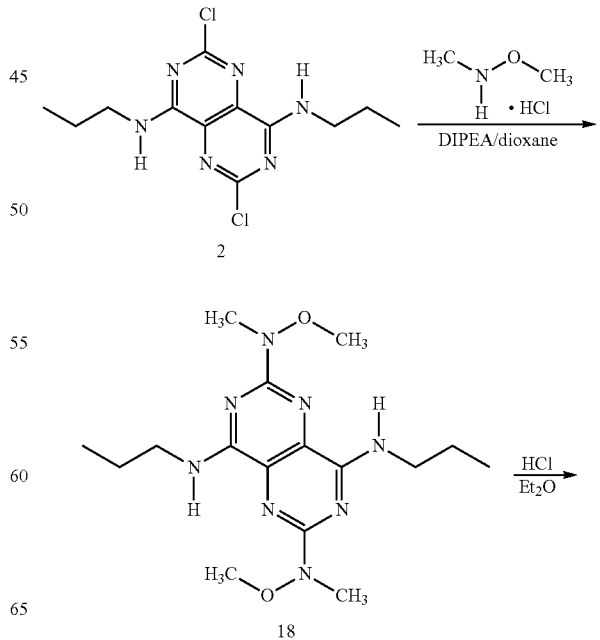

Scheme 11.

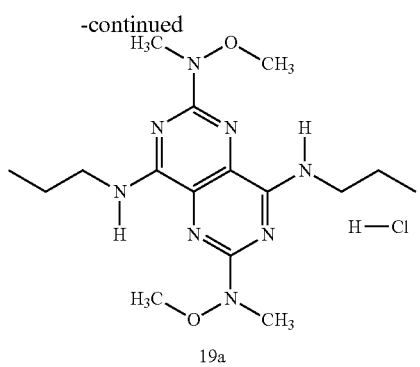

19a

Example 9

$N^2$-Methyl-$N^4$,$N^8$-di-n-propyl-pyrimido[5,4-d]pyrimidine-2,4,8-triamine (21) and corresponding hydrochloride salt (22a) (Scheme 12)

6-Chloro-$N^2$-methyl-$N^4$,$N^8$-di-n-propylpyrimido[5,4-d]pyrimidine-2,4,8-triamine (20)

A mixture of 2,6-dichloro-$N^4$,$N^8$-di-n-propyl-pyrimido[5,4-d]pyrimidine-4,8-diamine (2) (1.00 g, 3.17 mmol) and 2M methylamine/THF (8 mL) was heated at 60° C. for 21 h. The volatiles were removed by evaporation and the residue was partitioned between EtOAc (30 mL) and a saturated NaHCO$_3$ solution (30 mL). The water phase was extracted with EtOAc (2×20 mL). The combined organic extracts were washed with water (50 mL), and then with a brine solution (50 mL) and lastly dried over solid anhydrous Na$_2$SO$_4$. After filtration, the solvent was removed to yield 6-chloro-$N^2$-methyl-$N^4$,$N^8$-di-n-propylpyrimido [5,4-d]pyrimidine-2,4,8-triamine (20) (975 mg, 99% y). 400 MHz $^1$H NMR (CDCl$_3$, ppm) δ 6.80-6.71 (1H, m), 6.52 (1H, t, J=5.1 Hz), 4.93-4.85 (1H, m), 3.54 (2H, td, J=7.3, 6.1 Hz), 3.49-3.42 (2H, m), 3.00 (3H, d, J=5.1 Hz), 1.77-1.63 (4H, m), 1.03 (3H, t, J=7.4 Hz), 1.01 (3H, t, J=7.4 Hz). ESI-MS (m/z): 310, 312 [M+H]$^+$.

$N^2$-Methyl-$N^4$,$N^8$-di-n-propylpyrimido[5,4-d]pyrimidine-2,4,8-triamine (21)

A mixture of 6-chloro-$N^2$-methyl-$N^4$,$N^8$-di-n-propylpyrimido[5,4-d]pyrimidine-2,4,8-triamine (20) (440 mg, 1.42 mmol), KOH (319 mg, 5.68 mmol) and 10% Pd/C (310 mg) in THF (20 mL) was hydrogenated at 30 psi for 72 h. The reaction mixture was filtered, and the filtrate was evaporated. The residue was dissolved in EtOAc (80 mL), washed with water (3×30 mL), and then with a brine solution (30 mL) and lastly dried over solid anhydrous Na$_2$SO$_4$. After filtration the solvent was removed in vacuo and the residue was purified by flash column chromatography using gradient elution from CH$_2$Cl$_2$ to CH$_2$Cl$_2$/EtOH (98:2) to yield $N^2$-methyl-$N^4$,$N^8$-di-n-propylpyrimido[5,4-d]pyrimidine-2,4,8-triamine (21) (360 mg, 92% y). 400 MHz $^1$H NMR (CDCl$_3$, ppm): δ 8.25 (1H, s), 6.74-6.56 (2H, m), 4.92 (1H, br s), 3.56-3.48 (4H, m), 3.00 (3H, d, J=5.1 Hz), 1.78-1.63 (4H, m), 1.02 (3H, t, J=7.3 Hz), 1.00 (3H, t, J=7.3 Hz). ESI-MS (m/z): 276 [M+H]$^+$.

$N^2$-Methyl-$N^4$,$N^8$-di-n-propylpyrimido[5,4-d]pyrimidine-2,4,8-triamine hydrochloride (22a)

$N^2$-Methyl-$N^4$,$N^8$-di-n-propylpyrimido[5,4-d]pyrimidine-2,4,8-triamine (21) and 2M HCl/diethyl ether in diethyl ether were reacted using the procedure described for compound (4a) to yield $N^2$-methyl-$N^4$,$N^8$-di-n-propylpyrimido[5,4-d]pyrimidine-2,4,8-triamine hydrochloride (22a) in 91% yield. 400 MHz $^1$H NMR (DMSO-d$_6$, ppm): δ 13.8-13.0 (1H, br s), 9.78-8.83 (1H, m), 8.56 (1H, br s), 8.41 (1H, s), 7.33 (1H, br s), 3.55-3.35 (4H, m, overlapped with water), 2.99 (3H, s), 1.71-1.60 (4H, m), 0.95 (3H, t, J=7.3 Hz), 0.91 (3H, t, J=7.3 Hz). ESI-MS (m/z): 276 [M+H]$^+$; melting point: 139-142° C.

Scheme 12.

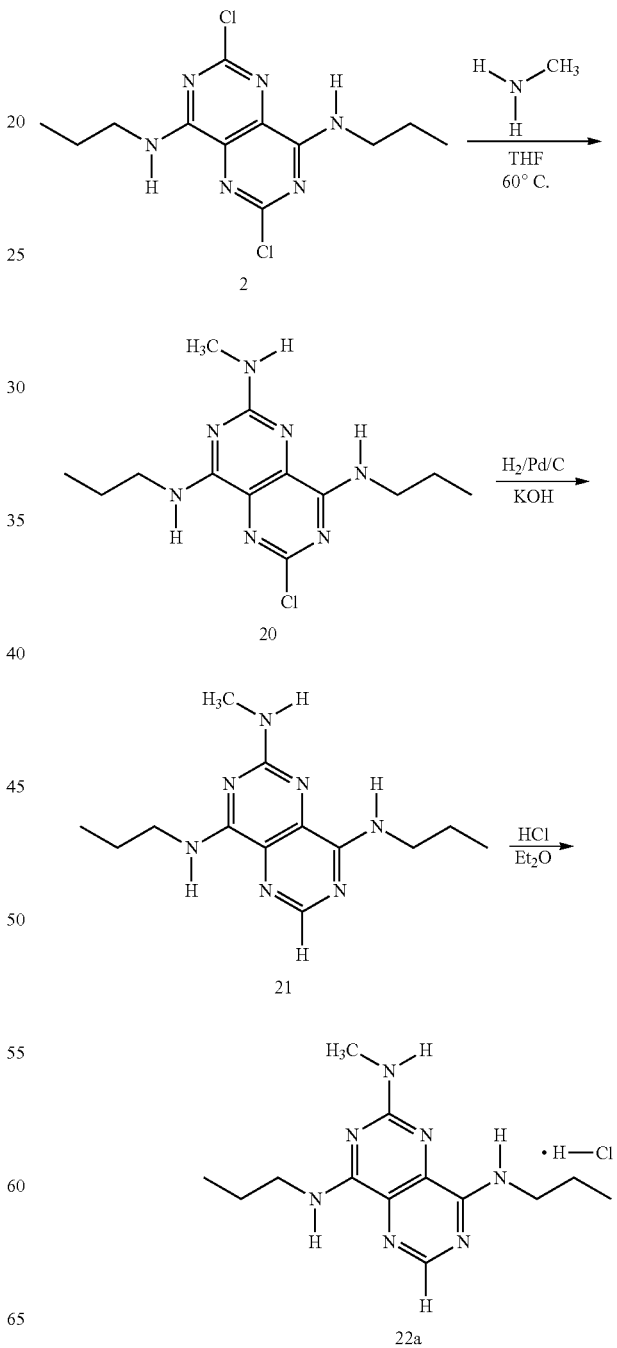

Example 10

O,N-Dimethyl-N-(6-methylamino-4,8-bis-n-propylamino-pyrimido[5,4-d]pyrimidin-2-yl)-hydroxylamine (23) and corresponding hydrochloride salt (24a)

O,N-Dimethyl-N-(6-methylamino-4,8-bis-n-propylamino-pyrimido[5,4-d]pyrimidin-2-yl)-hydroxylamine (23)

A mixture of 6-chloro-$N^2$-methyl-$N^4,N^8$-di-n-propylpyrimido[5,4-d]pyrimidine-2,4,8-triamine (20) (300 mg, 0.97 mmol), N,O-dimethylhydroxylamine hydrochloride (426 mg, 4.37 mmol) and N,N-diisopropylethylamine (722 µL, 4.37 mmol) in 1,4-dioxane (10 mL) was heated at 90° C. for 60 h. The reaction mixture was cooled, and a saturated NaHCO$_3$ solution (30 mL) was added. The resulting suspension was extracted with EtOAc (3×20 mL). The combined organic extracts were washed with water (30 mL), and then with a brine solution (20 mL) and lastly dried over solid anhydrous Na$_2$SO$_4$. After filtration, the solvent was removed and the residue was purified by flash column chromatography using gradient elution from CH$_2$Cl$_2$ to CH$_2$Cl$_2$/EtOH (95:5) to yield of O,N-dimethyl-N-(6-methylamino-4,8-bis-propylamino-pyrimido[5,4-d]pyrimidin-2-yl)-hydroxylamine (23) (175 mg, 54% y). 400 MHz $^1$H NMR (CDCl$_3$, ppm): δ 6.57 (2H, br s), 4.67 (1H, br s), 3.88 (3H, s), 3.54-3.43 (4H, m), 3.30 (3H, s), 2.98 (3H, d, J=5.1 Hz), 1.76-1.64 (4H, m), 1.01 (3H, t, J=7.4 Hz), 0.99 (3H, t, J=7.4 Hz). ESI-MS (m/z): 335 [M+H]$^+$.

O,N-Dimethyl-N-(6-methylamino-4,8-bis-n-propylamino-pyrimido[5,4-d]pyrimidin-2-yl)-hydroxylamine hydrochloride (24a)

O,N-Dimethyl-N-(6-methylamino-4,8-bis-n-propylamino-pyrimido[5,4-d]pyrimidin-2-yl)-hydroxylamine (23) and 2M HCl/diethyl ether in diethyl ether were reacted using the procedure described for compound (3a) to yield O,N-dimethyl-N-(6-methylamino-4,8-bis-n-propylamino-pyrimido[5,4-d]pyrimidin-2-yl)-hydroxylamine hydrochloride (24a) in 90% yield. 400 MHz $^1$H NMR (CDCl$_3$, ppm): 13.24 (0.2H, br s), 8.26 (1.8H, br s), 6.71-6.63 (1H, m), 3.89 (3H, s), 3.66-3.60 (2H, m), 3.57-3.51 (2H, m), 3.37 (3H, s), 3.06 (3H, d, J=4.8 Hz), 1.85-1.74 (4H, m), 1.03 (3H, t, J=7.4 Hz), 1.02 (3H, t, J=7.4 Hz). ESI-MS (m/z): 335 [M+H]$^+$; melting point: 182-185° C.

Example 11

$N^4,N^8$-Dimethyl-$N^2,N^6$-di-n-propyl-pyrimido[5,4-d]pyrimidine-2,4,6,8-tetraamine (26) and corresponding hydrochloride salt (27a) (Scheme 13)

2,6-Dichloro-$N^4,N^8$-dimethyl-pyrimido[5,4-d]pyrimidine-4,8-diamine (25)

A 2M methylamine/THF (2.10 mL, 4.2 mmol) solution was added to a solution of 2,4,6,8-tetrachloro-pyrimido[5,4-d]pyrimidine (1) (250 mg, 0.93 mmol) in THF (5 mL) at 0° C. The reaction mixture was stirred at room temperature for 1 h. After this time, water (10 mL) was added and the precipitate was filtered, washed with water (10 mL) and dried over P$_2$O$_5$ to yield 2,6-dichloro-$N^4,N^8$-dimethyl-pyrimido[5,4-d]pyrimidine-4,8-diamine (25) (230 mg, 95% y). 400 MHz $^1$H NMR (CDCl$_3$, ppm): δ 6.90 (2H, br s), 3.16 (6H, d, J=5.0 Hz). ESI-MS (m/z): 259, 261, 263 [M+H]$^+$.

$N^4,N^8$-Dimethyl-$N^2,N^6$-di-n-propyl-pyrimido[5,4-d]pyrimidine-2,4,6,8-tetraamine (26)

2,6-Dichloro-$N^4,N^8$-dimethyl-pyrimido[5,4-d]pyrimidine-4,8-diamine (25) and n-propylamine were reacted using the procedure described for compound 3 to yield $N^2,N^6$-di-n-propyl-$N^4,N^8$-dimethyl-pyrimido[5,4-d]pyrimidine-2,4,6,8-tetraamine (26) in 90% yield. 400 MHz $^1$H NMR (CDCl$_3$, ppm): δ 6.49-6.38 (2H, m), 4.64 (2H, t, J=5.2 Hz), 3.38-3.33 (4H, m), 3.06 (6H, d, J=5.2 Hz), 1.63 (4H, sextet, J=7.3 Hz), 0.99 (6H, t, J=7.3 Hz). ESI-MS (m/z): 305 [M+H]$^+$.

$N^4,N^8$-Dimethyl-$N^2,N^6$-di-n-propyl-pyrimido[5,4-d]pyrimidine-2,4,6,8-tetraamine hydrochloride (27a)

$N^2,N^6$-Di-n-propyl-$N^4,N^8$-dimethyl-pyrimido[5,4-d]pyrimidine-2,4,6,8-tetraamine (26) and 2M HCl/diethyl ether in diethyl ether/1,4-dioxane (5/1) were reacted using the procedure described for compound (4a) to yield $N^2,N^6$-di-n-propyl-$N^4,N^8$-dimethyl-pyrimido[5,4-d]pyrimidine-2,4,6,8-tetraamine hydrochloride (27a) in 88% yield. 400 MHz $^1$H NMR (CDCl$_3$, ppm): δ 14.00 (0.3H, s), 9.65 (0.7H, s), 7.70 (1H, s), 7.44 (1H, s), 6.65 (1.3H, s), 4.89 (0.7H, s), 3.50-3.43 (3H, m), 3.39-3.30 (1H, m), 3.21-3.20 (4H, m), 3.08-3.03 (2H, m), 1.71-1.59 (4H, m), 0.99 (6H, t, J=7.5 Hz). ESI-MS (m/z): 305 [M+H]$^+$; melting point: 237-240° C.

Scheme 13.

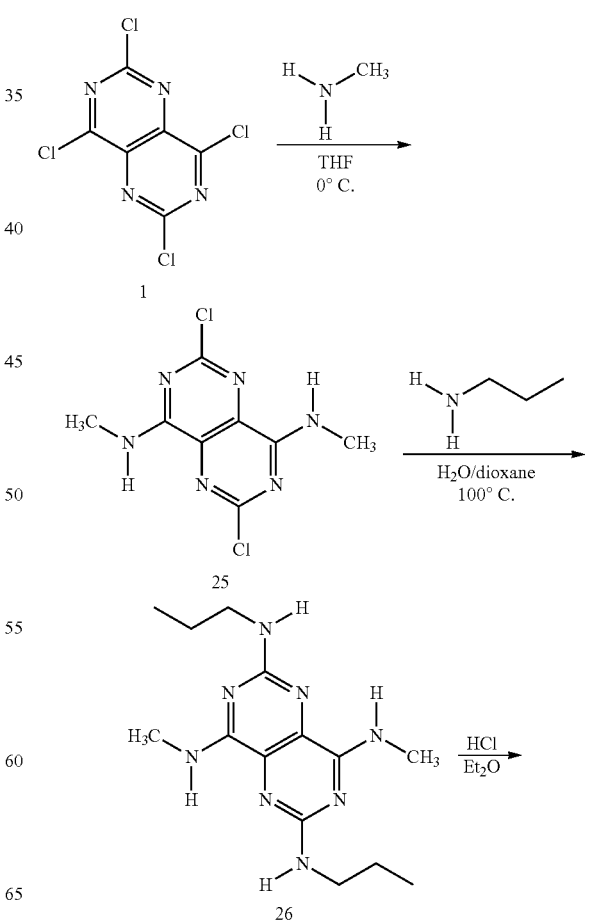

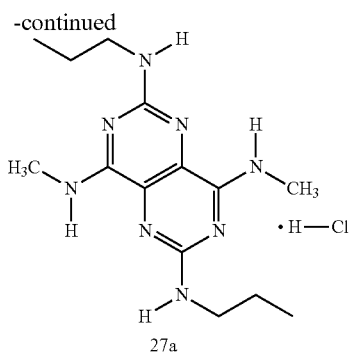

27a

Example 12

N²,N²,N⁶-Trimethyl-N⁴,N⁸-di-n-propyl-pyrimido[5,4-d]pyrimidine-2,4,6,8-tetraamine (28) and corresponding hydrochloride salt (29a) (Scheme 14)

6-Chloro-N²-methyl-N⁴,N⁸-di-n-propyl-pyrimido[5,4-d]pyrimidine-2,4,8-triamine hydrochloride (20a)

A 2M HCl/diethyl ether (260 μL, 0.52 mmol) was added to the solution of 6-chloro-N²-methyl-N⁴,N⁸-di-n-propylpyrimido[5,4-d]pyrimidine-2,4,8-triamine (20) (160 mg, 0.52 mmol) in diethyl ether (10 mL). The mixture was stirred for 0.5 h at 0° C., and the resultant precipitate was filtered, washed with diethyl ether (3 mL) and dried to yield 6-chloro-N²-methyl-N⁴,N⁸-di-$_n$-propylpyrimido[5,4-d]pyrimidine-2,4,8-triamine hydrochloride (20a) (160 mg, 89% y). 400 MHz $^1$H NMR (DMSO-d₆, ppm): δ 9.44 (1H, br s) 8.96 (1H, br s), 7.37 (1H, br s), 3.78-3.12 (4H, m, overlapped with water), 2.97 (3H, s), 1.71-1.56 (4H, m), 0.95 (3H, t, J=7.3 Hz), 0.89 (3H, t, J=7.3 Hz). ESI-MS (m/z): 310, 312 [M+H]⁺; melting point: 209-212° C.

N²,N²,N⁶-Trimethyl-N⁴,N⁸-di-n-propyl-pyrimido[5,4-d]pyrimidine-2,4,6,8-tetraamine (28)

A mixture of 6-chloro-N²-methyl-N⁴,N⁸-di-n-propylpyrimido[5,4-d]pyrimidine-2,4,8-triamine (20) (310 mg, 1.00 mmol) and dimethylamine (40% water solution, 2.25 mL) in 1,4-dioxane (2.5 mL) was heated at 105° C. for 16 h in a closed vial. The volatiles were removed by evaporation, and the residue was partitioned between CH₂Cl₂ (35 mL) and a saturated NaHCO₃ solution (30 mL). The water phase was extracted with CH₂Cl₂ (2×35 mL), and the combined organic extracts were washed with water (40 mL) and dried over solid anhydrous Na₂SO₄. After filtration, the solvent was removed and the residue was purified by flash column chromatography using gradient elution from PE/EtOAc (95:5) to PE/EtOAc (85:15) to yield N²,N²,N⁶-trimethyl-N⁴,N⁸-di-n-propyl-pyrimido[5,4-d]pyrimidine-2,4,6,8-tetraamine (28) (280 mg, 88% y). 400 MHz $^1$H NMR (CDCl₃, ppm): δ 400 MHz $^1$H NMR (CDCl₃, ppm): 6.61-6.40 (2H, m), 4.57 (1H, br s), 3.54-3.43 (4H, m), 3.15 (6H, s), 2.97 (3H, d, J=5.0 Hz), 1.76-1.65 (4H, m), 1.01 (3H, t, J=7.4 Hz), 1.00 (3H, t, J=7.4 Hz). ESI-MS (m/z): 319 [M+H]⁺.

N²,N²,N⁶-Trimethyl-N⁴,N⁸-di-n-propyl-pyrimido[5,4-d]pyrimidine-2,4,6,8-tetraamine hydrochloride (29a)

A 2M HCl/diethyl ether solution (0.41 mL, 0.82 mmol) was added to a solution of N²,N²,N⁶-trimethyl-N⁴,N⁸-di-n-propyl-pyrimido[5,4-d]pyrimidine-2,4,6,8-tetraamine (28) (264 mg, 0.83 mmol) in methanol (20 mL). The mixture was stirred for 0.5 h at 0° C., and then the volatiles were removed under reduced pressure to yield N²,N²,N⁶-trimethyl-N⁴,N⁸-di-n-propyl-pyrimido[5,4-d]pyrimidine-2,4,6,8-tetraamine hydrochloride (29a) (292 mg, ~100% y). 400 MHz $^1$H NMR (CDCl₃, ppm): δ 14.08 (1H, br s), 12.41 (0.3H, s), 8.4-7.2 (1.7H, br s), 6.59 (1H, s), 3.65-3.59 (2H, m), 3.56-3.48 (2H, m), 3.22 (6H, s), 3.04 (2H, d, J=4.8 Hz), 1.84-1.73 (4H, m), 1.03 (3H, t, J=7.4 Hz), 1.02 (3H, t, J=7.4 Hz). ESI-MS (m/z): 319 [M+H]⁺; melting point: 241-243° C.

Example 13

N²,N²-Diethyl-N⁶-methyl-N⁴,N⁸-di-n-propyl-pyrimido[5,4-d]pyrimidine-2,4,6,8-tetraamine (30) and corresponding hydrochloride salt (31a) (Scheme 14)

N²,N²-Diethyl-N⁶-methyl-N⁴,N⁸-di-n-propyl-pyrimido[5,4-d]pyrimidine-2,4,6,8-tetraamine (30)

A mixture of 6-chloro-N²-methyl-N⁴,N⁸-di-n-propylpyrimido[5,4-d]pyrimidine-2,4,8-triamine (20) (300 mg, 0.97 mmol) and diethylamine (500 μL) in 1,4-dioxane (2.5 mL) was heated in a closed vial at 120° C. for 48 h. An additional portion of diethylamine (500 μL) was added and heating at 120° C. was continued for 48 h. The volatiles were removed by evaporation, and the residue was partitioned between CH₂Cl₂ (35 mL) and a saturated NaHCO₃ solution (30 mL). The water phase was extracted with CH₂Cl₂ (2×30 mL), and the combined organic extracts were washed with water (40 mL) and dried over solid anhydrous Na₂SO₄. After filtration, the solvent was removed and the residue was purified by flash column chromatography using gradient elution from CH₂Cl₂ to CH₂Cl₂/EtOH (95:5) to give N²,N²-diethyl-N⁶-methyl-N⁴,N⁸-di-n-propyl-pyrimido[5,4-d]pyrimidine-2,4,6,8-tetraamine (30) (130 mg, 39% y). 400 MHz $^1$H NMR (CDCl₃, ppm): δ 6.52 (1H, br s), 6.45 (1H, br s), 4.53 (1H, br s), 3.67-3.57 (4H, m), 3.52-3.42 (4H, m), 2.97 (3H, d, J=4.4 Hz), 1.75-1.63 (4H, m), 1.19 (6H, t, J=7.0 Hz), 1.00 (3H, t, J=7.4 Hz), 0.99 (3H, t, J=7.4 Hz). ESI-MS (m/z): 347 [M+H]⁺.

N²,N²-Diethyl-N⁶-methyl-N⁴,N⁸-di-n-propyl-pyrimido[5,4-d]pyrimidine-2,4,6,8-tetraamine hydrochloride (31a)

N²,N²-Diethyl-N⁶-methyl-N⁴,N⁸-di-n-propyl-pyrimido[5,4-d]pyrimidine-2,4,6,8-tetraamine (30) (110 mg, 0.32 mmol) was treated with 2M HCl/diethyl ether using the procedure described for compound 20a to yield N²,N²-diethyl-N⁶-methyl-N⁴,N⁸-di-n-propyl-pyrimido[5,4-d]pyrimidine-2,4,6,8-tetraamine hydrochloride (31a) (110 mg, 89% y). 400 MHz $^1$H NMR (CDCl₃, ppm): δ 13.91 (1H, s), 7.56 (1H, br s), 7.51-7.43 (1H, m), 6.62-6.50 (1H, m), 3.65-3.54 (6H, m), 3.53-3.45 (2H, m), 3.04 (3H, d, J=4.8 Hz), 1.83-1.68 (4H, m), 1.18 (6H, t, J=7.0 Hz), 1.03 (3H, t, J=7.1 Hz), 1.01 (3H, t, J=7.1 Hz). ESI-MS (m/z): 347 [M+H]⁺; melting point: 202-204° C.

Example 14

2-(6-Methylamino-4,8-bis-n-propylamino-pyrimido[5,4-d]pyrimidin-2-yl-amino)-ethanol (32) and corresponding hydrochloride salt (33a) (Scheme 14)

6-Chloro-N²-methyl-N⁴,N⁸-di-n-propylpyrimido[5,4-d]pyrimidine-2,4,8-triamine (20) (257 mg, 0.83 mmol) and 2-aminoethanol were reacted using the procedure described for compound 40 to yield 2-(6-methylamino-4,8-bis-n-propylamino-pyrimido[5,4-d]pyrimidin-2-yl-amino)-ethanol (32) (200 mg, 72% y). 400 MHz $^1$H NMR (CDCl$_3$, ppm): δ 6.64 (1H, br s), 6.28 (1H, br s), 5.08 (1H, t, J=5.2 Hz), 4.86-4.37 (2H, m), 3.85-3.80 (2H, m), 3.60-3.53 (2H, m), 3.49-3.41 (4H, m), 2.96 (3H, d, J=5.2 Hz), 1.75-1.62 (4H, m), 1.01 (3H, t, J=7.4 Hz), 0.99 (3H, t, J=7.4 Hz). ESI-MS (m/z): 335 [M+H]$^+$.

2-(6-Methylamino-4,8-bis-n-propylamino-pyrimido[5,4-d]pyrimidin-2-yl-amino)-ethanol (32) (190 mg, 0.57 mmol)) was treated with 2M HCl/diethyl ether in methanol using the procedure described for compound (29a) (210 mg, ~100% y). 400 MHz $^1$H NMR (CDCl$_3$, ppm): δ 15.1-13.7 (1H, m), 8.00-7.31 (1.5H, m), 6.95 (0.5H, br s), 6.64 (1H, br s), 5.5-4.7 (1H, m), 3.86-3.81 (2H, m), 3.70-3.45 (6H, m), 3.04 (3H, s), 3.0-2.5 (1H, br s), 1.83-1.71 (4H, m), 1.03 (6H, t, J=7.4 Hz). ESI-MS (m/z): 335 [M+H]$^+$; melting point: 194-196° C.

Example 15

N$^2$-(2-Methoxyethyl)-N$^6$-methyl-N$^4$,N$^8$-di-n-propyl-pyrimido[5,4-d]pyrimidine-2,4,6,8-tetraamine (34) and corresponding hydrochloride salt (35a) (Scheme 14)

N$^2$-(2-Methoxy-ethyl)-N$^6$-methyl-N$^4$,N$^8$-di-n-propyl-pyrimido[5,4-d]pyrimidine-2,4,6,8-tetraamine (34) was prepared from 6-chloro-N$^2$-methyl-N$^4$,N$^8$-di-n-propylpyrimido[5,4-d]pyrimidine-2,4,8-triamine (20) (300 mg, 0.97 mmol) and 2-methoxy-ethylamine in n-butanol using the procedure described for compound (9) (215 mg, 64% y). 400 MHz $^1$H NMR (CDCl$_3$, ppm): δ 6.61-6.40 (2H, m), 4.93 (1H, s), 4.59 (1H, br s), 3.63-3.53 (4H, m), 3.50-3.41 (4H, m), 3.39 (3H, s), 2.97 (3H, d, J=5.2 Hz), 1.74-1.63 (4H, m), 1.00 (3H, t, J=7.4 Hz), 0.99 (3H, t, J=7.4 Hz). ESI-MS (m/z): 349 [M+H]$^+$.

N$^2$-(2-Methoxy-ethyl)-N$^6$-methyl-N$^4$,N$^8$-di-n-propyl-pyrimido[5,4-d]pyrimidine-2,4,6,8-tetraamine (34) (200 mg, 0.57 mmol)) was treated with 2M HCl/diethyl ether in methanol using the procedure described for compound (29a) (178 mg, 81% y). 400 MHz $^1$H NMR (DMSO-d$_6$, ppm): δ 9.3-8.0 (1H, m), 6.94 (2H, br s), 6.2-4.5 (2H, br s), 3.60-3.54 (2H, m), 3.51-3.41 (6H, m), 3.27 (3H, s), 2.92 (3H, s), 1.70-1.59 (4H, m), 0.93 (6H, t, J=7.4 Hz). ESI-MS (m/z): 349 [M+H]$^+$; melting point: 214-216° C.

Example 16

N$^2$-(2-Isopropoxy-ethyl)-N$^6$-methyl-N$^4$,N$^8$-di-n-propyl-pyrimido[5,4-d]pyrimidine-2,4,6,8-tetraamine (36) and corresponding hydrochloride salt (37a) (Scheme 14)

N$^2$-(2-Isopropoxy-ethyl)-N$^6$-methyl-N$^4$,N$^8$-di-n-propyl-pyrimido[5,4-d]pyrimidine-2,4,6,8-tetraamine (36) (249 mg, 0.80 mmol) was prepared from 6-chloro-N$^2$-methyl-N$^4$,N$^8$-di-n-propyl-pyrimido[5,4-d]pyrimidine-2,4,8-triamine (20) and 2-isopropyl-ethylamine using procedure described for compound (40) (165 mg 55% y). 400 MHz $^1$H NMR (CDCl$_3$, ppm): δ 6.55-6.42 (2H, m), 4.97-4.89 (1H, m), 4.60 (1H, br s), 3.66-3.54 (5H, m), 3.50-3.40 (4H, m), 2.96 (3H, d, J=5.0 Hz), 1.74-1.63 (4H, m), 1.18 (6H, d, J=6.3 Hz), 1.00 (3H, t, J=7.4 Hz), 0.99 (3H, t, J=7.4 Hz). ESI-MS (m/z): 377 [M+H]$^+$.

N$^2$-(2-Isopropoxy-ethyl)-N$^6$-methyl-N$^4$,N$^8$-di-n-propyl-pyrimido[5,4-d]pyrimidine-2,4,6,8-tetraamine (36) (140 mg, 0.37 mmol) was treated with 2M HCl/diethyl ether in methanol using the procedure described for compound (29a) (152 mg, ~100% y). 400 MHz $^1$H NMR (CDCl$_3$, ppm): 15.4-13.8 (1H, m), 10.1-9.2 (0.5H, m), 8.11-7.35 (1.5H, m), 7.01-6.56 (1H, m), 5.37-4.65 (1H, m), 3.70-3.42 (9H, m), 3.03 (3H, s), 1.85-1.70 (4H, m), 1.18 (6H, d, J=6.2 Hz), 1.03 (3H, t, J=7.4 Hz), 1.02 (3H, t, J=7.4 Hz). ESI-MS (m/z): 377 [M+H]$^+$; melting point: 154-156° C.

Example 17

N$^8$-Methyl-N$^4$,N$^6$-di-n-propyl-N$^2$-(3,3,3-trifluoropropyl)-pyrimido[5,4-d]pyrimidine-2,4,6,8-tetraamine (38) and corresponding hydrochloride salt (39a) (Scheme 14)

N$^8$-Methyl-N$^4$,N$^6$-di-n-propyl-N$^2$-(3,3,3-trifluoropropyl)-pyrimido[5,4-d]pyrimidine-2,4,6,8-tetraamine (38)

A mixture of 6-chloro-N$^2$-methyl-N$^4$,N$^8$-di-n-propylpyrimido[5,4-d]pyrimidine-2,4,8-triamine (20) (300 mg, 0.97 mmol), 3,3,3-trifluoropropylamine hydrochloride (435 mg, 2.91 mmol) and N,N-diisopropylethylamine (503 μL, 2.91 mmol) in n-butanol (1.5 mL) was heated in a closed vial at 140° C. for 24 h. A saturated NaHCO$_3$ solution (5 mL) was added and the resulting suspension was extracted with EtOAc (3×10 mL). The combined organic extracts were washed with water (20 mL), and then with a brine solution (10 mL) and dried over solid anhydrous Na$_2$SO$_4$. After filtration, the solvent was removed and the residue was purified by flash column chromatography using gradient elution from PE/EtOAc (5:1) to PE/EtOAc (3:1) to give N$^8$-methyl-N$^4$,N$^6$-di-n-propyl-N$^2$-(3,3,3-trifluoropropyl)-pyrimido[5,4-d]pyrimidine-2,4,6,8-tetraamine (38) (300 mg, 80% y). 400 MHz $^1$H NMR (CDCl$_3$, ppm): δ 6.58 (1H, br s), 6.45 (1H, br s), 4.79 (1H, s), 4.63 (1H, br s), 3.66 (2H, dt, J=7.4, 6.4 Hz), 3.49-3.43 (4H, m), 2.98 (3H, d, J=5.2 Hz), 2.55-2.43 (2H, m), 1.70 (2H, sextet, J=7.4 Hz), 1.69 (2H, sextet, J=7.4 Hz), 1.01 (6H, t, J=7.4 Hz). ESI-MS (m/z): 387 [M+H]$^+$.

N$^8$-Methyl-N$^4$,N$^6$-di-n-propyl-N$^2$-(3,3,3-trifluoropropyl)-pyrimido[5,4-d]pyrimidine-2,4,6,8-tetraamine hydrochloride (39a)

N$^8$-Methyl-N$^4$,N$^6$-di-n-propyl-N$^2$-(3,3,3-trifluoropropyl)-pyrimido[5,4-d]pyrimidine-2,4,6,8-tetraamine (38) (290 mg, 0.75 mmol) was treated with 2M HCl/diethyl ether in diethyl ether/ethanol (15/1) using the procedure described for compound (20a) to produce N$^8$-methyl-N$^4$,N$^6$-di-n-propyl-N$^2$-(3,3,3-trifluoropropyl)-pyrimido[5,4-d]pyrimidine-2,4,6,8-tetraamine hydrochloride (39a) (293 mg, 92% y). 400 MHz $^1$H NMR (CDCl$_3$, ppm): δ 9.75 (1H, br s), 9.50 (1H, br s), 6.87 (1H, br s), 6.62 (1H, s), 3.79 (2H, dt, J=7.4, 6.7 Hz), 3.68-3.59 (4H, m), 3.08 (3H, d, J=4.8 Hz), 2.54-2.41 (2H, m), 1.89-1.78 (4H, m), 1.06 (3H, t, J=7.4 Hz), 1.05 (3H, t, J=7.4 Hz). ESI-MS (m/z): 387 [M+H]$^+$; melting point: 259-260° C.

Example 18

N$^2$-Methyl-N$^4$,N$^8$-di-n-propyl-6-(morpholin-4-yl)-pyrimido[5,4-d]pyrimidine-2,4,8-triamine (40) and corresponding hydrochloride salt (41a) (Scheme 14)

N$^2$-Methyl-N$^4$N$^8$-di-n-propyl-6-(morpholin-4-yl)-pyrimido[5,4-d]pyrimidine-2,4,8-triamine A mixture of 6-chloro-N$^2$-methyl-N$^4$,N$^8$-di-n-propylpyrimido[5,4-d]pyrimidine-2,4,8-triamine (20) (250 mg, 0.81 mmol) and morpholine (2.0 mL) was heated in a closed vial at 105° C. for 16 h. A saturated NaHCO$_3$ solution (15 mL) was added and the resulting suspension was extracted with EtOAc (3×25 mL). The combined organic extracts were washed with water (2×15 mL), and then with a brine solution (20 mL), and dried over solid anhydrous Na$_2$SO$_4$. After filtration, the solvent was removed and the residue was purified by flash column chromatography using gradient elution from CH$_2$Cl$_2$ to CH$_2$Cl$_2$/EtOH (98:2) to give N$^2$-methyl-N$^4$,N$^8$-di-n-propyl-6-(morpholin-4-yl)-pyrimido[5,4-d]pyrimidine-2,4,8-triamine (40) (265 mg, 91% y). 400 MHz $^1$H NMR (CDCl$_3$, ppm): δ 6.65-6.37 (2H, m), 4.65 (1H, br s), 3.83-3.67 (8H, m), 3.54-3.40 (4H, m), 2.97 (3H, s), 1.76-1.63 (4H, m), 1.00 (3H, t, J=7.4 Hz), 0.99 (3H, t, J=7.4 Hz). ESI-MS (m/z): 361 [M+H]$^+$.

N$^2$-Methyl-N$^4$N$^8$-di-n-propyl-6-(morpholin-4-yl)-pyrimido[5,4-d]pyrimidine-2,4,8-triamine (41a)

N$^2$-Methyl-N$^4$,N$^8$-di-n-propyl-6-(morpholin-4-yl)-pyrimido[5,4-d]pyrimidine-2,4,8-triamine (40) (250 mg, 0.69 mmol) was treated with 2M HCl/diethyl ether in methanol using the procedure described for compound (20a) (226 mg, 82% y). 400 MHz $^1$H NMR (CDCl$_3$, ppm): δ 14.07 (1H, br s), 7.72 (1H, s), 7.48-7.39 (1H, m), 6.66-6.54 (1H, m), 3.82-3.71 (8H, m), 3.61 (2H, q, J=7.8 Hz), 3.53-3.45 (2H, m), 3.05 (3H, d, J=4.8 Hz), 1.82-1.70 (4H, m), 1.03 (3H, t, J=7.4 Hz), 1.02 (3H, t, J=7.4 Hz). ESI-MS (m/z): 361 [M+H]$^+$; melting point: 240-242° C.

Example 19

N$^2$-Methyl-N$^4$,N$^8$-di-n-propyl-6-(piperidin-1-yl)-pyrimido[5,4-d]pyrimidine-2,4,8-triamine (42) and corresponding hydrochloride salt (43a) (Scheme 14)

N$^2$-Methyl-N$^4$,N$^8$-di-n-propyl-6-(piperidin-1-yl)-pyrimido[5,4-d]pyrimidine-2,4,8-triamine was prepared from 6-chloro-N$^2$-methyl-N$^4$,N$^8$-di-n-propylpyrimido[5,4-d]pyrimidine-2,4,8-triamine (20) (250 mg, 0.81 mmol) and piperidine using procedure described for compound (40) (240 mg, 83% y). 400 MHz $^1$H NMR (CDCl$_3$, ppm): δ 6.49 (2H, br s), 4.59 (1H, br s), 3.83-3.65 (4H, m), 3.59-3.38 (4H, m), 2.96 (3H, s), 1.75-1.64 (4H, m), 1.64-1.54 (6H, m), 1.00 (3H, t, J=7.4 Hz), 0.99 (3H, t, J=7.4 Hz). ESI-MS (m/z): 359 [M+H]$^+$.

N$^2$-Methyl-N$^4$,N$^8$-di-n-propyl-6-(piperidin-1-yl)-pyrimido[5,4-d]pyrimidine-2,4,8-triamine (42) (220 mg, 0.61 mmol) was treated with 2M HCl/diethyl ether in methanol were reacted using the procedure described for compound (29a) (242 mg, ~100% y). 400 MHz $^1$H NMR (CDCl$_3$, ppm): δ 14.8-13.8 (1.2H, m), 12.51 (0.8H, br s), 6.65-6.54 (1H, m), 4.06-3.72 (4H, m), 3.66-3.58 (2H, m), 3.57-3.48 (2H, m), 3.05 (3H, d, J=4.8 Hz), 1.80 (4H, sextet, J=7.4 Hz), 1.73-1.62 (6H, m), 1.03 (3H, t, J=7.4 Hz), 1.02 (3H, t, J=7.4 Hz). ESI-MS (m/z): 359 [M+H]$^+$; melting point: 220-222° C.

Example 20

N$^2$-Methyl-N$^4$,N$^8$-di-n-propyl-6-pyrrolidin-1-yl-pyrimido[5,4-d]pyrimidine-2,4,8-triamine (44) and corresponding dihydrochloride salt (45a) (Scheme 14)

6-Chloro-N$^2$-methyl-N$^4$,N$^8$-di-n-propylpyrimido[5,4-d]pyrimidine-2,4,8-triamine (20) (160 mg, 0.52 mmol) and pyrrolidine were reacted using procedure described for compound (40) (135 mg, 76% y). 400 MHz $^1$H NMR (CDCl$_3$, ppm): δ 6.76-6.32 (2H, m), 4.58 (1H, br s), 3.74-3.34 (8H, m), 2.97 (3H, s), 1.98-1.90 (4H, m), 1.76-1.64 (4H, m), 1.00 (6H, t, J=7.4 Hz). ESI-MS (m/z): 345 [M+H]$^+$.

N$^2$-Methyl-N$^4$,N$^8$-di-n-propyl-6-pyrrolidin-1-yl-pyrimido[5,4-d]pyrimidine-2,4,8-triamine (44) (125 mg, 0.36 mmol) was treated with 2M HCl/diethyl ether in methanol using the procedure described for compound (20a) (76 mg, 50% y). 400 MHz $^1$H NMR (CDCl$_3$, ppm): δ 14.66 (1H, s), 12.34 (1H, s), 11.72 (1H, br s), 9.39 (1H, br s), 6.69-6.58 (1H, m), 4.26-3.95 (2H, m), 3.83-3.51 (6H, m), 3.06 (3H, d, J=4.7 Hz), 2.21-1.92 (4H, m), 1.91-1.75 (4H, m), 1.07-0.99 (6H, m). ESI-MS (m/z): 345 [M+H]$^+$; melting point: 243-245° C.

Example 21

N$^2$-Methyl-N$^4$,N$^8$-di-n-propyl-6-(4-methoxy-piperidin-1-yl)-pyrimido[5,4-d]pyrimidine-2,4,8-triamine (46) and corresponding hydrochloride salt (47a) (Scheme 14)

6-Chloro-N$^2$-methyl-N$^4$,N$^8$-di-n-propylpyrimido[5,4-d]pyrimidine-2,4,8-triamine (20) (260 mg, 0.84 mmol) and 4-methoxypiperidine were reacted using procedure described for compound 40 to produce N$^2$-methyl-N$^4$,N$^8$-di-n-propyl-6-(4-methoxy-piperidin-1-yl)-pyrimido[5,4-d]pyrimidine-2,4,8-triamine (46) (270 mg, 83% y). 400 MHz $^1$H NMR (CDCl$_3$, ppm): δ 6.49 (2H, s), 4.62 (1H, br s), 4.42-4.30 (2H, m), 3.54-3.35 (5H, m), 3.39 (3H, s), 3.29-3.17 (2H, m), 2.98 (3H, d, J=4.4 Hz), 2.01-1.91 (2H, m), 1.76-1.63 (4H, m), 1.62-1.50 (2H, m), 1.00 (3H, t, J=7.4 Hz), 0.99 (3H, t, J=7.4 Hz). ESI-MS (m/z): 389 [M+H]$^+$.

N$^2$-Methyl-N$^4$,N$^8$-di-n-propyl-6-(4-methoxy-piperidin-1-yl)-pyrimido[5,4-d]pyrimidine-2,4,8-triamine (46) (240 mg, 0.62 mmol) was treated with 2M HCl/diethyl ether in methanol using the procedure described for compound (20a) (262 mg, ~100% y). 400 MHz $^1$H NMR (CDCl$_3$, ppm): δ 13.99 (1H, br s), 7.66 (1H, br s), 7.47 (1H, br s), 6.63-6.56 (1H, m), 4.28-4.16 (2H, m), 3.64-3.57 (2H, m), 3.53-3.32 (5H, m), 3.39 (3H, s), 3.04 (3H, d, J=5.0 Hz), 1.98-1.89 (2H, m), 1.82-1.70 (4H, m), 1.64-1.52 (2H, m), 1.05-0.98 (6H, m). ESI-MS (m/z): 389 [M+H]$^+$; melting point: 221-223° C.

Example 22

N$^2$-(3-Chloro-2-methyl-benzyl)-N$^6$-methyl-N$^4$,N$^8$-di-n-propyl-pyrimido[5,4-d]pyrimidine-2,4,6,8-tetraamine (48) and corresponding hydrochloride salt (49a) (Scheme 14)

N$^2$-(3-Chloro-2-methyl-benzyl)-N$^6$-methyl-N$^4$,N$^8$-di-n-propyl-pyrimido[5,4-d]pyrimidine-2,4,6,8-tetraamine (48)

A mixture of 6-chloro-N$^2$-methyl-N$^4$,N$^8$-di-n-propylpyrimido[5,4-d]pyrimidine-2,4,8-triamine (20) (250 mg, 0.81 mmol) and 3-chloro-2-methyl-benzylamine (315 mg, 2.02 mmol) in n-butanol (2.0 mL) was heated in a closed vial at 145° C. for 23 h. The reaction mixture was cooled and a saturated NaHCO$_3$ solution (20 mL) was added. The resulting suspension was extracted with CH$_2$Cl$_2$ (3×15 mL). The combined organic extracts were washed with water (20 mL) and dried over solid anhydrous Na$_2$SO$_4$. After filtration, the solvent was removed and the residue was purified by flash column chromatography using gradient elution from CH$_2$Cl$_2$ to CH$_2$Cl$_2$/EtOH (98:2) to give N$^2$-(3-chloro-2-methyl-benzyl)-N$^6$-methyl-N$^4$,N$^8$-di-n-propyl-pyrimido[5,4-d]pyrimidine-2,4,6,8-tetraamine hydrochloride (48) (200 mg, 58%). 400 MHz $^1$H NMR (CDCl$_3$, ppm): δ 7.33-7.24 (2H, m), 7.07 (1H, dd, J=7.8, 7.8 Hz), 6.60-6.48 (1H, m), 6.47-6.34 (1H, m), 4.87-4.74 (1H, m), 4.65-4.54 (1H, m), 4.59 (2H, d, J=5.7 Hz), 3.49-3.39 (4H, m), 2.97 (3H, d, J=5.1 Hz), 2.43 (3H, s), 1.67 (2H, sextet, J=7.3 Hz), 1.66 (2H, sextet, J=7.3 Hz), 0.98 (3H, t, J=7.3 Hz), 0.98 (3H, t, J=7.3 Hz). ESI-MS (m/z): 429, 431 [M+H]$^+$.

N$^2$-(3-Chloro-2-methyl-benzyl)-N$^6$-methyl-N$^4$,N$^8$-di-n-propyl-pyrimido[5,4-d]pyrimidine-2,4,6,8-tetraamine hydrochloride (49a)

N$^2$-(3-chloro-2-methyl-benzyl)-N$^6$-methyl-N$^4$,N$^8$-di-n-propyl-pyrimido[5,4-d]pyrimidine-2,4,6,8-tetraamine hydrochloride (30) (140 mg, 0.33 mmol) was treated with 2M HCl/diethyl ether using the procedure described for compound (29a) to produce N$^2$-(3-chloro-2-methyl-benzyl)-N$^6$-methyl-N$^4$,N$^8$-di-n-propyl-pyrimido[5,4-d]pyrimidine-2,4,6,8-tetraamine hydrochloride (49a) (140 mg, 91% y). 400 MHz $^1$H NMR (CDCl$_3$, ppm): δ 15.5-14.8 (0.4H, m), 14.39-13.95 (0.6H, m), 9.8-9.4 (0.4H, m), 7.86-7.36 (1H, m), 7.31 (1H, d, J=7.8 Hz), 7.23-7.17 (1H, m), 7.2-7.0 (0.6H, m), 7.09 (1H, dd, J=7.8, 7.8 Hz), 6.72-6.49 (1H, m), 5.16-4.79 (1H, m), 4.77-4.47 (2H, m), 3.70-3.37 (4H, m), 3.13-2.89 (3H, m), 2.42 (3H, s), 1.89-1.61 (4H, m), 1.08-0.94 (6H, m). ESI-MS (m/z): 429, 431 [M+H]$^+$; melting point: 193-196° C.

Example 23

N$^2$-(3,4-Dichlorobenzyl)-N$^6$-methyl-N$^4$,N$^8$-di-n-propyl-pyrimido[5,4-d]pyrimidine-2,4,6,8-tetraamine (50) and corresponding hydrochloride salt (51a) (Scheme 14)

6-Chloro-N$^2$-methyl-N$^4$,N$^8$-di-n-propylpyrimido[5,4-d]pyrimidine-2,4,8-triamine (20) (250 mg, 0.81 mmol) and 3,4-dichlorobenzylamine were reacted in DMSO using the procedure described for compound (48) to produce N$^2$-(3,4-dichloro-benzyl)-N$^6$-methyl-N$^4$,N$^8$-di-n-propyl-pyrimido[5,4-d]pyrimidine-2,4,6,8-tetraamine (50) (260 mg, 71% y). 400 MHz $^1$H NMR (CDCl$_3$, ppm): δ 7.49 (1H, d, J=2.0 Hz), 7.36 (1H, d, J=8.2 Hz), 7.21 (1H, dd, J=8.2, 2.0 Hz), 6.58 (1H, s), 6.38 (1H, s), 5.08 (1H, s), 4.67 (1H, s), 4.54 (2H, d, J=6.0 Hz), 3.46-3.40 (4H, m), 2.96 (3H, d, J=5.1 Hz), 1.71-1.61 (4H, m), 0.98 (3H, t, J=7.4 Hz), 0.97 (3H, t, J=7.4 Hz). ESI-MS (m/z): 449, 451, 453 [M+H]$^+$.

N$^2$-(3,4-Dichloro-benzyl)-N$^6$-methyl-N$^4$,N$^8$-di-n-propyl-pyrimido[5,4-d]pyrimidine-2,4,6,8-tetraamine (50) (240 mg, 0.53 mmol) was treated with 2M HCl/diethyl ether in diethyl ether using the procedure described for compound (20a). The product was crystallized from ethanol to give N$^2$-(3,4-dichloro-benzyl)-N$^6$-methyl-N$^4$,N$^8$-di-n-propyl-pyrimido[5,4-d]pyrimidine-2,4,6,8-tetraamine hydrochloride (51a) (200 mg, 78% y). 400 MHz $^1$H NMR (DMSO-d$_6$, ppm): δ 13.5-12.3 (1H, m), 8.87 (1H, br s), 8.5-7.9 (1H, br s), 7.9-6.6 (3H, m), 7.68 (1H, s), 7.58 (1H, d, J=8.2 Hz), 4.57 (2H, s), 3.62-3.36 (4H, m, overlapped with water), 2.96 (3H, s), 1.75-1.41 (4H, m), 1.00-0.75 (6H, m). ESI-MS (m/z): 449, 451, 453 [M+H]$^+$; melting point: 176-179° C.

Example 24

N$^2$-(4-Fluorobenzyl)-N$^6$-methyl-N$^4$,N$^8$-di-n-propyl-pyrimido[5,4-d]pyrimidine-2,4,6,8-tetraamine (52) and corresponding hydrochloride salt (53a) (Scheme 14)

6-Chloro-N$^2$-methyl-N$^4$,N$^8$-di-n-propylpyrimido[5,4-d]pyrimidine-2,4,8-triamine (20) (360 mg, 1.16 mmol) and 4-fluorobenzylamine were reacted in n-butanol using the procedure described for compound (48) to produce N$^2$-(4-fluoro-benzyl)-N$^6$-methyl-N$^4$,N$^8$-di-n-propyl-pyrimido[5,4-d]pyrimidine-2,4,6,8-tetraamine (52) (169 mg, 37% y). 400 MHz $^1$H NMR (CDCl$_3$, ppm): 7.39-7.30 (2H, m), 7.06-6.93 (2H, m), 6.56 (1H, br s), 6.43 (1H, br s), 4.95 (1H, br s), 4.72-4.48 (3H, m), 3.50-3.37 (4H,), 2.97 (3H, d, J=5.2 Hz), 1.67 (4H, sextet, J=7.5 Hz), 0.98 (6H, t, J=7.5 Hz). ESI-MS (m/z): 399 [M+H]$^+$.

N$^2$-(4-Fluoro-benzyl)-N$^6$-methyl-N$^4$,N$^8$-di-n-propyl-pyrimido[5,4,-d]pyrimidine-2,4,8-triamine (52) (160 mg, 0.40 mmol) and 2M HCl/diethyl ether in methanol were reacted using the procedure described for (20a) (145 mg, 83% y). 400 MHz $^1$H NMR (CDCl$_3$, ppm): δ 15.32-14.86 (1.5H, m), 9.79-9.43 (1.5H, m), 7.35-7.21 (2H, m), 7.13 (1H, br s), 7.07-6.98 (2H, m), 6.61 (1H, s), 4.62 (2H, s), 3.69-3.49 (4H, m), 3.07 (3H, s), 1.89-1.69 (4H, m), 1.09-0.96 (6H, m). ESI-MS (m/z): 399 [M+H]$^+$; melting point: 187-189° C.

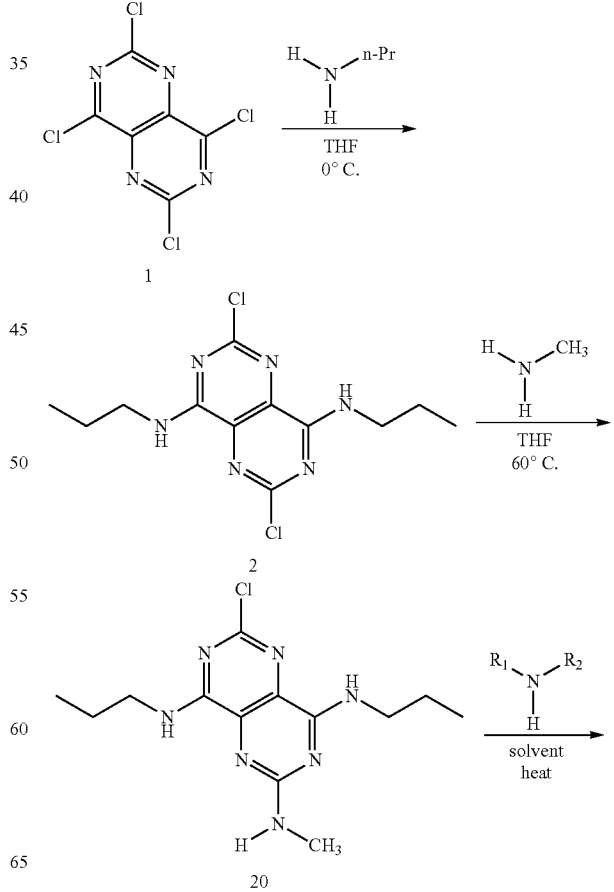

Scheme 14.

-continued

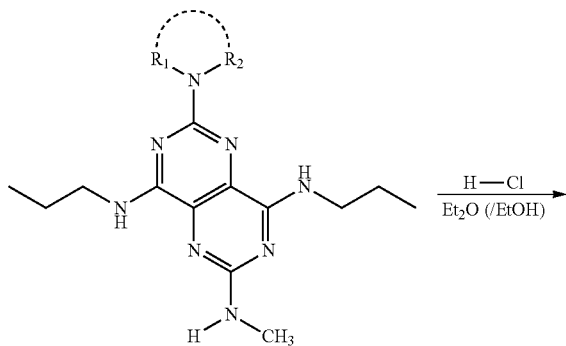

cmpds 28, 30, 32, 34, 36, 38, 40, 42, 44, 46, 48, 50, 52

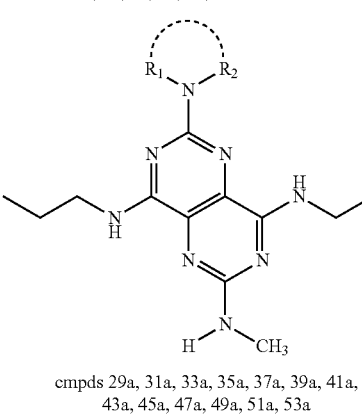

cmpds 29a, 31a, 33a, 35a, 37a, 39a, 41a, 43a, 45a, 47a, 49a, 51a, 53a

TABLE 1

2-Substituted $N^4,N^8$-di-n-propyl-$N^6$-methyl-pyrimido[5,4-d]pyrimidine-2,4,6,8-tetraamines and corresponding hydrochloride salts.

| Cmpd # | $R_1$—N—$R_2$/H—Cl |
|---|---|
| 28/29a | $CH_3$—N—$CH_3$ |
| 30/31a | $CH_3$—$CH_2$—N—$CH_2$—$CH_3$ |
| 32/33a | H—N—$CH_2$—$CH_2$—OH |
| 34/35a | H—N—$CH_2$—$CH_2$—O—$CH_3$ |
| 36/37a | H—N—$CH_2$—$CH_2$—O—$CH(CH_3)_2$ |
| 38/39a | H—N—$CH_2$—$CH_2$—$CF_3$ |
| 40/41a | morpholine |
| 42/43a | piperidine |
| 44/45a | pyrrolidine |
| 46/47a | 4-methoxypiperidine |

TABLE 1-continued

2-Substituted $N^4,N^8$-di-n-propyl-$N^6$-methyl-pyrimido[5,4-d]pyrimidine-2,4,6,8-tetraamines and corresponding hydrochloride salts.

| Cmpd # | $R_1$—N—$R_2$/H—Cl |
|---|---|
| 48/49a | 2-methyl-3-chlorobenzylamine |
| 50/51a | 3,4-dichlorobenzylamine |
| 52/53a | 4-fluorobenzylamine |

Example 25

$N^2,N^2,N^4,N^8$-Tetramethyl-$N^6$-n-propyl-pyrimido[5,4-d]pyrimidine-2,4,6,8-tetraamine (55) and hydrochloride salt (56a) (Scheme 15)

2,6-Dichloro-$N^4,N^8$-dimethyl-pyrimido[5,4-d]pyrimidine-4,8-diamine (25)

A 2M methylamine/THF (2.10 mL, 4.2 mmol) was added to a solution of 2,4,6,8-tetrachloro-pyrimido[5,4-d]pyrimidine (1) (250 mg, 0.93 mmol) in THF (5 mL) at 0° C. The reaction mixture was stirred at room temperature for 1 h. Water (10 mL) was then added and the resultant precipitate was filtered, washed with water (10 mL) and lastly dried over $P_2O_5$ to give 2,6-dichloro-$N^4,N^8$-dimethyl-pyrimido[5,4-d]pyrimidine-4,8-diamine (25) (230 mg, 95% y). 400 MHz $^1$H NMR (CDCl$_3$, ppm): δ 6.90 (2H, br s), 3.16 (6H, d, J=5.0 Hz). ESI-MS (m/z): 259, 261, 263 [M+H]$^+$.

6-Chloro-$N^4,N^8$-dimethyl-$N^2$-n-propyl-pyrimido[5,4-d]pyrimidine-2,4,8-triamine (54)

A mixture of 2,6-dichloro-$N^4,N^8$-dimethyl-pyrimido[5,4-d]pyrimidine-4,8-diamine (25) (325 mg, 3.17 mmol) and n-propylamine (206 μL, 2.5 mmol) in n-butanol (5 mL) was heated in a closed vial at 90° C. for 8 h. The volatiles were removed by evaporation, and the residue was partitioned between EtOAc (20 mL) and a saturated NaHCO$_3$ solution (20 mL). The aqueous phase was separated and then extracted with EtOAc (2×15 mL). The combined organic extracts were washed with water (30 mL), and then with a brine solution (30 mL) and lastly dried over solid anhydrous Na$_2$SO$_4$. After filtration, the solvent was removed and the residue was filtered through silica gel pad using PE/EtOAc (5:1) as eluent to give 6-chloro-$N^2$-n-propyl-$N^4,N^8$-dimethyl-pyrimido[5,4-d]pyrimidine-2,4,8-triamine (54) (320 mg, 91% y). 400 MHz $^1$H NMR (CDCl$_3$, ppm): δ 6.72 (1H, br s), 6.49 (1H, br s), 4.97 (1H, t, J=5.4 Hz), 3.42-3.35 (2H, m), 3.14 (3H, d, J=5.2 Hz), 3.04 (3H, d, J=5.0 Hz), 1.69-1.59 (2H, m), 0.99 (3H, t, J=7.4 Hz). ESI-MS (m/z): 282, 284 [M+H]$^+$.

$N^2,N^2,N^4,N^8$-Tetramethyl-$N^6$-n-propyl-pyrimido[5,4-d]pyrimidine-2,4,6,8-tetraamine (55)

A mixture of 6-chloro-$N^2$-n-propyl-$N^4,N^8$-dimethyl-pyrimido[5,4-d]pyrimidine-2,4,8-triamine (54) (300 mg, 1.06 mmol) and dimethylamine (40% water solution, 5.0 mL) in n-butanol (5.0 mL) was heated in a closed vial at 135° C. for 36 h. The volatiles were removed by evaporation and the residue was partitioned between $CH_2Cl_2$ (35 mL) and a saturated $NaHCO_3$ solution (30 mL). The aqueous phase was separated and extracted with $CH_2Cl_2$ (2×35 mL). The combined organic extracts were washed with water (40 mL) and dried over solid anhydrous $Na_2SO_4$. After filtration, the solvent was removed and the residue was purified by flash column chromatography using gradient elution from PE/EtOAc (99:1) to PE/EtOAc (1:99) to give $N^2,N^2,N^4,N^8$-tetramethyl-$N^6$-n-propyl-pyrimido[5,4-d]pyrimidine-2,4,6,8-tetraamine (55) (245 mg, 80% y). 400 MHz $^1$H NMR ($CDCl_3$, ppm): δ 6.48 (1H, s), 6.40 (1H, s), 4.64 (1H, s), 3.39-3.32 (2H, m), 3.16 (6H, s), 3.08 (3H, d, J=5.3 Hz), 3.06 (3H, d, J=5.3 Hz), 1.63 (2H, sextet, J=7.4 Hz), 0.99 (3H, t, J=7.4 Hz). ESI-MS (m/z): 291 [M+H]$^+$.

$N^2,N^2,N^4,N^6$-Tetramethyl-$N^6$-n-propyl-pyrimido[5,4-d]pyrimidine-2,4,6,8-tetraamine hydrochloride (56a)

$N^2,N^2,N^4,N^8$-tetramethyl-$N^6$-n-propyl-pyrimido[5,4-d]pyrimidine-2,4,6,8-tetraamine (55) (240 mg, 0.83 mmol) was treated with 2M HCl/diethyl ether in diethyl ether/ethanol (1/2) using the procedure described for compound (20a) (216 mg, 80% y). 400 MHz $^1$H NMR ($CDCl_3$, ppm): δ 13.87 (1H, s), 7.62 (1H, s), 7.46 (1H, s), 6.64 (1H, s), 3.49-3.42 (2H, m), 3.20 (3H, d, J=5.2 Hz), 3.15 (6H, s), 3.08 (3H, d, J=4.6 Hz), 1.66 (2H, sextet, J=7.2 Hz), 0.98 (3H, t, J=7.2 Hz). ESI-MS (m/z): 291 [M+H]$^+$; melting point: 285° C. (dec.).

Example 26

$N^2,N^2$-Diallyl-$N^4,N^8$-dimethyl-$N^6$-n-propyl-pyrimido[5,4-d]pyrimidine-2,4,6,8-tetraamine (57) and hydrochloride salt (58a) (Scheme 15)

A mixture of 6-chloro-$N^2$-n-propyl-$N^4,N^8$-dimethyl-pyrimido[5,4-d]pyrimidine-2,4,8-triamine (54) (225 mg, 0.80 mmol) and diallylamine (2.0 mL) was heated in a closed vial at 120° C. for 144 h. A saturated $NaHCO_3$ solution (15 mL) was added and the resulting suspension was extracted with EtOAc (3×25 mL). The combined organic extracts were washed with water (2×15 mL), and then with a brine solution (20 mL) and dried over solid anhydrous $Na_2SO_4$. After filtration, the solvent was removed and the residue was purified by flash column chromatography using gradient elution from PE/EtOAc (10:1) to PE/EtOAc (1:1) to give $N^2,N^2$-diallyl-$N^4,N^8$-dimethyl-$N^6$-n-propyl-pyrimido[5,4-d]pyrimidine-2,4,6,8-tetraamine (57) (170 mg, 62% y). 400 MHz $^1$H NMR ($CDCl_3$, ppm): δ 6.50-6.30 (2H, m), 5.90 (2H, ddt, J=17.2, 10.2, 5.8 Hz), 5.16 (2H, ddt, J=17.2, 1.6, 1.6 Hz), 5.11 (2H, ddt, J=10.2, 1.6, 1.6 Hz), 4.62 (1H, br s), 4.26-4.22 (4H, m), 3.39-3.32 (2H, m), 3.07 (3H, d, J=5.0 Hz), 3.06 (3H, d, J=5.0 Hz), 1.68-1.57 (2H, m) 0.99 (3H, t, J=7.4 Hz). ESI-MS (m/z): 343 [M+H]$^+$.

$N^2,N^2$-Diallyl-$N^4,N^8$-dimethyl-$N^6$-n-propyl-pyrimido[5,4-d]pyrimidine-2,4,6,8-tetraamine (57) (150 mg 0.44 mmol) was treated with 2M HCl/diethyl ether in 1,4-dioxane using the procedure described for compound (20a) (130 mg, 78% y). 400 MHz $^1$H NMR ($CDCl_3$, ppm): δ 13.91 (1H, s), 7.68 (1H, s), 7.39 (1H, s), 6.65 (1H, t, J=5.3 Hz), 5.92-5.78 (2H, m), 5.18-5.14 (2H, m), 5.14-5.11 (2H, m), 4.20 (4H, d, J=5.6 Hz), 3.47 (2H, q, J=6.7 Hz), 3.19 (3H, d, J=5.3 Hz), 3.07 (3H, d, J=4.6 Hz),1.71-1.60 (2H, m), 0.98 (3H, t, J=7.4 Hz). ESI-MS (m/z): 343 [M+H]$^+$; melting point: 199-201° C.

Example 27

2-[(4,8-Bis-methylamino-6-n-propylamino-pyrimido[5,4-d]pyrimidin-2-yl)-methyl-amino]-ethanol (59) and corresponding hydrochloride salt (60a) (Scheme 15)

A mixture of 6-chloro-$N^4,N^8$-dimethyl-$N^2$-n-propyl-pyrimido[5,4-d]pyrimidine-2,4,8-triamine (54) (300 mg, 1.06 mmol) and (2-hydroxyethyl)-methylamine (510 μL, 6.36 mmol) in n-butanol (5.0 mL) was heated in a closed vial at 115° C. for 48 h. The reaction mixture was cooled and a saturated $NaHCO_3$ solution (20 mL) was added. The resulting suspension was extracted with $CH_2Cl_2$ (3×15 mL). The combined organic extracts were washed with water (20 mL) and dried over solid anhydrous $Na_2SO_4$. After filtration, the solvent was removed and the residue was purified by flash column chromatography using gradient elution from PE/EtOAc (5:1) to PE/EtOAc (1:1) to give 2-[(4,8-bis-methylamino-6-n-propylamino-pyrimido[5,4-d]pyrimidin-2-yl)-methyl-amino]-ethanol (59) (300 mg, 88% y). 400 MHz $^1$H NMR ($CDCl_3$, ppm): δ 6.52 (1H, br s), 6.30 (1H, br s), 5.15-4.82 (1H, br s), 4.66 (1H, s), 3.95-3.84 (2H, m), 3.81-3.70 (2H, m), 3.44-3.30 (2H, m), 3.21 (3H, s), 3.08 (6H, s), 1.69-1.57 (2H, m), 0.99 (3H, t, J=7.4 Hz). ESI-MS (m/z): 321 [M+H]$^+$.

2-[(4,8-Bis-methylamino-6-n-propylamino-pyrimido[5,4-d]pyrimidin-2-yl)-methyl-amino]-ethanol (59) (300 mg, 0.94 mmol) was treated with 2M HCl/diethyl ether in 1,4-dioxane using the procedure described for compound (20a) (270 mg, 81% y). 400 MHz $^1$H NMR ($CDCl_3$, ppm): δ 13.83 (1H, s), 7.83 (1H, s), 7.44 (1H, s), 6.72-6.60 (1H, m), 3.92-3.85 (2H, m), 3.84-3.77 (2H, m), 3.50-3.40 (2H, m), 3.26 (1H, s), 3.22-3.17 (6H, m), 3.06 (3H, d, J=4.7 Hz), 1.71-1.60 (2H, m), 0.98 (3H, t, J=7.4 Hz). ESI-MS (m/z): 321 [M+H]$^+$; melting point: 246-248° C.

Example 28

$N^2$-(2-Isopropoxy-ethyl)-$N^4,N^8$-dimethyl-$N^6$-n-propyl-pyrimido[5,4-d]pyrimidine-2,4,6,8-tetraamine (61) and corresponding hydrochloride salt (62a) (Scheme 15)

6-Chloro-$N^2$-n-propyl-$N^4,N^8$-dimethyl-pyrimido[5,4-d]pyrimidine-2,4,8-triamine (54) (300 mg, 1.06 mmol) and 2-isopropoxy-ethylamine were heated for 144 h according to the procedure described for compound (59) to produce $N^2$-(2-isopropoxy-ethyl)-$N^4,N^8$-dimethyl-$N^6$-n-propyl-pyrimido[5,4-d]pyrimidine-2,4,6,8-tetraamine (61) (210 mg, 57% y). 400 MHz $^1$H NMR ($CDCl_3$, ppm): δ 6.43 (2H, br s), 5.01-4.91 (1H, m), 4.64 (1H, s), 3.67-3.54 (5H, m), 3.39-3.32 (2H, m), 3.07 (3H, d, J=4.5 Hz), 3.05 (3H, d, J=4.5 Hz), 1.68-1.58 (2H, m), 1.18 (6H, d, J=6.1 Hz), 0.99 (3H, t, J=7.4 Hz). ESI-MS (m/z): 349 [M+H]$^+$.

$N^2$-(2-Isopropoxy-ethyl)-$N^4,N^8$-dimethyl-$N^6$-n-propyl-pyrimido[5,4-d]pyrimidine-2,4,6,8-tetraamine (61) (190 mg, 0.55 mmol) was treated with 2M HCl/diethyl ether in 1,4-dioxane using the procedure described for compound (20a) (190 mg, 89% y). 400 MHz $^1$H NMR ($CDCl_3$, ppm):

δ 8.5-7.2 (2H, m), 7.0-6.3 (2H, m), 5.23 (1H, br s), 3.61-3.56 (4H, m), 3.62 (1H, septet, J=6.1 Hz), 3.50-3.37 (2H, m), 3.25-3.04 (6H, m), 1.72-1.60 (2H, m), 1.19 (6H, d, J=6.1 Hz), 0.99 (3H, t, J=7.4 Hz). ESI-MS (m/z): 349 [M+H]$^+$; melting point: 150-152° C.

Example 29

2-[N-(2-Dimethylamino-ethyl)-N-methyl]amino-N$^4$, N$^8$-dimethyl-N$^6$-n-propyl-pyrimido[5,4-d]pyrimidine-4,6,8-triamine (63) and corresponding hydrochloride salt (64a) (Scheme 15)

6-Chloro-N$^4$,N$^8$-dimethyl-N$^2$-n-propyl-pyrimido[5,4-d]pyrimidine-2,4,8-triamine (54) (300 mg, 1.06 mmol) was reacted with N,N,N'-trimethyl-ethane-1,2-diamine by heating for 78 h according to the procedure described for compound (60) to produce 2-[N-(2-dimethylamino-ethyl)-N-methyl]amino-N$^4$,N$^8$-dimethyl-N$^6$-n-propyl-pyrimido[5,4-d]pyrimidine-4,6,8-triamine (63) (310 mg, 84% y). 400 MHz $^1$H NMR (CDCl$_3$, ppm): δ 6.60 (1H, s), 6.45 (1H, s), 4.76 (1H, s), 3.82-3.76 (2H, m), 3.39-3.32 (2H, m), 3.16 (3H, s), 3.07 (3H, d, J=5.0 Hz), 3.06 (3H, d, J=5.0 Hz), 2.56-2.54 (2H, m), 2.34 (6H, s), 1.68-1.58 (2H, m), 0.99 (3H, t, J=7.4 Hz). ESI-MS (m/z): 348 [M+H]$^+$.

2-[N-(2-Dimethylamino-ethyl)-N-methyl]amino-N$^4$,N$^8$-dimethyl-N$^6$-n-propyl-pyrimido[5,4-d]pyrimidine-4,6,8-triamine (63) (292 mg, 0.84 mmol) was treated with 2M HCl/diethyl ether in diethyl ether/ethanol (1/1) using procedure described for compound (29a) (322 mg, ~100% y). 400 MHz $^1$H NMR (CDCl$_3$, ppm): δ 8.3-7.6 (1H, br s), 7.17 (1H, s), 5.75 (1H, s), 4.06-3.97 (2H, m), 3.45-3.38 (2H, m), 3.17 (3H, s), 3.14 (3H, d, J=4.9 Hz), 3.07 (3H, d, J=4.9 Hz), 2.95-2.86 (2H, m), 2.60 (6H, s), 1.69-1.59 (2H, m), 0.98 (3H, t, J=7.4 Hz). ESI-MS (m/z): 348 [M+H]$^+$.

Example 30

2-[(4,8-Bis-methylamino-6-n-propylamino-pyrimido [5,4-d]pyrimidin-2-yl)-(2-hydroxy-ethyl)-amino]-ethanol (65) and corresponding hydrochloride salt (66a) (Scheme 15)

2-[(4,8-Bis-methylamino-6-n-propylamino-pyrimido [5,4-d]pyrimidin-2-yl)-(2-hydroxy-ethyl)-amino]-ethanol (65)

A mixture of 6-chloro-N$^2$-n-propyl-N$^4$,N$^8$-dimethyl-pyrimido[5,4-d]pyrimidine-2,4,8-triamine (54) (275 mg, 0.98 mmol) and 2-(2-hydroxyethylamino)-ethanol (385 μL, 3.88 mmol) in n-butanol (5.0 mL) was heated in a closed vial at 135° C. for 100 h. The volatiles were removed by evaporation, and the residue was partitioned between CH$_2$Cl$_2$ (35 mL) and a saturated NaHCO$_3$ solution (30 mL). The aqueous phase was separated and extracted with CH$_2$Cl$_2$ (2×30 mL). The combined organic extracts were washed with water (20 mL) and dried over solid anhydrous Na$_2$SO$_4$. After filtration, the solvent was removed and the residue was purified by flash column chromatography using gradient elution from PE/EtOAc (99:1) to PE/EtOAc (1:99) to give 2-[(4,8-bis-methylamino-6-n-propylamino-pyrimido[5,4-d]pyrimidin-2-yl)-(2-hydroxy-ethyl)-amino]-ethanol (65) (217 mg, 63% y). 400 MHz $^1$H NMR (CDCl$_3$, ppm): δ 6.71-6.64 (1H, m), 6.12-6.06 (1H, m), 5.03-4.86 (2H, m), 4.75-4.66 (1H, m), 3.92-3.87 (4H, m), 3.82-3.76 (4H, m), 3.38-3.31 (2H, m), 3.07 (3H, d, J=5.2 Hz), 3.05 (3H, d, J=5.1 Hz), 1.62 (2H, sextet, J=7.4 Hz), 0.98 (3H, t, J=7.4 Hz). ESI-MS (m/z): 351 [M+H]$^+$.

2-[(4,8-Bis-methylamino-6-n-propylamino-pyrimido [5,4-d]pyrimidin-2-yl)-(2-hydroxy-ethyl)-amino]-ethanol hydrochloride (66a)

2-[(4,8-Bis-methylamino-6-propylamino-pyrimido[5,4-d]pyrimidin-2-yl)-(2-hydroxy-ethyl)-amino]-ethanol (65) (206 mg, 0.59 mmol) was treated with 2M HCl/diethyl ether in diethyl ether/ethanol (1/1) using procedure described for compound (20a) (215 mg, 95% y). 400 MHz $^1$H NMR (D$_2$O, ppm): δ 3.85-3.79 (4H, m), 3.76-3.71 (4H, m), 3.41-3.35 (2H, m), 3.08 (3H, s), 2.99 (3H, s), 1.65 (2H, sextet, J=7.4 Hz), 0.97 (3H, t, J=7.4 Hz). ESI-MS (m/z): 351 [M+H]$^+$; melting point: 220-222° C.

Example 31

N$^2$,N$^2$-Bis-(2-methoxyethyl)-N$^4$,N$^8$-dimethyl-N$^6$-n-propyl-pyrimido[5,4-d]pyrimidine-2,4,6,8-tetraamine (67) and corresponding hydrochloride salt (68a) (Scheme 15)

6-Chloro-N$^2$-n-propyl-N$^4$,N$^8$-dimethyl-pyrimido[5,4-d]pyrimidine-2,4,8-triamine (54) (275 mg, 0.97 mmol) was reacted with bis-(2-methoxyethyl)-amine by heating for 78 h according to the procedure described for compound (60) to produce N$^2$,N$^2$-bis-(2-methoxyethyl)-N$^4$,N$^8$-dimethyl-N$^6$-n-propyl-pyrimido[5,4-d]pyrimidine-2,4,6,8-tetraamine (67) (220 mg, 60% y). 400 MHz $^1$H NMR (CDCl$_3$, ppm): δ 6.46-6.31 (2H, m), 4.69-4.57 (1H, m), 3.86-3.80 (4H, m), 3.62 (4H, t, J=6.3 Hz), 3.39-3.32 (2H, m), 3.38 (6H, s), 3.09-3.03 (6H, m), 1.63 (2H, sextet, J=7.4 Hz), 0.99 (3H, t, J=7.4 Hz). ESI-MS (m/z): 379 [M+H]$^+$.

N$^2$,N$^2$-bis-(2-methoxyethyl)-N$^4$,N$^8$-dimethyl-N$^6$-n-propyl-pyrimido[5,4-d]pyrimidine-2,4,6,8-tetraamine (67) (205 mg, 0.65 mmol) was treated with 2M HCl/diethyl ether in diethyl ether using procedure described for compound (20a) (210 mg, 94% y). 400 MHz $^1$H NMR (CDCl$_3$, ppm): δ 6.66-6.60 (1H, m), 3.91-3.82 (4H, m), 3.59 (4H, t, J=6.0 Hz), 3.49-3.43 (2H, m), 3.35 (6H, s), 3.19 (3H, d, J=5.2 Hz), 3.07 (3H, d, J=4.7 Hz), 1.66 (2H, sextet, J=7.4 Hz), 0.98 (3H, t, J=7.4). ESI-MS (m/z): 379 [M+H]$^+$; melting point: 196-198° C.

Example 32

6-(4-Oxo-piperidin-1-yl)-N$^4$,N$^8$-dimethyl-N$^2$-n-propylamino-pyrimido-30 [5,4-d]pyrimidine-2,4,8-triamine (70) and corresponding hydrochloride salt (71a) (Scheme 15)

6-(1,4-Dioxa-8-aza-spiro[4.5]dec-8-yl)-N$^4$,N$^8$-dimethyl-N$^2$-n-propyl-pyrimido[5,4-d]pyrimidine-2,4,8-triamine (69)

6-Chloro-N$^4$,N$^8$-dimethyl-N$^2$-n-propyl-pyrimido[5,4-d]pyrimidine-2,4,8-triamine (54) (230 mg, 0.82 mmol) and 4-piperidone ethylene ketal (314 μL, 2.45 mmol) in n-butanol (5.0 mL) were heated at 120° C. in a closed vial for 24 h. The reaction mixture was cooled, and saturated NaHCO$_3$ solution (20 mL) was added. The resulting suspension was extracted with EtOAc (3×15 mL). The combined organic extracts were washed with water (40 mL), and then with a brine solution (30 mL), and dried over solid anhydrous Na$_2$SO$_4$. After filtration, the solvent was removed and the residue was purified by flash column chromatography using gradient elution from CH$_2$Cl$_2$ to CH$_2$Cl$_2$/EtOAc (3:2) to give 6-(1,4-dioxa-8-aza-spiro[4.5]dec-8-yl)-N$^4$,N$^8$-dimethyl-N$^2$-n-propyl pyrimido[5,4-d]pyrimidine-2,4,8-triamine (69) (309 mg, 97% y). 400 MHz $^1$H NMR (CDCl$_3$, ppm): δ 6.50-6.35 (2H, m), 4.66 (1H, br s), 4.00 (4H, s), 3.93-3.89 (4H, m), 3.36 (2H, td, J=7.2, 6.1 Hz), 3.07 (3H, d, J=5.1 Hz), 3.06 (3H, d, J=5.3 Hz), 1.77-1.72 (4H, m), 1.67-1.57 (2H, m), 0.99 (3H, t, J=7.4 Hz). ESI-MS (m/z): 389 [M+H]$^+$.

6-(4-Oxo-piperidin-1-yl)-N,N$^8$-dimethyl-N$^2$-n-propylamino-pyrimido-[5,4-d]pyrimidine-2,4,8-triamine (70)

A mixture of 6-(1,4-dioxa-8-aza-spiro[4.5]dec-8-yl)-N$^4$,N$^8$-dimethyl-N$^2$-propyl-pyrimido[5,4-d]pyrimidine-2,4,8-triamine (69) (300 mg, 0.77 mmol) and 4N HCl (6 mL) in THF (5 mL) was stirred at room temperature for 20 h. The pH of the solution was adjusted to 9 by the addition of a saturated NaHCO$_3$ solution. The resulting suspension was extracted with EtOAc (3×15 mL). The combined organic extracts were washed with water (40 mL), then with a brine solution (30 mL), and dried over solid anhydrous Na$_2$SO$_4$. After filtration, the solvent was removed and the residue was purified by flash column chromatography using gradient elution from CHCl$_3$ to CHCl$_3$/EtOAc (9:1) to give 6-(4-oxo-piperidin-1-yl)-N$^4$,N$^8$-dimethyl-N$^2$-n-propylamino-pyrimido-[5,4-d]pyrimidine-2,4,8-triamine (70) (213 mg, 80% y). 400 MHz $^1$H NMR (CDCl$_3$, ppm): δ 6.49 (1H, s), 6.41 (1H, s), 4.70 (1H, s), 4.15-4.08 (4H, m), 3.41-3.33 (2H, m), 3.10 (3H, d, J=5.1 Hz), 3.08 (3H, d, J=5.2 Hz), 2.49 (4H, t, J=6.1 Hz), 1.64 (2H, sextet, J=7.4 Hz), 1.00 (3H, t, J=7.4 Hz). ESI-MS (m/z): 345 [M+H]$^+$.

6-(4-Oxo-piperidin-1-yl)-N$^4$,N$^8$-dimethyl-6-n-propylamino-pyrimido-[5,4-d]pyrimidine-2,4,8-triamine hydrochloride (71a)

6-(4-Oxo-piperidin-1-yl)-N$^4$,N$^8$-dimethyl-N$^2$-n-propylamino-pyrimido-[5,4-d]pyrimidine-2,4,8-triamine (70) (213 mg, 0.62 mmol) was treated with 2M HCl/diethyl ether in diethyl ether using procedure described for compound (20a) (210 mg, 89% y). 400 MHz $^1$H NMR (CDCl$_3$, ppm): δ 14.08 (1H, s), 7.87 (1H, s), 7.41 (1H, s), 6.75-6.62 (1H, m), 4.15-4.07 (4H, m), 3.53-3.42 (2H, m), 3.22 (3H, d, J=5.1 Hz), 3.09 (3H, d, J=4.5 Hz), 2.51 (4H, t, J=6.1 Hz), 1.67 (2H, sextet, J=7.4 Hz), 0.99 (3H, t, J=7.4 Hz). ESI-MS (m/z): 345 [M+H]$^+$; melting point: 267° C. (dec.).

Example 33

N$^2$-(3-Trifluoromethyl-piperidin-1-yl)-N$^4$,N$^8$-dimethyl-6-n-propylamino-pyrimido[5,4-d]pyrimidine-2,4,8-triamine (72) and corresponding hydrochloride (73a) (Scheme 15)

6-Chloro-N$^4$,N$^8$-dimethyl-N$^2$-n-propyl-pyrimido[5,4-d]pyrimidine-2,4,8-triamine (54) (221 mg, 0.78 mmol) was reacted with 3-trifluoromethyl-piperidine (311 μL, 2.34 mmol) according to the procedure described for compound (69) to produce N$^2$-(3-trifluoromethyl-piperidin-1-yl)-N$^4$,N$^8$-dimethyl-6-n-propylamino-pyrimido[5,4-d]pyrimidine-2,4,8-triamine (72) (285 mg, 91% y). 400 MHz $^1$H NMR (CDCl$_3$, ppm): 6.52-6.32 (2H, m), 5.02-4.94 (1H, m), 4.82-4.74 (1H, m), 4.67 (1H, br s), 3.41-3.31 (2H, m), 3.08 (3H, d, J=5.0 Hz), 3.07 (3H, d, J=5.1 Hz), 2.84-2.71 (2H, m), 2.39-2.24 (1H, m), 2.13-2.01 (1H, m), 1.85-1.74 (1H, m), 1.70-1.47 (4H, m), 0.99 (3H, t, J=7.4 Hz). ESI-MS (m/z): 399 [M+H]$^+$.

N$^2$-(3-trifluoromethyl-piperidin-1-yl)-N$^4$,N$^8$-dimethyl-6-n-propylamino-pyrimido[5,4-d]pyrimidine-2,4,8-triamine (72) (283 mg, 0.71 mmol) was treated with 2M HCl/diethyl ether in diethyl ether using procedure described for compound (20a) (215 mg, 70% y). 400 MHz $^1$H NMR (CDCl$_3$, ppm): δ 14.21 (1H, s), 13.2-12.6 (0.5H, br s), 8.6-8.0 (1.5H, br s), 6.73-6.55 (1H, m), 4.91-4.83 (1H, m), 4.83-4.71 (1H, m), 3.52-3.42 (2H, m), 3.20 (3H, d, J=5.1 Hz), 3.11 (3H, d, J=4.6 Hz), 3.08-2.92 (2H, m), 2.38-2.22 (1H, m), 2.15-2.04 (1H, m), 1.94-1.83 (1H, m), 1.73-1.47 (4H, m), 0.99 (3H, t, J=7.4 Hz). ESI-MS (m/z): 399 [M+H]$^+$; melting point: 270° C. (dec.).

Example 34

N$^2$-6-n-Propylamino-N$^4$,N$^8$-dimethyl-2-(1,1-dioxothiomorpholin-4-yl)-pyrimido-[5,4-d]pyrimidine-2,4, 8-triamine (74) and corresponding hydrochloride salt (75a) (Scheme 15)

N$^2$-6-n-Propylamino-N$^4$,N$^8$-dimethyl-2-(1,1-dioxothiomorpholin-4-yl)-pyrimido-[5,4-d]pyrimidine-2,4, 8-triamine (74)

A mixture of 6-chloro-N$^2$-n-propyl-N$^4$,N$^8$-dimethyl-pyrimido[5,4-d]pyrimidine-2,4,8-triamine (54) (282 mg, 1.00 mmol) and thiomorpholine 1,1-dioxide (406 mg, 3.00 mmol) in n-butanol (5.0 mL) was heated in a closed vial at 130° C. for 48 h. The reaction mixture was cooled and a saturated NaHCO$_3$ solution (20 mL) was added. The resulting suspension was extracted with EtOAc (3×15 mL). The combined organic extracts were washed with water (30 mL), and then with a brine solution (30 mL) and dried over solid anhydrous Na$_2$SO$_4$. After filtration, the solvent was removed and the residue was purified by flash column chromatography using CHCl$_3$ as an eluent to give N$^2$-6-n-propylamino-N$^4$,N$^8$-dimethyl-2-(1,1-dioxo-thiomorpholin-4-yl)-pyrimido-[5,4-d]pyrimidine-2,4,8-triamine (74) (378 mg, 99%). 400 MHz $^1$H NMR (CDCl$_3$, ppm): δ 6.55 (1H, s), 6.31 (1H, s), 4.80-4.67 (1H, m), 4.43-4.24 (4H, m), 3.41-3.32 (2H, m), 3.07 (6H, d, J=5.1 Hz), 3.10-3.02 (4H, m), 1.69-1.55 (2H, m), 0.99 (3H, t, J=7.4 Hz). ESI-MS (m/z): 381 [M+H]$^+$.

N$^2$-6-n-Propylamino-N$^4$,N$^8$-dimethyl-2-(1,1-dioxothiomorpholin-4-yl)-pyrimido-[5,4-d]pyrimidine-2,4, 8-triamine hydrochloride (75a)

N$^2$-6-n-Propylamino-N$^4$,N$^8$-dimethyl-2-(1,1-dioxo-thiomorpholin-4-yl)-pyrimido-[5,4-d]pyrimidine-2,4,8-triamine (375 mg, 0.97 mmol) was treated with 2M HCl/diethyl ether in 1,4-dioxane using procedure described for compound (20a) (198 mg, 48% y). 400 MHz $^1$H NMR (CDCl$_3$/TFA, ppm): δ 9.79 (1H, s), 9.30-8.90 (1H, m), 7.65-7.14 (1H, m), 4.57-4.43 (4H, m), 3.51 (2H, t, J=7.4 Hz), 3.39-3.29 (4H, m), 3.23 (3H, s), 3.21 (3H, d, J=4.5 Hz), 1.68 (2H, sextet, J=7.4 Hz), 0.98 (3H, t, J=7.4 Hz). ESI-MS (m/z): 381 [M+H]$^+$; melting point >300° C.

Example 35

N²-n-Propyl-N⁴,N⁸-dimethyl-6-(4,4-difluoro-piperidin-1-yl)-pyrimido[5,4-d]pyrimidine-2,4,8-triamine (76) and corresponding hydrochloride salt (77a) (Scheme 15)

N²-n-Propyl-N⁴,N⁸-dimethyl-6-(4,4-difluoro-piperidin-1-yl)-pyrimido[5,4-d]pyrimidine-2,4,8-triamine (76)

A mixture of 6-chloro-N²-n-propyl-N⁴,N⁸-dimethyl-pyrimido[5,4-d]pyrimidine-2,4,8-triamine (54) (282 mg, 1.00 mmol), 4,4-difluoro-piperidine hydrochloride (158 mg, 2.91 mmol) and N,N-diisopropylethylamine (345 μL, 2.00 mmol) in 1,4-dioxane (4 mL) was heated in a closed vial at 120° C. for 48 h. Additional portions of 4,4-difluoro-piperidine hydrochloride (158 mg, 2.91 mmol) and N,N-diisopropylethylamine (345 μL, 2.00 mmol) were added and heating was continued for 18 h. After cooling, a saturated NaHCO₃ solution (5 mL) was added and the resulting suspension was extracted with CH₂Cl₂ (3×10 mL). The combined organic extracts were washed with water (20 mL), then with a brine solution (10 mL), and dried over solid anhydrous Na₂SO₄. After filtration, the solvent was removed and the residue was purified by flash column chromatography using gradient elution from PE/EtOAc (7:1) to PE/EtOAc (1:1) to give N²-n-propyl-N⁴,N⁸-dimethyl-6-(4,4-difluoro-piperidin-1-yl)-pyrimido[5,4-d]pyrimidine-2,4,8-triamine (76) (303 mg, 83% y). 400 MHz ¹H NMR (CDCl₃, ppm): δ 6.52-6.34 (2H, m), 4.69 (1H, br s), 3.96-3.91 (4H, m), 3.39-3.33 (2H, m), 3.08 (3H, d, J=5.1 Hz), 3.07 (3H, d, J=5.1 Hz), 2.04-1.94 (4H, m), 1.63 (2H, sextet, J=7.3 Hz), 0.99 (3H, t, J=7.3 Hz). ESI-MS (m/z): 367 [M+H]⁺.

N²-n-Propyl-N⁴,N⁸-dimethyl-6-(4,4-difluoro-piperidin-1-yl)-pyrimido[5,4-d]pyrimidine-2,4,8-triamine hydrochloride (77)

N²-n-propyl-N⁴,N⁸-dimethyl-6-(4,4-difluoro-piperidin-1-yl)-pyrimido[5,4-d]pyrimidine-2,4,8-triamine (76) (303 mg, 0.83 mmol) was treated with 2M HCl/diethyl ether in diethyl ether using procedure described for (20a) (319 mg, 96% y). 400 MHz ¹H NMR (CDCl₃, ppm): δ 8.20-7.40 (3H, m), 6.82-6.57 (1H, m), 3.97-3.90 (4H, m), 3.48-3.42 (2H, m), 3.19 (3H, d, J=5.1 Hz), 3.06 (3H, d, J=5.1 Hz), 2.05-1.93 (4H, m), 1.65 (2H, sextet, J=7.3 Hz), 0.97 (3H, t, J=7.3 Hz). ESI-MS (m/z): 367 [M+H]⁺; melting point: 290° C. (dec.).

Scheme 15.

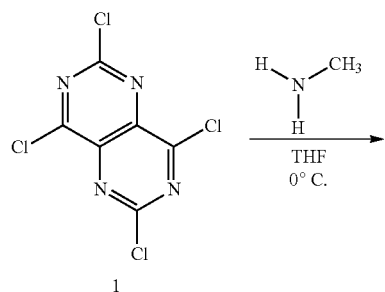

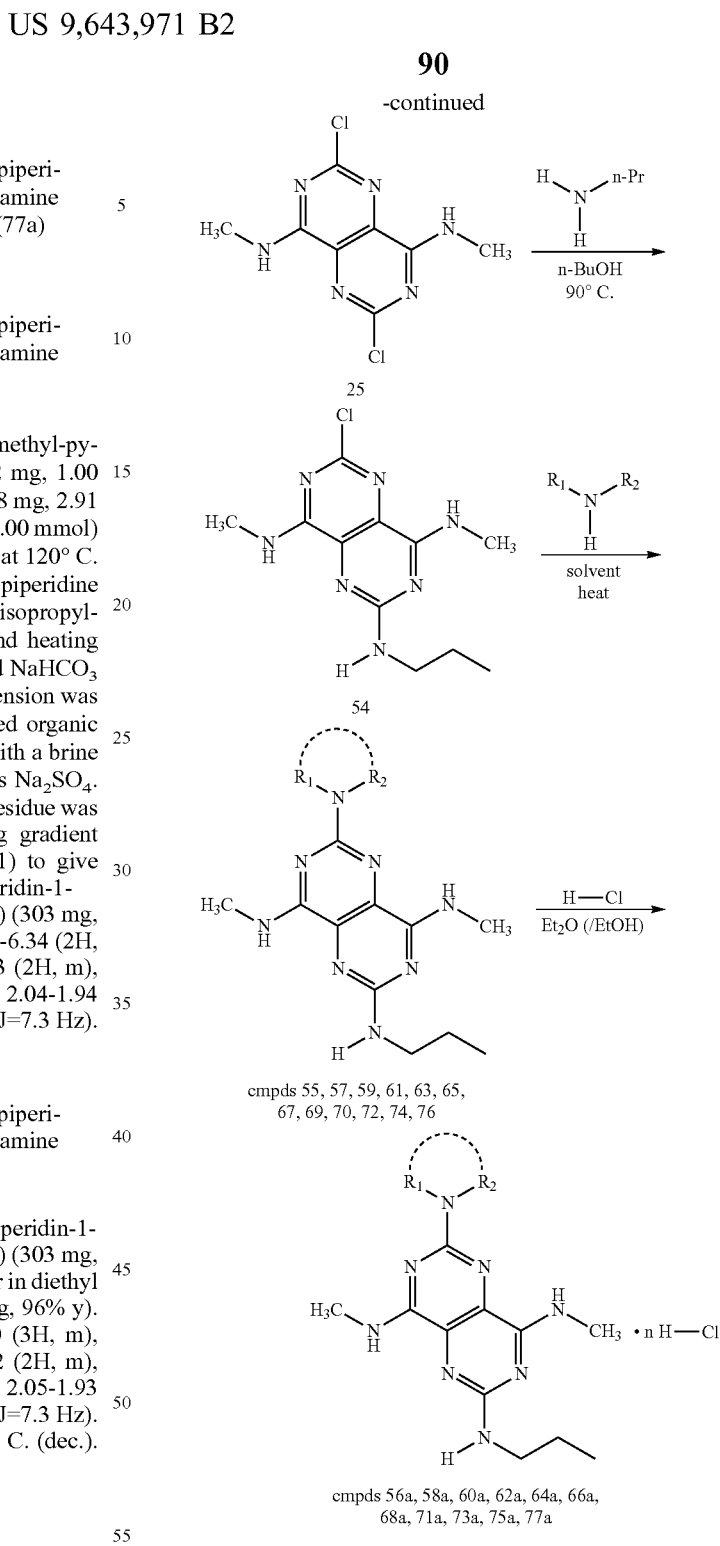

TABLE 2

2-Substituted N⁴,N⁸-dimethyl-N⁶-n-propyl-pyrimido[5,4-d]pyrimidine-2,4,6,8-tetraamines and corresponding hydrochloride salts

| Cmpd | $R_1$—N—$R_2$/H—Cl |
|---|---|
| 55/56a | CH₃—N—CH₃ |
| 57/58a | CH₂=CH—CH₂—N—CH₂—CH=CH₂ |
| 59/60a | CH₃—N—CH₂—CH₂—OH |
| 61/62a | H—N—CH₂—CH₂—O—CH(CH₃)₂ |

TABLE 2-continued

2-Substituted $N^4,N^8$-dimethyl-$N^6$-n-propyl-pyrimido[5,4-d]pyrimidine-2,4,6,8-tetraamines and corresponding hydrochloride salts

| Cmpd | $R_1$—N—$R_2$/H—Cl |
|---|---|
| 63/64a | $CH_3$—N—$CH_2$—$CH_2$—$N(CH_3)_2$ |
| 65/66a | H—N—$(CH_2$—$CH_2$—OH$)_2$ |
| 67/68a | H—N—$(CH_2$—$CH_2$—$OCH_3)_2$ |
| 69 | (1,4-dioxa-8-azaspiro[4.5]decane structure) |
| 70/71a | (4-oxopiperidine structure) |
| 72/73a | (3-trifluoromethylpiperidine structure) |
| 74/75a | (thiomorpholine 1,1-dioxide structure) |
| 1. 76/77a | 2. (4,4-difluoropiperidine structure) |

Example 36

$N^2,N^4,N^6,N^8$-Tetramethyl-pyrimido[5,4-d]pyrimidine-2,4,6,8-tetraamine hydrochloride (78) and corresponding hydrochloride salt (79a) (Scheme 16)

$N^2,N^4,N^6,N^8$-Tetramethyl-pyrimido[5,4-d]pyrimidine-2,4,6,8-tetraamine (78)

A mixture of 2,6-dichloro-$N^4,N^8$-dimethyl-pyrimido[5,4-d]pyrimidine-4,8-diamine (25) (310 mg, 1.35 mmol) and methylamine (40% water solution, 1.0 mL) in n-butanol (1.0 mL) was heated in a closed vial at 125° C. for 20 h. The reaction mixture was cooled, and water (10 mL) was added. The resulting precipitate was filtered, washed with water (10 mL), and dried. The product was purified by flash column chromatography using gradient elution from $CH_2Cl_2$ to $CH_2Cl_2$/MeOH (97:3) to give $N^2,N^4,N^6,N^8$-tetramethyl-pyrimido[5,4-d]pyrimidine-2,4,6,8-tetraamine (78) (230 mg, 69% y). 400 MHz $^1H$ NMR (CDCl$_3$, ppm): δ 6.48 (2H, br s), 4.62 (2H, br s), 3.07 (6H, d, J=5.1 Hz), 2.97 (6H, d, J=5.1 Hz). ESI-MS (m/z): 249 [M+H]$^+$.

$N^2,N^4,N^6,N^8$-Tetramethyl-pyrimido[5,4-d]pyrimidine-2,4,6,8-tetraamine hydrochloride (79a)

$N^2,N^4,N^6,N^8$-Tetramethyl-pyrimido[5,4-d]pyrimidine-2,4,6,8-tetraamine (78) (220 mg, 0.89 mmol) was treated with 2M HCl/diethyl ether in 1,4-dioxane using procedure described for compound (20a) (200 mg, 80% y). 400 MHz $^1H$ NMR (DMSO-d$_6$, ppm): δ 9.2-7.9 (3H, m), 7.5-6.3 (2H, br s), 2.99 (6H, s), 2.92 (6H, s). ESI-MS (m/z): 249 [M+H]$^+$; melting point >300° C.

Example 37

$N^2,N^6$-Diethyl-$N^4,N^8$-dimethyl-pyrimido[5,4-d]pyrimidine-2,4,6,8-tetraamine hydrochloride (80) and corresponding hydrochloride salt (81a) (Scheme 16)

$N^2,N^6$-Diethyl-$N^4,N^8$-dimethyl-pyrimido[5,4-d]pyrimidine-2,4,6,8-tetraamine (80)

A mixture of 2,6-dichloro-$N^4,N^8$-dimethyl-pyrimido[5,4-d]pyrimidine-4,8-diamine (25) and ethylamine (70% water solution, 1.0 mL) in n-butanol (1.0 mL) was heated in a closed vial at 140° C. for 24 h. After cooling, a saturated NaHCO$_3$ solution (20 mL) was added, and the resulting suspension was extracted with $CH_2Cl_2$ (3×20 mL). The combined organic extracts were washed with water (20 mL) and dried over solid anhydrous Na$_2$SO$_4$. After filtration, the solvent was removed and the residue was purified by flash column chromatography using gradient elution from $CH_2Cl_2$ to $CH_2Cl_2$/MeOH (98:2) to give $N^2,N^6$-diethyl-$N^4$,$N^8$-dimethyl-pyrimido[5,4-d]pyrimidine-2,4,6,8-tetraamine (80) (130 mg, 41% y). 400 MHz $^1H$ NMR (CDCl$_3$, ppm): δ 6.45 (2H, br s), 4.59 (2H, br s), 3.48-3.36 (4H, m), 3.06 (6H, d, J=5.0 Hz), 1.23 (6H, t, J=7.2). ESI-MS (m/z): 277 [M+H]$^+$.

$N^2,N^6$-Diethyl-$N^4,N^8$-dimethyl-pyrimido[5,4-d]pyrimidine-2,4,6,8-tetraamine hydrochloride (81a):

$N^2,N^6$-diethyl-$N^4,N^8$-dimethyl-pyrimido[5,4-d]pyrimidine-2,4,6,8-tetraamine (80) (120 mg, 0.43 mmol) was treated with 2M HCl/diethyl ether in 1,4-dioxane using procedure described for compound (20a) (90 mg, 67% y). 400 MHz $^1H$ NMR (DMSO-d$_6$, ppm): δ 9.2-8.2 (3H, m), 7.6-6.5 (2H, m), 3.49-3.37 (4H, m), 3.06-2.90 (6H, m), 1.14 (6H, t, J=7.2 Hz). ESI-MS (m/z): 277 [M+H]$^+$; melting point: 256-258° C.

Example 38

$N^2,N^6$-Di-n-butyl-$N^4,N^8$-dimethyl-pyrimido[5,4-d]pyrimidine-2,4,6,8-tetraamine (82) and corresponding hydrochloride salt (83a) (Scheme 16)

$N^2,N^6$-Di-n-butyl-$N^4,N^8$-dimethyl-pyrimido[5,4-d]pyrimidine-2,4,6,8-tetraamine (82)

2,6-Dichloro-$N^4,N^8$-dimethyl-pyrimido[5,4-d]pyrimidine-4,8-diamine (25) (250 mg, 0.96 mmol) and n-butylamine (6 eq.) in n-butanol were reacted according to the procedure described for compound (80). After recrystallization from EtOAc/petroleum ether, $N^2,N^6$-di-n-butyl-$N^4,N^8$-dimethyl-pyrimido[5,4-d]pyrimidine-2,4,6,8-tetraamine (82) was obtained (110 mg, 34% y). 400 MHz $^1$H NMR (CDCl$_3$, ppm): δ 6.43 (2H, br s), 4.61 (2H, br s), 3.43-3.53 (4H, m), 3.06 (6H, d, J=5.0 Hz), 1.64-1.54 (4H, m), 1.49-1.37 (4H, m), 0.96 (6H, t, J=7.4 Hz). ESI-MS (m/z): 333 [M+H]$^+$.

$N^2,N^6$-Di-n-butyl-$N^4,N^8$-dimethyl-pyrimido[5,4-d]pyrimidine-2,4,6,8-tetraamine hydrochloride (83a)

$N^2,N^6$-di-n-butyl-$N^4,N^8$-dimethyl-pyrimido[5,4-d]pyrimidine-2,4,6,8-tetraamine (82) (100 mg, 0.30 mmol) was treated with 2M HCl/diethyl ether in 1,4-dioxane using procedure described for compound (29a) (110 mg, ~100% y). 400 MHz $^1$H NMR (DMSO-d$_6$, ppm): δ 9.2-7.8 (3H, m), 7.4-6.5 (2H, m), 3.48-3.32 (4H, m), 2.99 (6H, s), 1.59-1.46 (4H, m), 1.42-1.27 (4H, m), 0.90 (6H, t, J=7.3 Hz). ESI-MS (m/z): 333 [M+H]$^+$; melting point: 199-201° C.

Example 39

$N^2,N^6$-Bis-cyclopropylmethyl-$N^4,N^8$-dimethyl-pyrimido[5,4-d]pyrimidine-2,4,6,8-tetraamine (84) and corresponding hydrochloride salt (85a) (Scheme 16)

$N^2,N^6$-Bis-cyclopropylmethyl-$N^4,N^8$-dimethyl-pyrimido[5,4-d]pyrimidine-2,4,6,8-tetraamine (84)

A mixture of 2,6-dichloro-$N^4,N^8$-dimethyl-pyrimido[5,4-d]pyrimidine-4,8-diamine (25) (2.0 g, 7.72 mmol) and cyclopropylmethylamine (4.0 mL, 46.31 mmol) in n-butanol (15.0 mL) was heated in a closed vial at 130° C. for 34 h. After cooling, a saturated NaHCO$_3$ solution (100 mL) and water (100 mL) was added, and the resulting suspension was extracted with CHCl$_3$ (3×200 mL). The combined organic extracts were washed with water (150 mL), and dried over solid anhydrous Na$_2$SO$_4$. After filtration, the solvent was removed and the residue was purified by flash column chromatography using gradient elution from CH$_2$Cl$_2$ to CH$_2$Cl$_2$/MeOH (96:4) to give $N^2,N^6$-bis-cyclopropylmethyl-$N^4,N^8$-dimethyl-pyrimido[5,4-d]pyrimidine-2,4,6,8-tetraamine (84) (1.35 g, 53% y). 400 MHz $^1$H NMR (CDCl$_3$, ppm): δ 6.43 (2H, br s), 4.78 (2H, br s), 3.25 (4H, dd, J=6.8, 5.6 Hz), 3.07 (6H, d, J=5.2 Hz), 1.15-1.04 (2H, m), 0.54-0.49 (4H, m), 0.27-0.22 (4H, m). ESI-MS (m/z): 329 [M+H]$^+$.

$N^2,N^6$-Bis-cyclopropylmethyl-$N^4,N^8$-dimethyl-pyrimido[5,4-d]pyrimidine-2,4,6,8-tetraamine hydrochloride (85a)

A 2.5 M HCl/EtOH solution (3.2 mL, 8.0 mmol) was added to the suspension of $N^2,N^6$-bis-cyclopropylmethyl-$N^4,N^8$-dimethyl-pyrimido[5,4-d]pyrimidine-2,4,6,8-tetraamine (84) (2.63 g, 8.01 mmol) in CH$_2$Cl$_2$/EtOH (100 mL/100 mL). The mixture was stirred for 0.5 h at room temperature and then volatiles were removed under reduced pressure. The residue was treated with diethyl ether (30 mL). The resultant precipitate were filtered, washed with diethyl ether (15 mL), then with petroleum ether (15 mL) and dried to give $N^2,N^6$-bis-cyclopropylmethyl-$N^4,N^8$-dimethyl-pyrimido[5,4-d]pyrimidine-2,4,6,8-tetraamine hydrochloride (85a) (2.75 g, 94% y). 400 MHz $^1$H NMR (CDCl$_3$, ppm): δ 13.1-12.7 (1H, br s), 8.85 (1H, s), 8.04 (1H, br s), 7.42-6.62 (2H, m), 3.30-3.18 (4H, m), 3.07-2.88 (6H, m), 1.15-1.03 (2H, m), 0.50-0.37 (4H, m), 0.33-0.17 (4H, m). ESI-MS (m/z): 329 [M+H]$^+$; melting point: 264-265° C.

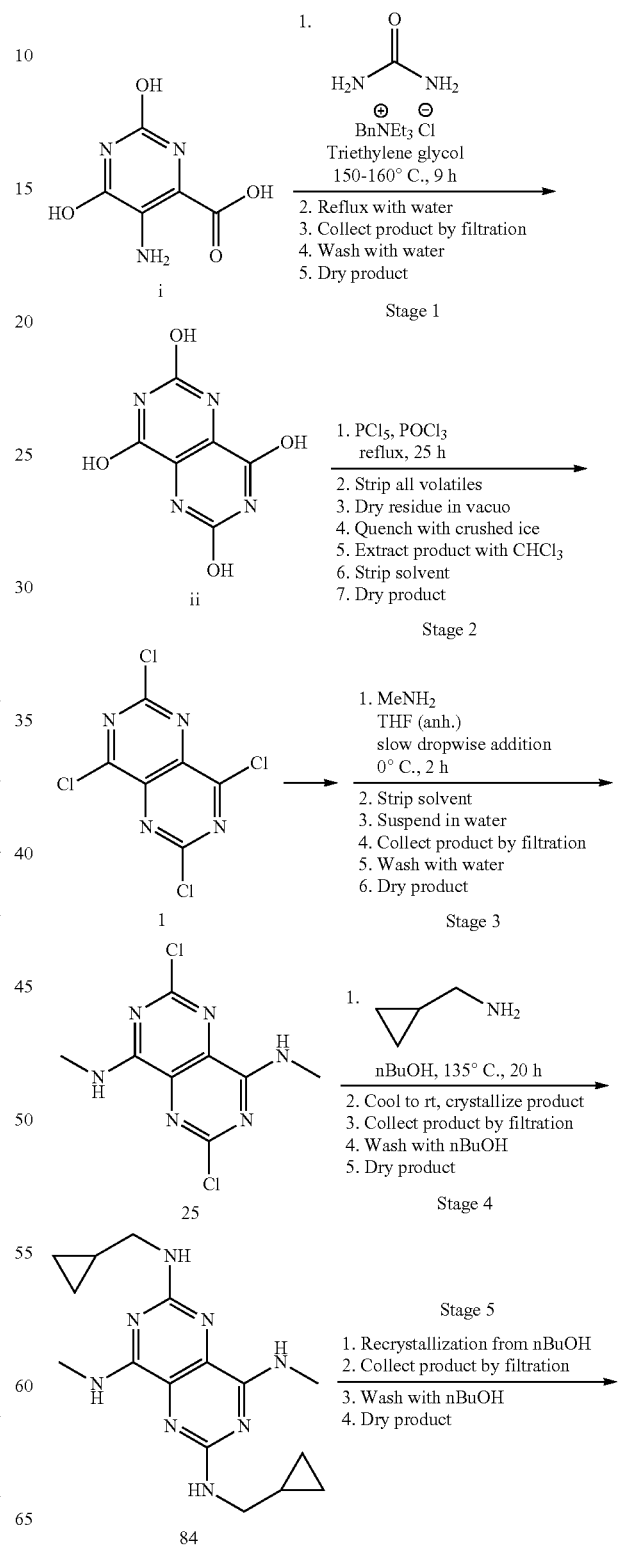

Scheme 16.

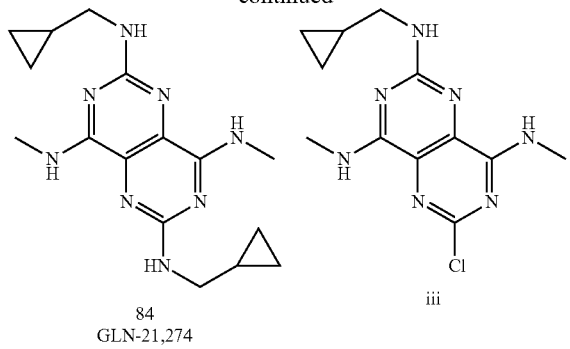

84
GLN-21,274

Example 39A

Preparation of $N^2$-$N^6$-Biscyclopropylmethyl-$N^4$,$N^8$-dimethyl-pyrimido [5,4-d]pyrimidine-2,4,6,8-tetraamine (84) (Scheme 16)

Stage 1. Pyrimido[5,4-d]pyrimidine-2,4,6,8-tetraol (ii)

A 250 mL, three-necked round bottom flask with a magnetic stir bar, temperature probe and an air condenser was charged with 5-aminoorotic acid (i) (15 g, 87.6 mmol, 1 equiv.), urea (42 g, 701 mmol, 8 equiv.), benzyltriethyl-ammonium chloride (0.3 g, 1.3 mmol, 0.015 equiv.) and triethylene glycol (13 mL). The suspension was heated with stirring and maintained at 150-160° C. (reaction mixture temperature) for 9 h. The initially viscous, heterogeneous mixture became more homogeneous and easily stirrable after heating for 10 minutes. After 3-4 h of heating the reaction mixture formed a thick, lumpy paste and toward the end of the heating period became unstirrable. Sublimation of urea occurred during the heating period. The course of the reaction was monitored by detecting the evolution of gaseous $NH_3$ with a wetted pH-indicator paper.

After reaction completion (no further $NH_3$ evolution), the mixture was cooled to 90° C. and water (120 mL) was added. The mixture was stirred at reflux for 1 h, during which time the initial pasty mass converted to a thin suspension. The mixture was cooled to room temperature, filtered, and the brown solid product washed with water (3×50 mL). The product was dried under air for 16 h at 60° C. yielding pyrimido[5,4-d]pyrimidine-2,4,6,8-tetraol (ii) (16.8 g, 98% y), as a brown powder. The product was used as is in the next step.

Stage 2: 2,4,6,8-Tetrachloro-pyrimido[5,4-d]pyrimidine (1)

A 1 L round bottom flask with a magnetic stir bar, a reflux condenser and a $CaCl_2$ drying tube was charged with pyrimido[5,4-d]pyrimidine-2,4,6,8-tetraol (ii) (23.9 g, 122 mmol, 1 equiv), $PCl_5$ (152 g, 732 mmol, 6 equiv) and $POCl_3$ (387.3 mL, 4150 mmol, 34 equi.). The resulting suspension was refluxed for 25 h at 145° C. At the end of the reflux period the reaction mixture became completely homogeneous. Precipitation of solids occurred upon cooling to room temperature. The reflux condenser was replaced by a distillation still head, and all volatiles were distilled off at atmospheric pressure and 145° C. When distillation ceased, the distilling flask was cooled to room temperature and water aspirator vacuum was applied to partially dry the product. The viscous product, while still in the distillation flask, was further dried for 30 min at 145° C. under vacuum. The product, while in the distillation flask, was cooled to room temperature, and crushed ice (350 mL) was introduced, resulting in the generation of heat and the boiling of the ice turned to water. The resulting slurry was cooled to room temperature, mixed with 400 mL of chloroform, and the emulsified mixture filtered through a glass frit. The filtrate comprised a clear lower organic layer, a middle emulsified layer and an upper aqueous layer. The organic layer was separated and saved and other two layers were combined and extracted with four additional 200 mL portions of chloroform. After the last extraction the middle emulsified layer was separated from upper aqueous layer. The emulsified layer was mixed with 200 mL of chloroform and celite and stirred at room temperature for 10 min, converting the emulsion to a suspension which was removed by filtration and washed with chloroform. The combined organic extracts were dried over solid anhydrous $Na_2SO_4$, filtered and evaporated to dryness in vacuo. The solid product was dried in a vacuum desiccator for 16 h at room temperatureyielding 2,4,6,8-tetrachloro-pyrimido[5,4-d]pyrimidine (1) (12.2 g, 37% y), as a yellow powder, mp: 254-256° C. Quality of the product may be verified by CHN elemental analysis.

TABLE 3

Representative Elemental Analysis of (1).

| | C | H | N |
|---|---|---|---|
| Theoretical: | 26.70 | 0.00 | 20.76 |
| Found 1 | 26.67 | 0.06 | 20.85 |
| Found 2 | 26.63 | 0.01 | 20.78 |

Stage 3: 2,6-Dichloro-$N^4$,$N^8$-dimethyl-pyrimido[5,4-d]pyrimidine-4,8-diamine (25)

A 0.5 L round bottom flask, equipped with a magnetic stir bar, temperature probe and a syringe pump, was charged with 2,4,6,8-tetrachloro-pyrimido[5,4-d]pyrimidine (1) (11.8 g, 43.9 mmol, 1 equiv) and anhydrous tetrahydrofuran (128 mL). The resulting suspension was cooled in an ice bath, then a 2M solution of $MeNH_2$ in tetrahydrofuran (98.6 mL, 197 mmol, 4.5 equiv) was added dropwise at 50 mL/h with a syringe pump. After the addition was complete, the reaction mixture was warmed to room temperature and stirred 0.5 h. LC-MS assay showed complete conversion. The tetrahydrofuran was stripped in vacuo and the orange semisolid residue was suspended in water (50 mL) and sonicated 30 min in an ultrasonic bath. The product was collected by filtration, washed with water (3×30 mL), and dried in air at 60° C. yielding 2,6-dichloro-$N^4$,$N^8$-dimethyl-pyrimido[5,4-d]pyrimidine-4,8-diamine (25) (10.9 g, 96% y), as an orange powder; mp: 257-258° C.

Stage 4: $N^2$-$N^6$-Bis-cyclopropylmethyl-$N^4$,$N^8$-dimethyl-pyrimido[5,4-d]pyrimidine-2,4,6,8-tetraamine (84)

An Ace glass pressure tube with a magnetic stir bar was charged with 2,6-dichloro-$N^4$,$N^8$-dimethyl-pyrimido[5,4-d]pyrimidine-4,8-diamine (25) (10.9 g, 42.1 mmol, 1 equiv.), cyclopropylmethylamine (18 g, 21.6 mL, 252 mmol, 6 equiv.) and nBuOH (65 mL). The tube was sealed with a Teflon plug and heated 20 h at 135° C. At the end of the heating period the product had begun to precipitate. The mixture was cooled to room temperature and stirred 2 h, giving rise to additional solid product. Upon manipulating the solid product in the mother liquor with a spatula, additional solid product formed. The mixture was left for an additional 2 h at room temperature, then the solids were collected by filtration, washed with nBuOH (3×30 mL) and light petroleum ether (2×50 mL) and dried on the filter for 2 h at room temperature, affording 7.0 g of $N^2$-$N^6$-bis-cyclopropylmethyl-$N^4$,$N^8$-dimethyl-pyrimido[5,4-d]pyrimidine-2,4,6,8-tetraamine (84), as a yellow crystalline solid.

The combined mother and wash liquors were evaporated to dryness; the resulting semisolid residue was suspended in diethyl ether (80 mL) and the mixture was sonicated for 1 h. The mixture was filtered to remove insolubles, and the filtrate was evaporated to dryness, affording a red oil consisting mainly of mono-chloro derivative iii, an intermediate of Stage 4. Crude iii can be treated under Stage 4 conditions with 3 molar equiv of cyclopropylmethylamine to produce additional $N^2$-$N^6$-bis-cyclopropylmethyl $N^4$,$N^8$-dimethyl-pyrimido[5,4-d]pyrimidine-2,4,6,8-tetraamine (84).

Stage 5: Recrystallization of $N^2$-$N^6$-biscyclopropylmethyl $N^4$,$N^8$-dimethyl-pyrimido[5,4-d]pyrimidine-2,4,6,8-tetraamine (84)

Figure 13:
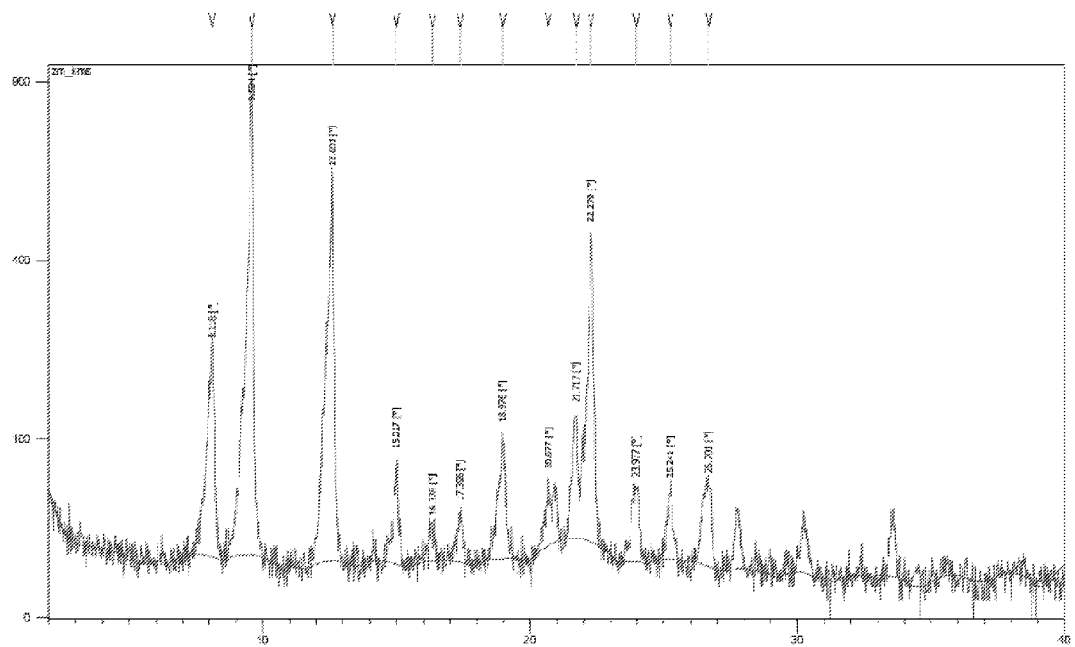
FIG. 13 is a graph illustrating the XRPD for $N^2$,$N^6$-bis-cyclopropylmethyl $N^4$,$N^8$-dimethyl-pyrimido[5,4-d]pyrimidine-2,4,6,8-tetraamine (84) as crystallized from n-butanol. The ordinate corresponds to intensity in arbitrary units, and the abscissa corresponds to position (2 Theta), Copper (Cu).
Figure 14:
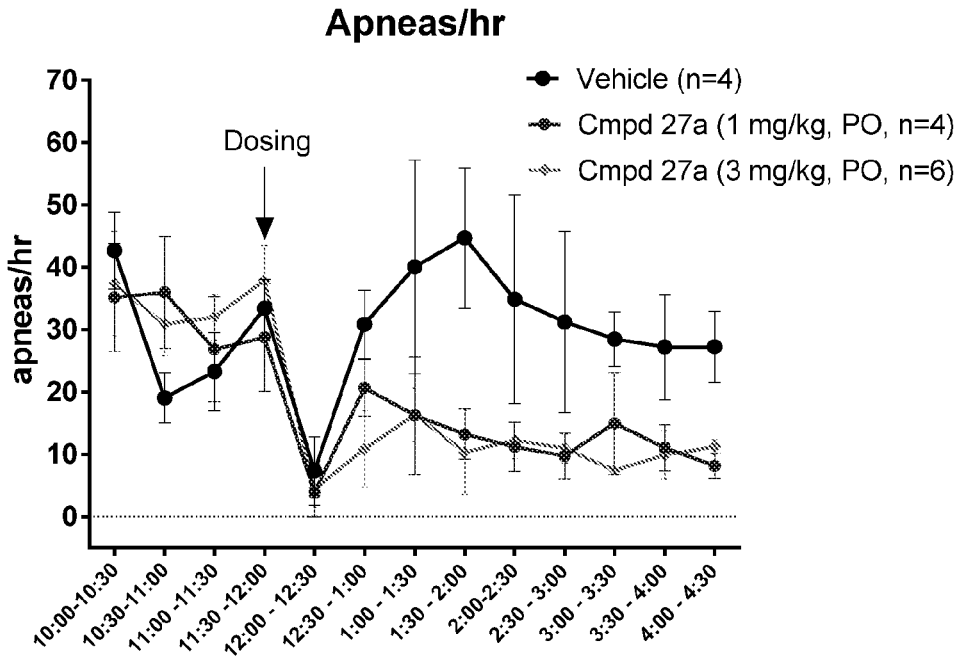
FIG. 14 is a graph illustrating the finding that compound (27a) reduced apnea frequency in rats chronically treated with morphine, versus treatment with a vehicle. The marked decrease in apnea at the 12:00-12:30 PM time bin, across all groups, was caused by overt stimulation (awakening) from dosing via oral gavage.
Figure 15:
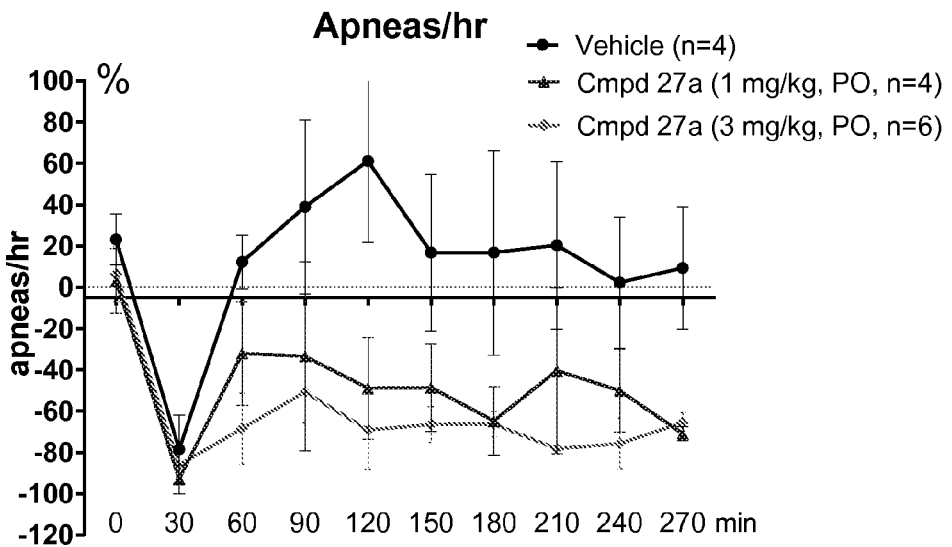
FIG. 15 is a graph illustrating the finding that compound (27a) reduced the number of apneas per hr expressed as a percent change from baseline (pre-drug) in rats chronically administered morphine, versus treatment with a vehicle. The marked decrease in apnea at the 30 min post-treatment time, across all groups, was caused by overt stimulation (awakening) from dosing via oral gavage.
Figure 16:
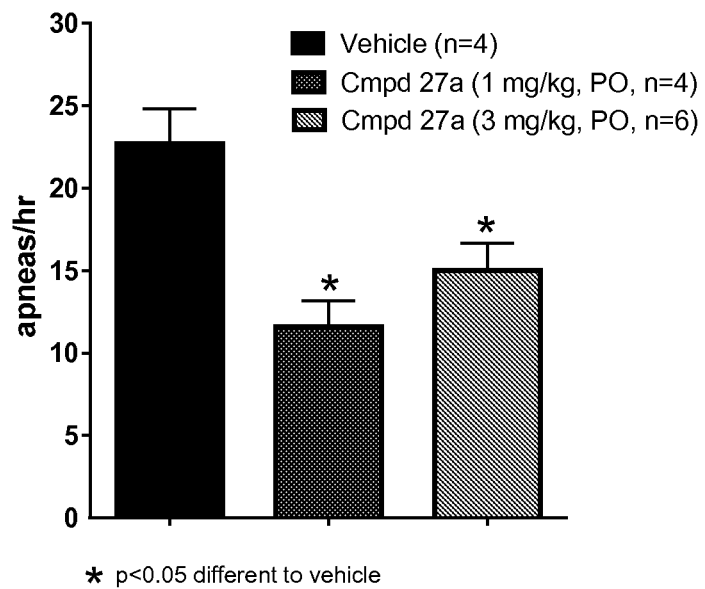
FIG. 16 is a bar graph illustrating the finding that compound (27a) reduced the the number of apneas per hr in rats chronically administered morphine, versus treatment with a vehicle.
Figure 17:
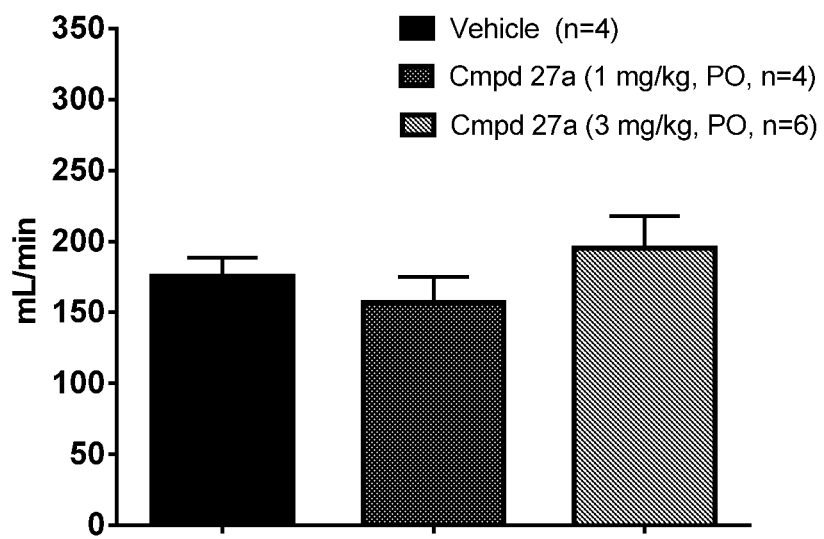
FIG. 17 is a bar graph illustrating the finding that compound (27a) did not cause an increase in minute volume compared to a vehicle-treated group.
Figure 18:
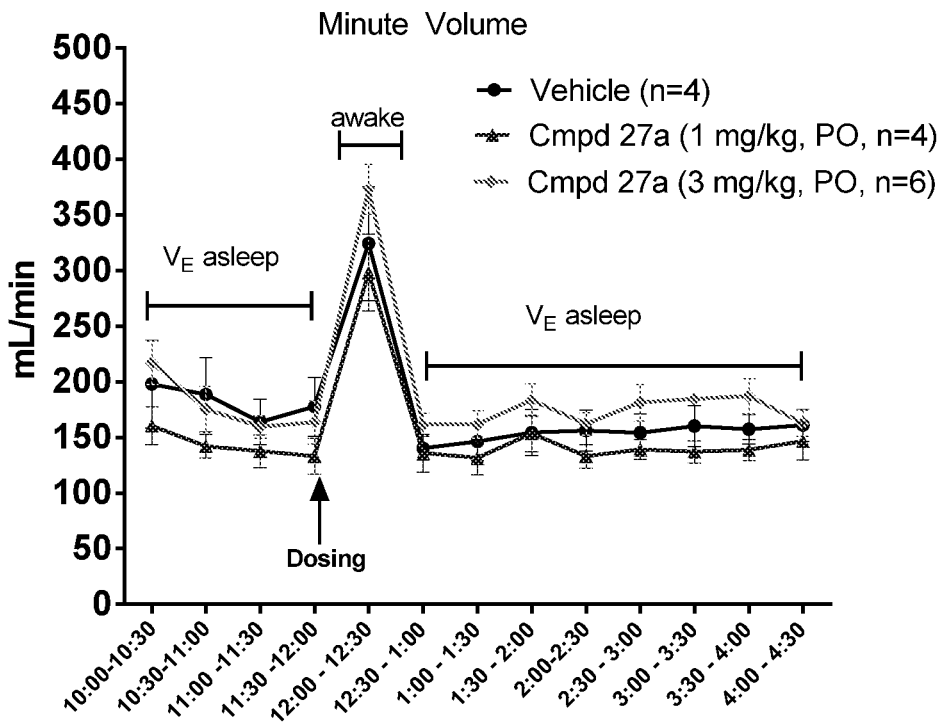
FIG. 18 is a graph illustrating the finding that compound (27a) did not cause an increase in ventilation per unit time compared to baseline, nor to treatment with a vehicle. The marked increase in minute volume at the (12:00-12:30) 30 min post-treatment time, across all groups, was caused by overt stimulation from dosing via oral gavage.
Figure 19:
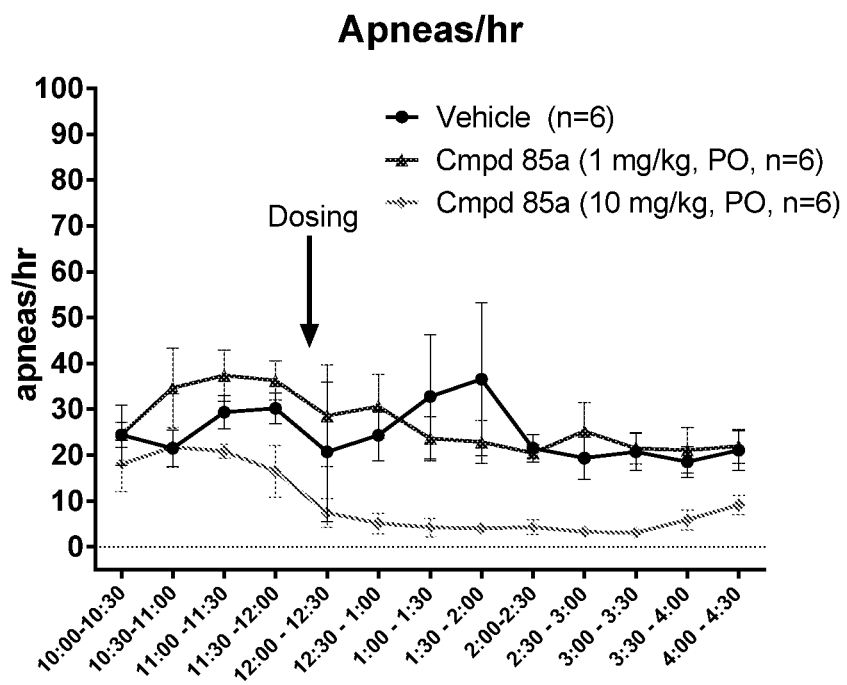
FIG. 19 is a graph illustrating the finding that compound (85a) reduced apnea frequency in rats chronically treated with morphine, versus treatment with a vehicle. The decrease in apnea at the 12:00-12:30 PM time bin, across all groups, was caused by overt stimulation (awakening) from dosing via oral gavage.
Figure 20:
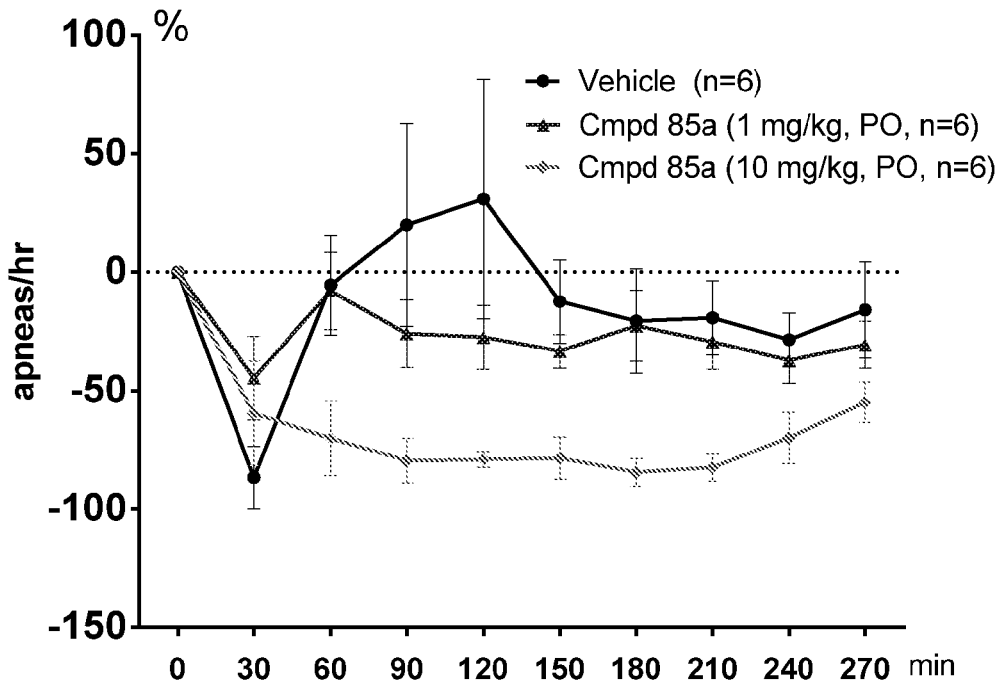
FIG. 20 is a graph illustrating the finding that compound (85a) reduced the number of apneas per hr expressed as a percent change from baseline (pre-drug), in rats chronically treated with morphine, versus treatment with a vehicle. The marked decrease in apnea at the 30 min post-treatment time, across all groups, was caused by overt stimulation (awakening) from dosing via oral gavage.
Figure 21:
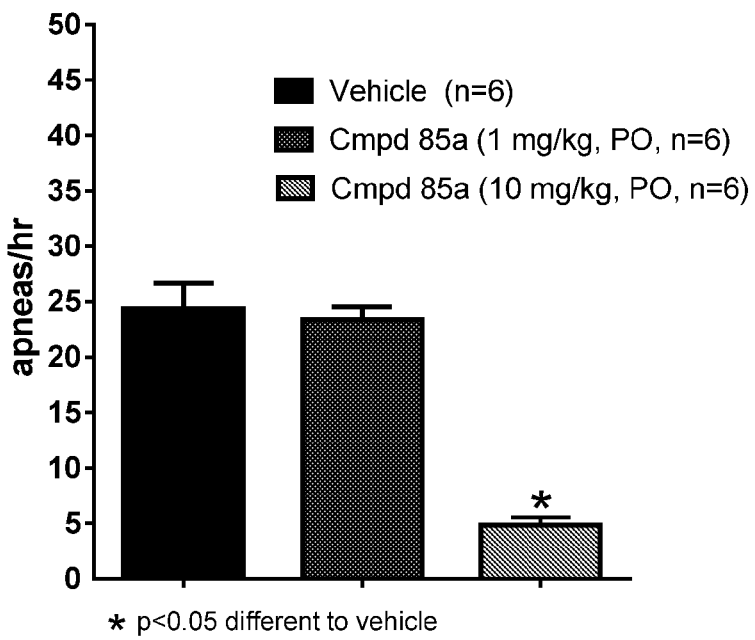
FIG. 21 is a bar graph illustrating the finding that compound (85a) reduced the number of apneas per hr in rats chronically treated with morphine, versus treatment with a vehicle.
Figure 22:
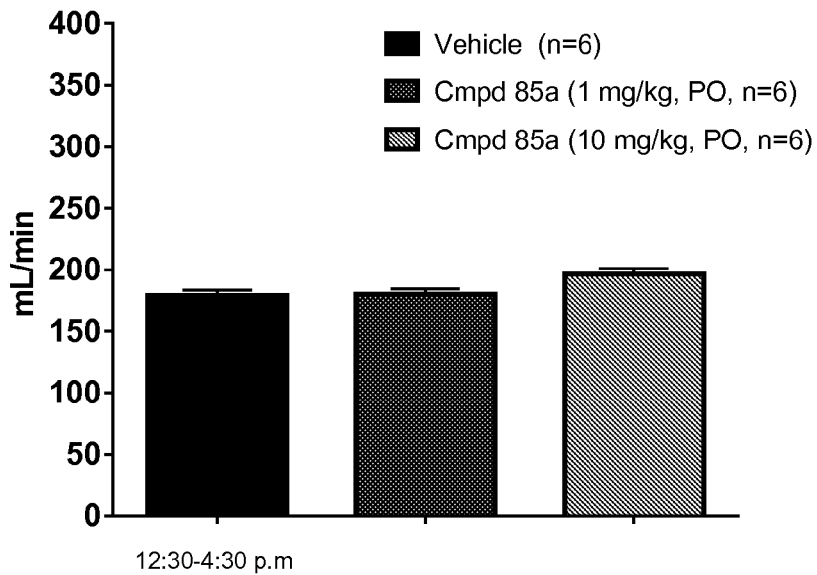
FIG. 22 is a bar graph illustrating the finding that compound (85a) did not cause an increase in minute volume compared to a vehicle-treated group.
Figure 23:
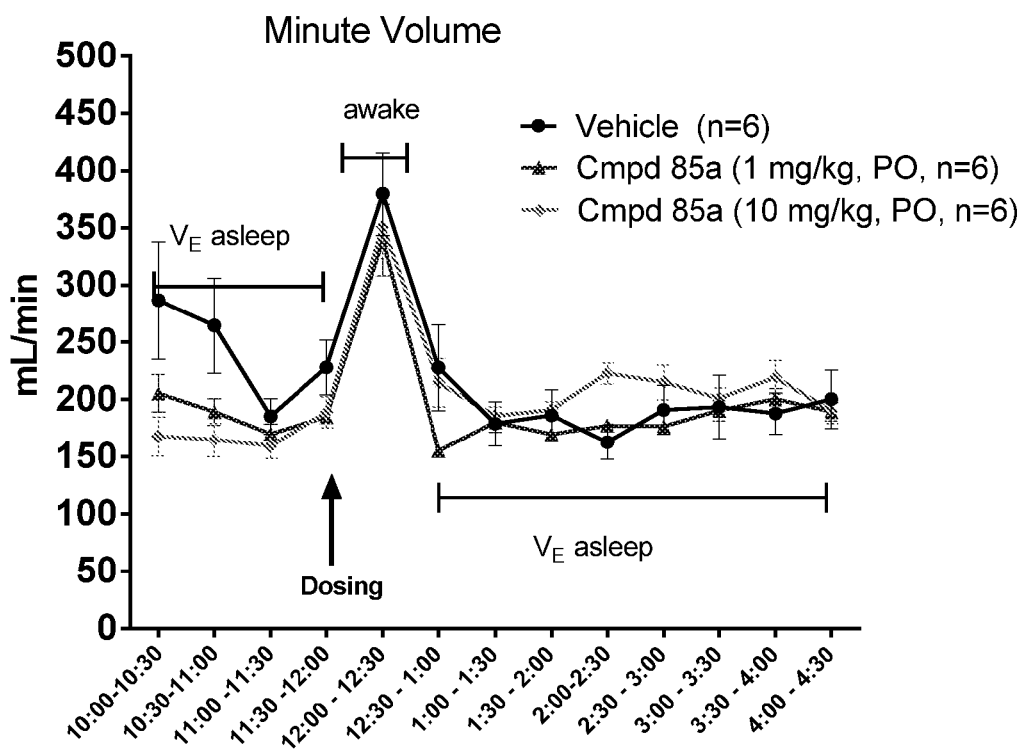
FIG. 23 is a graph illustrating the finding that compound (85a) did not cause an increase in ventilation per unit time compared to treatment with a vehicle. The marked increase in minute volume at the (12:00-12:30) 30 min post-treatment time, across all groups, was caused by overt stimulation from dosing via oral gavage.
Figure 24:
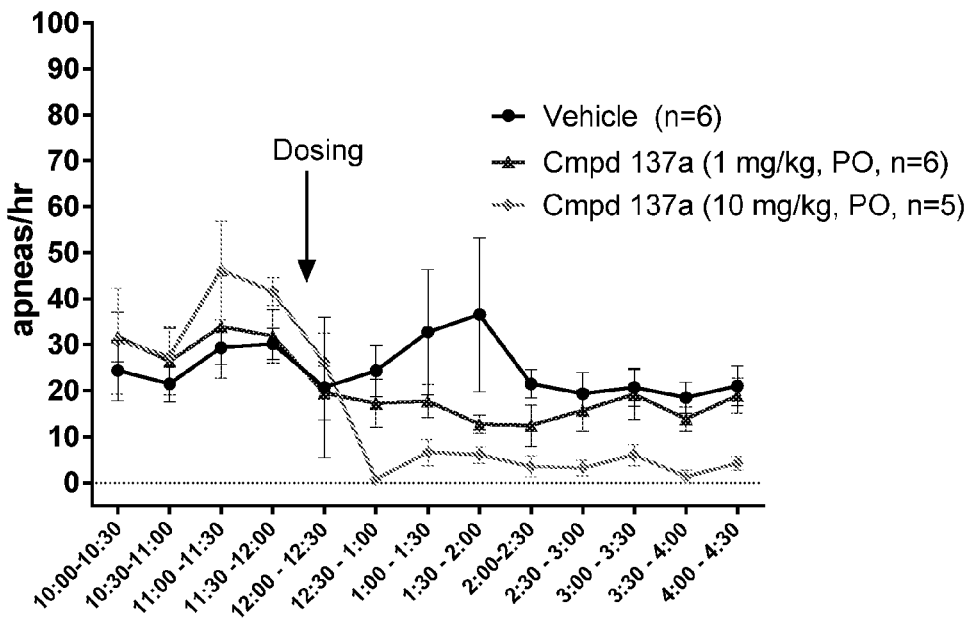
FIG. 24 is a graph illustrating the finding that compound (137a) reduced apnea frequency in rats chronically treated with morphine, versus treatment with a vehicle. (Note: The decrease in apnea at the 12:00-12:30 PM time bin, across all groups, is caused by overt stimulation (awakening) from dosing via oral gavage).
Figure 25:
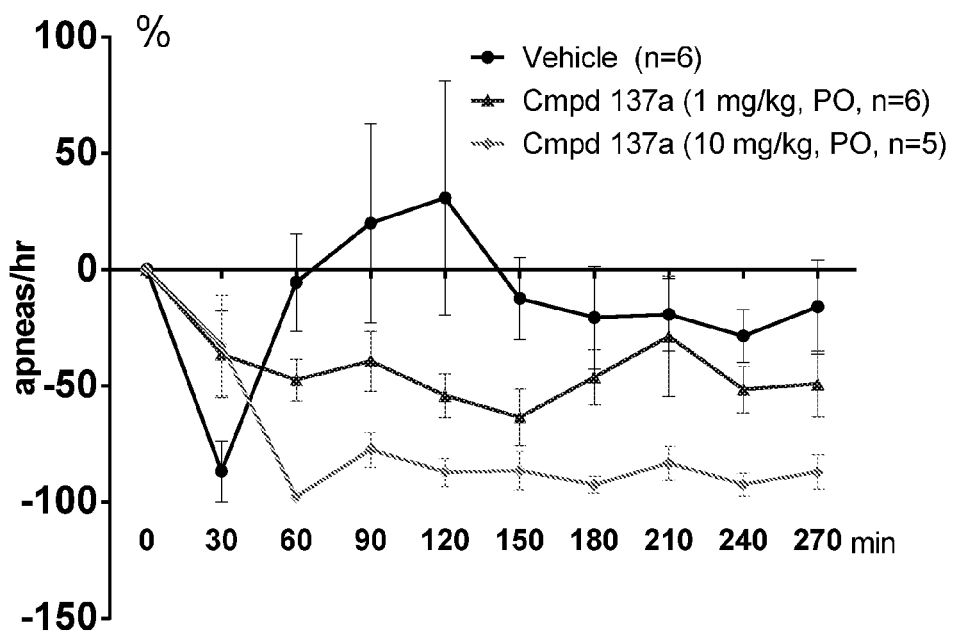
FIG. 25 is a graph illustrating the finding that compound (137a) reduced the number of apneas per hr expressed as a percent change from baseline (pre-drug), in rats chronically treated with morphine, versus treatment with a vehicle. The marked decrease in apnea at the 30 min post-treatment time, across all groups, was caused by overt stimulation (awakening) from dosing via oral gavage.
Figure 26:
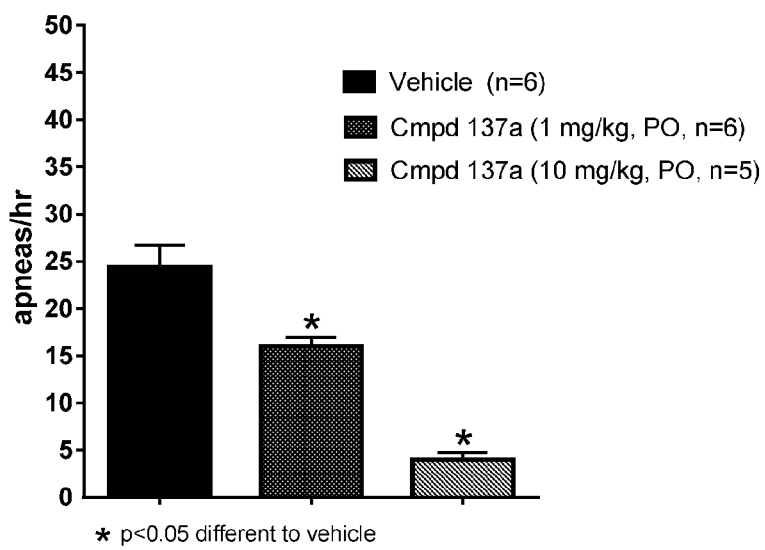
FIG. 26 is a bar graph illustrating the finding that compound (137a) reduced the number of apneas per hr in rats chronically treated with morphine, versus treatment with a vehicle.
Figure 27:
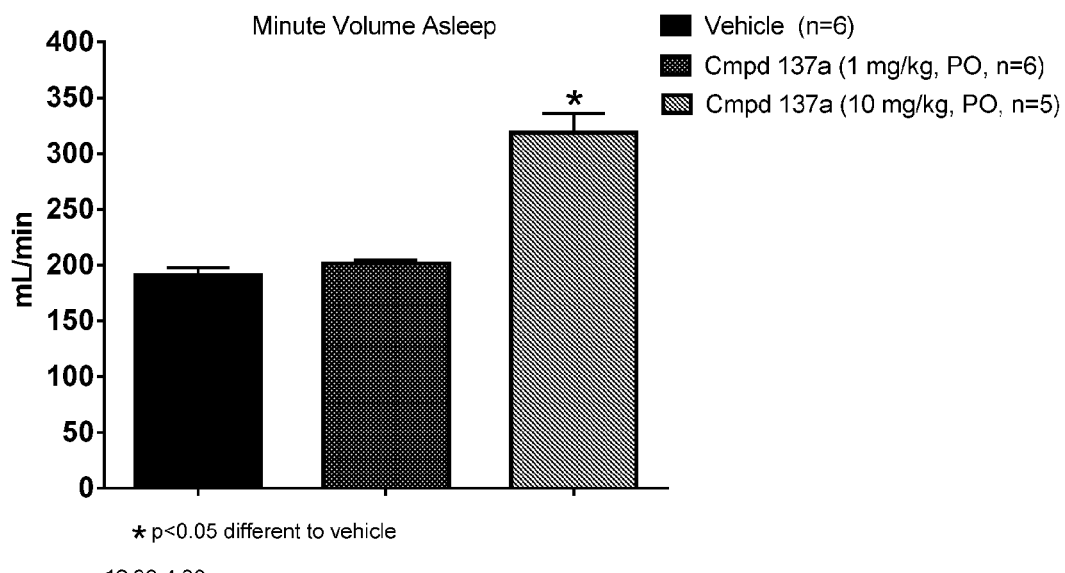
FIG. 27 is a bar graph illustrating the finding that compound (137a) at a low dose did not cause an increase in minute volume compared to a vehicle-treated group. Compound 137a caused an increase in minute volume at the higher dose.
Figure 28:
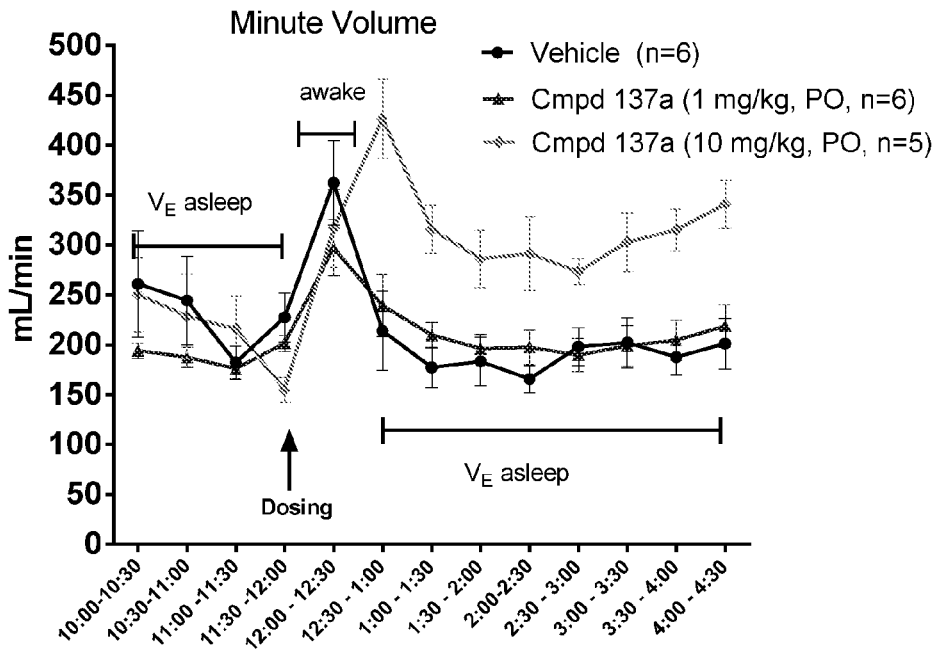
FIG. 28 is a graph illustrating the finding that compound (137a) did not cause an increase in ventilation per unit time compared to treatment with a vehicle. The marked increase in minute volume at the (12:00-12:30) 30 min post-treatment time, across all groups, was caused by overt stimulation from dosing via oral gavage.
Figure 29:
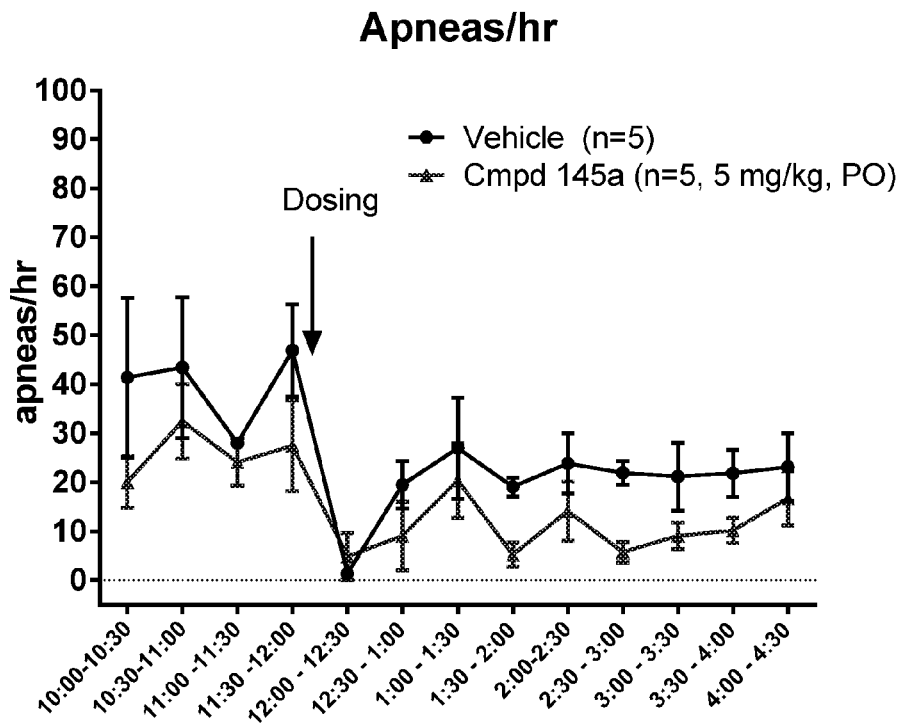
FIG. 29 is a graph illustrating the finding that compound (145a) reduced apnea frequency in rats chronically treated with morphine, versus treatment with a vehicle. The decrease in apnea at the 12:00-12:30 PM time bin, across all groups, is caused by overt stimulation (awakening) from dosing via oral gavage.
Figure 30:
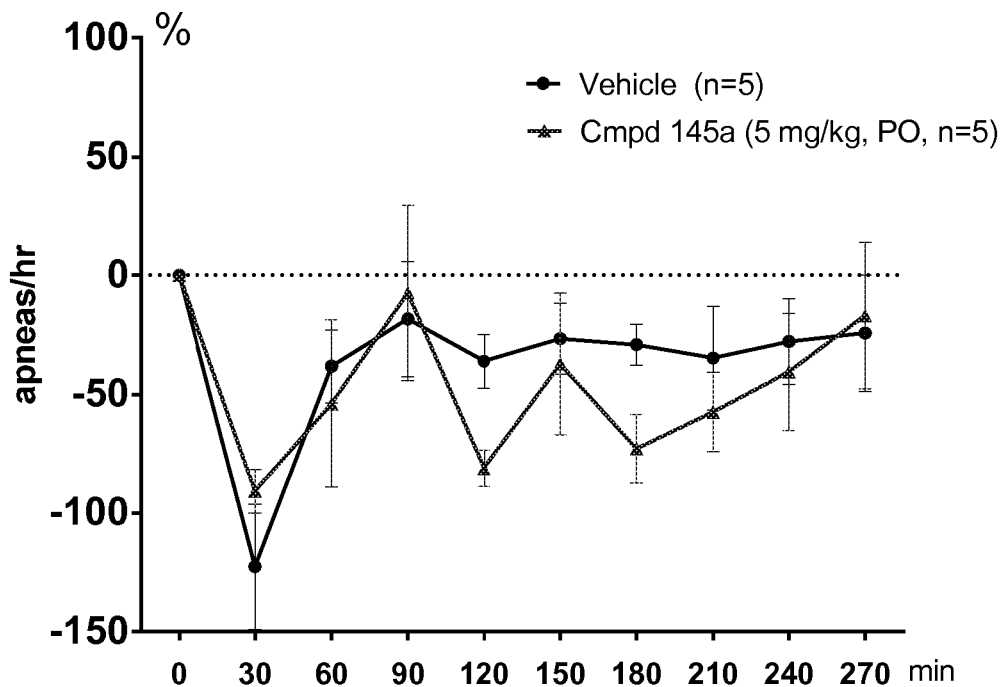
FIG. 30 is a graph illustrating the finding that compound (145a) reduced the number of apneas per hr expressed as a percent change from baseline (pre-drug), in rats chronically treated with morphine, versus treatment with a vehicle. The marked decrease in apnea at the 30 min post-treatment time, across all groups, was caused by overt stimulation (awakening) from dosing via oral gavage.
Figure 31:
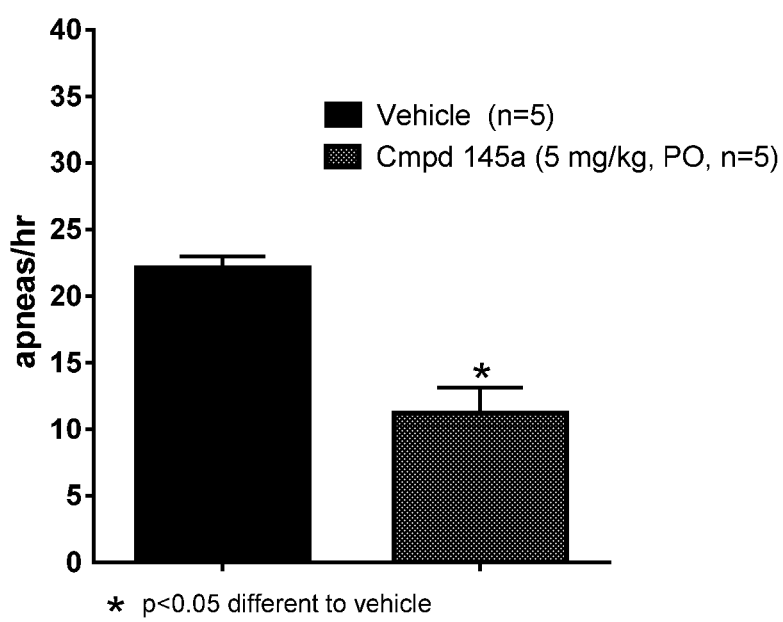
FIG. 31 is a bar graph illustrating the finding that compound (145a) reduced the number of apneas per hr in rats chronically treated with morphine, versus treatment with a vehicle.
Figure 32:
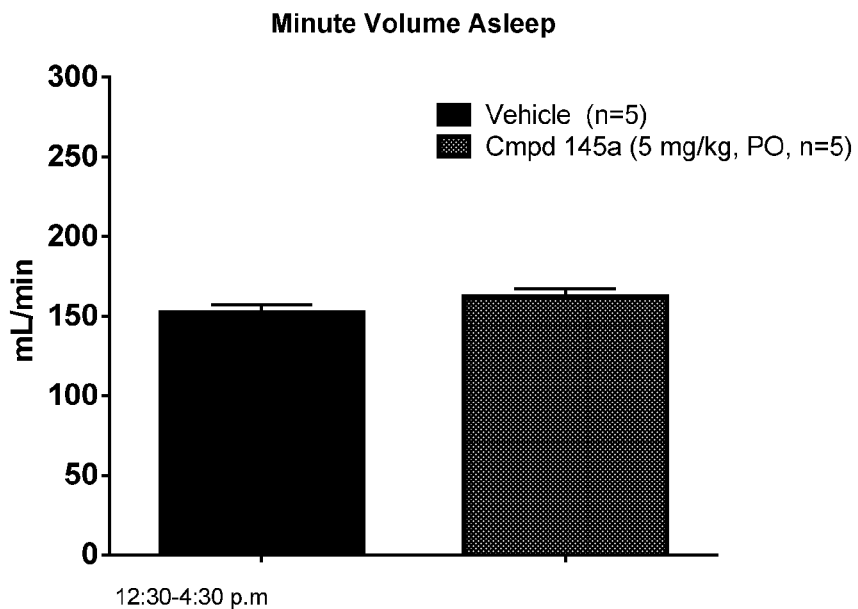
FIG. 32 is a bar graph illustrating the finding that compound (145a) did not cause an increase in minute volume compared to a vehicle-treated group.
Figure 33:
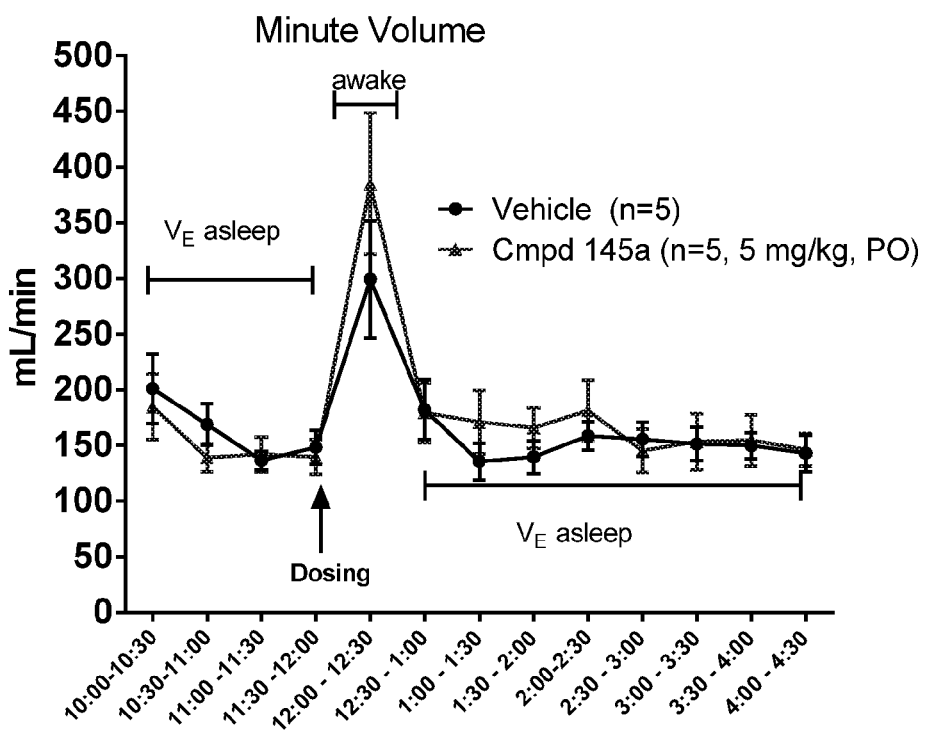
FIG. 33 is a graph illustrating the finding that compound (145a) did not cause an increase in ventilation per unit time compared to treatment with a vehicle. The marked increase in minute volume at the (12:00-12:30) 30 min post-treatment time, across all groups, was caused by overt stimulation from dosing via oral gavage).

$N^2$-$N^6$-biscyclopropylmethyl-$N^4$,$N^8$-dimethyl-pyrimido[5,4-d]pyrimidine-2,4,6,8-tetraamine (84) (7.0 g) obtained in Stage 4 was dissolved in n-BuOH (200 mL) at reflux and the solution was filtered through a sintered glass filter while hot to remove insoluble particulates. The filter was washed with n-BuOH (3×20 mL) and the combined filtrates were concentrated by distillation under atmospheric pressure to a final volume of 110 mL. The solution was cooled to and maintained at room temperature and stirred for 16 h. The product was collected by filtration, washed with n-BuOH (3×15 mL) and light petroleum ether (3×40 mL), and dried on the filter at room temperature yielding $N^2$,$N^6$-bis-cyclopropylmethyl-$N^4$,$N^8$-dimethyl-pyrimido[5,4-d]pyrimidine-2,4,6,8-tetraamine (84) (6.45 g, 47% y). mp: 264-268° C. XRPD as per FIG. 13 with key signals as per Table 5.

TABLE 4

Elemental Analysis of (84).

| | C | H | N |
|---|---|---|---|
| Theoretical: | 58.52 | 7.37 | 34.12 |
| Found 1 | 58.65 | 7.36 | 33.98 |
| Found 2 | 58.68 | 7.42 | 33.97 |

TABLE 5

Key XRPD Signals for (84) as crystallized from n-butanol.

| Pos. [°2Th.] | d-spacing [Å] | Rel. Int. [%] |
|---|---|---|
| 8.1179 | 10.88256 | 24.14 |
| 9.5941 | 9.21115 | 100.00 |
| 12.6010 | 7.01914 | 67.39 |
| 15.0171 | 5.89481 | 7.68 |
| 16.3278 | 5.42445 | 1.84 |
| 17.3962 | 5.09364 | 2.86 |
| 18.9758 | 4.67302 | 10.75 |
| 20.6773 | 4.29217 | 4.83 |
| 21.7166 | 4.08905 | 12.39 |
| 22.2793 | 3.98703 | 50.27 |

TABLE 5-continued

Key XRPD Signals for (84) as crystallized from n-butanol.

| Pos. [°2Th.] | d-spacing [Å] | Rel. Int. [%] |
|---|---|---|
| 23.9773 | 3.70839 | 4.78 |
| 25.2409 | 3.52554 | 4.60 |
| 26.7012 | 3.33594 | 5.35 |

Salt Screen Procedure

Free base $N^2$-$N^6$-bis-cyclopropylmethyl $N^4$,$N^8$-dimethyl-pyrimido[5,4-d]pyrimidine-2,4,6,8-tetraamine (84) (900 mg) and one molar equivalent of the salt former were dissolved in 30 mL 1:1 (vol/vol) chloroform/acetonitrile or chloroform/ethanol. The mixture was heated at 50° C. if necessary to form a clear solution and then the solution was concentrated to dryness in vacuo. The resulting solid residue was used as is, assuming that it is a 1:1 stoichiometric salt.

A 3 mL vial with a screw cap was charged with 50 mg of the solid salt and 1 mL of a solvent at room temperature. The mixture was heated if necessary to achieve a clear solution, in some examples producing a mixture comprising a clear portion and a melt or incompletely dissolved crystalline material. The hot mixture was cooled to room temperature. If crystallization did not occur or was incomplete at ambient temperature (small visible amount of crystals), the mixture was further cooled to about 0-5° C. Solid product was collected by filtration, dried at 45° C. in vacuo, and characterized by melting point and elemental analysis. Solvents evaluated include acetonitrile, methyl ethyl ketone, methyl isobutyl ketone, ethyl acetate, isopropyl acetate, water, heptane, methyl-tert-butyl ether, cyclohexane, toluene, methanol, ethanol, n-propanol, isopropanol, n-butanol, 2-butanol, isoamyl alcohol, and tetrahydrofuran. Salt formers evaluated include hydrochloric acid, sulphuric acid, phosphoric acid benzenesulphonic acid, methanesulphonic acid, p-toluenesulphonic acid, saccharin, malonic acid, L-aspartic acid, L-glutamic acid, maleic acid, L(+)-tartaric acid, fumaric acid, citric acid, malic acid, glycolic acid, mandelic acid, benzoic acid, succinic acid acetic acid, lactic acid, glycerophosphoric acid, D-glucuronic acid, and D-gluconic acid. Data for the salts isolated using various salt formers and solvents are provided in Tables 6A-6H.

TABLE 6A

Hydrogen chloride salt (85a)

| Solvent | Solubility, r.t. | Solubility, Reflux | Final Isolation Temp. | Base/acid molar ratio | Elemental Analysis | MP (° C.) |
|---|---|---|---|---|---|---|
| Ethanol | I | S | Ca. 0-5° C. | 1:1.11 | Theoretical C, 52.10, H, 6.86, N, 30.38 Found C, 52.17, H, 6.98, N, 30.20 C, 52.04, H, 6.88, N, 30.18 | 253-255 |
| n-Propanol | I | S | Ca. 0-5° C. | 1:1.15 | Theoretical C, 51.89, H, 6.84, N, 30.26 Found C, 52.12, H, 6.85, N, 29.89 C, 52.13, H, 6.91, N, 30.01 | 251-253 |
| n-Butanol | I | S | Ca. 0-5° C. | 1:1.15 | Theoretical C, 51.89, H, 6.84, N, 30.26 Found C, 52.00, H, 6.90, N, 30.08 C, 52.01, H, 6.93, N, 29.99 | 252-254 |

TABLE 6B

Sulfuric acid salt (85b)

| Solvent | Solubility r.t. | Solubility Reflux | Final Isolation Temp. | Base/acid molar ratio | Elemental Analysis | MP (° C.) |
|---|---|---|---|---|---|---|
| Methanol | I | S | Ca. 0-5° C. | 1:1 | Theoretical C, 45.06, H, 6.14, N, 26.27 Found C, 45.09, H, 6.39, N, 26.55 C, 45.14, H, 6.29, N, 26.54 | 228-230 |
| Ethanol | I | PS | r.t. | 1:1.04 | Theoretical C, 44.73, H, 6.18, N, 25.76 7.66 Found C, 44.29, H, 6.07, N, 26.00, C, 44.38, H, 6.23, N, 26.06 | 226-228 |

I = Insoluble,
S = Soluble,
PS = partially soluble.

TABLE 6C

Benzesulfonic acid salt (85c)

| Solvent | Solubility r.t. | Solubility Reflux | Final Isolation Temp. | Base/acid molar ratio | Elemental Analysis | MP (° C.) |
|---|---|---|---|---|---|---|
| Methyl isobutyl-ketone | I | S | Ca. 0-5° C. | 1:1 | Calculated C, 54.30, H, 6.21, N, 23.03, S, 6.59 Found C, 54.31, H, 6.22, N, 23.20, S, 6.53 C, 54.36, H, 6.24, N, 23.20, S, 6.57 | 149-150 |

TABLE 6C-continued

| | | | | Benzesulfonic acid salt (85c) | | |
|---|---|---|---|---|---|---|
| Solvent | Solubility r.t. | Solubility Reflux | Final Isolation Temp. | Base/acid molar ratio | Elemental Analysis | MP (° C.) |
| Ethyl Acetate | I | S | Ca. 0-5° C. | 1:1 | Calculated C, 54.30, H, 6.21, N, 23.03, S, 6.59 Found C, 54.07, H, 6.20, N, 23.07, S, 6.48 C, 54.21, H, 6.36, N, 23.14, S, 6.44 | 148-150 |
| Isopropyl acetate | I | S | Ca. 0-5° C. | 1:1 | Calculated C, 54.30, H, 6.21, N, 23.03, S, 6.59 Found C, 54.22, H, 6.20, N, 23.05, S, 6.43 C, 54.28, H, 6.34, N, 23.09, S, 6.53 | 146-148 |
| Toluene | I | S | Ca. 0-5° C. | 1:1 | Calculated C, 54.30, H, 6.21, N, 23.03, S, 6.59 Found C, 54.23, H, 6.32, N, 22.85, S, 6.18 C, 54.29, H, 6.20, N, 22.88, S, 6.23 | 147-149 |

TABLE 6D

| | | | | Toluenesulfonic salt (85d) | | |
|---|---|---|---|---|---|---|
| Solvent | Solubility r.t. | Solubility Reflux | Final Isolation Temp. | Base/acid molar ratio | Elemental Analysis | MP (° C.) |
| Isopropyl acetate | I | S | Ca. 0-5° C. | 1:1.13 | Theoretical C, 54.91, H, 6.37, N, 21.43, S, 6.93 Found C, 54.86, H, 6.40, N, 21.27, S, 6.65 C, 54.79, H, 6.39, N, 21.23, S, 6.68 | 142-144 |

TABLE 6E

| | | | | Malonic acid salt (85e) | | |
|---|---|---|---|---|---|---|
| Solvent | Solubility r.t. | Solubility Reflux | Final Isolation Temp. | Base/acid molar ratio | Elemental Analysis | MP (° C.) |
| Methanol | I | PS | r.t. | 1:1.06 | Theoretical C, 52.51, H, 6.49, N, 25.54 Found C, 52.47, H, 6.43, N, 25.56 C, 52.61, H, 6.39, N, 25.54 | 246-248 |
| Tetrahydro furan | I | PS | r.t. | 1:1.3 | Theoretical C, 51.55, H, 6.35, N, 24.17 Found C, 51.93, H, 6.49, N, 23.89 C, 52.20, H, 6.55, N, 24.03 | 247-249 |

TABLE 6F

Hydrogen tartrate salt (85f)

| Solvent | Solubility r.t. | Solubility Reflux | Final Isolation Temp. | Base/acid molar ratio | Elemental Analysis | MP (° C.) |
|---|---|---|---|---|---|---|
| Methanol | I | PS | r.t. | 1:0.79 | Theoretical<br>C, 51.48, H, 6.48, N, 25.07<br>Found<br>C, 51.24, H, 6.45, N, 25.28<br>C, 51.17, H, 6.45, N, 25.25 | 226-228 |
| n-Propanol | I | PS | r.t. | 1:0.83 | Theoretical<br>C, 51.23, H, 6.45, N, 24.74<br>Found<br>C, 51.25, H, 6.55, N, 24.66<br>C, 51.25, H, 6.56, N, 24.70 | 226-228 |
| n-Butanol | I | PS | r.t. | 1:0.83 | Theoretical<br>C, 51.23, H, 6.45, N, 24.74<br>Found<br>C, 51.50, H, 6.62, N, 24.37<br>C, 51.71, H, 6.67, N, 24.48 | 224-228 |

TABLE 6G

Maleic acid salt (85g)

| Solvent | Solubility r.t. | Solubility Reflux | Final Isolation Temp. | Base/acid molar ratio | Elemental Analysis | MP (° C.) |
|---|---|---|---|---|---|---|
| Methanol | I | S | r.t. | 1:1 | Theoretical<br>C, 54.04, H, 6.35, N, 25.21<br>Found<br>C, 53.68, H, 6.30, N, 25.09<br>C, 53.95, H, 6.30, N, 25.24 | 175-177 |
| n-Propanol | I | S | r.t. | 1:1 | Theoretical<br>C, 54.04, H, 6.35, N, 25.21<br>Found<br>C, 53.94, H, 6.36, N, 25.05<br>C, 53.89, H, 6.31, N, 25.02 | 174-176 |
| n-Butanol | I | S | r.t. | 1:1 | Theoretical<br>C, 54.04, H, 6.35, N, 25.21<br>Found<br>C, 53.77, H, 6.31, N, 24.94<br>C, 54.01, H, 6.31, N, 25.07 | 174-176 |
| Tetrahydrofuran | I | S | r.t. | 1:1 | Theoretical<br>C, 54.04, H, 6.35, N, 25.21<br>Found<br>C, 54.10, H, 6.32, N, 25.20<br>C, 54.08, H, 6.33, N, 25.25 | 194-196 |

TABLE 6H

Methanesulfonic acid salt (85h)

| Solvent | Solubility, r.t. | Solubility, Reflux | Final Isolation Temp. | Base/acid molar ratio | Elemental Analysis | MP (° C.) |
|---|---|---|---|---|---|---|
| Ethyl Acetate | I | S | r.t. | 1:1.1 | Theoretical<br>C, 47.31, H, 6.59, N, 25.81<br>Found<br>C, 47.16, H, 6.81, N, 25.41<br>C, 47.44, H, 6.81, N, 25.62 | 143-145 |

Example 40

$N^2,N^6$-Diisobutyl-$N^4,N^8$-dimethyl-pyrimido[5,4-d]pyrimidine-2,4,6,8-tetraamine (86) and corresponding hydrochloride salt (87a) (Scheme 17)

$N^2,N^6$-Diisobutyl-$N^4,N^8$-dimethyl-pyrimido[5,4-d]pyrimidine-2,4,6,8-tetraamine (86)

A mixture of 2,6-dichloro-$N^4,N^8$-dimethyl-pyrimido[5,4-d]pyrimidine-4,8-diamine (25) (350 mg, 1.35 mmol) and isobutylamine (805 µL, 8.10 mmol) in n-butanol (5.0 mL) was heated in a closed vial at 120° C. for 20 h. An additional portion of isobutylamine (805 µL, 8.10 mmol) was added and the heating was continued for 68 h. After cooling, a saturated NaHCO$_3$ solution (30 mL) was added and the resulting suspension was extracted with CH$_2$Cl$_2$ (3×30 mL). The combined organic extracts were washed with water (75 mL) and dried over solid anhydrous Na$_2$SO$_4$. After filtration, the solvent was removed and the residue was purified by flash column chromatography using gradient elution from CH$_2$Cl$_2$ to CH$_2$Cl$_2$/MeOH (9:1) to give $N^2,N^6$-diisobutyl-$N^4,N^8$-dimethyl-pyrimido[5,4-d]pyrimidine-2,4,6,8-tetraamine hydrochloride (86) (180 mg, 40% y). 400 MHz $^1$H NMR (DMSO-d$_6$, ppm): δ 7.00-6.90 (2H, m), 6.03 (2H, t, J=5.6 Hz), 3.16-3.09 (4H, m), 2.91 (6H, d, J=4.8 Hz), 1.91-1.76 (2H, m), 0.89 (12H, d, J=6.7 Hz). ESI-MS (m/z): 333 [M+H]$^+$.

$N^2,N^6$-Diisobutyl-$N^4,N^8$-dimethyl-pyrimido[5,4-d]pyrimidine-2,4,6,8-tetraamine hydrochloride (87a)

$N^2,N^6$-Diisobutyl-$N^4,N^8$-dimethyl-pyrimido[5,4-d]pyrimidine-2,4,6,8-tetraamine hydrochloride (86) (170 mg, 0.51 mmol) was treated with 2M HCl/diethyl ether in 1,4-dioxane/EtOH (1/1) using procedure described for compound (20a) (170 mg, 90% y). 400 MHz $^1$H NMR (CDCl$_3$, ppm): δ 14.96 (0.3H, s), 14.00 (1H, s), 9.60 (0.3H, s), 7.66 (0.7H, s), 7.41 (0.7H, s), 6.75 (1H, s), 4.93 (1H, s), 3.40-3.28 (2H, m), 3.28-3.13 (6H, m), 3.13-2.99 (2H, m), 2.00-1.81 (2H, m), 0.98 (12H, d, J=6.7 H). ESI-MS (m/z): 333 [M+H]$^+$; melting point: 208-210° C.

Example 41

$N^2,N^6$-Diallyl-$N^4,N^8$-dimethyl-pyrimido[5,4-d]pyrimidine-2,4,6,8-tetraamine (88) and corresponding hydrochloride salt (89a) (Scheme 17)

$N^2,N^6$-Diallyl-$N^4,N^8$-dimethyl-pyrimido[5,4-d]pyrimidine-2,4,6,8-tetraamine (88)

A mixture of 2,6-dichloro-$N^4,N^8$-dimethyl-pyrimido[5,4-d]pyrimidine-4,8-diamine (25) (350 mg, 1.35 mmol) and allylamine (293 µL, 8.10 mmol) in n-butanol (5.0 mL) was heated in a closed vial at 120° C. for 144 h. After cooling, a saturated NaHCO$_3$ solution (30 mL) was added and the resulting suspension was extracted with EtOAc (3×10 mL). The combined organic extracts were washed with water (30 mL), and then with a brine solution (30 mL), and dried over solid anhydrous Na$_2$SO$_4$. After filtration, the solvent was removed; the residue was purified by flash column chromatography using gradient elution from CHCl$_3$ to CHCl$_3$/EtOAc (4:1) to give $N^2,N^6$-diallyl-$N^4,N^8$-dimethyl-pyrimido[5,4-d]pyrimidine-2,4,6,8-tetraamine (88) (151 mg, 37%). 400 MHz $^1$H NMR (CDCl$_3$, ppm): δ 6.50-6.38 (2H, m), 6.00 (2H, ddt, J=17.1, 10.2, 5.7 Hz), 5.25 (2H, ddt, J=17.1, 1.6, 1.6 Hz), 5.11 (2H, ddt, J=10.2, 1.6, 1.6 Hz), 4.71 (2H, t, J=5.7 Hz), 4.05 (4H, ddt, J=5.7, 5.7, 1.6 Hz), 3.06 (6H, d, J=5.2 Hz). ESI-MS (m/z): 301 [M+H]$^+$.

$N^2,N^6$-Diallyl-$N^4,N^8$-dimethyl-pyrimido[5,4-d]pyrimidine-2,4,6,8-tetraamine hydrochloride (89a)

$N^2,N^6$-Diallyl-$N^4,N^8$-dimethyl-pyrimido[5,4-d]pyrimidine-2,4,6,8-tetraamine (88) (147 mg, 0.49 mmol) was treated with 2M HCl/diethyl ether in 1,4-dioxane using procedure described for compound (20a) (140 mg, 85% y). 400 MHz $^1$H NMR (CDCl$_3$, ppm): δ 15.10 (1H, br s), 14.31-14.03 (0.4H, m), 9.90-9.60 (1H, m), 8.05-7.31 (1H, m), 6.73 (1.6H, s), 6.06-5.88 (2H, m), 5.36-5.12 (4H, m), 4.25-3.95 (4H, m), 3.32-2.95 (6H, m). ESI-MS (m/z): 301 [M+H]$^+$; melting point: 212-214° C.

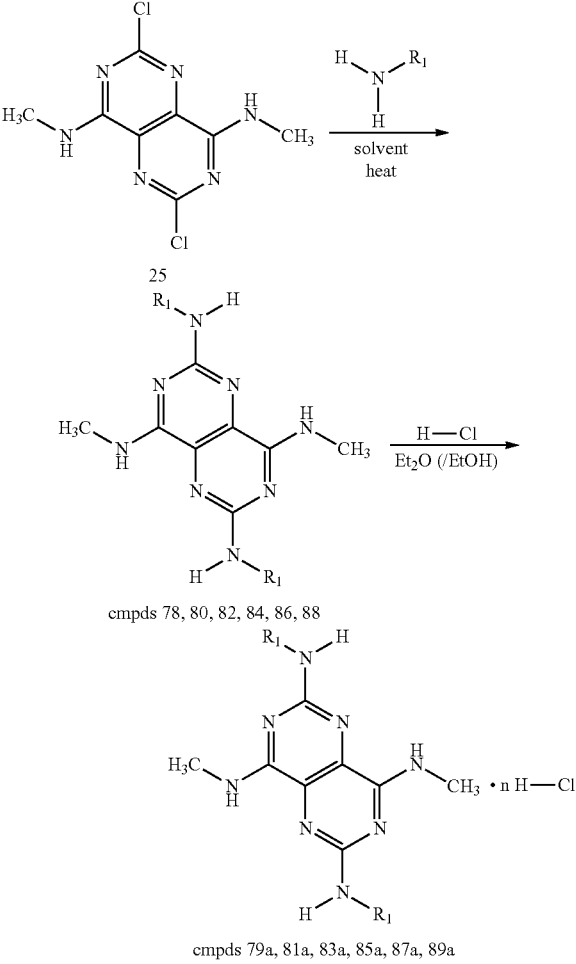

Scheme 17.

cmpds 78, 80, 82, 84, 86, 88 cmpds 79a, 81a, 83a, 85a, 87a, 89a

Example 42

2-Chloro-6-(N,N'-dimethyl-hydrazino)-$N^4,N^8$-dimethyl-pyrimido[5,4-d]pyrimidine-4,8-diamine (90), and 2,6-bis-(N,N'-dimethyl-hydrazino)-$N^4,N^8$-dimethyl-pyrimido[5,4-d]pyrimidine-4,8-diamine (91) (Scheme 18)

A mixture of 2,6-dichloro-$N^4,N^8$-dimethyl-pyrimido[5,4-d]pyrimidine-4,8-diamine (25) (600 mg, 2.32 mmol), N,N'- dimethyl-hydrazine dihydrochloride (926 mg, 6.96 mmol) and N,N-diisopropylethylamine (2.6 mL, 15.08 mmol) in 1,4-dioxane (15.0 mL) was heated at 80° C. for 20 h. Additional N,N'-dimethyl-hydrazine dihydrochloride (309 mg, 2.32 mmol) and N,N-diisopropylethylamine (0.87 mL, 5.03 mmol) was added, and heating was continued for 24 h. A saturated NaHCO₃ solution (30 mL) was added, and the suspension was extracted with CH₂Cl₂ (3×30 mL). The combined organic extracts were washed with water (75 mL) and dried over solid anhydrous Na₂SO₄. After filtration, the solvent was removed and the residue was purified by flash column chromatography using gradient elution from CH₂Cl₂ to CH₂Cl₂/MeOH (97:3) to give 2-chloro-6-(N,N'-dimethyl-hydrazino)-N⁴,N⁸-dimethyl-pyrimido[5,4-d]pyrimidine-4,8-diamine (90) (310 mg, 47% y) and 2,6-bis-(N,N'-dimethyl-hydrazino)-N⁴,N⁸-dimethyl-pyrimido[5,4-d]pyrimidine-4,8-diamine (91) (160 mg, 23% y). 400 MHz ¹H NMR (CDCl₃, ppm): δ 6.50-6.35 (2H, m), 5.35 (2H, s), 3.29 (6H, s), 3.11 (6H, d, J=5.0 Hz), 2.65 (6H, s). ESI-MS (m/z): 307 [M+H]⁺; melting point: 219-221° C.

Compound (90): 400 MHz ¹H NMR (CDCl₃, ppm): δ 6.67 (1H, s), 6.65 (1H, s), 5.36 (1H, s), 3.32 (3H, s), 3.16 (3H, d, J=5.2 Hz), 3.08 (3H, d, J=5.0 Hz), 2.66 (3H, s). ESI-MS (m/z): 283, 285 [M+H]+.

Example 43

6-(N,N'-Dimethyl-hydrazino)-N²,N²,N⁴,N⁸-tetramethyl-pyrimido[5,4-d]pyrimidine-2,4,8-triamine (92) and corresponding hydrochloride salt (93a) (Scheme 18)

A mixture of 2-chloro-6-(N,N'-dimethyl-hydrazino)-N⁴,N⁸-dimethyl-pyrimido[5,4-d]pyrimidine-4,8-diamine (90) (260 mg, 0.92 mmol) and 2M dimethylamine/THF (4.6 mL, 9.20 mmol) in 1,4-dioxane (5.0 mL) was heated in a closed vial at 135° C. for 20 h. The volatiles were removed, and the residue was partitioned between saturated NaHCO₃ solution (20 mL) and CH₂Cl₂ (20 mL). The aqueous phase was separated and extracted with CH₂Cl₂ (2×20 mL). The combined organic extracts were washed with water (30 mL) and dried over solid anhydrous Na₂SO₄. After filtration, the solvent was removed and the residue was purified by flash column chromatography using gradient elution from CH₂Cl₂ to CH₂Cl₂/MeOH (95:5) to give 6-(N,N'-dimethyl-hydrazino)-N²,N²,N⁴,N⁸-tetramethyl-pyrimido[5,4-d]pyrimidine-2,4,8-triamine (92) (180 mg, 67% y). 400 MHz ¹H NMR (CDCl₃, ppm): δ 6.50 (1H, s), 6.34 (1H, s), 5.38 (1H, br s), 3.28 (3H, s), 3.17 (6H, s), 3.11 (3H, d, J=5.1 Hz), 3.10 (3H, d, J=5.1 Hz), 2.65 (3H, s). ESI-MS (m/z): 292 [M+H]⁺.

6-(N,N'-Dimethyl-hydrazino)-N²,N²,N⁴,N⁸-tetramethyl-pyrimido[5,4-d]pyrimidine-2,4,8-triamine (92) (170 mg, 0.58 mmol) was treated with 2M HCl/diethyl ether in 1,4-dioxane using procedure described for compound (20a) (155 mg, 81% y). 400 MHz ¹H NMR (CDCl₃, ppm): δ 11.0-8.0 (2H, br s), 9.08 (2H, s), 3.45 (3H, s), 3.29 (6H, s), 3.11 (3H, d, J=4.6 Hz), 3.05 (3H, d, J=4.6 Hz), 2.86 (3H, s). ESI-MS (m/z): 292 [M+H]⁺; melting point: 273-275° C.

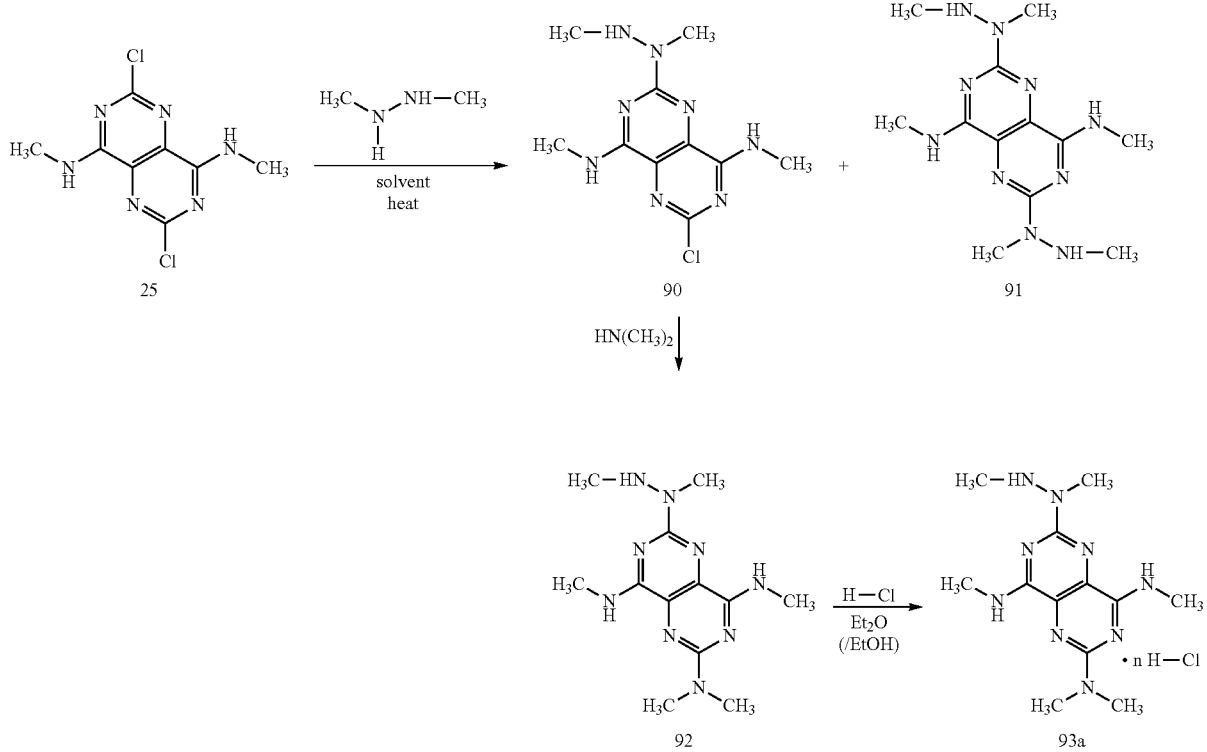

Scheme 18.

Example 44

N$^4$,N$^8$-Dimethyl-6-propoxy-N$^2$-n-propyl-pyrimido[5,4-d]pyrimidine-2,4,8-triamine (94) and corresponding hydrochloride salt (95a) (Scheme 19)

A NaH (60% suspension in mineral oil) (188 mg, 4.72 mmol) was added in portions to propanol (10 mL) at 0° C. The mixture was stirred for 10 min at 0° C., and then 6-chloro-N$^2$-n-propyl-N$^4$,N$^8$-dimethyl-pyrimido[5,4-d]pyrimidine-2,4,8-triamine (54) (250 mg, 0.89 mmol) was added. The mixture was heated at 110° C. for 16 h. The volatiles were removed and the residue was partitioned between a saturated NH$_4$Cl solution (30 mL) and CH$_2$Cl$_2$ (30 mL). The aqueous phase was separated and extracted with CH$_2$Cl$_2$ (2×30 mL). The combined organic extracts were washed with water (50 mL) and dried over solid anhydrous Na$_2$SO$_4$. After filtration the solvent was removed and the residue was purified by flash column chromatography using PE/EtOAc (1:1) as an eluent to give N$^4$,N$^8$-dimethyl-N$^2$-n-propyl-6-propoxy-pyrimido[5,4-d]pyrimidine-2,4,8-triamine (94) (227 mg, 84%). 400 MHz $^1$H NMR (CDCl$_3$, ppm): δ 6.64-6.57 (1H, m), 6.47-6.39 (1H, m), 4.82-4.75 (1H, m), 4.26 (2H, t, J=7.0 Hz), 3.40-3.34 (2H, m), 3.13 (3H, d, J=5.2 Hz), 3.07 (3H, d, J=5.2 Hz), 1.84 (2H, sextet, J=7.4 Hz), 1.63 (2H, sextet, J=7.4 Hz), 1.04 (3H, t, J=7.4 Hz), 0.99 (3H, t, J=7.4 Hz). ESI-MS (m/z): 306 [M+H]$^+$.

N$^4$,N$^8$-Dimethyl-N$^2$-n-propyl-6-propoxy-pyrimido[5,4-d]pyrimidine-2,4,8-triamine (94) (227 mg, 0.74 mmol) was treated with 2M HCl/diethyl ether in 1,4-dioxane using procedure described for compound (20a) (241 mg, 95% y). 400 MHz $^1$H NMR (CDCl$_3$, ppm): δ 8.15-8.09 (1H, m), 7.77-7.47 (1H, m), 6.80-6.72 (1H, m), 4.29 (2H, t, J=6.9 Hz), 3.53-3.46 (2H, m), 3.21 (3H, d, J=5.2 Hz), 3.15 (3H, d, J=4.7 Hz), 1.84 (2H, sextet, J=7.4 Hz), 1.68 (2H, sextet, J=7.4 Hz), 1.04 (3H, t, J=7.4 Hz), 1.00 (3H, t, J=7.4 Hz). ESI-MS (m/z): 306 [M+H]$^+$; melting point: 203-205° C.

Example 45

N$^4$,N$^8$-Dimethyl-N$^2$-n-propyl-6-propylsulfanyl-pyrimido[5,4-d]pyrimidine-2,4,8-triamine (96) and corresponding hydrochloride salt (97a) (Scheme 19)

Propanethiol (89 μL, 0.98 mmol) was dissolved in DMF (4 mL) and NaHMDS in THF (1.0 M, 1.06 mL, 1.06 mmol) was added at ambient temperature. After stirring for 15 min the clear solution was added to a solution of 6-chloro-N$^2$-n-propyl-N$^4$,N$^8$-dimethyl-pyrimido[5,4-d]pyrimidine-2,4,8-triamine (54) (250 mg, 0.89 mmol) in DMF (6 mL). Stirring was continued for 3 h at ambient temperature, and then the reaction was heated at 60° C. for 16 h. After this time, water (30 mL) was added, and the resulting suspension was extracted with EtOAc (3×30 mL). The combined organic extracts were washed with water (50 mL) and dried over solid anhydrous Na$_2$SO$_4$. After filtration, the solvent was removed and the residue was purified by flash column chromatography using PE/EtOAc (1:1) as an eluent to give N$^4$,N$^8$-dimethyl-N$^2$-n-propyl-N$^4$,N$^8$-dimethyl-6-propylsulfanyl-pyrimido[5,4-d]pyrimidine-2,4,8-triamine (96) (263 mg, 92% y). 400 MHz $^1$H NMR (CDCl$_3$, ppm): δ 6.55-6.47 (2H, m), 4.89-4.81 (1H, m), 3.41-3.34 (2H, m), 3.15-3.10 (5H, m), 3.07 (3H, d, J=5.2 Hz), 1.78 (2H, sextet, J=7.4 Hz), 1.63 (2H, sextet, J=7.4 Hz), 1.05 (3H, t, J=7.4 Hz), 0.99 (3H, t, J=7.4 Hz). ESI-MS (m/z): 322 [M+H]$^+$.

N$^4$,N$^8$-Dimethyl-N$^2$-n-propyl-6-propylsulfanyl-pyrimido[5,4-d]pyrimidine-2,4,8-triamine (96) (250 mg, 0.78 mmol) was treated with 2M HCl/diethyl ether in diethyl ether using procedure described for compound (20a) (262 mg, 94% y). 400 MHz $^1$H NMR (CDCl$_3$, ppm): δ 8.09-8.02 (1H, m), 7.65-7.56 (1H, m), 6.87-6.81 (1H, m), 3.53-3.45 (2H, m), 3.21 (3H, d, J=5.1 Hz), 3.14 (3H, d, J=4.6 Hz), 3.14-3.08 (2H, m), 1.77 (2H, sextet, J=7.4 Hz), 1.68 (2H, sextet, J=7.4 Hz), 1.05 (3H, t, J=7.4 Hz), 0.99 (3H, t, J=7.4 Hz). ESI-MS (m/z): 322 [M+H]$^+$; melting point: 218-220° C.

Example 46

6-Benzyloxy-N$^4$,N$^8$-Dimethyl-N$^2$-n-propyl-pyrimido[5,4-d]pyrimidine-2,4,8-triamine (98) and corresponding hydrochloride salt (99a) (Scheme 19)

Benzyl alcohol (1.0 mL, 9.60 mmol) was added to a suspension of NaH (60% in mineral oil) (416 mg, 10.4 mmol) in 1,4-dioxane (10 mL) at 0° C. The mixture was stirred for 30 min. at 0° C., then 6-chloro-N$^4$,N$^8$-dimethyl-N$^2$-n-propyl-pyrimido[5,4-d]pyrimidine-2,4,8-triamine (54) (450 mg, 1.60 mmol) was added. The mixture was heated at 110° C. for 1 h. The volatiles were removed and the residue was partitioned between a saturated NH$_4$Cl solution (30 mL) and CH$_2$Cl$_2$ (30 mL). The aqueous phase was separated and extracted with CH$_2$Cl$_2$ (2×30 mL). The combined organic extracts were washed with water (50 mL) and dried over solid anhydrous Na$_2$SO$_4$. After filtration, the solvent was removed and the residue was purified by flash column chromatography using gradient elution from PE/EtOAc (9:1) to PE/EtOAc (1:9) to give N$^4$,N$^8$-dimethyl-N$^2$-n-propyl-N$^4$,N$^8$-dimethyl-6-benzyloxy-pyrimido[5,4-d]pyrimidine-2,4,8-triamine (98) (465 mg, 82% y). 400 MHz $^1$H NMR (CDCl$_3$, ppm): δ 7.51-7.45 (2H, m), 7.38-7.32 (2H, m), 7.31-7.27 (1H, m), 6.68-6.58 (1H, m), 6.46-6.36 (1H, m), 5.39 (2H, s), 4.79 (1H, t, J=5.8 Hz), 3.37 (2H, td, J=7.3, 5.8 Hz), 3.13 (3H, d, J=5.2 Hz), 3.06 (3H, d, J=5.2 Hz), 1.7-1.58 (2H, m), 0.99 (3H, t, J=7.4 Hz). ESI-MS (m/z): 354 [M+H]$^+$.

N$^4$,N$^8$-Dimethyl-N$^2$-n-propyl-6-benzyloxy-pyrimido[5,4-d]pyrimidine-2,4,8-triamine (98) (100 mg, 0.28 mmol) was treated with 2M HCl/diethyl ether in diethyl ether using procedure described for compound (20a) (104 mg, 95% y). 400 MHz $^1$H NMR (CDCl$_3$, ppm): δ 8.27 (1H, br s), 7.76-7.59 (1H, m), 7.49-7.41 (2H, m), 7.40-7.29 (3H, m), 6.80-6.69 (1H, m), 5.41 (2H, s), 3.54-3.44 (2H, m), 3.20 (3H, d, J=5.2 Hz), 3.15 (3H, d, J=4.8 Hz), 1.74-1.62 (2H, m), 1.00 (3H, t, J=7.4 Hz). ESI-MS (m/z): 354 [M+H]$^+$; melting point: 194-196° C.

Example 47

4,8-Bis-methylamino-6-propylamino-pyrimido[5,4-d]pyrimidin-2-ol (100) and corresponding hydrochloride salt (101a) (Scheme 19)

A mixture of N$^4$,N$^8$-dimethyl-N$^2$-n-propyl-6-benzyloxy-pyrimido[5,4-d]pyrimidine-2,4,8-triamine (98) (330 mg, 0.93 mmol) and 10% Pd/C (25 mg) in EtOAc (7 mL) was hydrogenated at atmospheric pressure for 4 h. The reaction mixture was filtered through Celite, and the Celite pad was washed with hot MeOH. The filtrate was evaporated.

The residue were treated with EtOAc (80 mL) and the resultant precipitate were filtered and dried to give 4,8-bis-methylamino-6-propylamino-pyrimido[5,4-d]pyrimidin-2-ol (100) (160 mg, 65% y). 400 MHz $^1$H NMR (CD$_3$OD, ppm): δ 3.36 (2H, t, J=7.0 Hz), 3.06 (3H, s), 3.01 (3H, s), 1.67-1.55 (2H, m), 0.98 (3H, t J=7.5 Hz). ESI-MS (m/z): 264 [M+H]⁺.

4,8-Bis-methylamino-6-propylamino-pyrimido[5,4-d]pyrimidin-2-ol (100) (140 mg, 0.53 mmol) was treated with 2M HCl/EtOH in 1,4-dioxane/EtOH (1/1) using procedure described for compound (20a) (135 mg, 85% y). 400 MHz ¹H NMR (D₂O/acetic acid-d₄, ppm): δ 3.34 (2H, t, J=7.0 Hz), 3.14 (3H, s), 3.03 (3H, s), 1.63-1.50 (2H, m), 0.89 (3H, t, J=7.5 Hz). ESI-MS (m/z): 264 [M+H]⁺; melting point: 238-240° C.

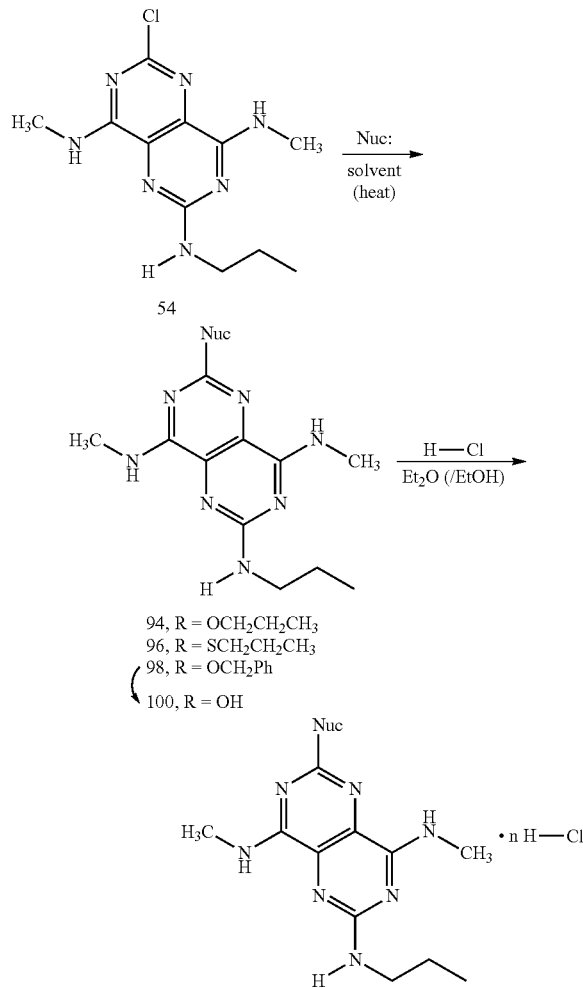

Example 48

4,8-Bis-methylamino-6-n-propylamino-pyrimido[5,4-d]pyrimidine-2-carbonitrile (102) and corresponding hydrochloride salt (103a) (Scheme 20)

To a solution of 6-chloro-N⁴,N⁸-dimethyl-N²-n-propyl-pyrimido[5,4-d]pyrimidine-2,4,8-triamine (54) (500 mg, 1.77 mmol) in DMSO (4 mL) was added KCN (243 mg, 3.73 mmol). The reaction mixture was heated at 140° C. for 40 h. The reaction mixture was poured into a saturated sodium chloride solution (100 mL). The resulting suspension was extracted with EtOAc (3×50 mL). The combined organic extracts were washed with water (50 mL) and dried over solid anhydrous Na₂SO₄. The solvent was removed and the residue was purified by flash column chromatography using gradient elution from PE/EtOAc (99:1) to PE/EtOAc (6:1) to give 4,8-bis-methylamino-6-n-propylamino-pyrimido[5,4-d]pyrimidine-2-carbonitrile (102) (450 mg, 94%). 400 MHz ¹H NMR (CDCl₃, ppm): δ 6.74-6.55 (2H, m), 5.20-5.12 (1H, m), 3.46-3.38 (2H, m), 3.14 (3H, d, J=5.02 Hz), 3.07 (3H, d, J=4.8 Hz), 1.70-1.60 (2H, m), 1.00 (3H, t, J=7.4 Hz). ESI-MS (m/z): 373 [M+H]⁺.

4,8-Bis-methylamino-6-n-propylamino-pyrimido[5,4-d]pyrimidine-2-carbonitrile (102) (140 mg, 0.51 mmol) was treated with 2M HCl/diethyl ether in methanol using procedure described for compound (20a) (125 mg, 79% y). 400 MHz ¹H NMR (CDCl₃, ppm): δ 14.86 (1H, s), 8.50 (1H, br s), 7.68 (1H, br s), 7.17-7.07 (1H, m), 3.57-3.50 (2H, m), 3.26 (3H, d, J=5.2 Hz), 3.17 (3H, d, J=4.8 Hz), 1.75-1.65 (2H, m), 1.01 (3H, t, J=7.4 Hz). ESI-MS (m/z): 373 [M+H]⁺; melting point: 201-204° C.

Example 49

N⁴,N⁸-Dimethyl-N²-n-propyl-6-(aminomethyl)-pyrimido[5,4-d]pyrimidine-2,4,8-triamine (104) and corresponding hydrochloride salt (105a) (Scheme 20)

A mixture of 4,8-bis-methylamino-6-n-propylamino-pyrimido[5,4-d]pyrimidine-2-carbonitrile (102) (200 mg, 0.73 mmol) and Re—Ni (50% slurry in H₂O, 75 mg) in EtOH (10 mL) was hydrogenated at 10 atm for 90 min. The reaction mixture was filtered through Celite and the filtrate was evaporated. The residue was purified by flash column chromatography using gradient elution from CH₂Cl₂/MeOH (9/1) to (1:1) to give N⁴,N⁸-dimethyl-N²-n-propyl-6-aminomethyl-pyrimido[5,4-d]pyrimidine-2,4,8-triamine (104) (110 mg, 55% y). 400 MHz ¹H NMR (CDCl₃, ppm): δ 6.72-6.62 (1H, m), 6.56-6.47 (1H, m), 4.95-4.87 (1H, m), 3.87 (2H, s), 3.44-3.35 (2H, m), 3.13 (3H, d, J=5.1 Hz), 3.08 (3H, d, J=5.1 Hz), 1.83 (2H, s), 1.70-1.59 (2H, m), 1.00 (3H, t, J=7.4). MS (m/z): 277 [M+H]+.

N⁴,N⁸-Dimethyl-N²-n-propyl-N⁴,N⁸-dimethyl-6-aminomethyl-pyrimido[5,4-d]pyrimidine-2,4,8-triamine (104) (110 mg, 0.40 mmol) was treated with 2M HCl/diethyl ether in 1,4-dioxane using procedure described for compound (29a) in quantitative yield (125 mg, ~100% y). 400 MHz ¹H NMR (CDCl₃, ppm): δ 12.76 (1H, br s), 9.08-8.62 (1H, m), 8.50 (1H, s), 7.80 (3H, br s), 4.60 (2H, s), 3.60-3.52 (2H, m), 3.29-3.17 (6H, m), 1.76-1.64 (2H, m), 0.99 (3H, t, J=7.3). ESI-MS (m/z): 277 [M+H]⁺; melting point: 290° C. (dec.).

Example 50

6-Carbamoyl-N⁴,N⁸-dimethyl-N²-n-propyl-pyrimido[5,4-d]pyrimidine-2,4,8-triamine (106) and corresponding hydrochloride salt (107a) (Scheme 20)

A mixture of 4,8-bis-methylamino-6-n-propylamino-pyrimido[5,4-d]pyrimidine-2-carbonitrile (102) (230 mg, 0.84 mmol) and 0.2 N NaOH (3 mL) in 1,4-dioxane (3 mL) was heated at 100° C. for 1 h. Water (15 mL) was added and the resulting suspension was extracted with EtOAc (3×20 mL). The combined organic extracts were washed with water (50 mL), and then with a brine solution (50 mL), and dried over solid anhydrous $Na_2SO_4$. After filtration, the solvent was removed and the residue was purified by flash column chromatography using gradient elution from $CHCl_3$/EtOAc (9:1) to $CHCl_3$/EtOAc/MeOH (4:2:1) to give 6-carbamoyl-$N^4,N^8$-dimethyl-$N^2$-n-propyl-pyrimido [5,4-d]pyrimidine-2,4,8-triamine (106) (185 mg, 76% y). 400 MHz $^1$H NMR ($CDCl_3$, ppm): δ 7.86 (1H, s), 7.06-6.88 (1H, m), 6.70-6.53 (1H, m), 6.00-5.83 (1H, m), 5.10 (1H, t, J=5.7 Hz), 3.46-3.36 (2H, m), 3.16 (3H, d, J=5.1 Hz), 3.05 (3H, d, J=5.1 Hz), 1.65 (2H, sextet, J=7.4 Hz), 1.00 (3H, t, J=7.4 Hz). MS (m/z): 291 [M+H]$^+$.

6-Carbamoyl-$N^4,N^8$-dimethyl-$N^2$-n-propyl-pyrimido[5,4-d]pyrimidine-2,4,8-triamine (106) (150 mg, 0.52 mmol) was treated with 4M HCl/1,4-dioxane in 1,4-dioxane using procedure described for compound (20a) (140 mg, 82% y). 400 MHz $^1$H NMR ($CDCl_3$/trifluoroacetic acid, ppm): δ 8.46-8.34 (1H, m), 8.23 (1H, s), 8.00-7.83 (2H, m), 7.21-7.10 (1H, m), 3.62-3.54 (2H, m), 3.26 (3H, d, J=5.1 Hz), 3.21 (3H, s), 1.71 (2H, sextet, J=7.4 Hz), 1.00 (3H, t, J=7.4 Hz). ESI-MS (m/z): 291 [M+H]$^+$; melting point: >300° C.

Example 51

4,8-Bis-methylamino-6-n-propylamino-pyrimido[5,4-d]pyrimidine-2-carboxylic acid (108) (Scheme 20)

A mixture of 4,8-bis-methylamino-6-n-propylamino-pyrimido[5,4-d]pyrimidine-2-carbonitrile (102) (300 mg, 1.10 mmol) and 2N NaOH (3 mL) in 1,4-dioxane (3 mL) was heated at 105° C. for 20 h. The reaction mixture was acidified (pH 4) with 5% $KHSO_4$ solution. A white precipitate formed upon addition of $CH_2Cl_2$ (10 mL), and it was filtered and then purified by reverse phase chromatography using gradient elution from 0.1% HCOOH to 95% MeCN in 0.1% HCOOH to give 4,8-bis-methylamino-6-n-propylamino-pyrimido[5,4-d]pyrimidine-2-carboxylic acid (108) (130 mg, 41% y). 400 MHz $^1$H NMR (DMSO-$d_6$, ppm): δ 8.24 (1H, br s), 7.82 (1H, br s), 7.24 (1H, s), 3.02 (6H, d, J=4.8 Hz), 3.04-2.81 (2H, m), 1.64-1.48 (2H, m), 0.91 (3H, t, J=7.4 Hz). ESI-MS (m/z): 292 [M+H]$^+$; melting point: 218-220° C.

Example 52

N-(n-Propyl)-[4,8-Bis-methylamino-6-n-propylamino-pyrimido[5,4-d]pyrimidin-2-yl]-amidine (109) and corresponding hydrochloride salt (110a) (Scheme 20)

A mixture of 4,8-bis-methylamino-6-n-propylamino-pyrimido[5,4-d]pyrimidine-2-carbonitrile (102) (270 mg, 0.99 mmol), NaOAc (123 mg, 1.5 mmol) and n-propylamine (124 μL, 1.5 mmol) in MeOH (5 mL) was heated at 110° C. for 2 h. The volatiles were removed and the residue was partitioned between a saturated $NaHCO_3$ solution (15 mL) and $CHCl_3$ (15 mL). The aqueous phase was separated and extracted with $CHCl_3$ (2×15 mL). The combined organic extracts were washed with water (50 mL) and dried over solid anhydrous $Na_2SO_4$. After filtration, the solvent was removed, and the residue was purified reverse phase chromatography using gradient elution from 10% MeOH in water to 95% MeOH to give N-(n-propyl)-[4,8-Bis-methylamino-6-n-propylamino-pyrimido[5,4-d]pyrimidin-2-yl]-amidine (109) (160 mg, 49% y). 400 MHz $^1$H NMR ($CDCl_3$, ppm): δ 8.3-7.8 (1H, br s), 6.75-6.65 (1H, m), 6.63-6.52 (2H, m), 5.01 (1H, t, J=5.6 Hz), 3.52-3.37 (4H, m), 3.18 (3H, d, J=5.2 Hz), 3.11 (3H, d, J=5.2 Hz), 1.78-1.69 (2H, m), 1.69-1.60 (2H, m), 1.03 (3H, t, J=7.5 Hz), 1.01 (3H, t, J=7.5 Hz). ESI-MS (m/z): 332 [M+H]+.

N-(n-Propyl)-[4,8-bis-methylamino-6-n-propylamino-pyrimido[5,4-d]pyrimidin-2-yl]-amidine (109) (150 mg, 0.45 mmol) was treated with 2M HCl/diethyl ether in 1,4-dioxane using procedure described for compound (20a) (160 mg, 97% y). 400 MHz $^1$H NMR ($CDCl_3$, ppm): δ 10.09 (1H, s), 9.87-9.46 (1H, m), 9.19-8.62 (2H, m), 6.71 (1H, s), 5.14 (1H, s), 3.93-3.80 (2H, m), 3.51-3.34 (2H, m), 3.21-3.03 (6H, m), 1.90-1.77 (2H, m), 1.71-1.60 (2H, m), 1.04 (3H, t, J=7.4 Hz), 1.00 (3H, t, J=7.4 Hz). ESI-MS (m/z): 332 [M+H]$^+$; melting point: 172° C. (dec.).

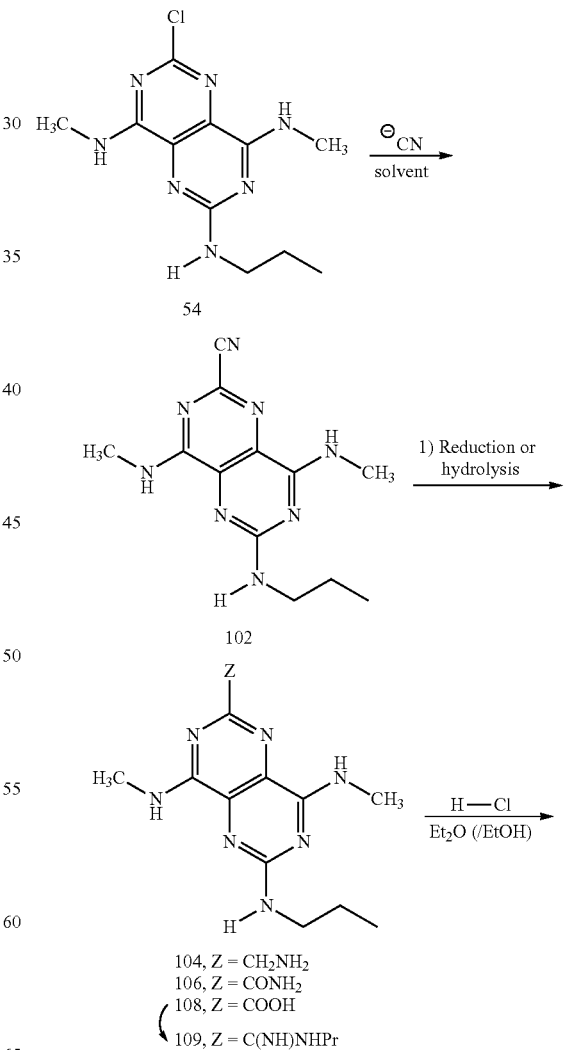

Scheme 20.

-continued

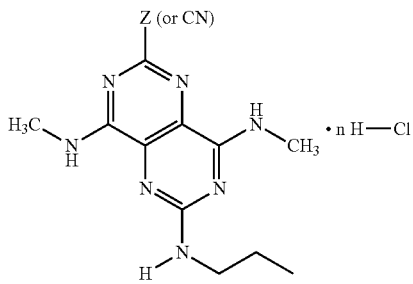

Example 53

N$^4$,N$^8$-Dimethyl-N$^2$-n-Propyl-6-(4-fluorophenyl)-pyrimido[5,4-d]pyrimidine-2,4,8-triamine (111) and corresponding hydrochloride salt (112a) (Scheme 21)

A mixture of 6-chloro-N$^2$-n-propyl-N$^4$,N$^8$-dimethyl-pyrimido[5,4-d]pyrimidine-2,4,8-triamine (54) (190 mg, 0.67 mmol), 4-fluorophenylboronic acid (141 mg, 1.01 mmol), 2M Na$_2$CO$_3$ solution (1.5 mL) and Pd(PPh$_3$)$_4$ (35 mg, 0.03 mmol) in dimethoxyethane was heated at 105° C. for 4 h under argon atmosphere. The reaction mixture was cooled, water (15 mL) was added, and the resulting suspension was extracted with EtOAc (3×15 mL). The combined organic extracts were washed with water (30 mL), and then with a brine solution (30 mL) and dried over solid anhydrous Na$_2$SO$_4$. After filtration, the solvent was removed and the residue was purified by flash column chromatography using gradient elution from PE/EtOAc (9:1) to PE/EtOAc (2:1) to give N$^4$,N$^8$-dimethyl-N$^2$-n-propyl-6-(4-fluoro-phenyl)-pyrimido[5,4-d]pyrimidine-2,4,8-triamine (111) (125 mg, 55% y). 400 MHz $^1$H NMR (CDCl$_3$, ppm): δ 8.48-8.42 (2H, m), 7.15-7.07 (2H, m), 6.83-6.75 (1H, m), 6.56-6.48 (1H, m), 4.94 (1H, t, J=5.6 Hz), 3.46-3.39 (2H, m), 3.24 (3H, d, J=5.0 Hz), 3.13 (3H, d, J=5.0 Hz), 1.72-1.62 (2H, m), 1.02 (3H, t, J=7.4 Hz). ESI-MS (m/z): 342 [M+H]$^+$.

N$^4$,N$^8$-Dimethyl-N$^2$-n-propyl-6-(4-fluoro-phenyl)-pyrimido[5,4-d]pyrimidine-2,4,8-triamine (111) (100 mg, 0.29 mmol) was treated with 2M HCl/diethyl ether in diethyl ether/methanol (10/1) using procedure described for compound (29a) in quantitative yield (110 mg, ~100% y). 400 MHz $^1$H NMR (DMSO-d$_6$, ppm): δ 13.2-12.7 (1H, br s), 9.60 (1H, br s), 8.66-8.59 (2H, m), 8.30 (1H, br s), 7.60 (1H, br s), 7.39-7.30 (2H, br s), 3.60-3.30 (2H, m, overlapped with water), 3.17-3.07 (6H, m), 1.70-1.60 (2H, m), 0.96 (3H, t, J=7.3 Hz). ESI-MS (m/z): 342 [M+H]$^+$; melting point: 270° C. (dec.).

Example 54

N$^2$-Methyl-N$^4$,N$^8$-di-n-propyl-6-(4-fluoro-phenyl)-pyrimido[5,4-d]pyrimidine-2,4,8-triamine (113) and corresponding hydrochloride salt (114a) (Scheme 21)

6-Chloro-N$^2$-methyl-N$^4$,N$^8$-di-n-propylpyrimido[5,4-d]pyrimidine-2,4,8-triamine (20) (250 mg, 0.81 mmol) and 4-fluorophenylboronic acid (166 mg, 1.2 mmol) were reacted using procedure described for compound (111) to produce N$^2$-methyl-N$^4$,N$^8$-di-n-propyl-6-(4-fluoro-phenyl)-pyrimido[5,4-d]pyrimidine-2,4,8-triamine (113) (200 mg, 67% y). 400 MHz $^1$H NMR (CDCl$_3$, ppm): δ 8.46-8.40 (2H, m), 7.15-7.08 (2H, m), 6.83 (1H, t, J=5.7 Hz), 6.60 (1H, t, J=5.7 Hz), 4.91-4.82 (1H, m), 3.69-3.62 (2H, m), 3.56-3.49 (2H, m), 3.03 (3H, d, J=5.1 Hz), 1.84-1.69 (4H, m), 1.06 (3H, t, J=7.5 Hz), 1.04 (3H, t, J=7.5 Hz). ESI-MS (m/z): 370 [M+H]$^+$.

N$^2$-Methyl-N$^4$,N$^8$-di-n-propyl-6-(4-fluorophenyl)-pyrimido[5,4-d]pyrimidine-2,4,8-triamine (113) (190 mg, 0.51 mmol) was treated with 2M HCl/diethyl ether in ethanol using procedure described for compound (29a) (207 mg, ~100% y). 400 MHz $^1$H NMR (CDCl$_3$, ppm): δ 8.42-8.35 (2H, m), 7.98-7.88 (1H, m), 7.88-7.79 (1H, m), 7.19-7.10 (2H, m), 6.99-6.88 (1H, m), 3.75-3.62 (4H, m), 3.11 (3H, d, J=4.8 Hz), 1.92-1.75 (4H, m), 1.08 (6H, t, J=7.4 Hz). ESI-MS (m/z): 370 [M+H]$^+$; melting point: 277-279° C.

Scheme 21.

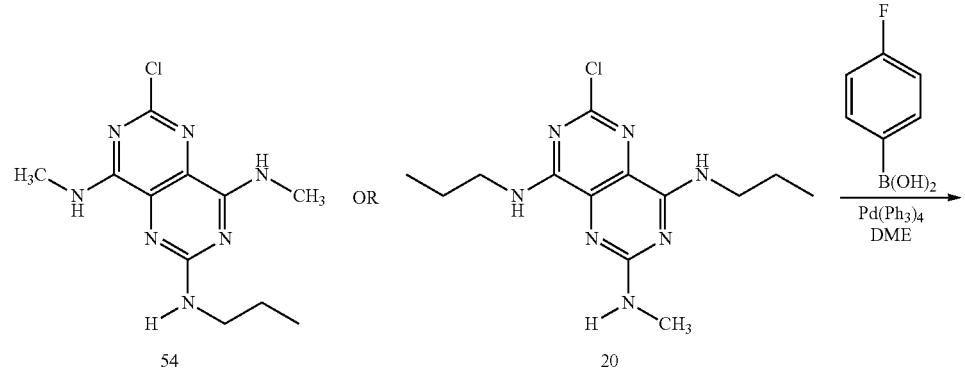

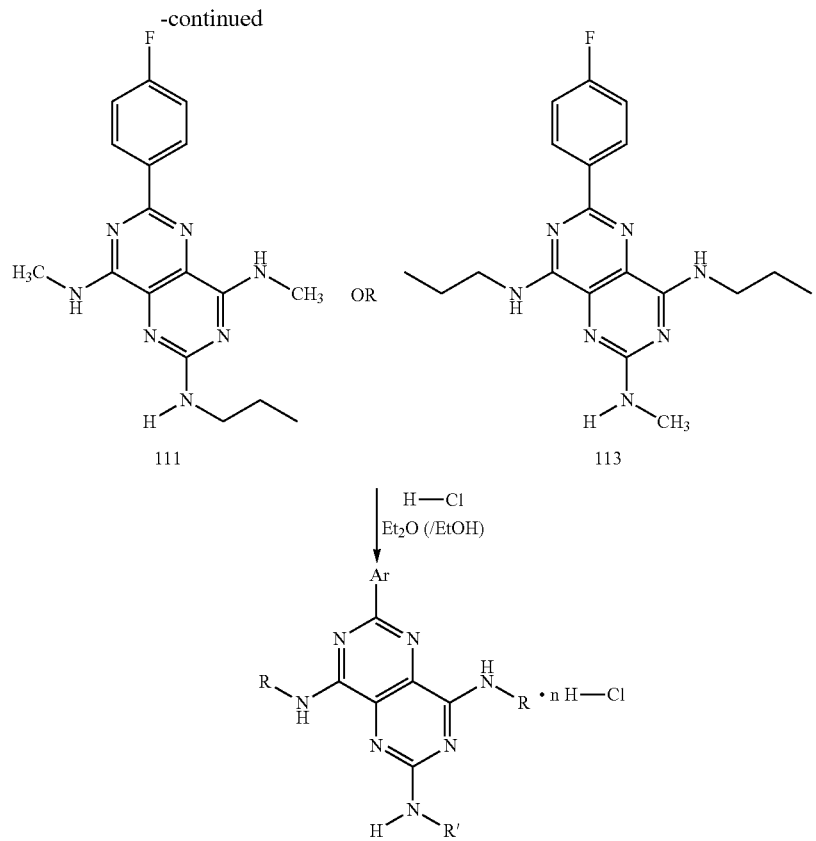

Example 55

N⁴,N⁸-Dimethyl-N²-n-propyl-pyrimido[5,4-d]pyrimidine-2,4,8-triamine (115) and corresponding hydrochloride salt (116a)

A mixture of 6-chloro-N²-n-propyl-N⁴,N⁸-dimethyl-pyrimido[5,4-d]pyrimidine-2,4,8-triamine (54) (440 mg, 1.42 mmol), triethylamine (185 μL, 1.32 mmol) and 10% Pd/C (160 mg) in EtOH (10 mL) was hydrogenated at 10 atmospheres for 24 h. The reaction mixture was filtered through Celite, and the filtrate was evaporated. The residue was dissolved in EtOAc (80 mL), washed with water (3×30 mL), and then with a brine solution (30 mL) and dried over solid anhydrous $Na_2SO_4$. After filtration, the solvent was removed; the residue was purified by flash column chromatography using gradient elution from PE/EtOAc (9:1) to PE/EtOAc (1:2) to give N⁴,N⁸-dimethyl-N²-n-propyl-pyrimido[5,4-d]pyrimidine-2,4,8-triamine (115) (185 mg, 84% y). 400 MHz ¹H NMR ($CDCl_3$, ppm): δ 8.26 (1H, s), 6.65 (1H, br s), 6.55 (1H, br s), 4.96 (1H, t, J=5.4 Hz), 3.44-3.37 (2H, m), 3.14 (3H, d, J=5.1 Hz), 3.07 (3H, d, J=5.0 Hz), 1.70-1.59 (2H, m), 1.00 (3H, t, J=7.4 Hz). ESI-MS (m/z): 248 [M+H]⁺.

N⁴,N⁸-Dimethyl-N²-n-propyl-pyrimido[5,4-d]pyrimidine-2,4,8-triamine (115) (175 mg, 0.71 mmol) was treated with 2M HCl/diethyl ether in diethyl ether using procedure described for compound (29a) in quantitative yield (200 mg, ~100% y). 400 MHz ¹H NMR ($CDCl_3$, ppm): δ 8.97-8.60 (2H, m), 8.43 (1H, s), 7.02-6.94 (1H, m), 3.52 (2H, td, J=6.8, 6.4 Hz), 3.24 (3H, d, J=5.1 Hz), 3.22 (3H, d, J=4.7 Hz), 1.75-1.64 (2H, m), 1.01 (3H, t, J=7.4 Hz). ESI-MS (m/z): 248 [M+H]⁺; melting point: 180-182° C.

Example 56

6-n-Butyl-N²-methyl-N⁴,N⁸-di-n-propyl-pyrimido[5,4-d]pyrimidine-2,4,8-triamine (117) and corresponding hydrochloride salt (118a)

A mixture of 6-chloro-N²-methyl-N⁴,N⁸-di-n-propylpyrimido[5,4-d]pyrimidine-2,4,8-triamine (20) (400 mg, 1.29 mmol), butylboronic acid (223 mg, 2.19 mmol), $K_2CO_3$ (535 mg, 3.87 mmol), $Ag_2O$ (748 mg, 3.23 mmol) and Pd(dppf)$Cl_2$×$CH_2Cl_2$ (114 mg, 0.14 mmol) in THF (1.0 mL) and 1,4-dioxane (7.0 mL) was heated at 115° C. for 20 h under argon atmosphere. Butylboronic acid (120 mg, 1.18 mmol) and Pd(dppf)$Cl_2$×$CH_2Cl_2$ (60 mg, 0.07 mmol) were added and heating was continued for 48 h. The reaction mixture was cooled and filtered through Celite. A saturated $NaHCO_3$ solution (20 mL) was added to the filtrate and the resulting suspension was extracted with $CH_2Cl_2$ (2×20 mL). The combined organic extracts were washed with water (30 mL) and dried over solid anhydrous $Na_2SO_4$. After filtration, the solvent was removed and the residue was purified by flash column chromatography using gradient elution from PE/EtOAc (20:1) to PE/EtOAc (5:2) to give 6-n-butyl-N²-methyl-N⁴,N⁸-di-n-propyl-pyrimido[5,4-d]pyrimidine-2,4,8-triamine (117) (240 mg, 56% y). 400 MHz H NMR ($CDCl_3$, ppm): δ 6.78-6.65 (1H, m), 6.52-6.42 (1H, m), 4.82-4.71 (1H, m), 3.57-3.50 (2H, m), 3.50-3.43 (2H, m), 2.99 (3H, d, J=5.1 Hz), 2.75-2.68 (2H, m), 1.83-1.65 (6H, m), 1.46-1.36 (2H, m), 1.01 (3H, t, J=7.3 Hz), 1.00 (3H, t, J=7.3 Hz), 0.95 (3H, t, J=7.4 Hz). ESI-MS (m/z): 332 [M+H]⁺.

6-n-Butyl-N²-methyl-N⁴,N⁸-di-n-propyl-pyrimido[5,4-d]pyrimidine-2,4,8-triamine (117 (230 mg, 0.69 mmol) was treated with 2M HCl/diethyl ether in diethyl ether using procedure described for compound (29a) (255 mg, ~100% y). 400 MHz $^1$H NMR (CDCl$_3$, ppm): δ 7.84-7.54 (2H, m), 6.88 (1H, br s), 3.71-3.51 (4H, m), 3.08 (3H, d, J=4.5 Hz), 2.83-2.63 (2H, m), 1.85-1.70 (6H, m), 1.47-1.34 (2H, m), 1.09-0.99 (6H, m), 0.95 (3H, t, J=7.3). ESI-MS (m/z): 332 [M+H]$^+$; melting point: 125-127° C.

Example 57

6-Methoxy-N$^2$-methyl-N$^4$,N$^8$-di-n-propyl-pyrimido[5,4-d]pyrimidine-2,4,8-triamine (119) and corresponding hydrochloride salt (120a)

A mixture of 6-chloro-N$^2$-methyl-N$^4$,N$^8$-di-n-propylpyrimido[5,4-d]pyrimidine-2,4,8-triamine (20) (300 mg, 0.97 mmol) and NaOMe (4M in MeOH; 620 µL) in methanol (5 mL) was heated at 105° C. for 48 h. The volatiles were removed and the residue was partitioned between a saturated NH$_4$Cl solution (30 mL) and CH$_2$Cl$_2$ (30 mL). The aqueous phase was separated and extracted with CH$_2$Cl$_2$ (2×30 mL). The combined organic extracts were washed with water (50 mL) and dried over solid anhydrous Na$_2$SO$_4$. After filtration, the solvent was removed and the residue was purified by flash column chromatography using gradient elution from CH$_2$Cl$_2$ to CH$_2$Cl$_2$/MeOH (97:3) to give 6-methoxy-N$^2$-methyl-N$^4$,N$^8$-di-n-propyl-pyrimido[5,4-d]pyrimidine-2,4,8-triamine (119) (225 mg, 76% y). 400 MHz $^1$H NMR (CDCl$_3$, ppm): δ 6.72-6.63 (1H, m), 6.51-6.43 (1H, m), 4.75-4.67 (1H, m), 3.95 (3H, s), 3.57-3.50 (2H, m), 3.50-3.44 (2H, m), 2.99 (3H, d, J=5.0 Hz), 1.77-1.64 (4H, m), 1.01 (3H, t, J=7.4 Hz), 1.00 (3H, t, J=7.4 Hz). ESI-MS (m/z): 306 [M+H]$^+$.

6-Methoxy-N$^2$-methyl-N$^4$,N$^8$-di-n-propyl-pyrimido[5,4-d]pyrimidine-2,4,8-triamine (119) (210 mg, 0.69 mmol) was treated with 2M HCl/diethyl ether in ethanol using procedure described for compound (29a) (235 mg, ~100% y). 400 MHz $^1$H NMR (CDCl$_3$, ppm): δ 8.38 (1H, s), 8.05 (1H, br s), 6.70 (1H, s), 4.00 (3H, m), 3.68-3.61 (4H, m), 3.08 (3H, d, J=4.1 Hz), 1.87-1.70 (4H, m), 1.04 (3H, t, J=7.3 Hz), 1.03 (3H, t, J=7.3 Hz). ESI-MS (m/z): 306 [M+H]$^+$; melting point: 201-204° C.

Example 58

6-Methylamino-4,8-bis-n-propylamino-pyrimido[5,4-d]pyrimidine-2-carbonitrile (121) and corresponding hydrochloride salt (122a)

6-Chloro-N$^2$-methyl-N$^4$,N$^8$-di-n-propylpyrimido[5,4-d]pyrimidine-2,4,8-triamine (20) (250 mg, 0.81 mmol) and KCN were reacted the using procedure described for compound (102) to produce 6-methylamino-4,8-bis-n-propylamino-pyrimido[5,4-d]pyrimidine-2-carbonitrile (121) (170 mg, 70% y). 400 MHz $^1$H NMR (CDCl$_3$, ppm): δ 6.71 (1H, br s), 6.64 (1H, br s), 5.10-5.03 (1H, m), 3.57-3.51 (2H, m), 3.51-3.42 (2H, m), 3.02 (3H, d, J=5.0 Hz), 1.77-1.64 (4H, m), 1.02 (3H, t, J=7.4 Hz), 1.01 (3H, t, J=7.4 Hz). ESI-MS (m/z): 301 [M+H]$^+$.

6-Methylamino-4,8-bis-n-propylamino-pyrimido[5,4-d]pyrimidine-2-carbonitrile (121) (160 mg, 0.53 mmol) was treated with 2M HCl/diethyl ether in methanol using procedure described for compound (20a) (130 mg, 73% y). 400 MHz $^1$H NMR (CDCl$_3$, ppm): δ 14.91 (0.8H, s), 14.64 (0.2H, s), 8.44 (0.8H, s), 8.34 (0.2H, s), 7.71-7.56 (1H, m), 7.07 (0.8H, s), 6.88 (0.2H, s), 3.69-3.63 (2H, m), 3.63-3.54 (2H, m), 3.16-3.07 (3H, m), 1.86-1.72 (4H, m), 1.06 (3H, t, J=7.4 Hz), 1.04 (3H, t, J=7.4 Hz). ESI-MS (m/z): 301 [M+H]$^+$; melting point: 204-206° C.

Example 59

N$^2$,N$^4$,N$^6$,N$^8$-Tetraethyl-pyrimido[5,4-d]pyrimidine-2,4,6,8-tetraamine (124) and corresponding hydrochloride salt (125a)

2,6-Dichloro-N$^4$,N$^8$-diethyl-pyrimido[5,4-d]pyrimidine-4,8-diamine (123)

A 2M ethylamine/THF (6.69 mL, 13.38 mmol) solution was added to a solution of 2,4,6,8-tetrachloro-pyrimido[5,4-d]pyrimidine (1) (800 mg, 2.96 mmol) in THF (10 mL) at 0° C. The reaction mixture was stirred at room temperature for 1 h. Water (30 mL) was added and the resultant precipitate was filtered, washed with water (10 mL) and dried over P$_2$O$_5$ to give 2,6-dichloro-N$^4$,N$^8$-diethyl-pyrimido[5,4-d]pyrimidine-4,8-diamine (123) (745 mg, 88%). 400 MHz $^1$H NMR (CDCl$_3$, ppm): δ 6.87 (2H, br s), 3.63 (4H, qd, J=7.3, 5.9 Hz), 1.32 (6H, t, J=7.3 Hz). ESI-MS (m/z): 287, 289, 291 [M+H]$^+$.

N$^2$,N$^4$,N$^6$,N$^8$-Tetraethyl-pyrimido[5,4-d]pyrimidine-2,4,6,8-tetraamine (124)

A mixture of 2,6-dichloro-N$^4$,N$^8$-diethyl-pyrimido[5,4-d]pyrimidine-4,8-diamine (123) and ethylamine (70% water solution, 2.00 mL) in n-butanol (3 mL) was heated at 100° C. for 44 h. The volatiles were removed by evaporation and the residue was partitioned between CH$_2$Cl$_2$ (20 mL) and a saturated NaHCO$_3$ solution (20 mL). The aqueous phase was separated and extracted with CH$_2$Cl$_2$ (2×20 mL). The combined organic extracts were washed with water (50 mL) and dried over solid anhydrous Na$_2$SO$_4$. After filtration, the solvent was removed and the residue was purified by flash column chromatography using gradient elution from CH$_2$Cl$_2$ to CH$_2$Cl$_2$/EtOH (98:2) to give N$^2$,N$^4$,N$^6$,N$^8$-tetraethyl-pyrimido[5,4-d]pyrimidine-2,4,6,8-tetraamine (124) (233 mg, 91% y). 400 MHz $^1$H NMR (CDCl$_3$, ppm): δ 6.42 (2H, s), 4.58 (2H, s), 3.57-3.48 (4H, m), 3.46-3.39 (4H, m), 1.28 (6H, t, J=7.3 Hz), 1.23 (6H, t, J=7.3 Hz). ESI-MS (m/z): 305 [M+H]$^+$.

N$^2$,N$^4$,N$^6$,N$^8$-Tetraethyl-pyrimido[5,4-d]pyrimidine-2,4,6,8-tetraamine hydrochloride (125a)

N$^2$,N$^4$,N$^6$,N$^8$-tetraethyl-pyrimido[5,4-d]pyrimidine-2,4,6,8-tetraamine (124) (220 mg, 0.72 mmol) was treated with 4M HCl/1,4-dioxane in 1,4-dioxane/EtOH (1/1) using procedure described for compound (29a) (245 mg, ~100% y). 400 MHz $^1$H NMR (CDCl$_3$, ppm): δ 9.63 (2H, s), 6.67 (2H, t, J=5.6 Hz), 3.74-3.66 (4H, m), 3.57-3.50 (4H, m), 1.41 (6H, t, J=7.3 Hz), 1.27 (6H, t, J=7.3 Hz). ESI-MS (m/z): 305 [M+H]$^+$; melting point: 247° C. (dec.).

Example 60

N$^4$,N$^8$-Diethyl-N$^2$,N$^6$-di-n-propyl-pyrimido[5,4-d]pyrimidine-2,4,6,8-tetraamine (126) and corresponding hydrochloride salt (127a)

A mixture of 2,6-dichloro-N$^4$,N$^8$-diethyl-pyrimido[5,4-d]pyrimidine-4,8-diamine (123) (245 mg, 0.85 mmol) and n-propylamine (352 µL, 4.27 mmol) in n-butanol (5.0 mL) was heated at 130° C. for 44 h. The volatiles were removed by evaporation, and the residue was partitioned between $CH_2Cl_2$ (20 mL) and a saturated $NaHCO_3$ solution (20 mL). The aqueous phase was separated and extracted with $CH_2Cl_2$ (2×20 mL). The combined organic extracts were washed with water (50 mL) and dried over solid anhydrous $Na_2SO_4$. After filtration, the solvent was removed and the residue was purified by flash column chromatography using gradient elution from $CH_2Cl_2$ to $CH_2Cl_2$/EtOH (98:2) to give $N^4,N^8$-diethyl-$N^2,N^6$-di-n-propyl-pyrimido[5,4-d]pyrimidine-2,4,6,8-tetraamine (126) (220 mg, 78% y). 400 MHz $^1$H NMR (CDCl$_3$, ppm): δ 6.48-6.37 (2H, m), 4.64 (2H, s), 3.57-3.48 (4H, m), 3.39-3.32 (4H, m), 1.67-1.57 (4H, m), 1.32-1.24 (6H, m), 1.02-0.96 (6H, m). ESI-MS (m/z): 333 [M+H]$^+$.

$N^4,N^8$-Diethyl-$N^2,N^6$-di-n-propyl-pyrimido[5,4-d]pyrimidine-2,4,6,8-tetraamine (126) (220 mg, 0.66 mmol) was treated with 4M HCl/1,4-dioxane in 1,4-dioxane/EtOH (1/1) using procedure described for compound (29a) (244 mg, ~100% y). 400 MHz $^1$H NMR (CDCl$_3$, ppm): δ 9.58 (2H, s), 6.75-6.68 (2H, m), 3.74-3.64 (4H, m), 3.49-3.41 (4H, m), 1.71-1.63 (4H, m), 1.41 (6H, t, J=7.2 Hz), 0.98 (6H, t, J=7.4 Hz). ESI-MS (m/z): 333 [M+H]$^+$; melting point: 248° C. (dec.).

Example 61

$N^2,N^6$-Bis-cyclopropylmethyl-$N^4,N^8$-diethyl-pyrimido[5,4-d]pyrimidine-2,4,6,8-tetraamine (128) and corresponding hydrochloride salt (129a)

A mixture of 2,6-dichloro-$N^4,N^8$-diethyl-pyrimido[5,4-d]pyrimidine-4,8-diamine (123) (245 mg, 0.85 mmol) and cyclopropylmethylamine (370 μL, 4.27 mmol) in n-butanol (5.0 mL) was heated in a closed vial at 130° C. for 44 h. The volatiles were removed by evaporation, and the residue was partitioned between $CH_2Cl_2$ (20 mL) and a saturated $NaHCO_3$ solution (20 mL). The aqueous phase was separated and extracted with $CH_2Cl_2$ (2×20 mL). The combined organic extracts were washed with water (50 mL) and dried over solid anhydrous $Na_2SO_4$. After filtration, the solvent was removed and the residue was purified by flash column chromatography using gradient elution from $CH_2Cl_2$ to $CH_2Cl_2$/MeOH (9:1) to give $N^2,N^6$-bis-cyclopropylmethyl-$N^4,N^8$-diethyl-pyrimido[5,4-d]pyrimidine-2,4,6,8-tetraamine (128) (135 mg, 45% y). 400 MHz $^1$H NMR (CDCl$_3$, ppm): δ 7.03-6.98 (2H, m), 6.10-6.03 (2H, m), 3.48-3.40 (4H, m), 3.21-3.14 (4H, m), 1.20-1.13 (6H, m), 1.09-1.02 (2H, m), 0.44-0.36 (4H, m), 0.23-0.18 (4H, m). ESI-MS (m/z): 357 [M+H]$^+$.

$N^2,N^6$-Bis-cyclopropylmethyl-$N^4,N^8$-diethyl-pyrimido[5,4-d]pyrimidine-2,4,6,8-tetraamine (128) (135 mg, 0.66 mmol) was treated with 4M HCl/1,4-dioxane in 1,4-dioxane/EtOH (1/1) using procedure described for compound (29a) (148 mg, ~100% y). 400 MHz $^1$H NMR (CDCl$_3$, ppm): δ 9.66 (2H, s), 6.78 (2H, s), 3.76-3.64 (4H, m), 3.39-3.36 (4H, m), 1.45-1.38 (6H, m), 1.13-1.04 (2H, m), 0.63-0.56 (4H, m), 0.31-0.26 (4H, m). ESI-MS (m/z): 357 [M+H]$^+$; melting point: 243-245° C.

Example 62

$N^2,N^6$-Diethyl-$N^4,N^8$-bis-cyclopropylmethyl-pyrimido[5,4-d]pyrimidine-2,4,6,8-tetraamine (131) and corresponding hydrochloride salt (132a)

2,6-Dichloro-$N^4,N^8$-bis-cyclopropylmethyl-pyrimido[5,4-d]pyrimidine-2,4,6,8-tetraamine (130)

Cyclopropylmethylamine (802 μL, 9.25 mmol) was added to a solution of 2,4,6,8-tetrachloro-pyrimido[5,4-d]pyrimidine (1) (500 mg, 1.85 mmol) in THF (8 mL) at 0° C. The reaction mixture was stirred at room temperature for 3 h. Water (30 mL) was then added and the resulting suspension was extracted with $CH_2Cl_2$ (3×20 mL). The combined organic extracts were washed with water (50 mL) and dried over solid anhydrous $Na_2SO_4$. After filtration, the solvent was removed and the residue was triturated with diethyl ether. The resultant precipitate were filtered and dried to give 2,6-dichloro-$N^4,N^8$-bis-cyclopropylmethyl-pyrimido[5,4-d]pyrimidine-2,4,6,8-tetraamine (130) (480 mg, 76% y). 400 MHz $^1$H NMR (CDCl$_3$, ppm): δ 6.96 (2H, t, J=5.7 Hz), 3.42 (4H, dd, J=7.3, 5.7 Hz), 1.16-1.05 (2H, m), 0.66-0.53 (4H, m), 0.38-0.25 (4H, m). ESI-MS (m/z): 339, 341, 343 [M+H]$^+$.

$N^2,N^6$-Diethyl-$N^4,N^8$-bis-cyclopropylmethyl-pyrimido[5,4-d]pyrimidine-2,4,6,8-tetraamine (131)

A mixture of 2,6-dichloro-$N^4,N^8$-bis-cyclopropylmethyl-pyrimido[5,4-d]pyrimidine-2,4,6,8-tetraamine (130) (220 mg, 0.65 mmol) and ethylamine (70% water solution, 1.00 mL) in 1,4-dioxane (5.0 mL) was heated at 130° C. for 144 h. The volatiles were removed by evaporation, and the residue was partitioned between $CH_2Cl_2$ (20 mL) and a saturated $NaHCO_3$ solution (20 mL). The aqueous phase was extracted with $CH_2Cl_2$ (2×30 mL). The combined organic extracts were washed with water (50 mL) and dried over solid anhydrous $Na_2SO_4$. After filtration, the solvent was removed and the residue was purified by flash column chromatography using gradient elution from PE/EtOAc (5:1) to PE/EtOAc (1:1) to give $N^2,N^6$-diethyl-$N^4,N^8$-bis-cyclopropylmethyl-pyrimido[5,4-d]pyrimidine-2,4,6,8-tetraamine (131) (190 mg, 82%). 400 MHz $^1$H NMR (DMSO-d$_6$+TFA, ppm): δ 3.45-3.32 (8H, m), 1.17-1.08 (8H, m), 0.52-0.45 (4H, m), 0.31-0.25 (4H, m). ESI-MS (m/z): 357 [M+H]$^+$.

$N^2,N^6$-Diethyl-$N^4$,N-bis-cyclopropylmethyl-pyrimido[5,4-d]pyrimidine-2,4,6,8-tetraamine hydrochloride (132a)

$N^2,N^6$-Diethyl-$N^4,N^8$-bis-cyclopropylmethyl-pyrimido[5,4-d]pyrimidine-2,4,6,8-tetraamine (131) (170 mg, 0.45 mmol) was treated with 2M HCl/diethyl ether in 1,4-dioxane using procedure described for compound (20a) (140 mg, 74% y). 400 MHz $^1$H NMR (CDCl$_3$, ppm): δ 14.90 (0.5H, s), 13.94 (1H, s), 9.70 (0.5H, s), 7.84 (0.5H, s), 7.53 (1H, s), 6.71 (1H, m), 4.80 (0.5H, s), 3.61-3.31 (8H, m), 1.33-1.08 (8H, m), 0.72-0.52 (4H, m), 0.44-0.28 (4H, m). ESI-MS (m/z): 357 [M+H]$^+$; melting point: 198-200° C.

Example 63

$N^2,N^2,N^6$-Triethyl-$N^4,N^8$-bis-cyclopropylmethyl-pyrimido[5,4-d]pyrimidine-2,4,6,8-tetraamine (134) and corresponding hydrochloride salt (135a)

6-Chloro-$N^2$-ethyl-$N^4,N^8$-bis-cyclopropylmethyl-pyrimido[54-d]pyrimidine-2,4,8-triamine (133)

A mixture of 2,6-dichloro-$N^4,N^8$-bis-cyclopropylmethyl-pyrimido[5,4-d]pyrimidine-2,4,6,8-tetraamine (130) (235 mg, 0.71 mmol) and ethylamine (70% water solution, 1.00 mL) in n-butanol (5.0 mL) was heated at 80° C. for 18 h. The volatiles were removed by evaporation and the residue was partitioned between $CH_2Cl_2$ (20 mL) and a saturated $NaHCO_3$ solution (20 mL). The aqueous phase was separated and extracted with CH$_2$Cl$_2$ (2×30 mL). The combined organic extracts were washed with water (50 mL) and dried over solid anhydrous Na$_2$SO$_4$. After filtration, the solvent was removed to give 6-chloro-N$^2$-ethyl-N$^4$,N$^8$-bis-cyclopropylmethyl-pyrimido[5,4-d]pyrimidine-2,4,8-triamine (133) (247 mg, 100%). ESI-MS (m/z): 348, 350 [M+H]$^+$.

N$^2$,N$^2$,N$^6$-Triethyl-N$^4$,N$^8$-bis-cyclopropylmethyl-pyrimido[5,4-d]pyrimidine-2,4,6,8-tetraamine (134)

A mixture of 6-chloro-N$^2$-ethyl-N$^4$,N$^8$-bis-cyclopropylmethyl-pyrimido[5,4-d]pyrimidine-2,4,8-triamine (133) (243 mg, 0.70 mmol) and diethylamine (1.0 mL) in n-butanol (4.0 mL) was heated in a closed vial at 130° C. for 110 h. The volatiles were removed by evaporation and the residue was partitioned between CH$_2$Cl$_2$ (35 mL) and a saturated NaHCO$_3$ solution (30 mL). The aqueous phase was separated and extracted with CH$_2$Cl$_2$ (2×30 mL). The combined organic extracts were washed with water (40 mL) and dried over solid anhydrous Na$_2$SO$_4$. The solvent was removed and the residue was purified by flash column chromatography using gradient elution from PE/EtOAc (9:1) to PE/EtOAc (1:1) to give N$^2$,N$^2$,N$^6$-triethyl-N$^4$,N$^8$-bis-cyclopropylmethyl-pyrimido[5,4-d]pyrimidine-2,4,6,8-tetraamine (134) (210 mg, 78% y). 400 MHz $^1$H NMR (CDCl$_3$, ppm): δ 6.74-6.29 (2H, m), 4.49 (1H, br s), 3.72-3.55 (4H, m), 3.51-3.26 (6H, m), 1.29-1.08 (11H, m), 0.62-0.48 (4H, m), 0.38-0.25 (4H, m). ESI-MS (m/z): 385 [M+H]$^+$.

N$^2$,N$^2$,N$^6$-Triethyl-N$^4$,N$^8$-bis-cyclopropylmethyl-pyrimido[5,4-d]pyrimidine-2,4,6,8-tetraamine hydrochloride (135a)

N$^2$,N$^2$,N$^6$-triethyl-N$^4$,N$^8$-bis-cyclopropylmethyl-pyrimido[5,4-d]pyrimidine-2,4,6,8-tetraamine (134) (190 mg, 0.49 mmol) and 2M HCl/diethyl ether in 1,4-dioxane using procedure described for compound (20a) (170 mg, 82% y). 400 MHz $^1$H NMR (CDCl$_3$, ppm): δ 13.91 (1H, s), 7.73 (1H, s), 7.56-7.47 (1H, m), 6.71-6.60 (1H, m), 3.60 (4H, q, J=7.1 Hz), 3.55-3.45 (4H, m), 3.40 (2H, dd, J=7.0, 5.2 Hz), 1.27-1.11 (2H, m), 1.25 (3H, t, J=7.0 Hz), 1.19 (6H, t, J=7.2 Hz), 0.66-0.60 (2H, m), 0.60-0.54 (2H, m), 0.38-0.29 (4H, m). ESI-MS (m/z): 385 [M+H]$^+$; melting point: 215-217° C.

Example 64

N$^2$,N$^6$-Diethyl-N$^4$,N$^8$-di-n-propyl-pyrimido[5,4-d]pyrimidine-2,4,6,8-tetraamine (136) and corresponding hydrochloride salt (137a)

2,6-Dichloro-N$^4$,N$^8$-di-n-propyl-pyrimido[5,4-d]pyrimidine-4,8-diamine (2) (250 mg, 0.79 mmol) and ethylamine (70% water solution) were reacted using procedure described for compound (32) to produce N$^2$,N$^6$-diethyl-N$^4$,N$^8$-di-n-propyl-pyrimido[5,4-d]pyrimidine-2,4,6,8-tetraamine (136) (175 mg, 67% y). 400 MHz $^1$H NMR (CDCl$_3$, ppm): δ 6.48 (2H, s), 4.55 (2H, s), 3.49-3.38 (8H, m), 1.69 (4H, sextet, J=7.4 Hz), 1.23 (6H, t, J=7.4 Hz), 1.00 (6H, t, J=7.4 Hz). ESI-MS (m/z): 333 [M+H]$^+$.

N$^2$,N$^6$-Diethyl-N$^4$,N$^8$-di-n-propyl-pyrimido[5,4-d]pyrimidine-2,4,6,8-tetraamine (136) (160 mg, 0.48 mmol) was treated with 2M HCl/diethyl ether in 1,4-dioxane using procedure described for compound (20a) (155 mg, 87% y). 400 MHz $^1$H NMR (CDCl$_3$, ppm): δ 13.92 (1H, s), 7.69 (1H, s), 7.47 (1H, s), 6.67 (1H, s), 4.80 (1H, s), 3.64-3.30 (8H, m), 1.82-1.68 (4H, m), 1.29-1.18 (6H, m), 1.02 (6H, t, J=7.4 Hz). ESI-MS (m/z): 333 [M+H]$^+$; melting point: 190-192° C.

Example 65

N$^2$,N$^6$-Dicyclopropyl-N$^4$,N$^8$-di-n-propyl-pyrimido[5,4-d]pyrimidine-2,4,6,8-tetraamine (138)

A mixture of 2,6-dichloro-N$^4$,N$^8$-di-n-propyl-pyrimido[5,4-d]pyrimidine-4,8-diamine (2) (300 mg, 0.95 mmol) and cyclopropylamine (396 µL, 5.71 mmol) in n-butanol (3.0 mL) was heated in a closed vial at 130° C. for 72 h. An additional portion of cyclopropylamine (263 µL, 3.80 mmol) was added and heating was continued for 48 h at 130° C. The volatiles were removed by evaporation and the residue was partitioned between CH$_2$Cl$_2$ (35 mL) and a saturated NaHCO$_3$ solution (30 mL). The aqueous phase was separated and extracted with CH$_2$Cl$_2$ (2×30 mL). The combined organic extracts were washed with water (40 mL) and dried over solid anhydrous Na$_2$SO$_4$. After filtration, the solvent was removed and the residue was purified by flash column chromatography using gradient elution from CH$_2$Cl$_2$ to CH$_2$Cl$_2$/EtOAc (1:1) to give N$^2$,N$^6$-dicyclopropyl-N$^4$,N$^8$-di-n-propyl-pyrimido[5,4-d]pyrimidine-2,4,6,8-tetraamine (138) (66 mg, 19% y). 400 MHz $^1$H NMR (DMSO-d$_6$, ppm): δ 6.93-6.88 (2H, m), 6.36-6.33 (2H, m), 3.41-3.34 (4H, m), 2.85-2.77 (2H, m), 1.60 (4H, sextet, J=7.3 Hz), 0.90 (6H, t, J=7.3 Hz), 0.64-0.57 (4H, m), 0.46-0.41 (4H, m). ESI-MS (m/z): 357 [M+H]$^+$; melting point: 210-212° C.

Example 66

N$^2$,N$^6$-Bis-cyclopropylmethyl-N$^4$,N$^8$-di-n-propyl-pyrimido[5,4-d]pyrimidine-2,4,6,8-tetraamine (139) and corresponding hydrochloride salt (140a)

A mixture of 2,6-dichloro-N,N'-di-n-propyl-pyrimido[5,4-d]pyrimidine-4,8-diamine (2) (300 mg, 0.95 mmol) and cyclopropylmethylamine (1.0 mL, 11.53 mmol) in DMSO (1.0 mL) was heated in a closed vial at 145° C. for 22 h. Water (10 mL) was added and the resultant precipitate were filtered and dried to give N$^2$,N$^6$-bis-cyclopropylmethyl-N$^4$,N$^8$-di-n-propyl-pyrimido[5,4-d]pyrimidine-2,4,6,8-tetraamine (139) (320 mg, 88% y). 400 MHz $^1$H NMR (DMSO-d6/trifluoroacetic acid, ppm): δ 9.0-7.0 (4H, br s), 3.50-3.40 (4H, m), 3.26 (4H, d, J=7.0 Hz), 1.69-1.58 (4H, m), 1.13-1.02 (2H, m), 0.93 (6H, t, J=7.4 Hz), 0.50-0.38 (4H, m), 0.31-0.19 (4H, m). ESI-MS (m/z): 385 [M+H]$^+$.

N$^2$,N$^6$-bis-cyclopropylmethyl-N$^4$,N$^8$-di-n-propyl-pyrimido[5,4-d]pyrimidine-2,4,6,8-tetraamine (139) (280 mg, 0.73 mmol) was treated with 2M HCl/diethyl ether in ethanol using procedure described for compound (29a). The product was crystallized from ethanol to give N$^2$,N$^6$-bis-cyclopropylmethyl-N$^4$,N$^8$-di-n-propyl-pyrimido[5,4-d]pyrimidine-2,4,6,8-tetraamine hydrochloride (305 mg, 99%). 400 MHz $^1$H NMR (DMSO-d$_6$, ppm): δ 9.3-6.7 (4H, m), 3.52-3.36 (4H, m), 3.28 (4H, d, J=6.8 Hz), 1.65 (4H, sextet, J=7.3 Hz), 1.15-1.04 (2H, m), 0.95 (6H, t, J=7.3 Hz), 0.54-0.40 (4H, m), 0.35-0.24 (4H, m). ESI-MS (m/z): 385 [M+H]$^+$; melting point: 221-224° C.

Example 67

N$^2$,N$^2$,N$^6$,N$^6$-Tetramethyl-N$^4$,N$^8$-di-n-propyl-pyrimido[5,4-d]pyrimidine-2,4,6,8-tetraamine (141) and corresponding dihydrochloride (142a)

A mixture of 2,6-dichloro-N$^4$,N$^8$-di-n-propyl-pyrimido[5,4-d]pyrimidine-4,8-diamine (2) (300 mg, 0.95 mmol) and 2M dimethylamine/THF (4.75 mL, 9.50 mmol) in n-butanol (5.0 mL) was heated in a closed vial at 110° C. for 40 h. The volatiles were removed and the residue was partitioned between a saturated NaHCO$_3$ solution (20 mL) and CH$_2$Cl$_2$ (20 mL). The aqueous phase was separated and extracted with CH$_2$Cl$_2$ (2×20 mL). The combined organic extracts were washed with water (30 mL) and dried over solid anhydrous Na$_2$SO$_4$. After filtration, the solvent was removed and the residue was purified by flash column chromatography using gradient elution from PE/EtOAc (9:1) to PE/EtOAc (1:1) to give $N^2,N^2,N^6,N^6$-tetramethyl-$N^4,N^8$-di-n-propyl-pyrimido[5,4-d]pyrimidine-2,4,6,8-tetraamine (141) (280 mg, 89% y). ESI-MS (m/z): 333 [M+H]$^+$.

$N^2,N^2,N^6,N^6$-Tetramethyl-$N^4,N^8$-di-n-propyl-pyrimido[5,4-d]pyrimidine-2,4,6,8-tetraamine (141) (270 mg, 0.81 mmol) was treated with 2M HCl/diethyl ether in 1,4-dioxane/ethanol (3/1) using procedure described for compound (3a) (270 mg, 82% y). 400 MHz $^1$H NMR (CDCl$_3$, ppm): δ 12.24 (2H, br s), 11.57 (2H, s), 3.67-3.56 (4H, m), 3.45 (12H, s), 1.90-1.77 (4H, m), 1.01 (6H, t, J=7.3 Hz). ESI-MS (m/z): 333 [M+H]$^+$; melting point: 240-242° C. Anal. Calcd for C$_{16}$H$_{30}$Cl$_2$N$_8$: C, 47.41; H, 7.46; N, 27.64. Found: C, 47.33; H, 7.46; N, 27.45.

Example 68

$N^4,N^8$-Diallyl-$N^2,N^6$-dimethyl-pyrimido[5,4-d]pyrimidine-2,4,6,8-tetraamine (144) and corresponding hydrochloride salt (145a)

$N^4,N^8$-Diallyl-2,6-dichloro-pyrimido[5,4-d]pyrimidine-4,8-diamine (143)

To a solution of 2,4,6,8-tetrachloro-pyrimido[5,4-d]pyrimidine (1) (700 mg, 2.59 mmol) in THF (20 mL), allylamine (815 μL, 10.89 mmol) in THF (5 mL) was added dropwise at 0° C. The reaction mixture was stirred at 0° C. for 90 min and then at room temperature for 30 min. A saturated NaHCO$_3$ solution (30 mL) was added and the resulting suspension was extracted with EtOAc (3×30 mL). The combined organic extracts were washed with water (50 mL), and then with a brine solution (50 mL) and dried over solid anhydrous Na$_2$SO$_4$. After filtration, the solvent was removed to give $N^4,N^8$-diallyl-2,6-dichloro-pyrimido[5,4-d]pyrimidine-4,8-diamine (143) (730 mg, 91% y). 400 MHz $^1$H NMR (CDCl$_3$, ppm): δ 7.00-6.91 (2H, m), 5.95 (2H, ddt, J=17.2, 10.2, 5.8 Hz), 5.32 (2H, ddt, J=17.2, 1.5, 1.5 Hz), 5.25 (2H, ddt, J=10.2, 1.5, 1.5 Hz), 4.23 (4H, ddt, J=5.8, 1.5 Hz). ESI-MS (m/z): 311, 313, 315 [M+H]$^+$.

$N^4,N^8$-Diallyl-$N^2,N^6$-dimethyl-pyrimido[5,4-d]pyrimidine-2,4,6,8-tetraamine (144)

A mixture of $N^4,N^8$-diallyl-2,6-dichloro-pyrimido[5,4-d]pyrimidine-4,8-diamine (143) (350 mg, 1.12 mmol) and methylamine (40% water solution, 1.0 mL) in n-butanol (1.0 mL) was heated in a closed vial at 130° C. for 40 h. The reaction mixture was cooled, a saturated NaHCO$_3$ solution (30 mL) was added and the resulting suspension was extracted with EtOAc (3×15 mL). The combined organic extracts were washed with water (30 mL), and then with a brine solution (30 mL) and dried over solid anhydrous Na$_2$SO$_4$. After filtration, the product was purified by flash column chromatography using gradient elution from PE/EtOAc (20:1) to PE/EtOAc (1:2) to give $N^4,N^8$-diallyl-$N^2,N^6$-dimethyl-pyrimido[5,4-d]pyrimidine-2,4,6,8-tetraamine (144) (225 mg, 67%). 400 MHz $^1$H NMR (CDCl$_3$, ppm): δ 6.57 (2H, s), 6.05-5.93 (2H, m), 5.32-5.23 (2H, m), 5.19-5.14 (2H, m), 4.61 (2H, s), 4.19-4.12 (4H, m), 2.96 (6H, d, J=5.1 Hz). ESI-MS (m/z): 301 [M+H]$^+$.

$N^4,N^8$-Diallyl-$N^2,N^6$-dimethyl-pyrimido[5,4-d]pyrimidine-2,4,6,8-tetraamine hydrochloride (145a)

$N^4,N^8$-Diallyl-$N^2,N^6$-dimethyl-pyrimido[5,4-d]pyrimidine-2,4,6,8-tetraamine (144) (220 mg, 0.73 mmol) was treated with 2M HCl/diethyl ether in 1,4-dioxane/ethanol (1/1) using procedure described for compound (20a) (130 mg, 89% y). 400 MHz $^1$H NMR (CDCl$_3$, ppm): δ 15.22-15.01 (0.2H, m), 14.30-14.02 (0.8H, m), 9.90-9.62 (0.2H, m), 7.90-7.75 (0.8H, m), 7.66-7.49 (1H, m), 6.66 (1H, s), 6.06-5.88 (2H, m), 5.44-5.10 (4H, m), 4.86 (1H, m), 4.36-4.08 (4H, m), 3.13-2.88 (6H, m). ESI-MS (m/z): 301 [M+H]$^+$; melting point: 224-226° C.

Example 69

$N^2,N^4,N^8$-Triallyl-6-[4-(4-fluorobenzyl)-piperazin-1-yl]-pyrimido[5,4-d]pyrimidine-2,4,8-triamine (147) and corresponding dihydrochloride salt (148a) (Scheme 22)

6-Chloro-$N^2,N^4,N^8$-triallyl-pyrimido[5,4-d]pyrimidine-2,4,8-triamine (146)

A mixture of 2,6-dichloro-$N^4,N^8$-diallyl-pyrimido[5,4-d]pyrimidine-4,8-diamine (143) (311 mg, 1.00 mmol) and allylamine (340 μL, 4.50 mmol) in n-butanol (1.0 mL) was heated in a closed vial at 70° C. for 16 h. A saturated NaHCO$_3$ solution (20 mL) was added and resulting suspension was extracted with EtOAc (3×15 mL). The combined organic extracts were washed with water (50 mL), and then with a brine solution (30 mL), and dried over solid anhydrous Na$_2$SO$_4$. After filtration, the product was purified by flash column chromatography using gradient elution from PE/EtOAc (20:1) to PE/EtOAc (1:2) to give 6-chloro-$N^2,N^4,N^8$-triallyl-pyrimido[5,4-d]pyrimidine-2,4,8-triamine (146) (230 mg, 69% y). 400 MHz $^1$H NMR (CDCl$_3$, ppm): δ 6.76 (1H, t, J=5.8 Hz), 6.61 (1H, t, J=5.8 Hz), 6.04-5.89 (3H, m), 5.33-5.12 (6H, m), 5.01 (1H, t, J=5.7 Hz), 4.22 (2H, ddt, J=5.8, 5.8, 1.5 Hz), 4.14 (2H, ddt, J=5.8, 5.8, 1.5 Hz), 4.07 (2H, ddt, J=5.7, 5.7, 1.6 Hz). ESI-MS (m/z): 332, 334 [M+H]+.

$N^2,N^4,N^8$-Triallyl-6-[4-(4-fluorobenzyl)-piperazin-1-yl]-pyrimido[5,4-d]pyrimidine-2,4,8-triamine (147)

A mixture of 6-chloro-$N^2,N^4,N^8$-triallyl-pyrimido[5,4-d]pyrimidine-2,4,8-triamine (146) (175 mg, 0.53 mmol) and 1-(4-fluorobenzyl)-piperazine (206 mg, 1.06 mmol) in n-butanol (5.0 mL) was heated in a closed vial at 70° C. for 60 h. A saturated NaHCO$_3$ solution (20 mL) was added and resulting suspension was extracted with EtOAc (3×25 mL). The combined organic extracts were washed with water (50 mL), and then with a brine solution (30 mL) and dried over solid anhydrous Na$_2$SO$_4$. After filtration, the product was purified by flash column chromatography using gradient elution from PE/EtOAc (20:1) to PE/EtOAc (2:1) to give $N^2,N^4,N^8$-triallyl-6-[4-(4-fluorobenzyl)-piperazin-1-yl]-pyrimido[5,4-d]pyrimidine-2,4,8-triamine (147) (210 mg, 81% y). 400 MHz $^1$H NMR (CDCl$_3$, ppm): δ 7.36-7.28 (2H, m), 7.05-6.96 (2H, m), 6.51 (2H, br s), 6.05-5.88 (3H, m), 5.32-5.20 (3H, m), 5.20-5.06 (3H, m), 4.69 (1H, br s), 4.20-4.10 (4H, m), 4.09-4.01 (2H, m), 3.82-3.70 (4H, m), 3.51 (2H, s), 2.53-2.42 (4H, m). ESI-MS (m/z): 490 [M+H]⁺.

$N^2,N^4,N^8$-Triallyl-6-[4-(4-fluorobenzyl)-piperazin-1-yl]-pyrimido[5,4-d]pyrimidine-2,4,8-triamine dihydrochloride(148a)

$N^2,N^4,N^8$-Triallyl-6-[4-(4-fluorobenzyl)-piperazin-1-yl]-pyrimido[5,4-d]pyrimidine-2,4,8-triamine (147) (200 mg, 0.41 mmol) was treated with 2M HCl/diethyl ether in 1,4-dioxane using procedure described for compound (20a) (105 mg, 45% y). 400 MHz ¹H NMR (CDCl₃, ppm): δ 7.19-7.10 (2H, m), 6.91-6.79 (1H, m), 5.99-5.79 (3H, m), 5.35-5.24 (4H, m), 5.23-5.14 (2H, m), 4.79-4.68 (2H, m), 4.31-4.20 (2H, m), 4.20-4.05 (6H, m), 3.88-3.75 (2H, m), 3.51-3.37 (2H, m), 2.84-2.69 (2H, m). ESI-MS (m/z): 490 [M+H]⁺; melting point: 239-241° C.

Example 70

$N^2,N^4,N^8$-Triallyl-6-{4-[bis-(4-fluorophenyl)-methyl]-piperazin-1-yl}-pyrimido[5,4-d]pyrimidine-2,4,8-triamine (149 and corresponding dihydrochloride salt (150a) (Scheme 22)

6-Chloro-$N^2,N^4,N^8$-triallyl-pyrimido[5,4-d]pyrimidine-2,4,8-triamine (146) (230 mg, 0.69 mmol) and 1-[bis-(4-fluorophenyl)-methyl]-piperazine were reacted using procedure described for compound (147) to produce $N^2,N^4,N^8$-triallyl-6-{4-[bis-(4-fluoro-phenyl)-methyl]-piperazin-1-yl}-pyrimido[5,4-d]pyrimidine-2,4,8-triamine (149) (260 mg, 64% y). 300 MHz ¹H-NMR (CDCl₃, ppm): δ 7.43-7.33 (4H, m), 7.04-6.93 (4H, m), 6.68-6.27 (2H, m), 6.07-5.86 (3H, m), 5.31-5.19 (3H, m), 5.19-5.06 (3H, m), 4.80-4.55 (1H, m), 4.24 (1H, m), 4.19-4.08 (4H, m), 4.08-3.99 (2H, m), 3.82-3.68 (4H, m), 2.49-2.35 (4H, m). ESI-MS (m/z): 584 [M+H]⁺.

$N^2,N^4,N^8$-triallyl-6-{4-[bis-(4-fluorophenyl)-methyl]-piperazin-1-yl}-pyrimido[5,4-d]pyrimidine-2,4,8-triamine (149) (250 mg, 0.43 mmol) was treated with 2M HCl/diethyl ether in 1,4-dioxane using procedure described for compound (20a) in 85% yield (240 mg, 85% y). 400 MHz ¹H NMR (CDCl₃, ppm): δ 13.64 (1H, s), 8.11 (1H, s), 8.05-7.88 (4H, m), 7.47 (1H, s), 7.18-7.07 (4H, m), 6.81 (1H, t, J=5.7 Hz), 5.97-5.78 (3H, m), 5.33-5.26 (2H, m), 5.26-5.10 (4H, m), 4.91-4.80 (1H, m), 4.70-4.51 (2H, m), 4.26-4.19 (2H, m), 4.17-4.01 (6H, m), 3.58-3.43 (2H, m), 2.93-2.72 (2H, m). ESI-MS (m/z): 584 [M+H]⁺; melting point: 240-242° C.

Scheme 22.

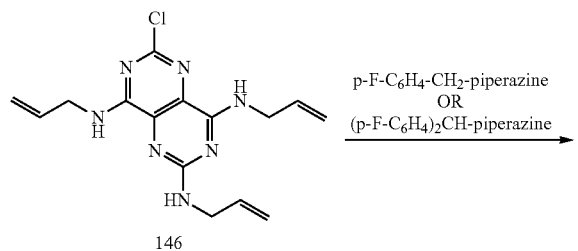

146

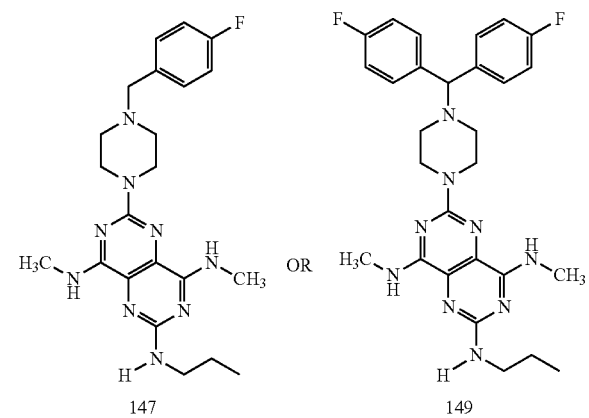

147          149

Example 71

$N^2,N^2,N^6$-Triethyl-$N^4,N^8$-di-n-propyl-pyrimido[5,4-d]pyrimidine-2,4,6,8-tetraamine (151) and corresponding hydrochloride salt (152a)

A mixture of 2,6-dichloro-$N^4,N^8$-di-n-propyl-pyrimido[5,4-d]pyrimidine-4,8-diamine (2) (215 mg, 0.68 mmol) and ethylamine (70% water solution, 1.00 mL) in n-butanol (2.0 mL) was heated at 80° C. for 18 h. A saturated NaHCO₃ solution (15 mL) was added and resulting suspension was extracted with EtOAc (3×15 mL). The combined organic extracts were washed with water (20 mL), and then with a brine solution (20 mL) and dried over solid anhydrous Na₂SO₄. After filtration, the solvent was removed. The residue was dissolved in n-butanol (2.0 mL), and diethylamine (1.0 mL) was added. The mixture was heated in a closed vial at 130° C. for 60 h. A saturated NaHCO₃ solution (15 mL) was added and the resulting suspension was extracted with EtOAc (3×20 mL). The combined organic extracts were washed with water (30 mL), and then with a brine solution (30 mL) and dried over solid anhydrous Na₂SO₄. After filtration, the solvent was removed and the residue was purified by flash column chromatography using gradient elution from PE/EtOAc (9:1) to PE/EtOAc (1:1) to give $N^2,N^2,N^6$-triethyl-$N^4,N^8$-di-n-propyl-pyrimido[5,4-d]pyrimidine-2,4,6,8-tetraamine (151) (222 mg, 91%). 400 MHz ¹H NMR (CDCl₃, ppm): δ 6.52 (1H, br s), 6.41 (1H, br s), 4.51 (1H, br s), 3.68-3.54 (4H, m), 3.52-3.34 (6H, m), 1.74-1.63 (4H, m), 1.22 (3H, t, J=7.2 Hz), 1.18 (6H, t, J=7.0 Hz), 0.99 (3H, t, J=7.4 Hz), 0.98 (3H, t, J=7.4 Hz). ESI-MS (m/z): 361 [M+H]⁺.

$N^2,N^2,N^6$-Triethyl-$N^4,N^8$-di-n-propyl-pyrimido[5,4-d]pyrimidine-2,4,6,8-tetraamine (151) (207 mg, 0.57 mmol) was treated with 2M HCl/diethyl ether in diethyl ether/ethanol (20/1) using procedure described for compound (20a) (220 mg, 97% y). 400 MHz ¹H NMR (CDCl₃, ppm): δ 13.91 (1H, br s), 7.9-7.2 (2H, m), 6.66-6.56 (1H, m), 3.75-3.45 (10H, m), 1.82-1.69 (4H, m), 1.25 (3H, t, J=7.2 Hz), 1.20 (6H, t, J=6.9 Hz), 1.02 (3H, t, J=7.4 Hz), 1.01 (3H, t, J=7.4 Hz). ESI-MS (m/z): 361 [M+H]⁺; melting point: 205-206° C.

Example 72

(4,8-Bis-methylamino-6-n-propylamino-pyrimido[5,4-d]pyrimidin-2-ylamino)-acetic acid tert-butyl ester (153) and (4,8-bis-methylamino-6-n-propylamino-pyrimido[5,4-d]pyrimidin-2-ylamino)-acetic acid (154) (Scheme 23)

A mixture of 6-chloro-$N^2$-n-propyl-$N^4$,$N^8$-dimethyl-pyrimido[5,4-d]pyrimidine-2,4,8-triamine (54) (300 mg, 1.06 mmol), glycine ethyl ester hydrochloride (297 mg, 2.13 mmol) and N,N-diisopropylethylamine (732 µL, 4.24 mmol) in n-butanol (4.0 mL) was heated in a closed vial at 130° C. for 90 h. A saturated NaHCO₃ solution (15 mL) was added and resulting suspension was extracted with CH₂Cl₂ (3×30 mL). The combined organic extracts were washed with water (50 mL) and dried over solid anhydrous Na₂SO₄. After filtration, the solvent was removed and the residue was purified by flash column chromatography using gradient elution from PE/EtOAc (9:1) to PE/EtOAc (1:3) to give (4,8-bis-methylamino-6-n-propylamino-pyrimido[5,4-d]pyrimidin-2-ylamino)-acetic acid tert-butyl ester (153) (150 mg, 38% y). ESI-MS (m/z): 377 [M+H]⁺.

A 1N NaOH solution (2 mL) was added to a solution of (4,8-bis-methylamino-6-n-propylamino-pyrimido[5,4-d]pyrimidin-2-ylamino)-acetic acid tert-butyl ester (153) (150 mg, 0.40 mmol) in 1,4-dioxane (2 mL). The mixture was stirred at ambient temperature for 1 h, and then neutralized with 1N HCl (pH 6-7). The resultant precipitate was filtered, washed with water (5 mL) and dried to give (4,8-bis-methylamino-6-n-propylamino-pyrimido[5,4-d]pyrimidin-2-ylamino)-acetic acid (154) (60 mg, 47% y). 400 MHz 1H NMR (DMSO-$d_6$, ppm): δ 12.36 (1H, br s), 7.19 (2H, br s), 6.27 (1H, s), 6.17 (1H, br s), 4.06-3.96 (2H, m), 3.34-3.21 (2H, m, overlapped with water), 2.98-2.84 (6H, m), 1.60-1.46 (2H, m), 0.90 (3H, t, J=7.2 Hz). ESI-MS (m/z): 321 [M+H]⁺; melting point: 210-212° C.

Scheme 23.

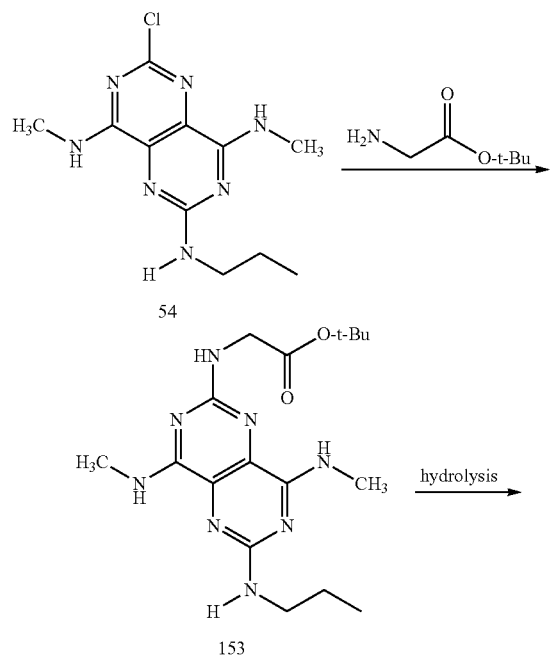

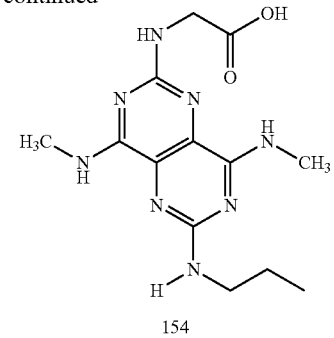

Example 73

N-n-Propyl-[2-(4,8-Bis-methylamino-6-propylamino-pyrimido[5,4-d]pyrimidin-2-ylamino)]-acetamide (156) and corresponding hydrochloride salt (157a)

(6-Chloro-4,8-bis-methylamino-pyrimido[5,4-d]pyrimidin-2-ylamino)-acetic acid ethyl ester (155)

A mixture of 2,6-dichloro-$N^4$,$N^8$-dimethyl-pyrimido[5,4-d]pyrimidine-4,8-diamine (25) (207 mg, 0.80 mmol), glycine ethyl ester hydrochloride (112 mg, 0.80 mmol) and N,N-diisopropylethylamine (276 µL, 1.60 mmol) in 1,4-dioxane (4.0 mL) was heated in a closed vial at 105° C. for 64 h. An additional portion of glycine ethyl ester hydrochloride (112 mg, 0.80 mmol) and N,N-diisopropylethylamine (276 µL, 1.60 mmol) were added, and the mixture was heated for 80 h. After cooling, a saturated NaHCO₃ solution (15 mL) was added and the resulting suspension was extracted with CH₂Cl₂ (3×20 mL). The combined organic extracts were washed with water (50 mL) and dried over solid anhydrous Na₂SO₄. After filtration, the solvent was removed and the residue was purified by flash column chromatography using gradient elution from PE/EtOAc (9:1) to PE/EtOAc (1:9) to give (6-chloro-4,8-bis-methylamino-pyrimido[5,4-d]pyrimidin-2-ylamino)-acetic acid ethyl ester (155). 400 MHz 1H NMR (CDCl₃, ppm): δ 6.72-6.64 (1H, m), 6.59-6.52 (1H, m), 5.43 (1H, t, J=5.6 Hz), 4.24 (2H, q, J=7.2 Hz), 4.18 (2H, d, J=5.6 Hz), 3.14 (3H, d, J=5.2 Hz), 3.05 (3H, d, J=5.2 Hz), 1.29 (3H, t, J=7.2 Hz). ESI-MS (m/z): 326, 328 [M+H]⁺.

N-Propyl-[2-(4,8-bis-methylamino-6-propylamino-pyrimido[5,4-d]pyrimidin-2-ylamino)]-acetamide (156)

A mixture of (6-chloro-4,8-bis-methylamino-pyrimido[5,4-d]pyrimidin-2-ylamino)-acetic acid ethyl ester (155) (204 mg, 0.63 mmol), n-propylamine (515 µL, 6.26 mmol) in n-butanol (4.0 mL) was heated in a closed vial at 125° C. for 96 h. A saturated NaHCO₃ solution (15 mL) was added and resulting suspension was extracted with CH₂Cl₂ (3×20 mL). The combined organic extracts were washed with water (40 mL) and dried over solid anhydrous Na₂SO₄. After filtration, the solvent was removed and the residue was purified by flash column chromatography using gradient elution from CH₂Cl₂/i-PrOH (97:3) to CH₂Cl₂/i-PrOH (97:3) (1:1) to give N-n-propyl-[2-(4,8-bis-methylamino-6-propylamino-pyrimido[5,4-d]pyrimidin-2-ylamino)]-acetamide (156) (125 mg, 55% y). 400 MHz ¹H NMR (CDCl₃, ppm): δ

6.66-6.60 (1H, m), 6.65 (1H, q, J=5.0 Hz), 6.37 (1H, q, J=5.0 Hz), 5.08-5.03 (1H, m), 4.76-4.71 (1H, m), 4.02 (2H, d, J=6.0 Hz), 3.38-3.32 (2H, m), 3.24-3.18 (2H, m), 3.06 (3H, d, J=5.1 Hz) 3.03 (3H, d, J=5.1 Hz) 1.62 (2H, sextet, J=7.3 Hz) 1.45 (2H, sextet, J=7.3 Hz) 0.98 (3H, t, J=7.3 Hz) 0.83 (3H, t, J=7.3 Hz). ESI-MS (m/z): 362 [M+H]$^+$.

N-n-Propyl-[2-(4,8-bis-methylamino-6-propylamino-pyrimido[5,4-d]pyrimidin-2-ylamino)]-acetamide hydrochloride (157a)

N-n-Propyl-[2-(4,8-bis-methylamino-6-propylamino-pyrimido[5,4-d]pyrimidin-2-ylamino)]-acetamide (156) (113 mg, 0.31 mmol) was treated with 2M HCl/diethyl ether in diethyl ether/ethanol (20/1) using procedure described for compound (20a) (105 mg, 85% y). 400 MHz $^1$H NMR (CDCl$_3$, ppm): δ 6.67 (1H, s), 6.22 (2H, br s), 4.14-4.08 (2H, m), 3.51-3.44 (2H, m), 3.27-3.21 (2H, m), 3.21-3.18 (3H, m), 3.15-3.09 (3H, m), 1.67 (2H, sextet, J=7.3 Hz), 1.50 (2H, sextet, J=7.3 Hz), 0.99 (3H, t, J=7.3 Hz), 0.87 (3H, t, J=7.3 Hz). ESI-MS (m/z): 362 [M+H]$^+$; melting point: 262° C. (dec.).

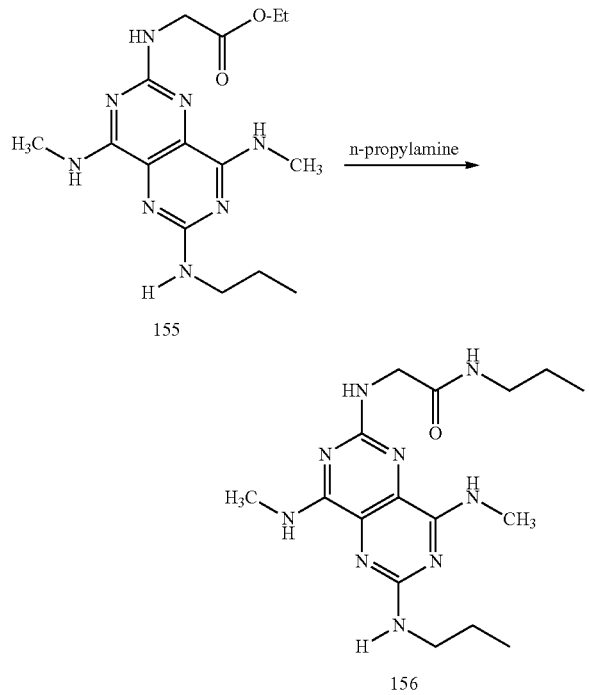

Scheme 24.

Example 74

In vitro Metabolic Stability of Select Compounds in Rat Liver Microsomes (RLM) and Human Liver Microsomes (HLM)

Assay Description:

Liver microsomes were incubated with the test compound for a series of time points. Control compound (verapamil), with a known high clearance rate, was included in every experiment for comparison with the test compound. Analysis was conducted by evaluating the disappearance of parent compound over time. Microsomes from various animal species may be used to conduct a species comparison with human data.

Materials and Reagent Preparation:

A 0.5 M stock of potassium phosphate buffer was diluted in deionized water to make up 50 mM working buffer. A large scale solution that was sufficient for several experiments was prepared, filtered-sterilized through a 0.2-micron filter using vacuum and stored at room temperature. A 8 mM NADPH solution was prepared by dissolving 100 mg NADPH sodium salt powder in 15 mL potassium phosphate buffer as prepared above to yield a final concentration of 8 mM (aliquoted and stored at −20° C.). Stock solution (5 mM) of test compounds were prepared by dissolving the material in methanol or 50/50 methanol/water. Separately, RLM (male, pooled) and/or HLM (mix-gender, pooled) with stock concentration of 20 mg/mL was obtained.

Procedure:

A 10 mL (or 20 mL) of the previously prepared 0.05 M potassium phosphate buffer was dispensed into a 50-mL conical tube and 1M MgCl$_2$ stock (20 μL or 40 μL) was added to a final concentration of 1.5 mM Mg$^{2+}$. The solution was then aliquoted into Falcon tubes (for each test compound). The 5 mM compound stock solutions (4 μL) were used to make up a final compound concentration of 5 μM. The final organic content in the assay was 0.1%. From this, 300 μL of the compounds-containing buffer solutions were divided into cluster tubes (duplicate reactions with microsomal incubations, and a singleton reaction for negative control). The 20 mg/mL microsomal stocks were diluted in potassium phosphate buffer to yield a concentration of 4 mg/mL. Then, 50 μL of the 4 mg/mL microsomal working solution were placed into the duplicate reaction wells. For the negative control wells, 50 μL of potassium phosphate buffer was used (without MgCl$_2$). The cluster tubes were pre-warmed for approximately 10 min in a 37° C. 50-rpm shaking incubator. In the meantime, the appropriate volume (1.5 mL or 3 mL) of the 8 mM NADPH solution was warmed. The enzyme reaction was started by the addition of 50 μL pre-warmed NADPH solution to all cluster tubes using a multi-channel pipette. From this, 50 μL aliquots were removed at pre-determined time points (0, 5, 10, 15, 30, and 60 minutes) into a collection plate containing 150 μL acetonitrile containing propranolol as internal standard. After collecting the last time point, the plate(s) was/were centrifuged for 10 min at 2000 g and the supernatant was transferred for LC-MS/MS analysis.

Data Interpretation:

The percent parent compound remaining was determined relative to 0-minute incubation samples for each replicate, from which the elimination half-life was calculated based on the natural log of % compound remaining vs. time plot. The following parameters were calculated to estimate the compounds in vitro metabolic stability:

$C_{mp}$=concentration of microsomal proteins (mg/mL)

$t_{1/2}$=the half-life (min), where $t_{1/2}$ is equal to 0.693/slope $CL_{int}$=the intrinsic hepatic clearance (uL/min/mg), where $CL_{int}$ is equal to $0.693/(t_{1/2} \times C_{mp})$ The metabolic stability of a test compound was categorized as follows:

Low clearance: $CL_{int}$ (μL/min/m g)<10 (RLM) or 5 (HLM)

Moderate clearance: 10≤$CL_{int}$(μL/min/mg)≤60 (RLM) or 5≤$CL_{int}$(μL/min/mg)≤35 (HLM)

High clearance: $CL_{int}$ (μL/min/mg) >60 (RLM) or 35 (HLM)

Example 75

Pharmacokinetic and Oral Bioavailability of Compound 4a in the Rat

In-Life Procedures:

Sprague-Dawley rats (200-300 g) were fed a standard laboratory rodent diet and housed in individual cages on a 12-hour light and 12-hour dark cycle with room temperature maintained at 22±3° C. and relative humidity at 50±20%. Rats were fasted overnight before dosing, with food returned after the 6 hour blood samples were obtained. Bedding was removed until after the 6 hour blood samples were obtained. Water was provided ad libitum throughout the study.

Oral Study:

Dosing solution of test compound was prepared in desired oral formulation for oral administration via gavage needle at 10-30 mg/kg (10 mL/kg) to three or four rats. All blood samples (250 µL per sample) were taken via jugular vein or femoral vein at 0 min (predose), 15 min, and 30 min and 1, 2, 4, 6, 8, and 24 h after oral dosing. Fluid replacement (1.5 mL of 0.9% sodium chloride injection, USP) were administered subcutaneously once after the 2 hr blood sampling. Blood samples were collected in BD Microtainer tubes coated with anticoagulant, placed on ice, and within 30 minutes, centrifuged at 15,000 g for 3 min to obtain plasma samples. All plasma samples were stored at −70° C. until analysis by LC-MS/MS.

Intravenous Study:

Dosing solution of test compound was prepared in desired intravenous formulation for intravenous bolus injection via tail vein, jugular vein, or femoral vein at 2-5 mg/kg (2 mL/kg) to three or four rats. All blood samples (250 uL per sample) were taken via jugular vein or femoral vein at 0 (predose), 5, 15, and 30 min and 1, 2, 4, 6, 8, and 24 h following intravenous administration. Fluid replacement (1.5 mL of 0.9% sodium chloride injection, USP) was administered subcutaneously once after the 2 hr blood sampling. Blood samples were collected in BD Microtainer tubes coated with anticoagulant, placed on ice, and within 30 minutes, centrifuged at 15,000 g for 3 minutes to obtain plasma samples. All plasma samples were stored at −70° C. until analysis by LC-MS/MS.

Bioanalytical Assay:

Plasma samples (incurred study samples, calibration standards, quality controls) were normally prepared as follows. Two volumes of acetonitrile containing an internal standard was added to one volume of plasma to precipitate plasma proteins. Samples were centrifuged (3,000 g for 5 min) and supernatant was removed for analysis by LC-MS-MS. Calibration standards were prepared by adding appropriate volumes of stock solution directly into blank plasma and treated identically to collected plasma samples. Calibration standards were typically prepared in the range of 2 ng/ml to 10 µg/mL for quantitation. Quality control samples were prepared in parallel at high, medium and low concentrations in an identical manner and they were used to ensure the quality of the assay results. No more that 2 of the 6 QC standards were allowed to differ by more than 20% of their nominal value. LC-MS-MS analysis was performed utilizing multiple reaction monitoring for detection of characteristic ions for each test compound, additional related analytes and internal standard. All ion source and tandem MS instrument parameters for the analytes were optimized for high sensitivity and selectivity.

Pharmacokinetic Data Analysis:

All pharmacokinetic parameters were determined based on a non-compartmental approach using WinNonlin software (Pharsight, Version 5.1). The terminal elimination half-life ($t_{1/2}$) was calculated as $\ln 2/\lambda z$ using the slope ($\lambda z$) from linear regression analysis of the terminal phase of the plasma concentration-time curve on a semi-log scale. The area under the plasma concentration-time curve ($AUC_{inf}$) was determined by non-compartmental analysis using the linear trapezoidal rule and extrapolated to infinity as $C_{last}/\lambda z$ using the last measurable concentration ($C_{last}$) and terminal slope ($\lambda z$). The plasma concentration at time zero ($C_0$) following intravenous administration was estimated by linear extrapolation from the first two time points after dosing. The mean residence time (MRT) was obtained by dividing the area under the first moment curve ($AUMC_{inf}$) by $AUC_{inf}$. The systemic plasma clearance ($CL_p$) was calculated as intravenous dose divided by $AUC_{inf}$. The volume of distribution at steady state ($V_{ss}$) was determined as the product of $CL_p$ and MRT. The time to reach maximum plasma concentration ($T_{max}$) was based on the time to reach observed maximum concentrations. The maximum plasma concentration ($C_{max}$) was the observed maximum concentration occurring at $T_{max}$. The absolute oral bioavailability (F) was calculated as the percentage ratio of mean dose-normalized oral $AUC_{inf}$ to dose-normalized intravenous $AUC_{inf}$.

Statistical Analysis:

Summary statistics for bioanalytical data and calculated pharmacokinetic parameters such as means, standard deviations, and coefficients of variation were determined using WinNonlin or Microsoft Excel applications.

In this assay compound 4a was found to have an oral bioavailability of 38%.

Example 76

Effect of Compounds of the Invention on Respiratory Rate (RR), Tidal Volume ($V_T$), and the Product Minute Volume Using an Anesthetized Rat Spirometry Screening Assay Anesthetized rats provide a quick method of screening compounds for respiratory and cardiovascular activity. In contrast to the conscious rat model, this model offers an experimental set up with less variation in the baseline cardiovascular and respiratory measures. Compounds screened in this assay may be examined in a conscious rat model.

Method Outline:

Rats were initially anesthetized with 3% isoflurane (inhaled) and femoral artery and vein cannulas were surgically inserted. Once cannulated, the rats were transitioned to urethane anesthesia (1.5 g/kg; i.v.) and a tracheal cut-down was performed. After placing the tracheal cannula, it was connected to a pneumotachometer to record respiratory airflow from which respiratory rate (RR), tidal volume ($V_T$), and their product minute volume were derived. After the surgical preparation was complete, animals were allowed to stabilize for 30 minutes while respiratory rate, tidal volume, minute volume, blood pressure and heart rate were recorded continuously. Arterial blood gases (ABG) were obtained from arterial blood collected from the femoral artery. ABG measurements were taken before and 6 minutes after vehicle and each dose of compound administered. Compounds being screened were administered via bolus injections through the venous cannula followed by a saline flush (total time of administration is approximately 30 seconds), and the animal was monitored for at least 6 minutes for changes in cardiovascular efforts. Compounds were prepared in formulations identified to ensure optimal solubility. As such, vehicle controls were matched for the formulation of each compound tested. Dosing of the compound being screened was 0.1 and 0.3 mg/kg. The next dose was not administered until all cardiovascular and respiratory measures had returned to baseline levels. The positive control compounds used were N-[4,6-di-(n-propylamino)-[1,3,5]triazin-2-yl]-N,O-dimethyl-hydroxylamine or N-[2,6-di-(n-propylamino)-[1,3]pyrimidin-4-yl]-N,O-dimethyl-hydroxylamine (both administered at the end of each screening experiment (0.3 mg/kg dose) to validate the experiment and also to serve as a measure with which the compound being screened could be compared.

Data Analysis:

Data were analyzed by collecting cardiovascular and respiratory data in 30 second averages (BINs). Data were plotted 2 minutes before challenge and then 6 minutes after challenge.

Figure 2:
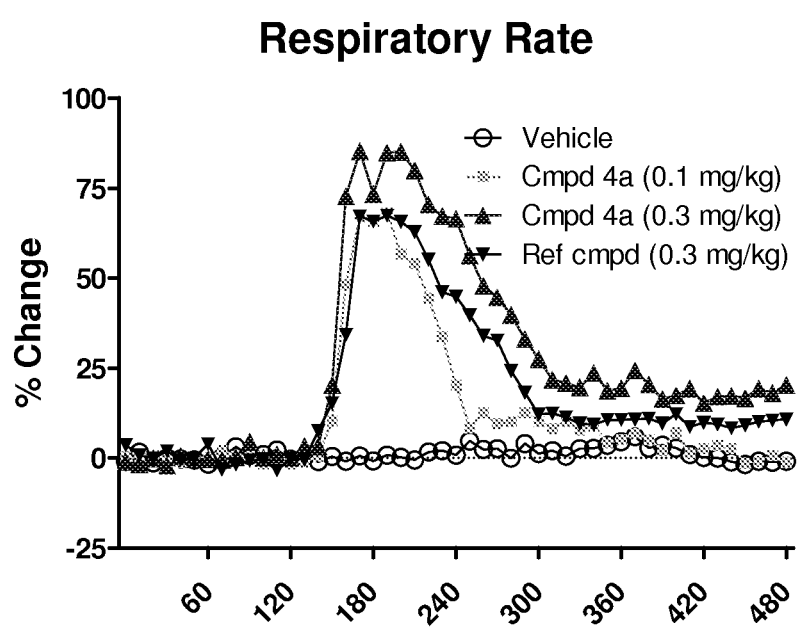
FIG. 2 is a graph illustrating the effect of compound (4a) on respiratory rate in an anesthetized rat spirometry screening assay.
Figure 3:
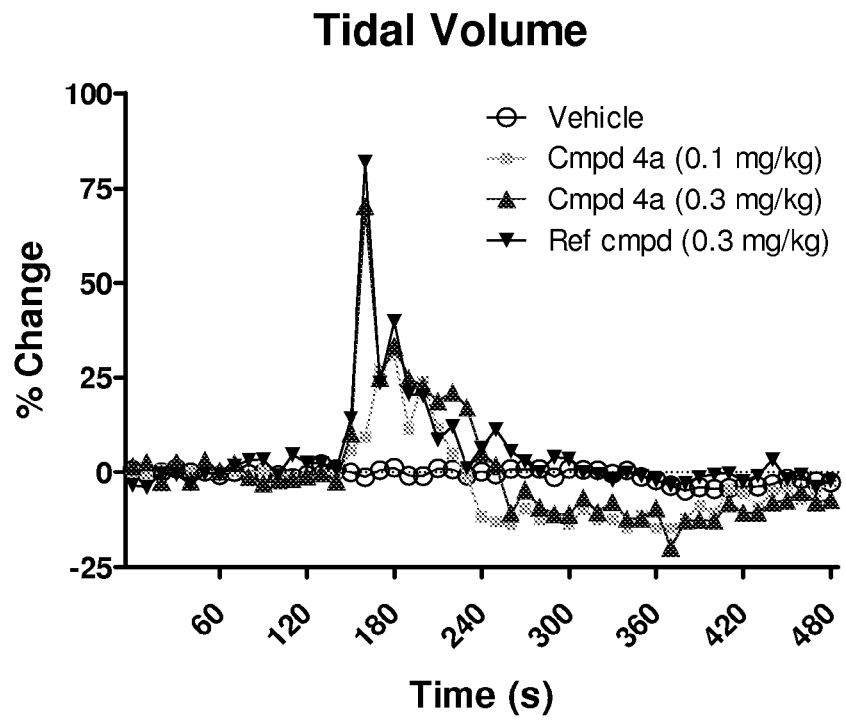
FIG. 3 is a graph illustrating the effect of compound (4a) on tidal volume in an anesthetized rat spirometry screening assay.
Figure 4:
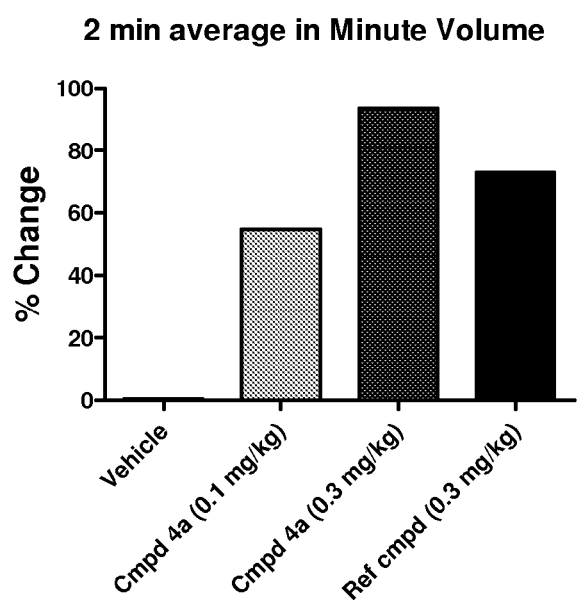
FIG. 4 is a bar graph illustrating the dose-dependent effect of compound (4a) on minute volume (based on a two-minute average) in an anesthetized rat spirometry screening assay.
Figure 5:
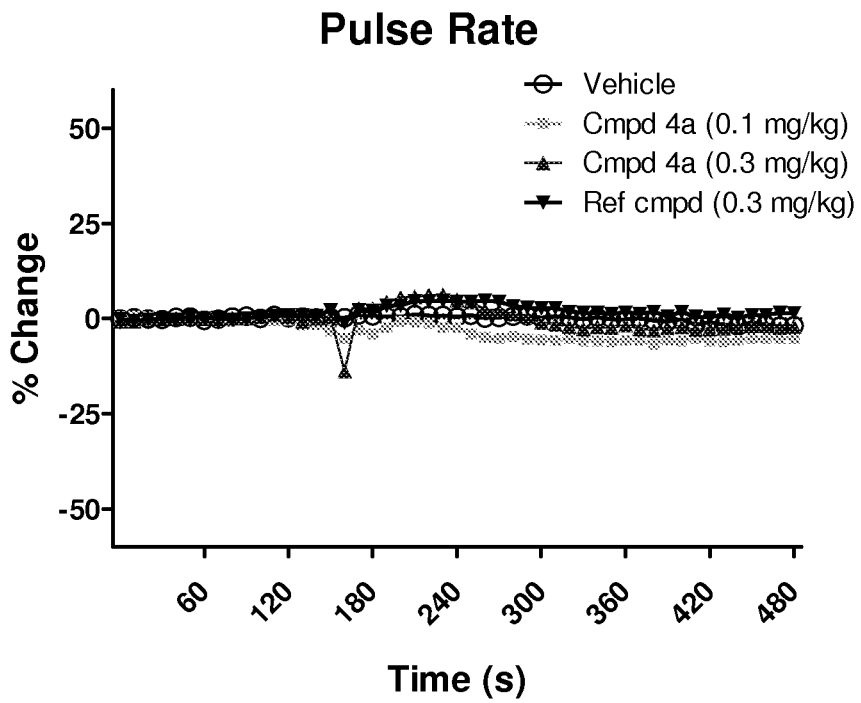
FIG. 5 is a graph illustrating the effect of compound (4a) on pulse rate in an anesthetized rat spirometry screening assay.
Figure 6:
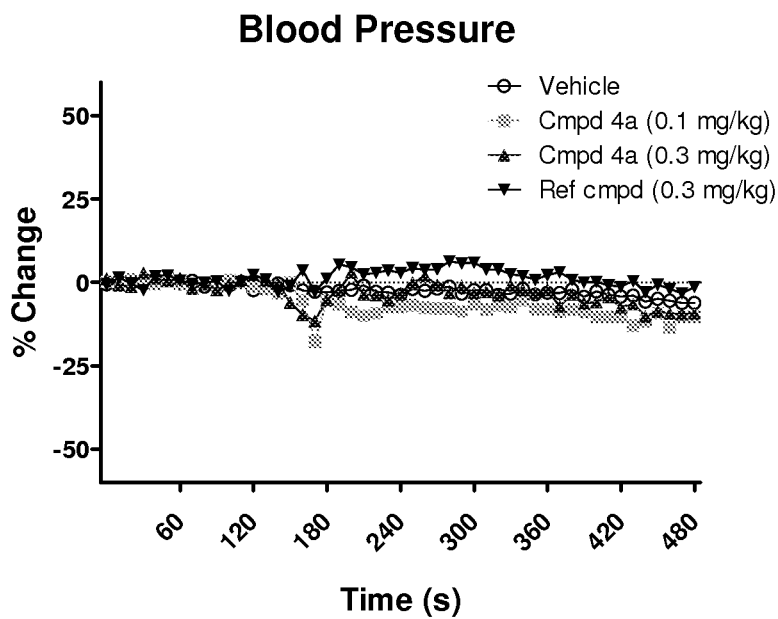
FIG. 6 is a graph illustrating the effect of compound (4a) on blood pressure in an anesthetized rat spirometry screening assay.

Results:

Compound (4a) caused an immediate and short term (approximately 2 minutes duration) increase in minute ventilation (FIG. 1) above baseline values. This increase was due to stimulatory effects on respiratory rate primarily (FIG. 2), rather than tidal volume (FIG. 3). Compound (4a) produced negligible effects on pulse rate (FIG. 5) and blood pressure (FIG. 6). Compound (4a) produced a greater effect compared to a reference compound as measured by area-under-curve (FIG. 4).

Figure 7:
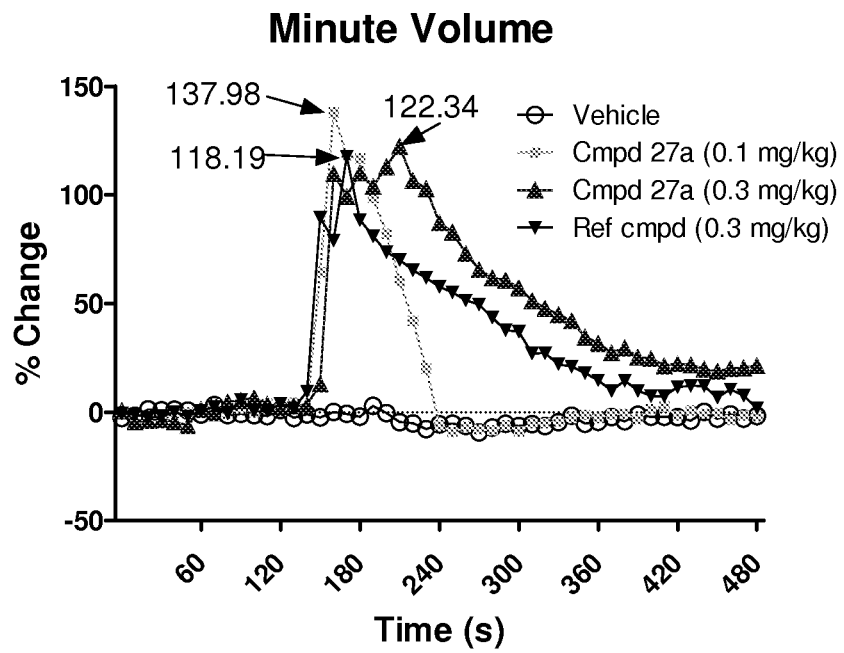
FIG. 7 is a graph illustrating the effect of compound (27a) on minute volume in an anesthetized rat spirometry screening assay.
Figure 8:
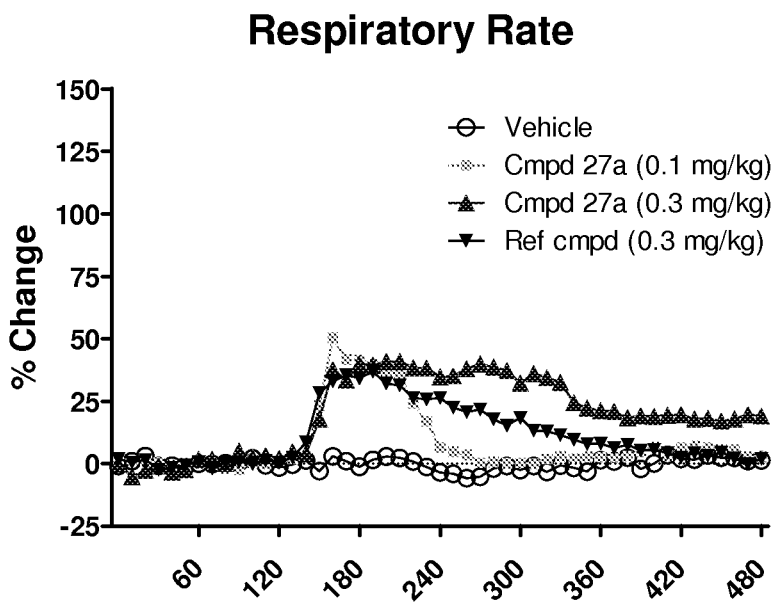
FIG. 8 is a graph illustrating the effect of compound (27a) on respiratory rate in an anesthetized rat spirometry screening assay.
Figure 9:
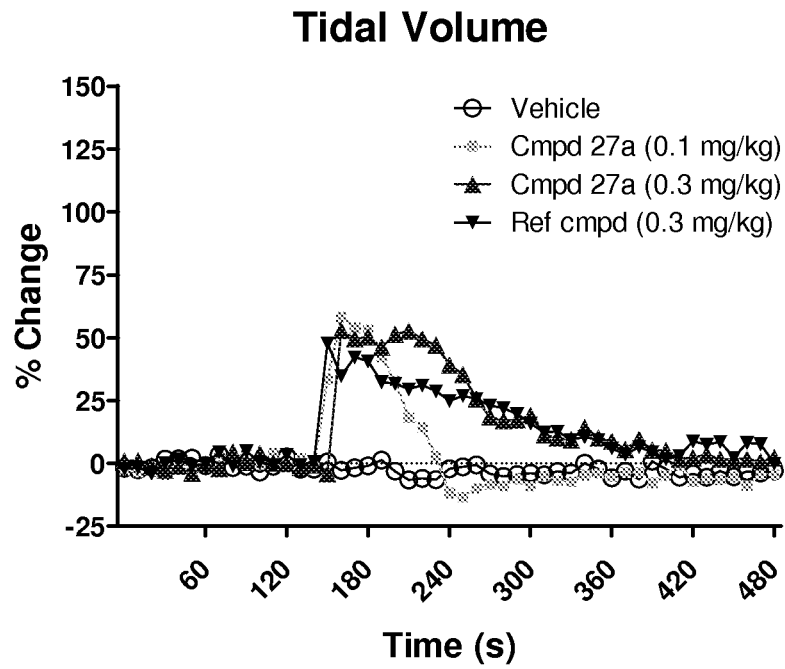
FIG. 9 is a graph illustrating the effect of compound (27a) on tidal volume in an anesthetized rat spirometry screening assay.
Figure 10:
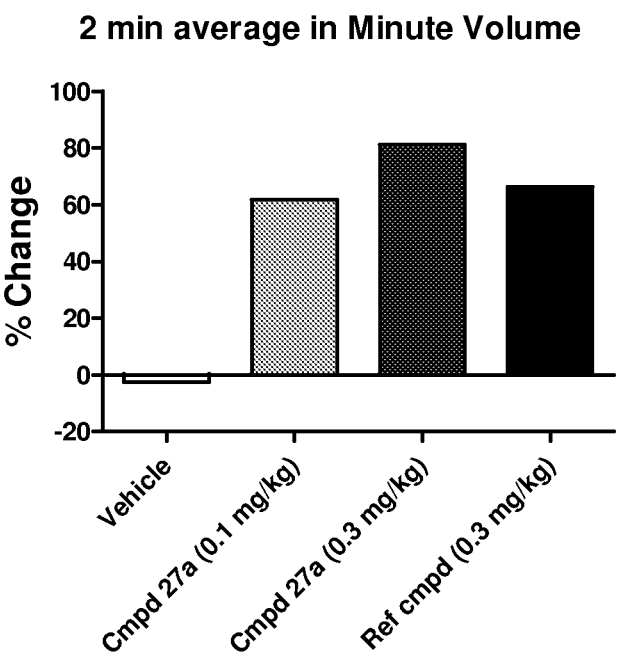
FIG. 10 is a bar graph illustrating the dose-dependent effect of compound (27a) on minute volume (based on a two-minute average) in an anesthetized rat spirometry screening assay.
Figure 11:
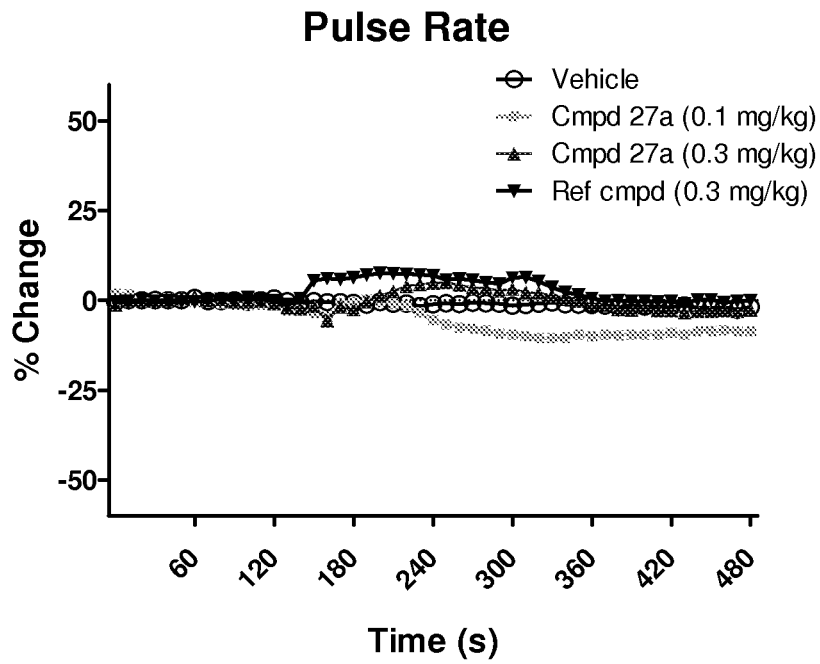
FIG. 11 is a graph illustrating the effect of compound (27a) on pulse rate in an anesthetized rat spirometry screening assay.
Figure 12:
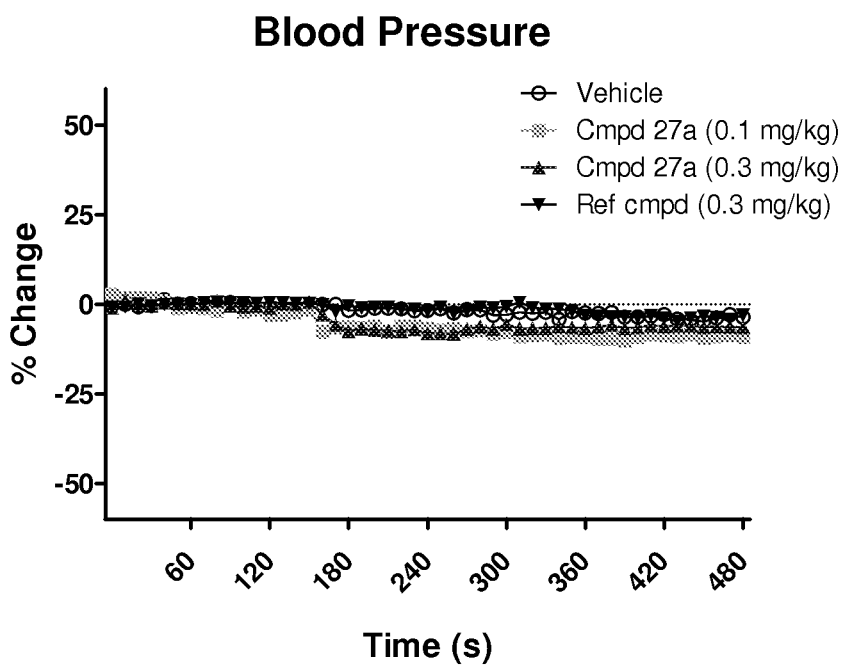
FIG. 12 is a graph illustrating the effect of compound (27a) on blood pressure in an anesthetized rat spirometry screening assay.

Compound (27a) caused an immediate and short term (approximately 2 minutes duration) increase in minute ventilation (FIG. 7) above baseline values. This increase was due to stimulatory effects on respiratory rate (FIG. 8), as well as tidal volume (FIG. 9). Compound (27a) produced minimal effects on pulse rate (FIG. 11) and blood pressure (FIG. 12). Compound (27a) produces a greater effect compared to a reference compound as measured by area-under-curve (FIG. 10).

Example 77

Microsomal Stability and Ventilatory Activity of Compounds of the Invention

Representative data are illustrated in Table 7, which summarizes the effects of individual compounds on peak minute ventilation (increase in $V_E$), overall increase in 2 minute area under the curve (AUC) which is a cumulative measure of effect, along with compound stability (half-life) in rat and human microsomes.

TABLE 7

Microsomal stability and ventilatory activity of compounds of the invention.

| Cmpd # | $V_E$ Peak (% Inc.) | AUC MV Inc (2 min) (ratio vs. std*) | RLM T½ (min) | HLM T½ (min) |
|---|---|---|---|---|
| 4a | 176 | 1.28 | 273 | 411 |
| 6a | 60 | 0.54 | 416 | >500 |
| 8a | 44 | 0.14 | 331 | >500 |
| 10a | 11 | 0.07 | 162 | 462 |
| 13a | 131 | 0.56 | 204 | 342 |
| 15a | 6 | 0.00 | 34 | 91 |
| 17a | 2 | 0.05 | 25 | 29 |
| 19a | 4 | 0.00 | 106 | 110 |

TABLE 7-continued

Microsomal stability and ventilatory activity of compounds of the invention.

| Cmpd # | $V_E$ Peak (% Inc.) | AUC MV Inc (2 min) (ratio vs. std*) | RLM T½ (min) | HLM T½ (min) |
|---|---|---|---|---|
| 22a | 9 | 0.01 | 9 | 21 |
| 24a | 123 | 0.43 | 162 | 119 |
| 27a | 122 | 1.22 | 136 | 127 |
| 29a | 135 | 0.95 | 44 | 94 |
| 31a | 3 | 0.01 | 108 | 417 |
| 33a | 88 | 0.29 | 106 | 115 |
| 35a | 279 | 1.33 | 102 | 225 |
| 37a | 128 | 1.23 | 76 | 135 |
| 39a | 120 | 0.71 | 154 | 238 |
| 41a | 57 | 0.36 | 100 | 187 |
| 43a | 26 | 0.20 | 69 | 98 |
| 45a | 87 | 0.41 | >500 | >500 |
| 47a | 4 | 0.00 | 106 | 110 |
| 49a | 19 | 0.11 | 84 | 190 |
| 51a | 20 | 0.08 | 72 | 127 |
| 53a | 15 | 0.06 | 94 | 79 |
| 54 | 30 | 0.09 | 40 | 82 |
| 56a | 116 | 0.79 | ND | ND |
| 58a | 32 | 0.18 | ND | ND |
| 60a | 192, 172 | 0.46, 0.83 | ND | ND |
| 62a | 85 | 0.55 | ND | ND |
| 64a | 9 | 0.01 | ND | ND |
| 66a | 12 | 0.14 | ND | ND |
| 68a | 3 | 0.00 | ND | ND |
| 71a | 36 | 0.13 | ND | ND |
| 73a | 1 | 0.00 | ND | ND |
| 75a | 2 | 0.02 | ND | ND |
| 77a | 50 | 0.55 | ND | ND |
| 79a | 3 | 0.00 | 388 | >500 |
| 81a | 0 | 0.00 | 274 | 198 |
| 83a | 95 | 1.05 | 335 | 249 |
| 85a | 104 | 0.51 | 386 | 389 |
| 87a | 18 | 0.18 | ND | ND |
| 89a | 169 | 0.92 | ND | ND |
| 91 | 9 | 0.08 | 24 | 102 |
| 93a | 7 | 0.03 | 14 | 81 |
| 95a | 115 | 0.36 | ND | ND |
| 97a | 38 | 0.26 | ND | ND |
| 99a | 24 | 0.19 | ND | ND |
| 101 | 3 | 0.00 | ND | ND |
| 103a | 0 | 0.00 | ND | ND |
| 105a | 7 | 0.00 | ND | ND |
| 107a | 0 | 0.00 | ND | ND |
| 108 | 11 | 0.05 | ND | ND |
| 110a | 0 | 0.00 | ND | ND |
| 112a | 20 | 0.14 | 104 | 121 |
| 114a | 6 | 0.05 | 249 | 305 |
| 116a | 0 | 0.00 | ND | ND |
| 118a | 5 | 0.05 | 34 | 72 |
| 120a | 70 | 0.36 | 82 | 114 |
| 122a | 6 | 0.00 | ND | ND |
| 125a | 133 | 0.80 | ND | ND |
| 127a | 125 | 0.86 | ND | ND |
| 129a | 21 | 0.25 | ND | ND |
| 132a | 76 | 0.98 | ND | ND |
| 135a | 0 | 0.00 | ND | ND |
| 137a | 197 | 0.88 | 97 | 227 |
| 138 | 77 | 0.53 | 331 | >500 |
| 140a | 3,7 | 0.01, 0.05 | 50 | 71 |
| 142a | 5 | 0.05 | ND | ND |
| 145a | 146 | 0.88 | ND | ND |
| 148a | 0 | 0.00 | ND | ND |
| 150a | 0 | 0.00 | ND | ND |
| 152a | 1 | 0.00 | ND | ND |
| 154 | 0 | 0.00 | ND | ND |
| 157a | 5 | 0.04 | ND | ND |

*N-[2,6-di-(n-propylamino)-[1,3]pyrimidin-4-yl]-N,O-dimethyl-hydroxylamine used as comparator compound.

Example 78

Effects of Compounds of Thes Invention on Apnea, Sleep Architecture and Ventilatory Response

The objective of this study was to quantify the effects of selected compounds of this invention on apnea, ventilation and sleep structure in a rat model. The study consisted of two treatment conditions: (1) chronic morphine and test compound administered orally, and (2) chronic morphine and oral vehicle.

Adult male lean Zucker rats were anesthetized for electroencephalogram (EEG) and electromyogram (EMG) telemeter implantation. At least one week was permitted post-surgery before animals were used further. Morphine sulfate was added to the drinking water of singly housed rats beginning with 0.1 mg/ml morphine and increasing the concentration in increments, so that a final concentration of 0.6 mg/ml was achieved within 2 weeks. All respiratory measurements were made while animals were unrestrained in whole-body plethysmography chambers to permit animals to sleep and move freely. To avoid eliciting withdrawal, morphine water was continuously available during each plethysmography experiment. Minute volume and the number of central sleep apneas (CSA) were measured during all treatment conditions. A period of at least 1 to 1.5 h was permitted for animals to acclimate to the chamber before data collection began. The biopotential telemeters and their receivers were placed directly under the plethysmographic chambers and were used to continuously to capture EEG, EMG, and body temperature signals. Only data collected between the hours of 10 am to 4:30 pm were used in the final analysis to control for the effects of circadian rhythm on breathing.

Test compound in vehicle or an equivalent volume of vehicle was administered via an oral gavage tube at 12 pm. Data collected between 10 am and 12 pm represented baseline (pre-drug) conditions. Data collected between 12 μm and 4:30 μm represented post-drug conditions. Analyses of the EEG and EMG waveforms for the purpose of staging sleep-wake behavior in rats as awake, NREM sleep, and REM sleep were based on previous sleep studies involving rodents. Central apneas were defined as a respiratory cycle period that was more than or equal to twice the average cycle period during baseline recordings. Percent time in each sleep-wake state, minute volume, and central sleep apnea counts were compared between treatment groups using a two-way ANOVA (factors: drug treatment and time). Breathing data during wakefulness was not analyzed because movement prevents measurement of accurate volumes when using whole-body plethysmography. When differences were detected with ANOVA, Student-Neuman-Keuls post hoc tests were run for all main effects and interactions. Differences were considered significant when $p<0.05$. Values are expressed as means±SE.

Compounds of this invention reduce apneas in rats, that were chronically administered opioid, at doses at which ventilatory stimulation (increase in minute volume) does not occur. As a non-limiting example, compounds (27a), (85a), (137a) and (145a) decreased apnea frequency (FIGS. 14, 19, 24 and 29), decreased the number of apneas per hr with respect to baseline (FIGS. 15, 20, 25 and 30), and decreased the number of apneas per hr with respect to vehicle (FIGS. 16, 21, 26 and 31). Furthermore, as a non-limiting example, compounds (27a), (85a), (137a) and (145a) do not cause increases in minute volume (FIGS. 17, 22, 27 and 32) and do not cause an increase in ventilation per unit time (FIGS. 18, 23, 28 and 33).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A compound selected from the group consisting of:
   $N^2,N^6$-Dimethyl-$N^4,N^8$-di-n-propyl-pyrimido[5,4-d]pyrimidine-2,4,6,8-tetraamine;
   $N^2,N^4,N^6,N^8$-Tetra-n-propyl-pyrimido[5,4-d]pyrimidine-2,4,6,8-tetraamine;
   $N^2,N^6$-Di-n-butyl-$N^4,N^8$-di-n-propyl-pyrimido[5,4-d]pyrimidine-2,4,6,8-tetraamine;
   $N^2,N^6$-Di-i-propyl-$N^4,N^8$-di-n-propyl-pyrimido[5,4-d]pyrimidine-2,4,6,8-tetraamine;
   $N^2,N^6$-Dimethyl-$N^4$-n-propyl-$N^8$-prop-2-ynyl-pyrimido[5,4-d]pyrimidine-2,4,6,8-tetraamine;
   $N^2,N^6$-Bis-(N-methoxy(N-methyl)amino)-$N^4,N^8$-bis-n-propylamino-pyrimido[5,4-d]pyrimidine;
   N-(6-Chloro-4,8-bis-propylamino-pyrimido[5,4-d]pyrimidin-2-yl)-O,N-dimethyl-hydroxylamine;
   $N^2,N^6$-Bis-(N-Methoxy(N-methyl)amino)-$N^4,N^8$-bis-n-propylamino-pyrimido[5,4-d]pyrimidine hydrochloride;
   $N^2$-Methyl-$N^4,N^8$-di-n-propyl-pyrimido[5,4-d]pyrimidine-2,4,8-triamine;
   O,N-Dimethyl-N-(6-methylamino-4,8-bis-n-propylamino-pyrimido[5,4-d] pyrimidin-2-yl)-hydroxylamine;
   $N^4,N^8$-Dimethyl-$N^2,N^6$-di-n-propyl-pyrimido[5,4-d]pyrimidine-2,4,6,8-tetraamine;
   $N^2,N^2,N^6$-Trimethyl-$N^4,N^8$-di-n-propyl-pyrimido[5,4-d]pyrimidine-2,4,6,8-tetraamine;
   6-Chloro-$N^2$-methyl-$N^4,N^8$-di-n-propylpyrimido[5,4-d]pyrimidine-2,4,8-triamine;
   $N^2,N^2$-Diethyl-$N^6$-methyl-$N^4,N^8$-di-n-propyl-pyrimido[5,4-d]pyrimidine-2,4,6,8-tetraamine;
   2-(4,8-Bis-n-propylamino-6-methylamino-pyrimido[5,4-d]pyrimidin-2-yl-amino)-ethanol;
   $N^2$-(2-Methoxy-ethyl)-$N^6$-methyl-$N^4,N^8$-di-n-propyl-pyrimido[5,4-d]pyrimidine-2,4,6,8-tetraamine;
   $N^2$-(2-Isopropoxy-ethyl)-$N^6$-methyl-$N^4,N^8$-di-n-propyl-pyrimido[5,4-d]pyrimidine-2,4,6,8-tetraamine;
   $N^8$-Methyl-$N^4,N^6$-di-n-propyl-$N^2$-(3,3,3-trifluoropropyl)-pyrimido[5,4-d]pyrimidine-2,4,6,8-tetraamine
   $N^2$-Methyl-$N^4,N^8$-di-n-propyl-6-(morpholin-4-yl)-pyrimido[5,4-d]pyrimidine-2,4,8-triamine;
   $N^2$-Methyl-$N^4,N^8$-di-n-propyl-6-(piperidin-1-yl)-pyrimido[5,4-d]pyrimidine-2,4,8-triamine;
   $N^2$-Methyl-$N^4,N^8$-di-n-propyl-6-pyrrolidin-1-yl-pyrimido[5,4-d]pyrimidine-2,4,8-triamine;
   $N^2$-Methyl-$N^4,N^8$-di-n-propyl-6-(4-methoxy-piperidin-1-yl)-pyrimido[5,4,-d]pyrimidine-2,4,8-triamine;
   $N^2$-(3-Chloro-2-methyl-benzyl)-$N^6$-methyl-$N^4,N^8$-di-n-propyl-pyrimido[5,4-d]pyrimidine-2,4,6,8-tetraamine;
   $N^2$-(3,4-Dichlorobenzyl)-$N^6$-methyl-$N^4,N^8$-di-n-propyl-pyrimido[5,4-d]pyrimidine-2,4,6,8-tetraamine;
   $N^2$-(4-Fluorobenzyl)-$N^6$-methyl-$N^4,N^8$-di-n-propyl-pyrimido[5,4-d]pyrimidine-2,4,6,8-tetraamine;

6-Chloro-$N^4,N^8$-dimethyl-$N^2$-n-propyl-pyrimido[5,4-d]pyrimidine-2,4,8-triamine;
$N^2,N^2,N^4,N^8$-Tetramethyl-$N^6$-n-propyl-pyrimido[5,4-d]pyrimidine-2,4,6,8-tetraamine;
$N^2,N^2$-Diallyl-$N^4,N^8$-dimethyl-$N^6$-n-propyl-pyrimido[5,4-d]pyrimidine-2,4,6,8-tetraamine;
2-[(4,8-Bis-methylamino-6-n-propylamino-pyrimido[5,4-d]pyrimidin-2-yl)-methyl-amino]-ethanol;
$N^2$-(2-Isopropoxy-ethyl)-$N^4,N^8$-dimethyl-$N^6$-n-propyl-pyrimido[5,4-d]pyrimidine-2,4,6,8-tetraamine;
2-[N-(2-Dimethylamino-ethyl)-N-methyl]amino-$N^4,N^8$-dimethyl-$N^6$-n-propyl-pyrimido[5,4-d]pyrimidine-4,6,8-triamine;
2-[(4,8-Bis-methylamino-6-n-propylamino-pyrimido[5,4-d]pyrimidin-2-yl)-(2-hydroxy-ethyl)-amino]-ethanol;
$N^2,N^2$-Bis-(2-methoxyethyl)-$N^4,N^8$-dimethyl-$N^6$-n-propyl-pyrimido[5,4-d]pyrimidine-2,4,6,8-tetraamine;
6-(4-Oxo-piperidin-1-yl)-$N^4,N^8$-dimethyl-$N^2$-n-propylamino-pyrimido-[5,4-d]pyrimidine-2,4,8-triamine;
$N^2$-(3-Trifluoromethyl-piperidin-1-yl)-$N^4,N^8$-dimethyl-6-n-propylamino-pyrimido-[5,4-d]pyrimidine-2,4,8-triamine;
$N^2$-6-n-Propylamino-$N^4,N^8$-dimethyl-2-(1,1-dioxo-thiomorpholin-4-yl)-pyrimido-[5,4-d]pyrimidine-2,4,8-triamine;
$N^2$-n-Propyl-$N^4,N^8$-dimethyl-6-(4,4-difluoro-piperidin-1-yl)-pyrimido[5,4-d]pyrimidine-2,4,8-triamine;
$N^2,N^4,N^6,N^8$-Tetramethyl-pyrimido[5,4-d]pyrimidine-2,4,6,8-tetraamine;
$N^2,N^6$-Diethyl-$N^4,N^8$-dimethyl-pyrimido[5,4-d]pyrimidine-2,4,6,8-tetraamine;
$N^2,N^6$-Di-n-butyl-$N^4,N^8$-dimethyl-pyrimido[5,4-d]pyrimidine-2,4,6,8-tetraamine;
$N^2,N^6$-Bis-cyclopropylmethyl-$N^4,N^8$-dimethyl-pyrimido[5,4-d]pyrimidine-2,4,6,8-tetraamine;
$N^2,N^6$-Diisobutyl-$N^4,N^8$-dimethyl-pyrimido[5,4-d]pyrimidine-2,4,6,8-tetraamine;
$N^2,N^6$-Diallyl-$N^4,N^8$-dimethyl-pyrimido[5,4-d]pyrimidine-2,4,6,8-tetraamine;
2-Chloro-6-(N,N'-dimethyl-hydrazino)-$N^4,N^8$-dimethyl-pyrimido[5,4-d]pyrimidine-4,8-diamine;
6-(N,N'-Dimethyl-hydrazino)-$N^2,N^2,N^4,N^8$-tetramethyl-pyrimido[5,4-d]pyrimidine-2,4,8-triamine;
$N^4,N^8$-Dimethyl-6-propoxy-$N^2$-n-propyl-pyrimido[5,4-d]pyrimidine-2,4,8-triamine;
$N^4,N^8$-Dimethyl-$N^2$-n-propyl-6-propylsulfanyl-pyrimido[5,4-d]pyrimidine-2,4,8-triamine;
6-Benzyloxy-$N^4,N^8$-dimethyl-$N^2$-n-propyl-pyrimido[5,4-d]pyrimidine-2,4,8-triamine;
4,8-Bis-methylamino-6-n-propylamino-pyrimido[5,4-d]pyrimidin-2-ol;
4,8-Bis-methylamino-6-n-propylamino-pyrimido[5,4-d]pyrimidine-2-carbonitrile;
$N^4,N^8$-Dimethyl-$N^2$-n-propyl-6-(aminomethyl)-pyrimido[5,4-d]pyrimidine-2,4,8-triamine;
6-Carbamoyl-$N^4,N^8$-dimethyl-$N^2$-n-propyl-pyrimido[5,4-d]pyrimidine-2,4,8-triamine;
4,8-Bis-methylamino-6-n-propylamino-pyrimido[5,4-d]pyrimidine-2-carboxylic acid;
N-(n-Propyl)-[4,8-bis-methylamino-6-n-propylamino-pyrimido[5,4-d]pyrimidin-2-yl]-amidine;
$N^4,N^8$-Dimethyl-$N^2$-n-propyl-6-(4-fluorophenyl)-pyrimido[5,4-d]pyrimidine-2,4,8-triamine;
$N^2$-Methyl-$N^4,N^8$-di-n-propyl-6-(4-fluorophenyl)-pyrimido[5,4-d]pyrimidine-2,4,8-triamine;
$N^4,N^8$-Dimethyl-$N^2$-n-propyl-pyrimido[5,4-d]pyrimidine-2,4,8-triamine;
6-n-Butyl-$N^2$-methyl-$N^4,N^8$-di-n-propyl-pyrimido[5,4-d]pyrimidine-2,4,8-triamine;
6-Methoxy-$N^2$-Methyl-$N^4,N^8$-di-n-propyl-pyrimido[5,4-d]pyrimidine-2,4,8-triamine;
6-Methylamino-4,8-bis-n-propylamino-pyrimido[5,4-d]pyrimidine-2-carbonitrile;
$N^2,N^4,N^6,N^8$-Tetraethyl-pyrimido[5,4-d]pyrimidine-2,4,6,8-tetraamine 2,6-Dichloro-$N^4,N^8$-diethyl-pyrimido[5,4-d]pyrimidine-4,8-diamine;
$N^4,N^8$-Diethyl-$N^2,N^6$-Di-n-propyl-pyrimido[5,4-d]pyrimidine-2,4,6,8-tetraamine;
$N^2,N^6$-Bis-cyclopropylmethyl-$N^4,N^8$-diethyl-pyrimido[5,4-d]pyrimidine-2,4,6,8-tetraamine;
$N^2,N^6$-Diethyl-$N^4,N^8$-bis-cyclopropylmethyl-pyrimido[5,4-d]pyrimidine-2,4,6,8-tetraamine;
$N^2,N^2,N^6$-Triethyl-$N^4,N^8$-bis-cyclopropylmethyl-pyrimido[5,4-d]pyrimidine-2,4,6,8-tetraamine;
6-Chloro-$N^2$-ethyl-$N^4,N^8$-bis-cyclopropylmethyl-pyrimido[5,4-d]pyrimidine-2,4,8-triamine;
$N^2,N^6$-Diethyl-$N^4,N^8$-di-n-propyl-pyrimido[5,4-d]pyrimidine-2,4,6,8-tetraamine;
$N^2,N^6$-Dicyclopropyl-$N^4,N^8$-di-n-propyl-pyrimido[5,4-d]pyrimidine-2,4,6,8-tetraamine;
$N^2,N^6$-Bis-cyclopropylmethyl-$N^4,N^8$-di-n-propyl-pyrimido[5,4-d]pyrimidine-2,4,6,8-tetraamine;
$N^2,N^2,N^6,N^6$-Tetramethyl-$N^4,N^8$-di-n-propyl-pyrimido[5,4-d]pyrimidine-2,4,6,8-tetraamine;
$N^4,N^8$-Diallyl-$N^2,N^6$-dimethyl-pyrimido[5,4-d]pyrimidine-2,4,6,8-tetraamine;
$N^2,N^4,N^8$-Triallyl-6-[4-(4-fluorobenzyl)-piperazin-1-yl]-pyrimido[5,4-d]pyrimidine-2,4,8-triamine;
6-Chloro-$N^2,N^4,N^8$-triallyl-pyrimido[5,4-d]pyrimidine-2,4,8-triamine;
$N^2,N^4,N^8$-Triallyl-6-{4-[bis-(4-fluorophenyl)-methyl]-piperazin-1-yl}-pyrimido[5,4-d]pyrimidine-2,4, 8-triamine;
$N^2,N^2,N^6$-Triethyl-$N^4,N^8$-di-n-propyl-pyrimido[5,4-d]pyrimidine-2,4,6,8-tetraamine;
(4,8-Bis-methylamino-6-n-propylamino-pyrimido[5,4-d]pyrimidin-2-ylamino)-acetic acid tert-butyl ester;
(4,8-Bis-methylamino-6-n-propylamino-pyrimido[5,4-d]pyrimidin-2-ylamino)-acetic acid;
N-n-Propyl-[2-(4,8-bis-methylamino-6-propylamino-pyrimido[5,4-d]pyrimidin-2-ylamino)]-acetamide;
(6-Chloro-4,8-bis-methylamino-pyrimido[5,4-d]pyrimidin-2-ylamino)-acetic acid ethyl ester;
a salt or solvate thereof, and any combinations thereof.

2. The compound of claim 1, wherein the salt is selected from the group consisting of sulfate, hydrogen sulfate, hemisulfate, chloride, bromide, iodide, nitrate, carbonate, phosphate, hydrogen phosphate, dihydrogen phosphate, formate, acetate, propionate, succinate, glycolate, gluconate, lactate, malate, tartrate, citrate, ascorbate, glucuronate, maleate, fumarate, pyruvate, aspartate, glutamate, benzoate, anthranilate, 4-hydroxybenzoate, phenylacetate, mandelate, pamoate, methanesulfonate, ethanesulfonate, benzenesulfonate, pantothenate, trifluoromethanesulfonate, 2-hydroxyethanesulfonate, p-toluenesulfonate, sulfanilate, cyclohexylaminosulfonate, stearate, alginate, β-hydroxybutyrate, salicylate, galactarate, galacturonate, saccharin, saccharate, glycerophosphonate, and any combinations thereof.

3. A pharmaceutical composition comprising at least one pharmaceutically acceptable carrier and at least one compound selected from the group consisting of:

$N^2,N^6$-Dimethyl-$N^4,N^8$-di-n-propyl-pyrimido[5,4-d]pyrimidine-2,4,6,8-tetraamine;
$N^2,N^4,N^6,N^8$-Tetra-n-propyl-pyrimido[5,4-d]pyrimidine-2,4,6,8-tetraamine;
$N^2,N^6$-Di-n-butyl-$N^4,N^8$-di-n-propyl-pyrimido[5,4-d]pyrimidine-2,4,6,8-tetraamine;
$N^2,N^6$-Di-i-propyl-$N^4,N^8$-di-n-propyl-pyrimido[5,4-d]pyrimidine-2,4,6,8-tetraamine;
$N^2,N^6$-Dimethyl-$N^4$-n-propyl-$N^8$-prop-2-ynyl-pyrimido[5,4-d]pyrimidine-2,4,6,8-tetraamine;
$N^2,N^6$-Bis-(N-methoxy(N-methyl)amino)-$N^4,N^8$-bis-n-propylamino-pyrimido[5,4-d]pyrimidine;
N-(6-Chloro-4,8-bis-propylamino-pyrimido[5,4-d]pyrimidin-2-yl)-O,N-dimethyl-hydroxylamine;
$N^2,N^6$-Bis-(N-Methoxy(N-methyl)amino)-$N^4,N^8$-bis-n-propylamino-pyrimido[5,4-d]pyrimidine hydrochloride;
$N^2$-Methyl-$N^4,N^8$-di-n-propyl-pyrimido[5,4-d]pyrimidine-2,4,8-triamine;
O,N-Dimethyl-N-(6-methylamino-4,8-bis-n-propylamino-pyrimido[5,4-d]pyrimidin-2-yl)-hydroxylamine;
$N^4,N^8$-Dimethyl-$N^2,N^6$-di-n-propyl-pyrimido[5,4-d]pyrimidine-2,4,6,8-tetraamine;
$N^2,N^2,N^6$-Trimethyl-$N^4,N^8$-di-n-propyl-pyrimido[5,4-d]pyrimidine-2,4,6,8-tetraamine;
6-Chloro-$N^2$-methyl-$N^4,N^8$-di-n-propylpyrimido[5,4-d]pyrimidine-2,4,8-triamine;
$N^2,N^2$-Diethyl-$N^6$-methyl-$N^4,N^8$-di-n-propyl-pyrimido[5,4-d]pyrimidine-2,4,6,8-tetraamine;
2-(4,8-Bis-n-propylamino-6-methylamino-pyrimido[5,4-d]pyrimidin-2-yl-amino)-ethanol;
$N^2$-(2-Methoxy-ethyl)-$N^6$-methyl-$N^4,N^8$-di-n-propyl-pyrimido[5,4-d]pyrimidine-2,4,6,8-tetraamine;
$N^2$-(2-Isopropoxy-ethyl)-$N^6$-methyl-$N^4,N^8$-di-n-propyl-pyrimido[5,4-d]pyrimidine-2,4,6,8-tetraamine;
$N^8$-Methyl-$N^4,N^6$-di-n-propyl-$N^2$-(3,3,3-trifluoropropyl)-pyrimido[5,4-d]pyrimidine-2,4,6,8-tetraamine
$N^2$-Methyl-$N^4,N^8$-di-n-propyl-6-(morpholin-4-yl)-pyrimido[5,4-d]pyrimidine-2,4,8-triamine;
$N^2$-Methyl-$N^4,N^8$-di-n-propyl-6-(piperidin-1-yl)-pyrimido[5,4-d]pyrimidine-2,4,8-triamine;
$N^2$-Methyl-$N^4,N^8$-di-n-propyl-6-pyrrolidin-1-yl-pyrimido[5,4-d]pyrimidine-2,4,8-triamine;
$N^2$-Methyl-$N^4,N^8$-di-n-propyl-6-(4-methoxy-piperidin-1-yl)-pyrimido[5,4,-d]pyrimidine-2,4,8-triamine;
$N^2$-(3-Chloro-2-methyl-benzyl)-$N^6$-methyl-$N^4,N^8$-di-n-propyl-pyrimido[5,4-d]pyrimidine -2,4,6,8-tetraamine;
$N^2$-(3,4-Dichlorobenzyl)-$N^6$-methyl-$N^4,N^8$-di-n-propyl-pyrimido[5,4-d]pyrimidine-2,4,6,8-tetraamine;
$N^2$-(4-Fluorobenzyl)-$N^6$-methyl-$N^4,N^8$-di-n-propyl-pyrimido[5,4-d]pyrimidine-2,4,6,8-tetraamine;
6-Chloro-$N^4,N^8$-dimethyl-$N^2$-n-propyl-pyrimido[5,4-d]pyrimidine-2,4,8-triamine;
$N^2,N^2,N^4,N^8$-Tetramethyl-$N^6$-n-propyl-pyrimido[5,4-d]pyrimidine-2,4,6,8-tetraamine;
$N^2,N^2$-Diallyl-$N^4,N^8$-dimethyl-$N^6$-n-propyl-pyrimido[5,4-d]pyrimidine-2,4,6,8-tetraamine;
2-[(4,8-Bis-methylamino-6-n-propylamino-pyrimido[5,4-d]pyrimidin-2-yl)-methyl-amino]-ethanol;
$N^2$-(2-Isopropoxy-ethyl)-$N^4,N^8$-dimethyl-$N^6$-n-propyl-pyrimido[5,4-d]pyrimidine-2,4,6,8-tetraamine;
2-[N-(2-Dimethylamino-ethyl)-N-methyl]amino-$N^4,N^8$-dimethyl-$N^6$-n-propyl-pyrimido[5,4-d]pyrimidine-4,6,8-triamine;
2-[(4,8-Bis-methylamino-6-n-propylamino-pyrimido[5,4-d]pyrimidin-2-yl)-(2-hydroxy-ethyl)-amino]-ethanol;
$N^2,N^2$-Bis-(2-methoxyethyl)-$N^4,N^8$-dimethyl-$N^6$-n-propyl-pyrimido[5,4-d]pyrimidine-2,4,6,8-tetraamine;
6-(4-Oxo-piperidin-1-yl)-$N^4,N^8$-dimethyl-$N^2$-n-propylamino-pyrimido-[5,4-d]pyrimidine-2,4,8-triamine;
$N^2$-(3-Trifluoromethyl-piperidin-1-yl)-$N^4,N^8$-dimethyl-6-n-propylamino-pyrimido-[5,4-d]pyrimidine-2,4,8-triamine;
$N^2$-6-n-Propylamino-$N^4,N^8$-dimethyl-2-(1,1-dioxo-thiomorpholin-4-yl)-pyrimido-[5,4-d]pyrimidine-2,4,8-triamine;
$N^2$-n-Propyl-$N^4,N^8$-dimethyl-6-(4,4-difluoro-piperidin-1-yl)-pyrimido[5,4-d]pyrimidine-2,4,8-triamine;
$N^2,N^4,N^6,N^8$-Tetramethyl-pyrimido[5,4-d]pyrimidine-2,4,6,8-tetraamine;
$N^2,N^6$-Diethyl-$N^4,N^8$-dimethyl-pyrimido[5,4-d]pyrimidine-2,4,6,8-tetraamine;
$N^2,N^6$-Di-n-butyl-$N^4,N^8$-dimethyl-pyrimido[5,4-d]pyrimidine-2,4,6,8-tetraamine;
$N^2,N^6$-Bis-cyclopropylmethyl-$N^4,N^8$-dimethyl-pyrimido[5,4-d]pyrimidine-2,4,6,8-tetraamine;
$N^2,N^6$-Diisobutyl-$N^4,N^8$-dimethyl-pyrimido[5,4-d]pyrimidine-2,4,6,8-tetraamine;
$N^2,N^6$-Diallyl-$N^4,N^8$-dimethyl-pyrimido[5,4-d]pyrimidine-2,4,6,8-tetraamine;
2-Chloro-6-(N,N'-dimethyl-hydrazino)-$N^4,N^8$-dimethyl-pyrimido[5,4-d]pyrimidine-4,8-diamine;
6-(N,N'-Dimethyl-hydrazino)-$N^2,N^2,N^4,N^8$-tetramethyl-pyrimido[5,4-d]pyrimidine-2,4,8-triamine;
$N^4,N^8$-Dimethyl-6-propoxy-$N^2$-n-propyl-pyrimido[5,4-d]pyrimidine-2,4,8-triamine;
$N^4,N^8$-Dimethyl-$N^2$-n-propyl-6-propylsulfanyl-pyrimido[5,4-d]pyrimidine-2,4,8-triamine;
6-Benzyloxy-$N^4,N^8$-dimethyl-$N^2$-n-propyl-pyrimido[5,4-d]pyrimidine-2,4,8-triamine;
4,8-Bis-methylamino-6-n-propylamino-pyrimido[5,4-d]pyrimidin-2-ol;
4,8-Bis-methylamino-6-n-propylamino-pyrimido[5,4-d]pyrimidine-2-carbonitrile;
$N^4,N^8$-Dimethyl-$N^2$-n-propyl-6-(aminomethyl)-pyrimido[5,4-d]pyrimidine-2,4,8-triamine;
6-Carbamoyl-$N^4,N^8$-dimethyl-$N^2$-n-propyl-pyrimido[5,4-d]pyrimidine-2,4,8-triamine;
4,8-Bis-methylamino-6-n-propylamino-pyrimido[5,4-d]pyrimidine-2-carboxylic acid;
N-(n-Propyl)-[4,8-bis-methylamino-6-n-propylamino-pyrimido[5,4-d]pyrimidin-2-yl]-amidine;
$N^4,N^8$-Dimethyl-$N^2$-n-propyl-6-(4-fluorophenyl)-pyrimido[5,4-d]pyrimidine-2,4,8-triamine;
$N^2$-Methyl-$N^4,N^8$-di-n-propyl-6-(4-fluorophenyl)-pyrimido[5,4-d]pyrimidine-2,4,8-triamine;
$N^4,N^8$-Dimethyl-$N^2$-n-propyl-pyrimido[5,4-d]pyrimidine-2,4,8-triamine;
6-n-Butyl-$N^2$-methyl-$N^4,N^8$-di-n-propyl-pyrimido[5,4-d]pyrimidine-2,4,8-triamine;
6-Methoxy-$N^2$-Methyl-$N^4,N^8$-di-n-propyl-pyrimido[5,4-d]pyrimidine-2,4,8-triamine;
6-Methylamino-4,8-bis-n-propylamino-pyrimido[5,4-d]pyrimidine-2-carbonitrile;
$N^2,N^4,N^6,N^8$-Tetraethyl-pyrimido[5,4-d]pyrimidine-2,4,6,8-tetraamine
2,6-Dichloro-$N^4,N^8$-diethyl-pyrimido[5,4-d]pyrimidine-4,8-diamine;
$N^4,N^8$-Diethyl-$N^2,N^6$-Di-n-propyl-pyrimido[5,4-d]pyrimidine-2,4,6,8-tetraamine;

N²,N⁶-Bis-cyclopropylmethyl-N⁴,N⁸-diethyl-pyrimido[5,4-d]pyrimidine-2,4,6,8-tetraamine;
N²,N⁶-Diethyl-N⁴,N⁸-bis-cyclopropylmethyl-pyrimido[5,4-d]pyrimidine-2,4,6,8-tetraamine;
N²,N²,N⁶-Triethyl-N⁴,N⁸-bis-cyclopropylmethyl-pyrimido[5,4-d]pyrimidine-2,4,6,8-tetraamine;
6-Chloro-N²-ethyl-N⁴,N⁸-bis-cyclopropylmethyl-pyrimido[5,4-d]pyrimidine-2,4,8-triamine;
N²,N⁶-Diethyl-N⁴,N⁸-di-n-propyl-pyrimido[5,4-d]pyrimidine-2,4,6,8-tetraamine;
N²,N⁶-Dicyclopropyl-N⁴,N⁸-di-n-propyl-pyrimido[5,4-d]pyrimidine-2,4,6,8-tetraamine;
N²,N⁶-Bis-cyclopropylmethyl-N⁴,N⁸-di-n-propyl-pyrimido[5,4-d]pyrimidine-2,4,6,8-tetraamine;
N²,N²,N⁶,N⁶-Tetramethyl-N⁴,N⁸-di-n-propyl-pyrimido[5,4-d]pyrimidine-2,4,6,8-tetraamine;
N⁴,N⁸-Diallyl-N²,N⁶-dimethyl-pyrimido[5,4-d]pyrimidine-2,4,6,8-tetraamine;
N²,N⁴,N⁸-Triallyl-6-[4-(4-fluorobenzyl)-piperazin-1-yl]-pyrimido[5,4-d]pyrimidine-2,4,8-triamine;
6-Chloro-N²,N⁴,N⁸-triallyl-pyrimido[5,4-d]pyrimidine-2,4,8-triamine;
N²,N⁴,N⁸-Triallyl-6-{4-[bis-(4-fluorophenyl)-methyl]-piperazin-1-yl}-pyrimido[5,4-d]pyrimidine-2,4,8-triamine;
N²,N²,N⁶-Triethyl-N⁴,N⁸-di-n-propyl-pyrimido[5,4-d]pyrimidine-2,4,6,8-tetraamine;
(4,8-Bis-methylamino-6-n-propylamino-pyrimido[5,4-d]pyrimidin-2-ylamino)-acetic acid tert-butyl ester;
(4,8-Bis-methylamino-6-n-propylamino-pyrimido[5,4-d]pyrimidin-2-ylamino)-acetic acid;
N-n-Propyl-[2-(4,8-bis-methylamino-6-propylamino-pyrimido[5,4-d]pyrimidin-2-ylamino)]-acetamide;
(6-Chloro-4,8-bis-methylamino-pyrimido[5,4-d]pyrimidin-2-ylamino)-acetic acid ethyl ester;
a salt or solvate thereof, and any combinations thereof.

4. The composition of claim 3, further comprising at least one agent selected from the group consisting of doxapram and enantiomers thereof, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, armodafinil, and inhaled therapeutics.

5. The composition of claim 4, wherein the compound and the agent are physically mixed in the composition.

6. The composition of claim 4, wherein the compound and the agent are physically separated in the composition.

7. The composition of claim 3, further comprising at least one agent known to cause changes in breathing control.

8. The composition in claim 7, wherein the at least one agent is selected from the group consisting of opioid narcotics, benzodiazepines, sedatives, sleeping aids, hypnotics, propofol, and any combinations thereof.

9. The composition of claim 7, wherein the compound and the agent are physically mixed in the composition.

10. The composition of claim 7, wherein the compound and the agent are physically separated in the composition.

11. The composition of claim 3, which is formulated for oral administration to a subject.

12. The composition of claim 11, wherein the composition minimizes delivery of the compound to the stomach of the subject and maximizes delivery of the compound to the intestine of the subject.

13. The composition of claim 11, wherein the composition includes an enteric coating.

14. The composition of claim 11, wherein the compound is contained in a pharmaceutically suitable capsule.

15. The composition of claim 14, wherein the capsule contains granules or powder of the compound, or an admixture of the compound with an excipient.

16. The composition of claim 15, wherein the excipient comprises a binder, disintegrant, diluent, buffer, lubricant, glidant, antioxidant, antimicrobial preservative, colorant, or flavorant.

17. The composition of claim 15, wherein the capsule is enterically coated but the granules or powders of the compound are not enterically coated.

18. The composition of claim 15, wherein the granules or powders of the compound are coated with an enteric coating before being placed into the capsule.

19. The composition of claim 18, wherein the granules or powders of the compound are coated with a multiplicity of enteric coatings, as to provide delivery of drug to different regions of the intestine of the subject.

20. The composition of claim 15, wherein at least a portion of the granules or powders of the compound are enterically coated.

21. The composition of claim 20, wherein the capsule is coated with an enteric coating that is different from the enteric coating that coats the granules or powders of the compound.

22. The composition of claim 11, wherein the compound is coated onto a base particle, whereby a core comprising the drug as a coating over the base particle is formed.

23. The composition of claim 22, wherein the core is coated with an enteric coating, thereby forming an enterically coated bead.

24. The composition of claim 23, wherein the enterically coated bead is contained in a pharmaceutically acceptable capsule.

25. The composition of claim 24, wherein the capsule contains beads coated with a multiplicity of enteric coatings, so that the capsule provides delivery of the compound to different regions of the intestine of the subject.

26. The composition of claim 15, wherein the granules or powder of the compound, or an admixture of the compound with an excipient, contained within the capsule are dissolved or suspended in a pharmaceutically acceptable liquid as to provide a liquid-filled capsule.

27. The composition of claim 26, wherein the capsule is enterically coated but the liquid formulation contained within does not comprise an enteric coating.

28. The composition of claim 26, wherein the granules or powders of the compound are enterically coated.

29. The composition of claim 28, wherein the granules or powders of the compound are coated with a multiplicity of enteric coatings, as to provide delivery of drug to different regions of the intestine of the subject.

30. The composition of claim 28, wherein the enteric coating applied to the capsule differs from the enteric coating applied to any of the granules or powders of the compound.

31. The composition of claim 14, wherein the compound is coated onto a base particle to form a core comprising the compound as a coating over the base particle, wherein the core is suspended in a pharmaceutically acceptable liquid, and wherein the suspended core is placed in a capsule.

32. The composition of claim 31, wherein the capsule and the core are enterically coated.

33. A method of treating a breathing control disorder or disease in a subject in need thereof, the method comprising administering to the subject an effective amount of a pharmaceutical composition comprising at least one pharmaceutically acceptable carrier and at least one compound or salt thereof selected from the group consisting of:

$N^2,N^6$-Dimethyl-$N^4,N^8$-di-n-propyl-pyrimido[5,4-d]pyrimidine-2,4,6,8-tetraamine;

$N^2,N^4,N^6,N^8$-Tetra-n-propyl-pyrimido[5,4-d]pyrimidine-2,4,6,8-tetraamine;

$N^2,N^6$-Di-n-butyl-$N^4,N^8$-di-n-propyl-pyrimido[5,4-d]pyrimidine-2,4,6,8-tetraamine;

$N^2,N^6$-Di-i-propyl-$N^4,N^8$-di-n-propyl-pyrimido[5,4-d]pyrimidine-2,4,6,8-tetraamine;

$N^2,N^6$-Dimethyl-$N^4$-n-propyl-$N^8$-prop-2-ynyl-pyrimido[5,4-d]pyrimidine-2,4,6,8-tetraamine;

$N^2,N^6$-Bis-(N-methoxy(N-methyl)amino)-$N^4,N^8$-bis-n-propylamino-pyrimido[5,4-d]pyrimidine;

N-(6-Chloro-4,8-bis-propylamino-pyrimido[5,4-d]pyrimidin-2-yl)-O,N-dimethyl-hydroxylamine;

$N^2,N^6$-Bis-(N-Methoxy(N-methyl)amino)-$N^4,N^8$-bis-n-propylamino-pyrimido[5,4-d]pyrimidine hydrochloride;

$N^2$-Methyl-$N^4,N^8$-di-n-propyl-pyrimido[5,4-d]pyrimidine-2,4,8-triamine;

O,N-Dimethyl-N-(6-methylamino-4,8-bis-n-propylamino-pyrimido[5,4-d]pyrimidin-2-yl)-hydroxylamine;

$N^4,N^8$-Dimethyl-$N^2,N^6$-di-n-propyl-pyrimido[5,4-d]pyrimidine-2,4,6,8-tetraamine;

$N^2,N^2,N^6$-Trimethyl-$N^4,N^8$-di-n-propyl-pyrimido[5,4-d]pyrimidine-2,4,6,8-tetraamine;

6-Chloro-$N^2$-methyl-$N^4,N^8$-di-n-propylpyrimido[5,4-d]pyrimidine-2,4,8-triamine;

$N^2,N^2$-Diethyl-$N^6$-methyl-$N^4,N^8$-di-n-propyl-pyrimido[5,4-d]pyrimidine-2,4,6,8-tetraamine;

2-(4,8-Bis-n-propylamino-6-methylamino-pyrimido[5,4-d]pyrimidin-2-yl-amino)-ethanol;

$N^2$-(2-Methoxy-ethyl)-$N^6$-methyl-$N^4,N^8$-di-n-propyl-pyrimido[5,4-d]pyrimidine-2,4,6,8-tetraamine;

$N^2$-(2-Isopropoxy-ethyl)-$N^6$-methyl-$N^4,N^8$-di-n-propyl-pyrimidine[5,4-d]pyrimidine-2,4,6,8-tetraamine;

$N^8$-Methyl-$N^4,N^6$-di-n-propyl-$N^2$-(3,3,3-trifluoropropyl)-pyrimido[5,4-d]pyrimidine-2,4,6,8-tetraamine;

$N^2$-Methyl-$N^4,N^8$-di-n-propyl-6-(morpholin-4-yl)-pyrimido[5,4-d]pyrimidine-2,4,8-triamine;

$N^2$-Methyl-$N^4,N^8$-di-n-propyl-6-(piperidin-1-yl)-pyrimido[5,4-d]pyrimidine-2,4,8-triamine;

$N^2$-Methyl-$N^4,N^8$-di-n-propyl-6-pyrrolidin-1-yl-pyrimido[5,4-d]pyrimidine-2,4,8-triamine;

$N^2$-Methyl-$N^4,N^8$-di-n-propyl-6-(4-methoxy-piperidin-1-yl)-pyrimido[5,4,-d]pyrimidine-2,4,8-triamine;

$N^2$-(3-Chloro-2-methyl-benzyl)-$N^6$-methyl-$N^4,N^8$-di-n-propyl-pyrimido[5,4-d]pyrimidine-2,4,6,8-tetraamine;

$N^2$-(3,4-Dichlorobenzyl)-$N^6$-methyl-$N^4,N^8$-di-n-propyl-pyrimido[5,4-d]pyrimidine-2,4,6,8-tetraamine;

$N^2$-(4-Fluorobenzyl)-$N^6$-methyl-$N^4,N^8$-di-n-propyl-pyrimido[5,4-d]pyrimidine-2,4,6,8-tetraamine;

6-Chloro-$N^4,N^8$-dimethyl-$N^2$-n-propyl-pyrimido[5,4-d]pyrimidine-2,4,8-triamine;

$N^2,N^2,N^4,N^8$-Tetramethyl-$N^6$-n-propyl-pyrimido[5,4-d]pyrimidine-2,4,6,8-tetraamine;

$N^2,N^2$-Diallyl-$N^4,N^8$-dimethyl-$N^6$-n-propyl-pyrimido[5,4-d]pyrimidine-2,4,6,8-tetraamine;

2-[(4,8-Bis-methylamino-6-n-propylamino-pyrimido[5,4-d]pyrimidin-2-yl)-methyl-amino]-ethanol;

$N^2$-(2-Isopropoxy-ethyl)-$N^4,N^8$-dimethyl-$N^6$-n-propyl-pyrimido[5,4-d]pyrimidine-2,4,6,8-tetraamine;

2[N-(2-Dimethylamino-ethyl)-N-methyl]amino-$N^4,N^8$-dimethyl-$N^6$-n-propyl-pyrimido[5,4-d]pyrimidine-4,6,8-triamine;

2-[(4,8-Bis-methylamino-6-n-propylamino-pyrimido[5,4-d]pyrimidin-2-yl)-(2-hydroxy-ethyl)-amino]-ethanol;

$N^2,N^2$-Bis-(2-methoxyethyl)-$N^4,N^8$-dimethyl-$N^6$-n-propyl-pyrimido[5,4-d]pyrimidine-2,4,6,8-tetraamine;

6-(4-Oxo-piperidin-1-yl)-$N^4,N^8$-dimethyl-$N^2$-n-propylamino-pyrimido-[5,4-d]pyrimidine-2,4,8-triamine;

$N^2$-(3-Trifluoromethyl-piperidin-1-yl)-$N^4,N^8$-dimethyl-6-n-propylamino-pyrimido-[5,4-d]pyrimidine-2,4,8-triamine;

$N^2$-6-n-Propylamino-$N^4,N^8$-dimethyl-2-(1,1-dioxo-thiomorpholin-4-yl)-pyrimido-[5,4-d]pyrimidine-2,4,8-triamine;

$N^2$-n-Propyl-$N^4,N^8$-dimethyl-6-(4,4-difluoro-piperidin-1-yl)-pyrimido[5,4-d]pyrimidine-2,4,8-triamine;

$N^2,N^4,N^6,N^8$-Tetramethyl-pyrimido[5,4-d]pyrimidine-2,4,6,8-tetraamine;

$N^2,N^6$-Diethyl-$N^4,N^8$-dimethyl-pyrimido[5,4-d]pyrimidine-2,4,6,8-tetraamine;

$N^2,N^6$-Di-n-butyl-$N^4,N^8$-dimethyl-pyrimido[5,4-d]pyrimidine-2,4,6,8-tetraamine;

$N^2,N^6$-Bis-cyclopropylmethyl-$N^4,N^8$-dimethyl-pyrimido[5,4-d]pyrimidine-2,4,6,8-tetraamine;

$N^2,N^6$-Diisobutyl-$N^4,N^8$-dimethyl-pyrimido[5,4-d]pyrimidine-2,4,6,8-tetraamine;

$N^2,N^6$-Diallyl-$N^4,N^8$-dimethyl-pyrimido[5,4-d]pyrimidine-2,4,6,8-tetraamine;

2-Chloro-6-(N,N'-dimethyl-hydrazino)-$N^4,N^8$-dimethyl-pyrimido[5,4-d]pyrimidine-4,8-diamine;

6-(N,N'-Dimethyl-hydrazino)-$N^2,N^2,N^4,N^8$-tetramethyl-pyrimido[5,4-d]pyrimidine-2,4,8-triamine;

$N^4,N^8$-Dimethyl-6-propoxy-$N^2$-n-propyl-pyrimido[5,4-d]pyrimidine-2,4,8-triamine;

$N^4,N^8$-Dimethyl-$N^2$-n-propyl-6-propylsulfanyl-pyrimido[5,4-d]pyrimidine-2,4,8-triamine;

6-Benzyloxy-$N^4,N^8$-dimethyl-$N^2$-n-propyl-pyrimido[5,4-d]pyrimidine-2,4,8-triamine;

4,8-Bis-methylamino-6-n-propylamino-pyrimido[5,4-d]pyrimidin-2-ol;

4,8-Bis-methylamino-6-n-propylamino-pyrimido[5,4-d]pyrimidine-2-carbonitrile;

$N^4,N^8$-Dimethyl-$N^2$-n-propyl-6-(aminomethyl)-pyrimido[5,4-d]pyrimidine-2,4,8-triamine;

6-Carbamoyl-$N^4,N^8$-dimethyl-$N^2$-n-propyl-pyrimido[5,4-d]pyrimidine-2,4,8-triamine;

4,8-Bis-methylamino-6-n-propylamino-pyrimido[5,4-d]pyrimidine-2-carboxylic acid;

N-(n-Propyl)-[4,8-bis-methylamino-6-n-propylamino-pyrimido[5,4-d]pyrimidin-2-yl]-amidine;

$N^4,N^8$-Dimethyl-$N^2$-n-propyl-6-(4-fluorophenyl)-pyrimido[5,4-d]pyrimidine-2,4,8-triamine;

$N^2$-Methyl-$N^4,N^8$-di-n-propyl-6-(4-fluorophenyl)-pyrimido[5,4-d]pyrimidine-2,4,8-triamine;

$N^4,N^8$-Dimethyl-$N^2$-n-propyl-pyrimido[5,4-d]pyrimidine-2,4,8-triamine;

6-n-Butyl-$N^2$-methyl-$N^4,N^8$-di-n-propyl-pyrimido[5,4-d]pyrimidine-2,4,8-triamine;

6-Methoxy-$N^2$-Methyl-$N^4,N^8$-di-n-propyl-pyrimido[5,4-d]pyrimidine-2,4,8-triamine;

6-Methylamino-4,8-bis-n-propylamino-pyrimido[5,4-d]pyrimidine-2-carbonitrile;

$N^2,N^4,N^6,N^8$-Tetraethyl-pyrimido [5,4-d]pyrimidine-2,4,6,8-tetraamine
2,6-Dichloro-$N^4,N^8$-diethyl-pyrimido[5,4-d]pyrimidine-4,8-diamine;
$N^4,N^8$-Diethyl-$N^2,N^6$-Di-n-propyl-pyrimido[5,4-d]pyrimidine-2,4,6,8-tetraamine;
$N^2,N^6$-Bis-cyclopropylmethyl-$N^4,N^8$-diethyl-pyrimido [5,4-d]pyrimidine-2,4,6,8-tetraamine;
$N^2,N^6$-Diethyl-$N^4,N^8$-bis-cyclopropylmethyl-pyrimido [5,4-d]pyrimidine-2,4,6,8-tetraamine;
$N^2,N^2,N^6$-Triethyl-$N^4,N^8$-bis-cyclopropylmethyl-pyrimido [5,4-d]pyrimidine-2,4,6,8-tetraamine;
6-Chloro-$N^2$-ethyl-$N^4,N^8$-bis-cyclopropylmethyl-pyrimido[5,4-d]pyrimidine-2,4,8-triamine;
$N^2,N^6$-Diethyl-$N^4,N^8$-di-n-propyl-pyrimido [5,4-d]pyrimidine-2,4,6,8-tetraamine;
$N^2,N^6$-Dicyclopropyl-$N^4,N^8$-di-n-propyl-pyrimido[5,4-d]pyrimidine-2,4,6,8-tetraamine;
$N^2,N^6$-Bis-cyclopropylmethyl-$N^4,N^8$-di-n-propyl-pyrimido[5,4-d]pyrimidine-2,4,6,8-tetraamine;
$N^2,N^2,N^6,N^6$-Tetramethyl-$N^4,N^8$-di-n-propyl-pyrimido [5,4-d]pyrimidine-2,4,6,8-tetraamine;
$N^4,N^8$-Diallyl-$N^2,N^6$-dimethyl-pyrimido[5,4-d]pyrimidine-2,4,6,8-tetraamine;
$N^2,N^4,N^8$-Triallyl-6-[4-(4-fluorobenzyl)-piperazin-1-yl]-pyrimido[5,4-d]pyrimidine-2,4,8-triamine;
6-Chloro-$N^2,N^4,N^8$-triallyl-pyrimido[5,4-d]pyrimidine-2,4,8-triamine;
$N^2,N^4,N^8$-Triallyl-6-{4-[bis-(4-fluorophenyl)-methyl]-piperazin-1-yl}-pyrimido[5,4-d]pyrimidine-2,4,8-triamine;
$N^2,N^2,N^6$-Triethyl-$N^4,N^8$-di-n-propyl-pyrimido [5,4-d]pyrimidine-2,4,6,8-tetraamine;
(4,8-Bis-methylamino-6-n-propylamino-pyrimido[5,4-d]pyrimidin-2-ylamino)-acetic acid tert-butyl ester;
(4,8-Bis-methylamino-6-n-propylamino-pyrimido[5,4-d]pyrimidin-2-ylamino)-acetic acid;
N-n-Propyl-[2-(4,8-bis-methylamino-6-propylamino-pyrimido[5,4-d]pyrimidin-2-ylamino)]acetamide;
(6-Chloro-4,8-bis-methylamino-pyrimido[5,4-d]pyrimidin-2-ylamino)-acetic acid ethyl ester;
a salt or solvate thereof, and any combinations thereof.

34. The method of claim 33, wherein the breathing control disorder or disease is selected from the group consisting of respiratory depression, sleep apnea, apnea of prematurity, obesity-hypoventilation syndrome, primary alveolar hypoventilation syndrome, dyspnea, altitude sickness, hypoxia, hypercapnia, chronic obstructive pulmonary disease (COPD), sudden infant death syndrome (SIDS), congenital central hypoventilation syndrome, Alzheimer's disease, Parkinson's disease, stroke, Duchenne muscular dystrophy, and brain and spinal cord traumatic injury.

35. The method of claim 34, wherein the respiratory depression is caused by an anesthetic, a sedative, a sleeping aid, an anxiolytic agent, a hypnotic agent, alcohol or a narcotic.

36. The method of claim 33, wherein the subject is further administered at least one additional agent useful for treating the breathing disorder or disease.

37. The method of claim 36, wherein the at least one additional agent is selected from the group consisting of doxapram and enantiomers thereof, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, armodafinil, and inhaled therapeutics.

38. The method of claim 36, wherein the compound and the agent are separately administered to the subject.

39. The method of claim 36, wherein the compound and the agent are co-administered to the subject.

40. The method of claim 33, wherein the subject is further administered at least one additional therapeutic agent known to change normal breathing control in the subject.

41. The method of claim 40, wherein at least one additional agent is selected from the group consisting of opioid narcotics, benzodiazepines, sedatives, sleeping aids, hypnotics, propofol, and any combinations thereof.

42. The method of claim 33, wherein the composition is administered in conjunction with the use of a mechanical ventilation device or positive airway pressure device on the subject.

43. The method of claim 33, wherein the subject is a mammal or bird.

44. The method of claim 43, wherein the mammal is a human.

45. The method of claim 33, wherein the composition is administered to the subject by a nasal, inhalational, topical, oral, buccal, rectal, pleural, peritoneal, vaginal, intramuscular, subcutaneous, transdermal, epidural, intratracheal, otic, intraocular, intrathecal or intravenous route.

46. The method of claim 33, wherein the composition is orally administered to the subject.

47. The method of claim 33, wherein the salt is selected from the group consisting of sulfate, hydrogen sulfate, chloride, bromide, iodide, nitrate, carbonate, phosphate, hydrogen phosphate, dihydrogen phosphate, formate, acetate, propionate, succinate, glycolate, gluconate, lactate, malate, tartrate, citrate, ascorbate, glucuronate, maleate, fumarate, pyruvate, aspartate, glutamate, benzoate, anthranilate, 4-hydroxybenzoate, phenylacetate, mandelate, pamoate, methanesulfonate, ethanesulfonate, benzenesulfonate, pantothenate, trifluoromethanesulfonate, 2-hydroxyethanesulfonate, p-toluenesulfonate, sulfanilate, cyclohexylaminosulfonate, stearate, alginate, β-hydroxybutyrate, salicylate, galactarate, galacturonate, saccharin, saccharate, and glycerophosphonate.

48. A method of stabilizing breathing rhythm in a subject in need thereof, the method comprising administering to the subject an effective amount of a pharmaceutical composition comprising at least one pharmaceutically acceptable carrier and at least one compound or salt thereof selected from the group consisting of:
$N^2,N^6$-Dimethyl-$N^4,N^8$-di-n-propyl-pyrimido[5,4-d]pyrimidine-2,4,6,8-tetraamine;
$N^2,N^4,N^6,N^8$-Tetra-n-propyl-pyrimido[5,4-d]pyrimidine-2,4,6,8-tetraamine;
$N^2,N^6$-Di-n-butyl-$N^4,N^8$-di-n-propyl-pyrimido[5,4-d]pyrimidine-2,4,6,8-tetraamine;
$N^2,N^6$-Di-i-propyl-$N^4,N^8$-di-n-propyl-pyrimido[5,4-d]pyrimidine-2,4,6,8-tetraamine;
$N^2,N^6$-Dimethyl-$N^4$-n-propyl-$N^8$-prop-2-ynyl-pyrimido [5,4-d]pyrimidine-2,4,6,8-tetraamine;
$N^2,N^6$-Bis-(N-methoxy(N-methyl)amino)-$N^4,N^8$-bis-n-propylamino-pyrimido[5,4-d]pyrimidine;
N-(6-Chloro-4,8-bis-propylamino-pyrimido[5,4-d]pyrimidin-2-yl)-O,N-dimethyl-hydroxylamine;
$N^2,N^6$-Bis-(N-Methoxy(N-methyl)amino)-$N^4,N^8$-bis-n-propylamino-pyrimido[5,4-d]pyrimidine hydrochloride;

$N^2$-Methyl-$N^4$,$N^8$-di-n-propyl-pyrimido[5,4-d]pyrimidine-2,4,8-triamine;

O,N-Dimethyl-N-(6-methylamino-4,8-bis-n-propylamino-pyrimido[5,4-d]pyrimidin-2-yl)-hydroxylamine;

$N^4$,$N^8$-Dimethyl-$N^2$,$N^6$-di-n-propyl-pyrimido[5,4-d]pyrimidine-2,4,6,8-tetraamine;

$N^2$,$N^2$,$N^6$-Trimethyl-$N^4$,$N^8$-di-n-propyl-pyrimido[5,4-d]pyrimidine-2,4,6,8-tetraamine;

6-Chloro-$N^2$-methyl-$N^4$,$N^8$-di-n-propylpyrimido[5,4-d]pyrimidine-2,4,8-triamine;

$N^2$,$N^2$-Diethyl-$N^6$-methyl-$N^4$,$N^8$-di-n-propyl-pyrimido[5,4-d]pyrimidine-2,4,6,8-tetraamine;

2-(4,8-Bis-n-propylamino-6-methylamino-pyrimido[5,4-d]pyrimidin-2-yl-amino)-ethanol;

$N^2$-(2-Methoxy-ethyl)-$N^6$-methyl-$N^4$,$N^8$-di-n-propyl-pyrimido[5,4-d]pyrimidine-2,4,6,8-tetraamine;

$N^2$-(2-Isopropoxy-ethyl)-$N^6$-methyl-$N^4$,$N^8$-di-n-propyl-pyrimido[5,4-d]pyrimidine-2,4,6,8-tetraamine;

$N^8$-Methyl-$N^4$,$N^6$-di-n-propyl-$N^2$-(3,3,3-trifluoropropyl)-pyrimido[5,4-d]pyrimidine-2,4,6,8-tetraamine $N^2$-Methyl-$N^4$,$N^8$-di-n-propyl-6-(morpholin-4-yl)-pyrimido[5,4-d]pyrimidine-2,4,8-triamine;

$N^2$-Methyl-$N^4$,$N^8$-di-n-propyl-6-(piperidin-1-yl)-pyrimido[5,4-d]pyrimidine-2,4,8-triamine;

$N^2$-Methyl-$N^4$,$N^8$-di-n-propyl-6-pyrrolidin-1-yl-pyrimido[5,4-d]pyrimidine-2,4,8-triamine;

$N^2$-Methyl-$N^4$,$N^8$-di-n-propyl-6-(4-methoxy-piperidin-1-yl)-pyrimido[5,4,-d]pyrimidine-2,4,8-triamine;

$N^2$-(3-Chloro-2-methyl-benzyl)-$N^6$-methyl-$N^4$,$N^8$-di-n-propyl-pyrimido[5,4-d]pyrimidine-2,4,6,8-tetraamine;

$N^2$-(3,4-Dichlorobenzyl)-$N^6$-methyl-$N^4$,$N^8$-di-n-propyl-pyrimido[5,4-d]pyrimidine-2,4,6,8-tetraamine;

$N^2$-(4-Fluorobenzyl)-$N^6$-methyl-$N^4$,$N^8$-di-n-propyl-pyrimido[5,4-d]pyrimidine-2,4,6,8-tetraamine;

6-Chloro-$N^4$,$N^8$-dimethyl-$N^2$-n-propyl-pyrimido[5,4-d]pyrimidine-2,4,8-triamine;

$N^2$,$N^2$,$N^4$,$N^8$-Tetramethyl-$N^6$-n-propyl-pyrimido[5,4-d]pyrimidine-2,4,6,8-tetraamine;

$N^2$,$N^2$-Diallyl-$N^4$,$N^8$-dimethyl-$N^6$-n-propyl-pyrimido[5,4-d]pyrimidine-2,4,6,8-tetraamine;

2-[(4,8-Bis-methylamino-6-n-propylamino-pyrimido[5,4-d]pyrimidin-2-yl)-methyl-amino]-ethanol;

$N^2$-(2-Isopropoxy-ethyl)-$N^4$,$N^8$-dimethyl-$N^6$-n-propyl-pyrimido[5,4-d]pyrimidine-2,4,6,-tetraamine;

2[N-(2-Dimethylamino-ethyl)-N-methyl]amino-$N^4$,$N^8$-dimethyl-$N^6$-n-propyl-pyrimido[5,4-d]pyrimidine-4,6,8-triamine;

2-[(4,8-Bis-methylamino-6-n-propylamino-pyrimido[5,4-d]pyrimidin-2-yl)-(2-hydroxy-ethyl)-amino]-ethanol;

$N^2$,$N^2$-Bis-(2-methoxyethyl)-$N^4$,$N^8$-dimethyl-$N^6$-n-propyl-pyrimido[5,4-d]pyrimidine-2,4,6,8-tetraamine;

6-(4-Oxo-piperidin-1-yl)-$N^4$,$N^8$-dimethyl-$N^2$-n-propylamino-pyrimido-[5,4-d]pyrimidine-2,4,8-triamine;

$N^2$-(3-Trifluoromethyl-piperidin-1-yl)-$N^4$,$N^8$-dimethyl-6-n-propylamino-pyrimido-[5,4-d]pyrimidine-2,4,8-triamine;

$N^2$-6-n-Propylamino-$N^4$,$N^8$-dimethyl-2-(1,1-dioxo-thiomorpholin-4-yl)-pyrimido-[5,4-d]pyrimidine-2,4,8-triamine;

$N^2$-n-Propyl-$N^4$,$N^8$-dimethyl-6-(4,4-difluoro-piperidin-1-yl)-pyrimido[5,4-d]pyrimidine-2,4,8-triamine;

$N^2$,$N^4$,$N^6$,$N^8$-Tetramethyl-pyrimido[5,4-d]pyrimidine-2,4,6,8-tetraamine;

$N^2$,$N^6$-Diethyl-$N^4$,$N^8$-dimethyl-pyrimido[5,4-d]pyrimidine-2,4,6,8-tetraamine;

$N^2$,$N^6$-Di-n-butyl-$N^4$,$N^8$-dimethyl-pyrimido[5,4-d]pyrimidine-2,4,6,8-tetraamine;

$N^2$,$N^6$-Bis-cyclopropylmethyl-$N^4$,$N^8$-dimethyl-pyrimido[5,4-d]pyrimidine-2,4,6,8-tetraamine;

$N^2$,$N^6$-Diisobutyl-$N^4$,$N^8$-dimethyl-pyrimido[5,4-d]pyrimidine-2,4,6,8-tetraamine;

$N^2$,$N^6$-Diallyl-$N^4$,$N^8$-dimethyl-pyrimido[5,4-d]pyrimidine-2,4,6,8-tetraamine;

2-Chloro-6-(N,N'-dimethyl-hydrazino)-$N^4$,$N^8$-dimethyl-pyrimido[5,4-d]pyrimidine-4,8-diamine;

6-(N,N'-Dimethyl-hydrazino)-$N^2$,$N^2$,$N^4$,$N^8$-tetramethyl-pyrimido[5,4-d]pyrimidine-2,4,8-triamine;

$N^4$,$N^8$-Dimethyl-6-propoxy-$N^2$-n-propyl-pyrimido[5,4-d]pyrimidine-2,4,8-triamine;

$N^4$,$N^8$-Dimethyl-$N^2$-n-propyl-6-propylsulfanyl-pyrimido[5,4-d]pyrimidine-2,4,8-triamine;

6-Benzyloxy-$N^4$,$N^8$-dimethyl-$N^2$-n-propyl-pyrimido[5,4-d]pyrimidine-2,4,8-triamine;

4,8-Bis-methylamino-6-n-propylamino-pyrimido[5,4-d]pyrimidin-2-ol;

4,8-Bis-methylamino-6-n-propylamino-pyrimido[5,4-d]pyrimidine-2-carbonitrile;

$N^4$,$N^8$-Dimethyl-$N^2$-n-propyl-6-(aminomethyl)-pyrimido[5,4-d]pyrimidine-2,4,8-triamine;

6-Carbamoyl-$N^4$,$N^8$-dimethyl-$N^2$-n-propyl-pyrimido[5,4-d]pyrimidine-2,4,8-triamine;

4,8-Bis-methylamino-6-n-propylamino-pyrimido[5,4-d]pyrimidine-2-carboxylic acid;

N-(n-Propyl)-[4,8-bis-methylamino-6-n-propylamino-pyrimido[5,4-d]pyrimidin-2-yl]-amidine;

$N^4$,$N^8$-Dimethyl-$N^2$-n-propyl-6-(4-fluorophenyl)-pyrimido[5,4-d]pyrimidine-2,4,8-triamine;

$N^2$-Methyl-$N^4$,$N^8$-di-n-propyl-6-(4-fluorophenyl)-pyrimido[5,4-d]pyrimidine-2,4,8-triamine;

$N^4$,$N^8$-Dimethyl-$N^2$-n-propyl-pyrimido[5,4-d]pyrimidine-2,4,8-triamine;

6-n-Butyl-$N^2$-methyl-$N^4$,$N^8$-di-n-propyl-pyrimido[5,4-d]pyrimidine-2,4,8-triamine;

6-Methoxy-$N^2$-Methyl-$N^4$,$N^8$-di-n-propyl-pyrimido[5,4-d]pyrimidine-2,4,8-triamine;

6-Methylamino-4,8-bis-n-propylamino-pyrimido[5,4-d]pyrimidine-2-carbonitrile;

$N^2$,$N^4$,$N^6$,$N^8$-Tetraethyl-pyrimido[5,4-d]pyrimidine-2,4,6,8-tetraamine 2,6-Dichloro-$N^4$,$N^8$-diethyl-pyrimido[5,4-d]pyrimidine-4,8-diamine;

$N^4$,$N^8$-Diethyl-$N^2$,$N^6$-Di-n-propyl-pyrimido[5,4-d]pyrimidine-2,4,6,8-tetraamine;

$N^2$,$N^6$-Bis-cyclopropylmethyl-$N^4$,$N^8$-diethyl-pyrimido[5,4-d]pyrimidine2,4,6,8-tetraamine;

$N^2$,$N^6$-Diethyl-$N^4$,$N^8$-bis-cyclopropylmethyl-pyrimido[5,4-d]pyrimidine-2,4,6,8-tetraamine;

$N^2$,$N^2$,$N^6$-Triethyl-$N^4$,$N^8$-bis-cyclopropylmethyl-pyrimido[5,4-d]pyrimidine-2,4,6,8-tetraamine;

6-Chloro-$N^2$-ethyl-$N^4$,$N^8$-bis-cyclopropylmethyl-pyrimido[5,4-d]pyrimidine-2,4,8-triamine;

$N^2$,$N^6$-Diethyl-$N^4$,$N^8$-di-n-propyl-pyrimido[5,4-d]pyrimidine-2,4,6,8-tetraamine;

$N^2$,$N^6$-Dicyclopropyl-$N^4$,$N^8$-di-n-propyl-pyrimido[5,4-d]pyrimidine-2,4,6,8-tetraamine;

$N^2$,$N^6$-Bis-cyclopropylmethyl-$N^4$,$N^8$-di-n-propyl-pyrimido[5,4-d]pyrimidine-2,4,6,8-tetraamine;

$N^2$,$N^2$,$N^6$,$N^6$-Tetramethyl-$N^4$,$N^8$-di-n-propyl-pyrimido[5,4-d]pyrimidine-2,4,6,8-tetraamine;

$N^4$,$N^8$-Diallyl-$N^2$,$N^6$-dimethyl-pyrimido[5,4-d]pyrimidine-2,4,6,8-tetraamine;

$N^2,N^4,N^8$-Triallyl-6-[4-(4-fluorobenzyl)-piperazin-1-yl]-pyrimido[5,4-d]pyrimidine-2,4,8-triamine;

6-Chloro-$N^2,N^4,N^8$-triallyl-pyrimido[5,4-d]pyrimidine-2,4,8-triamine;

$N^2,N^4,N^8$-Triallyl-6-{4-[bis-(4-fluorophenyl)-methyl]-piperazin-1-yl}-pyrimido[5,4-d]pyrimidine-2,4, 8-triamine;

$N^2,N^2,N^6$-Triethyl-$N^4,N^8$-di-n-propyl-pyrimido[5,4-d]pyrimidine-2,4,6,8-tetraamine;

(4,8-Bis-methylamino-6-n-propylamino-pyrimido[5,4-d]pyrimidin-2-ylamino)-acetic acid tert-butyl ester;

(4,8-Bis-methylamino-6-n-propylamino-pyrimido[5,4-d]pyrimidin-2-ylamino)-acetic acid;

N-n-Propyl-[2-(4,8-bis-methylamino-6-propylamino-pyrimido[5,4-d]pyrimidin-2-ylamino)]-acetamide;

(6-Chloro-4,8-bis-methylamino-pyrimido[5,4-d]pyrimidin-2-ylamino)-acetic acid ethyl ester;

a salt or solvate thereof, and any combinations thereof.

49. The method of claim 48, wherein the subject has a breathing control disorder or disease selected from the group consisting of respiratory depression, sleep apnea, apnea of prematurity, obesity-hypoventilation syndrome, primary alveolar hypoventilation syndrome, dyspnea, altitude sickness, hypoxia, hypercapnia, chronic obstructive pulmonary disease (COPD), sudden infant death syndrome (SIDS), congenital central hypoventilation syndrome, Alzheimer's disease, Parkinson's disease, stroke, Duchenne muscular dystrophy, and brain and spinal cord traumatic injury.

50. The method of claim 49, wherein the respiratory depression is caused by an anesthetic, a sedative, a sleeping aid, an anxiolytic agent, a hypnotic agent, alcohol or a narcotic.

51. The method of claim 49, wherein the subject is further administered at least one additional agent useful for treating the breathing disorder or disease.

52. The method of claim 51, wherein the at least one additional agent is selected from the group consisting of doxapram and enantiomers thereof, acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, armodafinil, and inhaled therapeutics.

53. The method of claim 51, wherein the compound and the agent are separately administered to the subject.

54. The method of claim 51, wherein the compound and the agent are co-administered to the subject.

55. The method of claim 48, wherein the subject is further administered at least one additional therapeutic agent known to change normal breathing control in the subject.

56. The method of claim 55, wherein at least one additional agent is selected from the group consisting of opioid narcotics, benzodiazepines, sedatives, sleeping aids, hypnotics, propofol, and any combinations thereof.

57. The method of claim 48, wherein the composition is administered in conjunction with the use of a mechanical ventilation device or positive airway pressure device on the subject.

58. The method of claim 48, wherein the subject is a mammal or bird.

59. The method of claim 58, wherein the mammal is a human.

60. The method of claim 48, wherein the composition is administered to the subject by a nasal, inhalational, topical, oral, buccal, rectal, pleural, peritoneal, vaginal, intramuscular, subcutaneous, transdermal, epidural, intratracheal, otic, intraocular, intrathecal or intravenous route.

61. The method of claim 48, wherein the composition is orally administered to the subject.

62. The method of claim 48, wherein the salt is selected from the group consisting of sulfate, hydrogen sulfate, chloride, bromide, iodide, nitrate, carbonate, phosphate, hydrogen phosphate, dihydrogen phosphate, formate, acetate, propionate, succinate, glycolate, gluconate, lactate, malate, tartrate, citrate, ascorbate, glucuronate, maleate, fumarate, pyruvate, aspartate, glutamate, benzoate, anthranilate, 4-hydroxybenzoate, phenylacetate, mandelate, pamoate, methanesulfonate, ethanesulfonate, benzenesulfonate, pantothenate, trifluoromethanesulfonate, 2-hydroxyethanesulfonate, p-toluenesulfonate, sulfanilate, cyclohexylaminosulfonate, stearate, alginate, β-hydroxybutyrate, salicylate, galactarate, galacturonate, saccharin, saccharate, and glycerophosphonate.

63. A method of preparing $N^2$-$N^6$-bis-cyclopropylmethyl $N^4$, $N^8$-dimethyl-pyrimido[5,4-d]pyrimidine-2,4,6,8-tetraamine (84), comprising reacting 2,6-dichloro-$N^4,N^8$-dimethyl-pyrimido[5,4-d]pyrimidine-4,8-diamine and cyclopropylmethylamine in a solvent.

64. The method of claim 63, wherein the reaction is run under heating and wherein (84) precipitates from the solvent once the reaction system is cooled to room temperature.

65. The method of claim 63, wherein the solvent comprises n-butanol.

66. The method of claim 64, wherein the precipitated (84) is recrystallized from n-butanol.

67. The method of claim 66, wherein the recrystallized (84) has a X-ray powder diffraction spectrum comprising 2Θ values (in degrees) of about 8.12, 9.59, 12.60, 15.02, 16.33, 17.40, 18.98, 20.68, 21.72, 22.28, 23.98, 25.24, and 26.70.

68. The method of claim 63, wherein the 2,6-dichloro-$N^4,N^8$-dimethyl-pyrimido[5,4-d]pyrimidine-4,8-diamine is prepared by reacting 2,4,6,8-tetrachloro-pyrimido[5,4-d]pyrimidine and methylamine in a solvent.

69. The method of claim 68, wherein the ratio of equivalents of 2,4,6,8-tetrachloro-pyrimido[5,4-d]pyrimidine to methylamine is about 1:4.5.

70. Compound $N^2$-$N^6$-bis-cyclopropylmethyl-$N^4,N^8$-dimethyl-pyrimido[5,4-d]pyrimidine-2,4,6,8-tetraamine, which X-ray powder diffraction spectrum comprises 2Θ values (in degrees) of about 8.12, 9.59, 12.60, 15.02, 16.33, 17.40, 18.98, 20.68, 21.72, 22.28, 23.98, 25.24, and 26.70.

* * * * *